(12) United States Patent
Kubo et al.

(10) Patent No.: US 6,797,823 B1
(45) Date of Patent: Sep. 28, 2004

(54) QUINOLINE DERIVATIVES AND QUINAZOLINE DERIVATIVES

(75) Inventors: Kazuo Kubo, Takasaki (JP); Yasunari Fujiwara, Takasaki (JP); Toshiyuki Isoe, Takasaki (JP)

(73) Assignee: Kirin Beer Kabushiki Kaisha, Tokyo-To (JP)

( * ) Notice: Subject to any disclaimer, the term of this patent is extended or adjusted under 35 U.S.C. 154(b) by 0 days.

(21) Appl. No.: 09/889,858

(22) PCT Filed: Jan. 20, 2000

(86) PCT No.: PCT/JP00/00255
§ 371 (c)(1),
(2), (4) Date: Jul. 23, 2001

(87) PCT Pub. No.: WO00/43366
PCT Pub. Date: Jul. 27, 2000

(30) Foreign Application Priority Data

| Jan. 22, 1999 | (JP) | 11-014858 |
| Feb. 3, 1999 | (JP) | 11-026691 |
| May 21, 1999 | (JP) | 11-142493 |
| Sep. 7, 1999 | (JP) | 11-253624 |

(51) Int. Cl.$^7$ .............. C07D 239/88; C07D 215/233; A61K 31/47; A61K 31/517; A61P 35/00
(52) U.S. Cl. .............. 544/287; 544/288; 544/117; 544/119; 544/183; 546/153
(58) Field of Search .............. 544/287, 288, 544/183, 235, 117, 119; 514/259, 234.5, 235.2, 266.21, 266.3, 248, 243, 312; 546/153

(56) References Cited

U.S. PATENT DOCUMENTS

| 5,480,883 A | 1/1996 | Spada |
| 6,143,764 A | * 11/2000 | Kubo et al. ............... 514/235.2 |
| 2003/0087907 A1 | * 5/2003 | Kubo et al. ................ 544/287 |

FOREIGN PATENT DOCUMENTS

| EP | 0 860 433 | 8/1998 |
| JP | 10-505600 | 6/1998 |
| JP | 11-158149 | 6/1999 |
| WO | WO 200147890 | * 7/2001 |

OTHER PUBLICATIONS

Ghosh, Acta Crystallographica C57, 76 (2001).
Vollhardt, "Organic Chemistry" (1987), pp. 1179.
Funa, Jikken, Igaku 9(2) 139–143 (1991).

* cited by examiner

*Primary Examiner*—Mark L. Berch
(74) *Attorney, Agent, or Firm*—Oblon, Spivak, McClelland, Maier & Neustadt, P.C.

(57) ABSTRACT

An object of the present invention is to provide compounds which have antitumor activity and do not change cytomorphosis. Disclosed are compounds represented by formula (I) and a pharmaceutically acceptable salts and solvates thereof and pharmaceutical compositions comprising said compounds:

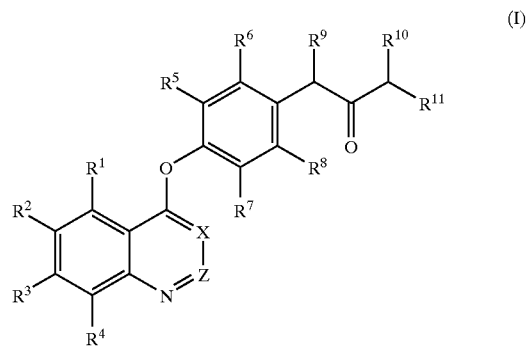

(I)

wherein X and Z each independently represent CH or N; $R^1$ to $R^3$ represent H, substituted alkoxy, unsubstituted alkoxy or the like; $R^4$ represents H; $R^5$ to $R^8$ represent H, halogen, alkyl, alkoxy, alkylthio, nitro, or amino, provided that $R^5$ to $R^8$ do not simultaneously represent H; $R^9$ and $R^{10}$ represent H, alkyl, or alkylcarbonyl; and $R^{11}$ represents alkyl, alkenyl, alkynyl, or aralkyl.

8 Claims, No Drawings

QUINOLINE DERIVATIVES AND QUINAZOLINE DERIVATIVES

This is a U.S. National Phase application of PCT/JP00/00255 file Jan. 20, 2000.

BACKGROUND OF THE INVENTION

1. Field of the Invention

The present invention relates to quinoline derivatives and quinazoline derivatives having antitumor activity. More particularly, the present invention relates to quinoline derivatives and quinazoline derivatives that are useful for the treatment of diseases such as tumor, diabetic retinopathy, chronic rheumatism, psoriasis, atherosclerosis, and Kaposi's sarcoma.

2. Background Art

WO 97/17329 describes quinoline derivatives and quinazoline derivatives having antitumor activity. WO 97/17329, however, discloses neither the effects of these quinoline derivatives and quinazoline derivatives on cytomorphosis nor the compounds according to the present invention.

SUMMARY OF THE INVENTION

The present inventors have found that a group of quinoline derivatives and quinazoline derivatives has antitumor activity and, at the same time, has no significant effect on cytomorphosis. The activity of increasing the cell size may be regarded as activity of inducing tissue disorders.

An object of the present invention is to provide compounds which have antitumor activity and, at the same time, have no significant effect on cytomorphosis.

According to the present invention, there is provided a compound represented by formula (I) or a pharmaceutically acceptable salt or solvate thereof:

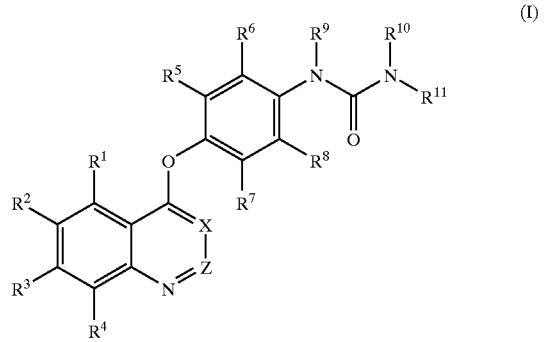

wherein

X and Z each represent CH or N;

$R^1$, $R^2$, and $R^3$, which may be the same or different, represent a hydrogen atom, $C_{1-6}$ alkyl, $C_{1-6}$ alkoxy, $C_{2-6}$ alkenyl, $C_{2-6}$ alkynyl, nitro, or amino, which $C_{1-6}$ alkyl, $C_{1-6}$ alkoxy, $C_{2-6}$ alkenyl, and $C_{2-6}$ alkynyl are optionally substituted by a halogen atom; hydroxyl; $C_{1-4}$ alkoxy; $C_{1-4}$ alkoxycarbonyl; amino on which one or two hydrogen atoms are optionally substituted by $C_{1-4}$ alkyl optionally substituted by hydroxyl or $C_{1-4}$ alkoxy; group $R^{12}R^{13}N—C(=O)—O—$ wherein $R^{12}$ and $R^{13}$, which may be the same or by different, represent a hydrogen atom or $C_{1-4}$ alkyl which alkyl is optionally substituted by hydroxyl or $C_{1-4}$ alkoxy; or group $R^{14}—(S)m-$ wherein $R^{14}$ represents a saturated or unsaturated three- to seven-membered carbocyclic or heterocyclic group optionally substituted by $C_{1-4}$ alkyl and m is 0 or 1;

$R^4$ represents a hydrogen atom;

$R^5$, $R^6$, $R^7$, and $R^8$, which may be the same or different, represent a hydrogen atom, a halogen atom, $C_{1-4}$ alkyl, $C_{1-4}$ alkoxy, $C_{1-4}$ alkylthio, nitro, or amino, provided that $R^5$, $R^6$, $R^7$, and $R^8$ do not simultaneously represent a hydrogen atom;

$R^9$ and $R^{10}$, which may be the same or different, represent a hydrogen atom, $C_{1-6}$ alkyl, or $C_{1-4}$ alkylcarbonyl, the alkyl portion of which $C_{1-6}$ alkyl or $C_{1-4}$ alkylcarbonyl is optionally substituted by a halogen atom; $C_{1-4}$ alkoxy; amino which is optionally substituted by $C_{1-4}$ alkyl optionally substituted by $C_{1-4}$ alkoxy; or a saturated or unsaturated three- to seven-membered carbocyclic or heterocyclic group; and $R^{11}$ represents $C_{1-6}$ alkyl, $C_{2-6}$ alkenyl, or $C_{2-6}$ alkynyl (which $C_{1-6}$ alkyl, $C_{2-6}$ alkenyl, and $C_{2-6}$ alkynyl each are optionally substituted by a halogen atom or $C_{1-6}$ alkoxy), or $R^{15}—(CH_2)n—$ wherein n is an integer of 0 to 4 and $R^{15}$ represents a saturated or unsaturated three- to seven-membered carbocyclic or heterocyclic group which is optionally substituted by a halogen atom, $C_{1-6}$ alkyl, or $C_{1-6}$ alkoxy and is optionally condensed with other saturated or unsaturated three- to seven-membered carbocyclic ring or heterocyclic ring to form a bicyclic ring.

The compound according to the present invention is useful, for example, for the treatment of tumor, diabetic retinopathy, chronic rheumatism, psoriasis, atherosclerosis, Kaposi's sarcoma, and solid tumor.

DETAILED DESCRIPTION OF THE INVENTION

Compound

As used herein, the term "$C_{1-6}$ alkyl" and "$C_{1-6}$ alkoxy" as a group or a part of a group respectively mean straight chain or branched chain alkyl and alkoxy having 1 to 6, preferably 1 to 4 carbon atoms.

As used herein, the term "$C_{2-6}$ alkenyl" and "$C_{2-6}$ alkynyl" as a group or a part of a group respectively mean straight chain or branched chain alkenyl and alkynyl having 2 to 6, preferably 2 to 4 carbon atoms.

Examples of $C_{1-6}$ alkyl include methyl, ethyl, n-propyl, isopropyl, n-butyl, i-butyl, s-butyl, t-butyl, n-pentyl, and n-hexyl.

Examples of $C_{1-6}$ alkoxy include methoxy, ethoxy, n-propoxy, i-propoxy, n-butoxy, i-butoxy, s-butoxy, and t-butoxy.

Examples of $C_{2-6}$ alkenyl include allyl, butenyl, pentenyl, and hexenyl.

Examples of $C_{2-6}$ alkynyl include 2-propynyl, butynyl, pentynyl, and hexynyl.

The term "halogen atom" means a fluorine, chlorine, bromine, or iodine atom.

The saturated or unsaturated three- to seven-membered carbocyclic or heterocyclic ring is preferably five- to seven-membered, more preferably five- or six-membered, saturated or unsaturated carbocyclic or heterocyclic ring.

Examples of saturated or unsaturated three- to seven-membered carbocyclic groups include phenyl, cycloheptyl, cyclohexyl, and cyclopentyl.

The saturated or unsaturated three- to seven-membered heterocyclic ring contains at least one hetero-atom selected from oxygen, nitrogen, and sulfur atoms. The term "hetero-atom" used herein means an oxygen, nitrogen, or sulfur atom. Examples of saturated or unsaturated three- to seven-membered heterocyclic groups include pyridyl, piperidino, piperazino, morpholino, imidazolyl, triazolyl, tetrazolyl, oxazolyl, thiazolyl, pyrrolidinyl, and pyrazolyl.

The saturated or unsaturated heterocyclic group, which may be represented by $R^{15}$ and $R^{32}$, may be condensed with other saturated or unsaturated heterocyclic ring to form a bicyclic ring. Such condensed cyclic groups include naphthyl, indanyl, quinolyl, and quinazolinyl.

$R^1$ preferably represents a hydrogen atom.

$R^2$ and $R^3$ preferably represents optionally substituted $C_{1-6}$ alkoxy.

$C_{1-6}$ alkyl, $C_{1-6}$ alkoxy, $C_{2-6}$ alkenyl, and $C_{2-6}$ alkynyl, which may be represented by $R^1$, $R^2$, and $R^3$, may be substituted by group $R^{14}$—(S)m- .

The carbocyclic or heterocyclic group, which may be represented by $R^{14}$, preferably represents a saturated or unsaturated five- or six-membered carbocyclic or heterocyclic group. The carbocyclic group more preferably represents phenyl. The heterocyclic group more preferably represents a saturated or unsaturated five-membered heterocyclic group containing one to four nitrogen atoms or a saturated or unsaturated six-membered heterocyclic group (preferably pyridyl) containing one or two hetero-atoms selected from nitrogen and oxygen atoms. More specifically, the hetero-atom constituting the six-membered heterocyclic group may be one nitrogen atom and one oxygen atom, or one or two nitrogen atoms.

When m is 0 (zero), —(S)m- represents a bond.

The substituted $C_{1-6}$ alkoxy group, which may be represented by $R^1$, $R^2$, and $R^3$, preferably represents group $R^{31}$—(CH$_2$)p-O— wherein $R^{31}$ represents a halogen atom, hydroxyl, $C_{1-4}$ alkoxy, $C_{1-4}$ alkoxycarbonyl, amino on which one or two hydrogen atoms each are optionally substituted by $C_{1-4}$ alkyl optionally substituted by hydroxyl or $C_{1-4}$ alkoxy, group $R^{12}R^{13}$N—C(=O)—O— wherein $R^{12}$ and $R^{13}$ are as defined in formula (I), or group $R^{14}$—(S)m- wherein $R^{14}$ may be as defined in formula (I); p is an integer of 1 to 6, preferably 1 to 4, more preferably 1 or 2, particularly preferably 1.

A group of preferred compounds represented by formula (I) include:
  compounds wherein $R^1$ represents a hydrogen atom and $R^2$ and $R^3$ represent unsubstituted $C_{1-4}$ alkoxy, preferably methoxy;
  compounds wherein $R^1$ represents a hydrogen atom, $R^2$ represents substituted $C_{1-4}$ alkoxy, preferably group $R^{31}$—(CH$_2$)p-O—, and $R^3$ represents unsubstituted $C_{1-4}$ alkoxy, preferably methoxy; and
  compounds wherein $R^1$ represents a hydrogen atom, $R^2$ represents unsubstituted $C_{1-4}$ alkoxy, preferably methoxy, and $R^3$ represents substituted $C_{1-4}$ alkoxy, preferably group $R^{31}$—(CH$_2$)p-O—.

Another group of preferred compounds represented by formula (I) include:
  compounds wherein at least one of $R^5$, $R^6$, $R^7$, and $R^8$ represents a halogen atom, preferably a chlorine atom or a fluorine atom;
  compounds wherein at least one of $R^{5,\ R6,\ R7,\ and\ R8}$ represents $C_{1-4}$ alkyl;
  compounds wherein two of $R^5$, $R^6$, $R^7_1$ and $R^8$ represent methyl and the remaining two represent a hydrogen atom;
  compounds wherein at least one of $R^5$, $R^6$, $R^7$, and $R^8$ repersents nitro, amino, $C_{1-4}$ alkoxy, or $C_{1-4}$ alkylthio;
  compounds wherein $R^5$, $R^7$, and $R^8$ represent a hydrogen atom and $R^6$ represents a halogen atom, more preferably a chlorine atom or a fluorine atom;
  compounds wherein $R^5$ and $R^6$ represent $C_{1-4}$ alkyl, more preferably methyl, and $R^7$ and $R^8$ represent a hydrogen atom;
  compounds wherein $R^5$ and $R^8$ represent a hydrogen atom and $R^6$ and $R^7$ represent $C_{1-4}$ alkyl, more preferably methyl; and
  compounds wherein $R^5$, $R^7$, and $R^8$ represent a hydrogen atom and $R^6$ represents $C_{1-4}$ alkyl, $C_{1-4}$ alkoxy, $C_{1-4}$ alkylthio, nitro, or amino.

In $R^9$ and $R^{10}$, the saturated or unsaturated three- to seven-membered carbocyclic or heterocyclic group as the substituent preferably represents a saturated or unsaturated five- or six-membered carbocyclic or heterocyclic group.

$R^9$ and $R^{10}$ preferably represent a hydrogen atom, methyl, ethyl, propyl, methoxymethyl, formyl, acetyl, benzyl, or phenetyl.

Still another group of preferred compounds represented by formula (I) include:
  compounds wherein $R^1$, $R^9$, and $R^{10}$ represent a hydrogen atom; and
  compounds wherein $R^1$ represents a hydrogen atom and any one of or both $R^9$ and $R^{10}$ represent a group other than a hydrogen atom.

In group $R^{15}$—(CH,)n— which may be represented by $R^{11}$, n is preferably an integer of 0 to 2, more preferably 0 or 1. Preferred examples of $R^{15}$ include an optionally substituted saturated or unsaturated six-membered carbocyclic group, more preferably phenyl, and an optionally substituted saturated or unsaturated six-membered heterocyclic group, more preferably pyridyl. The hetero-atom(s) constituting the six-membered heterocyclic group may more specifically consist of one nitrogen atom or one nitrogen atom and one oxygen atom.

A further group of preferred compounds represented by formula (I) include compounds wherein X represents N or CH and Z represents CH.

A still further group of preferred compounds represented by formula (I) include compounds represented by formula (Ia):

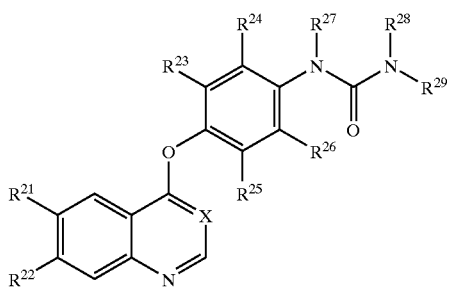

(Ia)

wherein
X represents CH or N;
R$^{21}$ and R$^{22}$, which may be the same or different, represent unsubstituted C$_{1-6}$ alkoxy or group R$^{31}$—(CH$_2$)p-O— wherein R$^{31}$ represents a halogen atom, hydroxyl, C$_{1-4}$ alkoxy, C$_{1-4}$ alkoxycarbonyl, amino on which one or two hydrogen atoms are optionally substituted by C$_{1-4}$ alkyl optionally substituted by hydroxyl or C$_{1-4}$ alkoxy, group R$^{12}$R$^{13}$N—C(=O)—O— wherein R$^{12}$ and R$^{13}$, which may be the same or different, represent a hydrogen atom or C$_{1-4}$ alkyl which alkyl is optionally substituted by hydroxyl or C$_{1-4}$ alkoxy, or group R$^{14}$—(S)m- wherein R$^{14}$ represents a saturated or unsaturated three- to seven-membered carbocyclic or heterocyclic group optionally substituted by C$_{1-4}$ alkyl and m is 0 or 1; and p is an integer of 1 to 6;
R$^{23}$, R$^{24}$, R$^{25}$, and R$^{26}$, which may be the same or different, represent a hydrogen atom, a halogen atom, C$_{1-4}$ alkyl, C$_{1-4}$ alkoxy, C$_{1-4}$ alkylthio, nitro, or amino, provided that R$^{23}$, R$^{24}$, R$^{25}$, and R$^{26}$ do not simultaneously represent a hydrogen atom;
R$^{27}$ and R$^{28}$, which may be the same or different, represent a hydrogen atom, C$_{1-6}$ alkyl, or C$_{1-4}$ alkylcarbonyl, the alkyl portion of which C$_{1-6}$ alkyl or C$_{1-4}$ alkylcarbonyl is optionally substituted by a halogen atom; C$_{1-4}$ alkoxy; amino which is optionally substituted by C$_{1-4}$ alkyl optionally substituted by C$_{1-4}$ alkoxy; or a saturated or unsaturated three- to seven-membered carbocyclic or heterocyclic group; and
R$^{29}$ represents C$_{1-6}$ alkyl, C$_{2-6}$ alkenyl, or C$_{2-6}$ alkynyl (which C$_{1-6}$ alkyl, C$_{2-6}$ alkenyl, and C$_{2-6}$ alkynyl each are optionally substituted by a halogen atom or C$_{1-4}$ alkoxy), or R$^{32}$—(CH$_2$)q- wherein q is an integer of 0 to 4 and R$^{32}$ represents a saturated or unsaturated six-membered carbocyclic or heterocyclic group which is optionally substituted by a halogen atom, C$_{1-4}$ alkyl, or C$_{1-4}$ alkoxy and is optionally condensed with other saturated or unsaturated five- or six-membered carbocyclic ring or heterocyclic ring to form a bicyclic ring.

R$^{21}$ and R$^{22}$ may represent unsubstituted C$_{1-6}$ alkoxy, preferably methoxy.

Any one of R$^{21}$ and R$^{22}$ may represent unsubstituted C$_{1-6}$ alkoxy, preferably methoxy and the other represents group R$^{31}$—(CH$_2$)p-O—.

In group R$^{31}$—(CH$_2$)p-O—, p is preferably 1 to 4, more preferably 1 or 2, particularly preferably 1.

A group of preferred compounds represented by formula (Ia) include:
compounds wherein at least one of R$^{23}$, R$^{24}$, R$^{25}$, and R$^{26}$ represents a halogen atom, preferably a chlorine atom or a fluorine atom;
compounds wherein at least one of R$^{23}$, R$^{24}$, R$^{25}$, and R$^{26}$ represents C$_{1-4}$ alkyl;
compounds wherein two of R$^{23}$, R$^{24}$, R$^{25}$, and R$^{26}$ represent methyl and the remaining two represent a hydrogen atom;
compounds wherein at least one of R$^{23}$, R$^{24}$, R$^{25}$, and R$^{26}$ represents nitro, amino, C$_{1-4}$ alkoxy, or C$_{1-4}$ alkylthio;
compounds wherein R$^{23}$, R$^{25}$, and R$^{26}$ represent a hydrogen atom and R$^{24}$ represents a halogen atom, more preferably a chlorine atom or a fluorine atom;
compounds wherein R$^{23}$ and R$^{24}$ represent C$_{1-4}$ alkyl, more preferably methyl and R$^{25}$ and R$^{26}$ represent a hydrogen atom;
compounds wherein R$^{23}$ and R$^{26}$ represent a hydrogen atom and R$^{24}$ and R$^{25}$ represent C$_{1-4}$ alkyl, more preferably methyl; and
compounds wherein R$^{23}$, R$^{25}$, and R$^{26}$ represent a hydrogen atom and R$^{24}$ represents C$_{1-4}$ alkyl, C$_{1-4}$ alkoxy, C$_{1-4}$ alkylthio, nitro, or amino.

Another group of preferred compounds represented by formula (Ia) include compounds wherein R$^{27}$ and R$^{28}$ represent a hydrogen atom.

Still another group of preferred compounds represented by formula (Ia) include compounds wherein any one of or both R$^{27}$ and R$^{28}$ represent a group other than a hydrogen atom.

In R$^{32}$—(CH$_2$)q- which may be represented by R$^{29}$, q is preferably an integer of 0 to 2, more preferably 0 or 1. Examples of preferred R$^{32}$ include optionally substituted phenyl and an optionally substituted saturated or unsaturated six-membered heterocyclic group, more preferably pyridyl. The hetero-atom(s) constituting the six-membered heterocyclic group may more specifically consist of one nitrogen atom or one nitrogen atom and one oxygen atom. The saturated or unsaturated six-membered carbocyclic group or heterocyclic group, which may be represented by R$^{32}$, is preferably condensed with other saturated or unsaturated six-membered carbocyclic ring or heterocyclic ring to form a bicyclic ring.

A still further group of preferred compounds represented by formula (Ia) include:
compounds wherein
X represents CH or N,
R$^{21}$ and R$^{22}$ represent unsubstituted C$_{1-4}$ alkoxy,
R$^{23}$, R$^{25}$, and R$^{26}$ represent a hydrogen atom,
R$^{24}$ represents a halogen atom, C$_{1-4}$ alkyl, C$_{1-4}$ alkoxy, or nitro,
R$^{27}$ and R$^{28}$ represent a hydrogen atom, and
R$^{29}$ represents C$_{1-6}$ alkyl, C$_{2-6}$ alkenyl, or C$_{2-6}$ alkynyl (which C$_{1-6}$ alkyl, C$_{2-6}$ alkenyl, and C$_{2-6}$ alkynyl each are optionally substituted by a halogen atom or C$_{1-4}$ alkoxy), or —(CH$_2$)q-R$^{32}$ wherein q is an integer of 0 or 1 and R$^{32}$ represents phenyl, pyridyl, or naphthyl which phenyl, pyridyl, and naphthyl are optionally substituted by a halogen atom, C$_{1-4}$ alkyl, or C$_{1-4}$ alkoxy;
compounds wherein
X represents CH or N,
R$^{21}$ and R$^{22}$ represent unsubstituted C$_{1-4}$ alkoxy,
R$^{23}$, R$^{25}$, and R$^{26}$ represent a hydrogen atom,
R$^{24}$ represents a halogen atom, C$_{1-4}$ alkyl, C$_{1-4}$ alkoxy, or nitro, any one of or both $R^{27}$ and $R^{28}$ represent a group other than a hydrogen atom, and $R^{29}$ represents $C_{1-6}$ alkyl, $C_{2-6}$ alkenyl, or $C_{2-6}$ alkynyl (which $C_{1-6}$ alkyl, $C_{2-6}$ alkenyl, and $C_{2-6}$ alkynyl each are optionally substituted by a halogen atom or $C_{1-4}$ alkoxy), or —($CH_2$)q-$R^{32}$ wherein q is an integer of 0 or 1 and $R^{32}$ represents phenyl, pyridyl, or naphthyl which phenyl, pyridyl, and naphthyl are optionally substituted by a halogen atom, $C_{1-4}$ alkyl, or $C_{1-4}$ alkoxy;

compounds wherein

X represents CH or N, $R^{21}$ and $R^{22}$ represent unsubstituted $C_{1-4}$ alkoxy, $R^{23}$, $R^{25}$, and $R^{26}$ represent a hydrogen atom, $R^{24}$ represents a halogen atom, $C_{1-4}$ alkyl, $C_{1-4}$ alkoxy, or nitro, $R^{27}$ represents a hydrogen atom, $R^{28}$ represents a group other than a hydrogen atom, and $R^{29}$ represents $C_{1-6}$ alkyl, $C_{2-6}$ alkenyl, or $C_{2-6}$ alkynyl (which $C_{1-6}$ alkyl, $C_{2-6}$ alkenyl, and $C_{2-6}$ alkynyl each are optionally substituted by a halogen atom or $C_{1-4}$ alkoxy), or —($CH_2$)q-$R^{32}$ wherein q is an integer of 0 or 1 and $R^{32}$ represents phenyl, pyridyl, or naphthyl which phenyl, pyridyl, and naphthyl are optionally substituted by a halogen atom, $C_{1-4}$ alkyl, or $C_{1-4}$ alkoxy;

compounds wherein

X represents CH or N, any one of $R^{21}$ and $R^{22}$ represents unsubstituted $C_{1-4}$ alkoxy and the other represents group $R^{32}$—($CH_2$)p-O—, preferably $R^{21}$ represents unsubstituted $C_{1-4}$ alkoxy and $R^{22}$ represents group $R^{31}$—($CH_2$)p-O—, $R^{23}$, $R^{25}$, and $R^{26}$ represent a hydrogen atom, $R^{24}$ represents a halogen atom, $C_{1-4}$ alkyl, $C_{1-4}$ alkoxy, or nitro, $R^{27}$ and $R^{28}$ represent a hydrogen atom, and $R^{29}$ represents $C_{1-6}$ alkyl, $C_{2-6}$ alkenyl, or $C_{2-6}$ alkynyl (which $C_{1-6}$ alkyl, $C_{2-6}$ alkenyl, and $C_{2-6}$ alkynyl each are optionally substituted by a halogen atom or $C_{1-4}$ alkoxy), or —($CH_2$)q-$R^{32}$ wherein q is an integer of 0 or 1 and $R^{32}$ represents phenyl, pyridyl, or naphthyl which phenyl, pyridyl, and naphthyl are optionally substituted by a halogen atom, $C_{1-4}$ alkyl, or $C_{1-4}$ alkoxy;

compounds wherein

X represents CH or N, any one of $R^{21}$ and $R^{22}$ represents unsubstituted $C_{1-4}$ alkoxy and the other represents group $R^3$—($CH_2$)p-O—, preferably $R^{21}$ represents unsubstituted $C_{1-4}$ alkoxy and $R^{22}$ represents group $R^{31}$—($CH_2$)p-O—, $R^{23}$, $R^{25}$, and $R^{26}$ represent a hydrogen atom, $R^{24}$ represents a halogen atom, $C_{1-4}$ alkyl, $C_{1-4}$ alkoxy, or nitro, any one of or both $R^{27}$ and $R^{28}$ represent a group other than a hydrogen atom, and $R^{29}$ represents $C_{1-6}$ alkyl, $C_{2-6}$ alkenyl, or $C_{2-6}$ alkynyl (which $C_{1-6}$ alkyl, $C_{2-6}$ alkenyl, and $C_{2-6}$ alkynyl each are optionally substituted by a halogen atom or $C_{1-4}$ alkoxy), or —($CH_2$)q-$R^{32}$ wherein q is an integer of- 0 or 1 and $R^{32}$ represents phenyl, pyridyl, or naphthyl which phenyl, pyridyl, and naphthyl are optionally substituted by a halogen atom, $C_{1-4}$ alkyl, or $C_{1-4}$ alkoxy;

compounds wherein

X represents CH or N, any one of $R^{21}$ and $R^{22}$ represents unsubstituted $C_{1-4}$ alkoxy and the other represents group $R^{31}$—($CH_2$)p-O—, preferably $R^{21}$ represents unsubstituted $C_{1-4}$ alkoxy and $R^{22}$ represents group $R^{31}$—($CH_2$)p-O—, $R^{23}$, $R^{25}{}_1$, and $R^{26}$ represent a hydrogen atom, $R^{24}$ represents a halogen atom, $C_{1-4}$ alkyl, $C_{1-4}$ alkoxy, or nitro, $R^{27}$ represents a hydrogen atom, $R^{28}$ represents a group other than a hydrogen atom, and $R^{29}$ represents $C_{1-6}$ alkyl, $C_{2-6}$ alkenyl, or $C_{2-6}$ alkynyl (which $C_{1-6}$ alkyl, $C_{2-6}$ alkenyl, and $C_{2-6}$ alkynyl each are optionally substituted by a halogen atom or $C_{1-4}$ alkoxy), or —($CH_2$)q-$R^{32}$ wherein q is an integer of 0 or 1 and $R^{32}$ represents phenyl, pyridyl, or naphthyl which phenyl, pyridyl, and naphthyl are optionally substituted by a halogen atom, $C_{1-4}$ alkyl, or $C_{1-4}$ alkoxy; and compounds wherein X represents CH or N, any one of $R^{21}$ and $R^{22}$ represents unsubstituted $C_{1-4}$ alkoxy and the other represents group $R^{31}$—($CH_2$)p-O—, preferably $R^{21}$ represents unsubstituted $C_{1-4}$ alkoxy and $R^{22}$ represents group $R^{31}$—($CH_2$)p-O—, $R^{23}$ and $R^{26}$ represent a hydrogen atom, $R^{24}$ and $R^{25}$ represent a halogen atom, $C_{1-4}$ alkyl, $C_{1-4}$ alkoxy, or nitro, $R^{27}$ and $R^{28}$ represent a hydrogen atom, and $R^{29}$ represents $C_{1-6}$ alkyl, $C_{2-6}$ alkenyl, or $C_{2-6}$ alkynyl (which $C_{1-6}$ alkyl, $C_{2-6}$ alkenyl, or $C_{2-6}$ alkynyl each are optionally substituted by a halogen atom or $C_{1-4}$ alkoxy), or —($CH_2$)q-$R^{32}$ wherein q is an integer of 0 or 1 and $R^{32}$ represents phenyl, pyridyl, or naphthyl which phenyl, pyridyl, and naphthyl are optionally substituted by a halogen atom, $C_{1-4}$ alkyl, or $C_{1-4}$ alkoxy.

Examples of preferred compounds according to the present invention include compounds described in Examples 1 to 186.

Another examples of preferred compounds according to the present invention include the following compounds:

N-{2-chloro-4-[(6,7-dimethyl-4-quinazolinyl)oxy]-phenyl}-N'-isobutylurea;

N-(4-{[7-(benzyloxy)-6-methoxy-4-quinazolinyl]oxy}-2-chlorophenyl)-N'-propylurea;

N-(4-{[6-(benzyloxy)-7-methoxy-4-quinazolinyl]oxy}-2-chlorophenyl)-N'-propylurea;

N-(2-chloro-4-{[7-methoxy-6-(3-morpholinopropoxy)-4-quinazolinyl]oxy}phenyl)-N'-propylurea;

N-[2-chloro-4-({6-methoxy-7-[2-(1H-1-imidazolyl)-ethoxy]-4-quinazolinyl}oxy)phenyl]-N'-ethylurea;

N-[2-chloro-4-({6-methoxy-7-[2-(1H-1,2,3-triazol-1-yl)ethoxy]-4-quinazolinyl}oxy)phenyl]-N'-ethylurea;

N-[2-chloro-4-({6-methoxy-7-[3-(1H-1,2,3-triazol-1-yl)propoxy]-4-quinazolinyl}oxy)phenyl]-N'-ethylurea;

N-[2-chloro-4-({6-methoxy-7-[2-(4-methyl-piperazino)ethoxy]-4-quinazolinyl}oxy)phenyl]-N'-ethylurea;

N-(2-chloro-4-{[6-methoxy-7-(2-morpholinoethoxy)-4-quinazolinyl]oxy}phenyl)-N'-ethylurea;

N-(2-chloro-4-{[6-methoxy-7-(3-morpholinopropoxy)-4-quinazolinyl]oxy}phenyl)-N'-ethylurea;

N-[2-chloro-4-({6-methoxy-7-[2-(dimethylamino)-ethoxy]-4-quinazolinyl}oxy)phenyl]-N'-ethylurea;

N-[2-chloro-4-({6-methoxy-7-[2-(1H-1-imidazolyl)-ethoxy]-4-quinazolinyl}oxy)phenyl]-N'-propylurea;

N-[2-chloro-4-({6-methoxy-7-[2-(1H-1,2,3-triazol-1-yl 4-quinazolinyl}oxy)phenyl]-N'-propylurea;

N-[2-chloro-4-({6-methoxy-7-[3-(1H-1,2,3-triazol-1-yl)propoxy]-4-quinazolinyl}oxy)phenyl]-N'-propylurea;

N-(2-chloro-4-{[6-methoxy-7-(3-morpholinopropoxy)-4-quinazolinyl]oxy}phenyl)-N'-propylurea;

N-[2-chloro-4-({6-methoxy-7-[2-(dimethylamino)-ethoxy]-4-quinazolinyl}oxy)phenyl]-N'-propylurea;

N-[2-chloro-4-({6-methoxy-7-[2-(1H-1-imidazolyl)-ethoxy)-4-quinazolinyl}oxy)phenyl]-N'-butylurea;

N-[2-chloro-4-({6-methoxy-7-[2-(1H-1,2,3-triazol-1-yl)ethoxy]-4-quinazolinyl}oxy)phenyl]-N'-butylurea;

N-[2-chloro-4-({6-methoxy-7-[3-(1H-1,2,3-triazol-1-yl)propoxy]-4-quinazolinyl}oxy)phenyl]-N'-butylurea;

N-[2-chloro-4-({6-methoxy-7-[2-(4-methyl-piperazino)ethoxy]-4-quinazolinyl}oxy)phenyl]-N'-butylurea;

N-(2-chloro-4-{[6-methoxy-7-(2-morpholinoethoxy)-4-quinazolinyl]oxy}phenyl)-N'-butylurea;

N-(2-chloro-4-{[6-methoxy-7-(3-morpholinopropoxy)-4-quinazolinyl]oxy}phenyl)-N'-butylurea;

N-[2-chloro-4-({6-methoxy-7-[2-(dimethylamino)-ethoxy]-4-quinazolinyl}oxy)phenyl]-N'-butylurea; and N-[2-chloro-4-({6-methoxy-7-[2-(dimethylamino)-ethoxy]-4-quinolyl}oxy)phenyl]-N'-propylurea.

Examples of particularly preferred compounds according to the present invention include:

(13) N-{2-chloro-4-[(6,7-dimethoxy-4-quinolyl)oxy]-phenyl}-N'-propylurea;

(51) N-(2-chloro-4-{[6-methoxy-7-(2-morpholino-ethoxy)-4-quinolyl]oxy}phenyl)-N'-(2,4-difluorophenyl) urea;

(62) N-{2-chloro-4-[(6,7-dimethoxy-4-quinazolinyl)-oxy]phenyl}-N'-propylurea;

(76) N-{2-chloro-4-[(6,7-dimethoxy-4-quinazolinyl)-oxy]phenyl}-N'-ethylurea;

(117) N-{2-chloro-4-[(6,7-dimethoxy-4-quinazolinyl)oxy]phenyl}-N'-methylurea;

(119) N-(2-chloro-4-{[6-methoxy-7-(3-morpholino-propoxy)-4-quinazolinyl]oxy}phenyl)-N'-propylurea;

(135) N-(2-chloro-4-{[6-methoxy-7-(3-piperidino-propoxy)-4-quinazolinyl]oxy}phenyl)-N'-propylurea;

(142) N-(2-chloro-4-{[6-methoxy-7-(3-pyridyl-methoxy)-4-quinolyl]oxy}phenyl)-N'-propylurea;

(143) N-(2-chloro-4-{[6-methoxy-7-(4-pyridyl-methoxy)-4-quinolyl]oxy}phenyl)-N'-propylurea;

(144) N-(2-chloro-4-{[6-methoxy-7-(2-morpholino-ethoxy)-4-quinolyl]oxy}phenyl)-N'-propylurea;

(145) N-[2-chloro-4-({6-methoxy-7-[2-(1H-1,2,3-triazol-1-yl)ethoxyl]-4-quinolyl}oxy)phenyl]-N'-propylurea (146) N-[2-chloro-4-(7-{[2-(1H-1-imidazolyl)-ethoxyl]-6-methoxy-4-quinolyl}oxy)phenyl]-N '-propylurea (148) N-[2-chloro-4-({6-methoxy-7-[2-(4-methyl-piperazino)ethoxy]4-quinolyl}oxy)phenyl]-N'-propylurea.

(149) N-(2-chloro-4-{(7-(2-hydroxyethoxy)-6-methoxy-4-quinolyl]oxy}phenyl)-N'-propylurea;

(151) N-(2-chloro-4-{[6-methoxy-7-(3-morpholino-propoxy)-4-quinolyl]oxy}phenyl)-N'-propylurea;

(152) N-[2-chloro-4-(6-methoxy-7-{-([3-(4-methyl-piperazino)propoxy]-4-quinolyl}oxy)phenyl]-N'-propylurea;

(153) N-[2-chloro-4-(6-methoxy-7-{[3-(1H-1,2,3-triazol-1-yl)propoxy]-4-quinolyl}oxy)phenyl]-N'-propylurea;

(157) N-{2-chloro-4-[(7-{3-[(2-hydroxyethyl)-(methyl)amino]propoxy}-6-methoxy-4-quinolyl)oxy]-phenyl}-N'-propylurea;

(159) N-{2-chloro-4-[(6-methoxy-7-{(5-(1H-1,2,3-triazol-1-yl)pentyl]oxy}-4-quinolyl)oxy]phenyl}-N'-propylurea;

(160) N-[2-chloro-4-({7-[4-(1H-1-imidazolyl)-butoxy]-6-methoxy-4-quinolyl}oxy)phenyl]-N'-propylurea (162) N-(2-chloro-4-{[6-methoxy-7-(2-morpholino-ethoxy)-4-quinazolinyl]oxy}phenyl)-N'-(2,4-difluorophenyl)urea;

(163) N-(2-chloro-4-{[6-methoxy-7-(3-morpholino-propoxy)-4-quinazolinyl]oxy}phenyl)-N'-(2,4-difluorophenyl)urea;

(164) N-[2-chloro-4-({6-methoxy-7-[3-(4-methyl-piperazino)propoxy]-4-quinazolinyl}oxy)phenyl]-N'-(2,4-difluorophenyl)urea (165) N-{2-chloro-4-[(7-{3-[(2-hydroxyethyl)-(methyl)amino]propoxy}-6-methoxy-4-quinazolinyl)oxy]-phenyl}-N'-(2,4-difluorophenyl)urea;

(168) N-(2-chloro-4-{[6-methoxy-7-(3-morpholino-propoxy)-4-quinolyl]oxy}phenyl)-N'-(2,4-difluorophenyl)-urea;

(169) N-(2-chloro-4-{[6-methoxy-7-(3-pyridyl-methoxy)-4-quinolyl]oxy}phenyl)-N'-(2,4-difluorophenyl)-urea;

(170) N-[2-chloro-4-({6-methoxy-7-[2-(1H-1,2,3-triazol-1-yl)ethoxyl]-4-quinolyl}oxy) phenyl]-N'-(2,4-difluorophenyl)urea.

(184) N-(2-chloro-4-{[6-methoxy-7-(3-piperidino-propoxy)-4-quinazolinyl]oxy}phenyl)-N'-methylurea;

(185) N-(2-chloro-4-{[6-methoxy-7-(3-piperidino-propoxy)-4-quinazolinyl]oxy}phenyl)-N'-ethylurea; and (186) N-(2-chloro-4-{[6-methoxy-7-(4-pyridyl-methoxy)-4-quinolyl]oxy}phenyl)-N'-(2,4-difluorophenyl)-urea.

Examples of more preferred compounds according to the present invention include the following compounds:

(62) N-{2-chloro-4-[(6,7-dimethoxy-4-quinazolinyl)-oxy]phenyl}-N'-propylurea;

(142) N-(2-chloro-4-{[6-methoxy-7-(3-pyridyl-methoxy)-4-quinolyl]oxy}phenyl)-N'-propylurea; and (169) N-(2-chloro-4-{[6-methoxy-7-(3-pyridyl-methoxy)-4-quinolyl]oxy}phenyl)-N'-(2,4-difluorophenyl)-urea.

The compounds according to the present invention may form pharmaceutically acceptable salts thereof. Preferred examples of such salts include: alkali metal or alkaline earth metal salts such as sodium salts, potassium salts or calcium salts; hydrohalogenic acid salts such as hydrofluoride salts, hydrochloride salts, hydrobromide salts, or hydroiodide salts; inorganic acid salts such as nitric acid salts, perchloric acid salts, sulfuric acid salts, or phosphoric acid salts; lower alkylsulfonic acid salts such as methanesulfonic acid salts, trifluoromethanesulfonic acid salts, or ethanesulfonic acid salts; arylsulfonic acid salts such as benzenesulfonic acid salts or p-toluenesulfonic acid salts; organic acid salts such as fumaric acid salts, succinic acid salts, citric acid salts, tartaric acid salts, oxalic acid salts, maleic acid salts, acetic acid salts, malic acid salts, lactic acid salts, or ascorbic acid salts; and amino acid salts such as glycine salts, phenylalanine salts, glutamic acid salts, or aspartic acid salts.

Further, the compounds according to the present invention may form solvates (for example, hydrates).

Production of Compounds

The compounds according to the present invention may be produced, for example, according to scheme 1 and scheme 2.

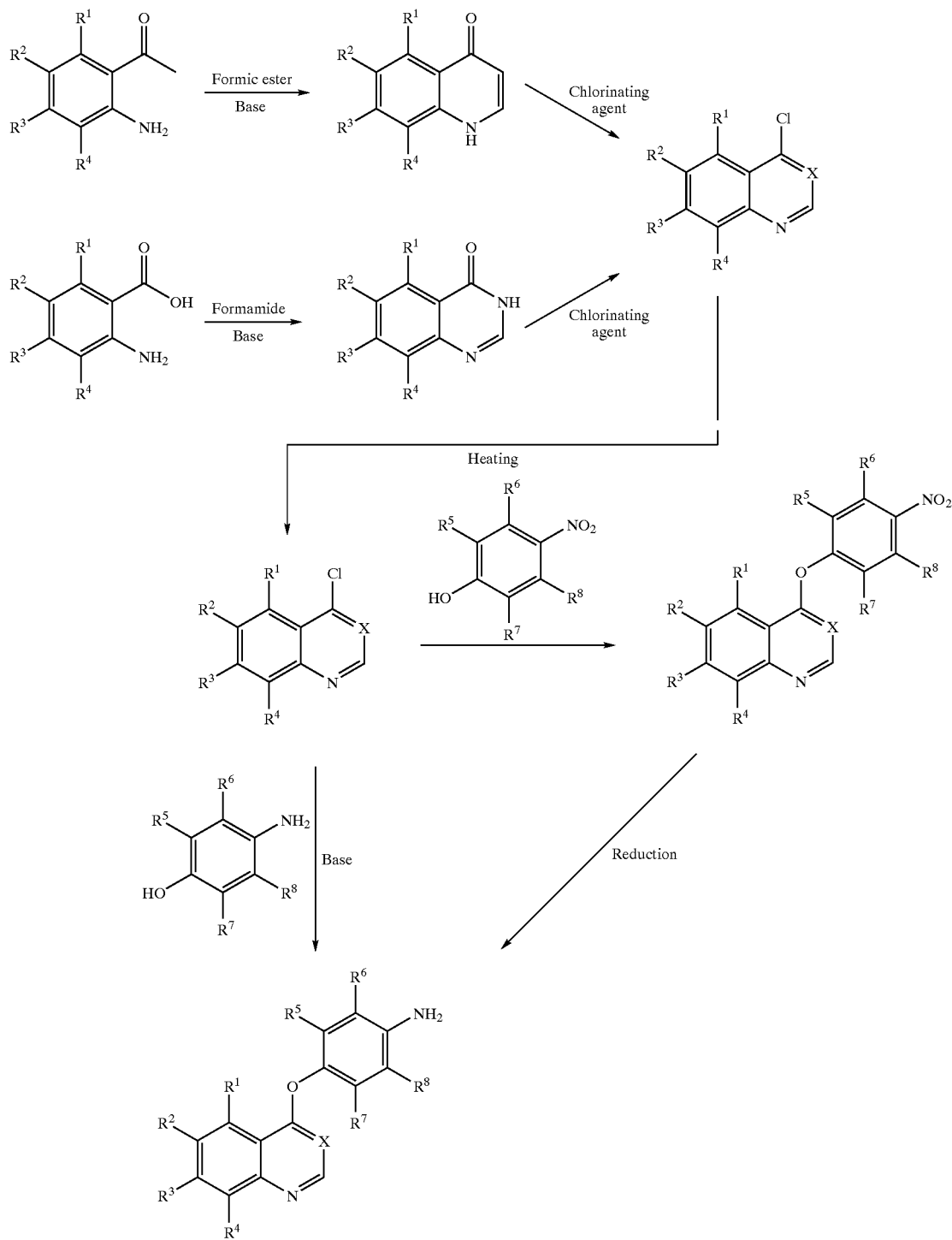

Starting compounds necessary for the synthesis of the compounds according to the present invention may be commercially available, or alternatively may be produced according to a conventional process. For example, a 4-chloroquinoline derivative may be synthesized by a conventional process as described in Org. Synth. Col. Vol. 3, 272 (1955), Acta Chim. Hung., 112, 241 (1983) or WO 98/47873. A 4-chloroquinazoline derivative may be synthesized by a conventional process as described in J. Am. Chem. Soc., 68, 1299 (1946) or J. Am. Chem. Soc., 68, 1305 (1946).

Alternatively, the 4-chloroquinazoline derivative may be produced by a process which comprises the steps of: (1) first reacting a benzoic ester with formamide to prepare a quinazolone derivative (see Production Example 34) and (2) then heating the 4-quinazolone derivative using toluene or sulfolane as a solvent in the presence of phosphorus oxychloride (see Production Examples 35 and 36). The quinazolone derivative is generally synthesized in the presence of a benzoic ester, sodium methoxide, formamide, and a solvent such as DMF or methanol. In the step (1), the reaction proceeds in a system where only the benzoic ester and formaldehyde are present. This is advantageous in that the synthesis can be carried out using a small number of starting compounds. The 4-quinazolone derivative is generally halogenated by heating the quinazolone derivative and phosphorus oxychloride. In this case, in many cases, due to high reactivity of the quinazoline derivative, the influence of the solvent has caused the quinazoline derivative to be returned to the starting compound and consequently made it impossible to complete the reaction. In the step (2), the reaction is completed in the presence of toluene or sulfolane, and, thus, this is advantageous from the viewpoint of an increase in yield.

Next, 4-chloroquinoline derivative or a corresponding quinazoline derivative is allowed to act on nitrophenol in the presence of a suitable solvent or in the absence of a solvent to synthesize a 4-(nitrophenoxy)quinoline derivative or a corresponding quinazoline derivative which is then stirred in a suitable solvent, for example, N,N-dimethylformamide, in the presence of a catalyst, for example, palladium hydroxide-carbon or palladium-carbon, in a hydrogen atmosphere to give a 4-(aminophenoxy)quinoline derivative or a corresponding quinazoline derivative. Alternatively, a 4-chloroquinoline derivative or a corresponding quinazoline derivative may be allowed to act on aminophenol in the presence of a base, for example, sodium hydride, to give a 4-(aminophenoxy)quinoline derivative or a corresponding quinazoline derivative.

Alternatively, the 4-(aminophenoxy)quinoline derivative or the corresponding quinazoline derivative may also be produced by dissolving aminophenol in an aqueous sodium hydroxide solution and then subjecting the solution to a two-phase reaction with a solution of a 4-chloroquinazoline derivative or a corresponding quinazoline derivative in an organic solvent in the presence of a phase transfer catalyst or in the absence of a catalyst (see Production Examples 37 and 38). In this reaction, for example, phenol remaining unreacted and a decomposition product of 4-chloroquinazoline are left in the aqueous layer, while the target product is present in the organic layer. That is, the organic layer contains only the target product. Therefore, the post-treatment is advantageously simple. Further, the production of N-alkylaminophenoxy-quinazoline as a by-product can be advantageously suppressed.

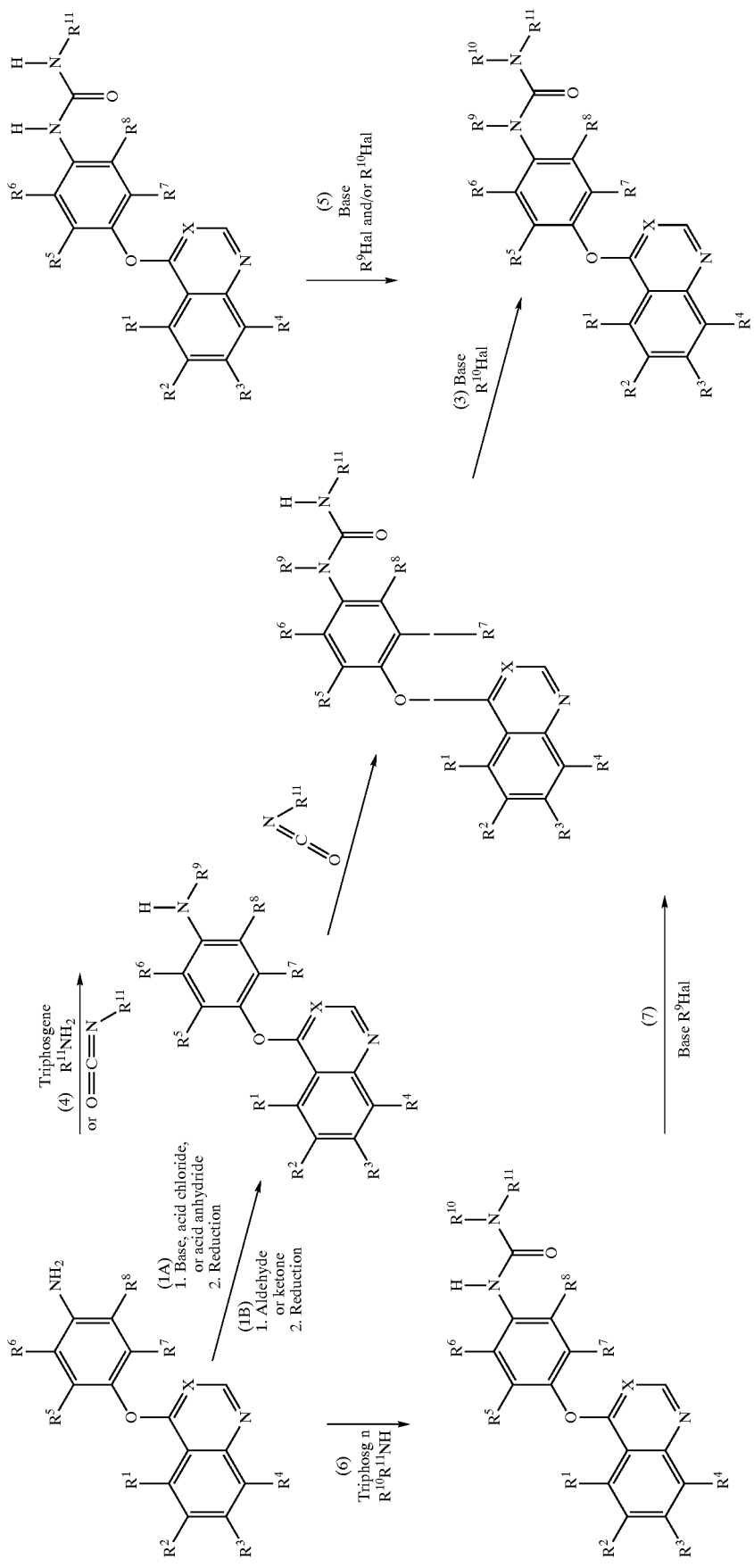

The 4-(aminophenoxy)quinoline derivative or the corresponding quinazoline derivative thus obtained may be reacted with an acid chloride or an acid anhydride in the presence of a base, followed by reduction, for example, with lithium aluminum hydride to introduce a substituent into $R^9$ (step 1A).

Alternatively, the 4-(aminophenoxy)quinoline derivative or the corresponding quinazoline derivative may be reacted with an aldehyde or a ketone to produce an imine, followed by reduction, for example, with sodiumboroncyanohydride to introduce a substituent into $R^9$ (step 1B).

The derivative with a substituent introduced into $R^9$ is allowed to act on an isocyanate derivative (O=C=N—$R^{11}$) by a conventional method (step 2), and a suitable alkylating agent ($R^{10}$Hal) is allowed to act in the presence of a base, for example, sodium hydride (step 3) to produce the compound of formula (I).

Alternatively, $R^9$ and $R^{10}$ may also be introduced by allowing a suitable alkylating agent ($R^9$Hal, $R^{10}$Hal) to act on a urea derivative, wherein $R^9$ and/or $R^{10}$ represent a hydrogen atom, in the presence of a base, for example, sodium hydride (steps 5 and 7).

The urea derivative, wherein $R^9$ and/or $R^{10}$ represent a hydrogen atom, may be produced by allowing an isocyanate derivative to act on the 4-(aminophenoxy)quinoline derivative or the corresponding quinazoline derivative, produced in scheme 1, according to a conventional method, or by adding a triphosgene to the 4-(aminophenoxy)quinoline derivative or the corresponding quinazoline derivative in the presence of a base, for example, triethylamine, and then reacting the mixture with a suitable alkylamine ($R^{11}NH_2$, $R^{10}R^{11}NH$) (steps 4 and 6).

The derivative having a specific substituent at the 7-position of the quinoline ring may be produced, for example, according to scheme 3.

Scheme 3

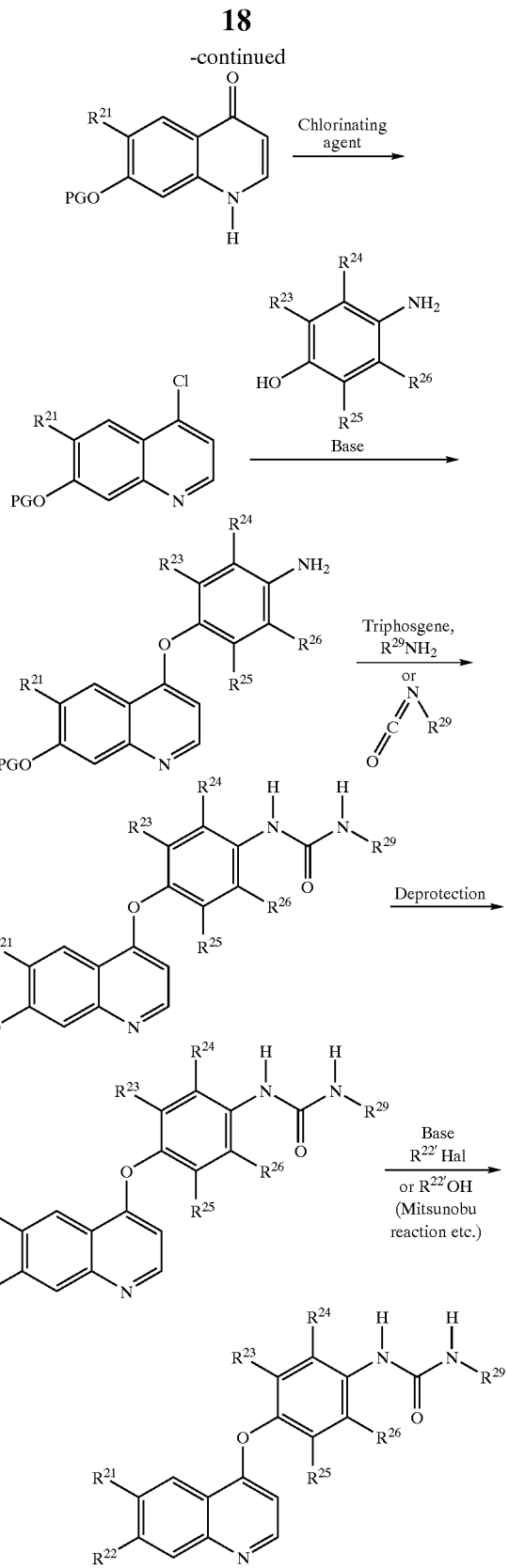

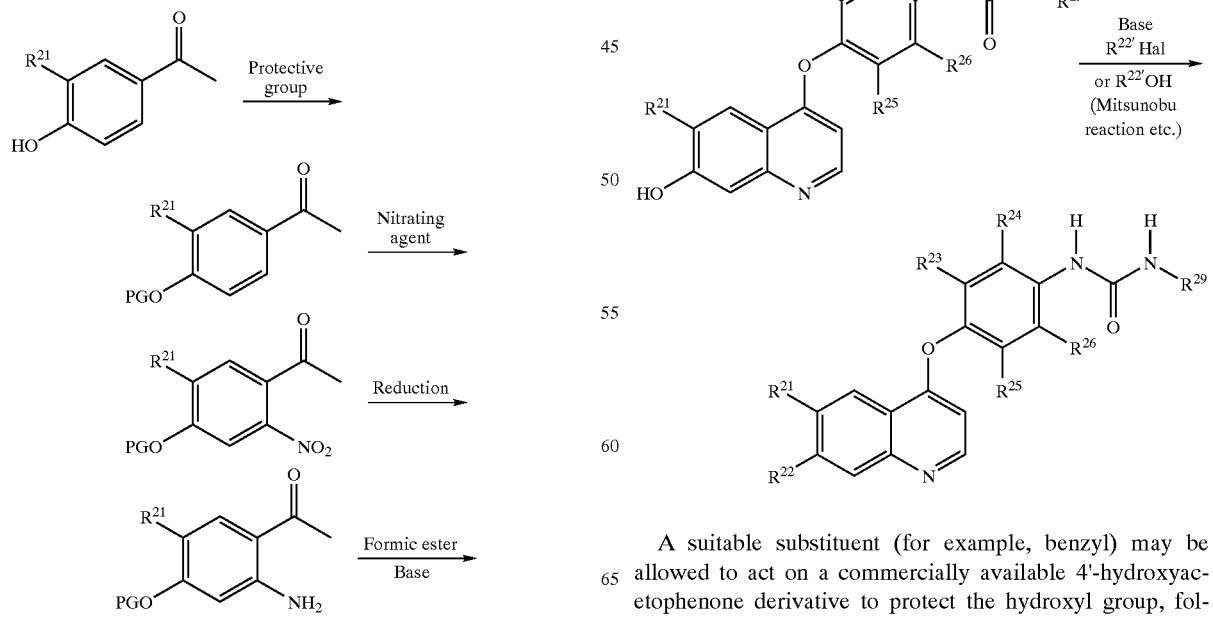

A suitable substituent (for example, benzyl) may be allowed to act on a commercially available 4'-hydroxyacetophenone derivative to protect the hydroxyl group, followed by action of a nitrating agent (for example, nitric acid-acetic acid) to introduce a nitro group.

The nitro group may be then reduced to an amino group which is then reacted with a formic ester in the presence of a base to form a quinolone ring, followed by action of a chlorinating agent, for example, phosphorus oxychloride, to produce a 4-chloroquinoline derivative.

The 4-chloroquinoline derivative thus obtained may be allowed to act on aminophenol in the presence of a base, for example, sodium hydride, to produce a 4-(aminophenoxy)quinoline derivative.

The urea portion may be synthesized by allowing an isocyanate derivative (O=C=N—$R^{29}$) to act on the derivative thus obtained according to a conventional method, or by treating the derivative with triphosgene and then allowing an aromatic amine or alkylamine ($R^{29}NH_2$) to act on the treated derivative.

Next, the protective group (PG) for the hydroxyl group at the 7-position of the quinoline ring may be removed, followed by action of an alkyl halide ($R^{22'}$ Hal wherein $R^{22'}$ represents an alkyl portion when $R^{22}$ represents alkoxy) in the presence of a base, or by action of an alcohol derivative ($R^{22'}$ OH) according to a conventional method, for example, Mitsunobu reaction, to produce a compound, according to the present invention, having an alkoxy group at the 7-position of the quinoline ring.

The alkyl halide used in the substitution reaction may be commercially available or produced according to a process described, for example, in J. Am. Chem. Soc., 1945, 67, 736.

The alcohol derivative used in the substitution reaction may be commercially available or produced according to a process described, for example, in J. Antibiot. (1993), 46(1), 177 and Ann. Pharm. Fr. 1977, 35, 503.

The derivative having a specific substituent at the 6-position of the quinoline ring may be produced using 3'-hydroxyacetophenone derivative as the starting compound according to scheme 3.

The derivative having a specific substituent at the 7-position of the quinazoline ring may be produced according to scheme 4.

Scheme 4

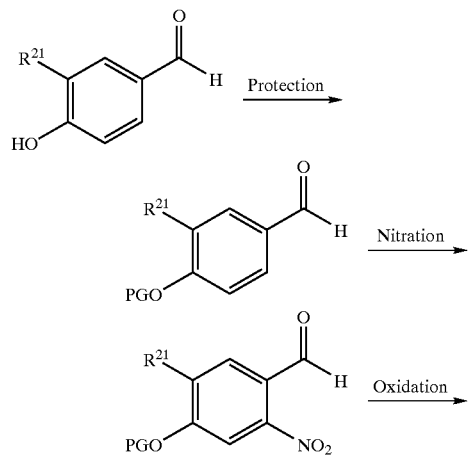

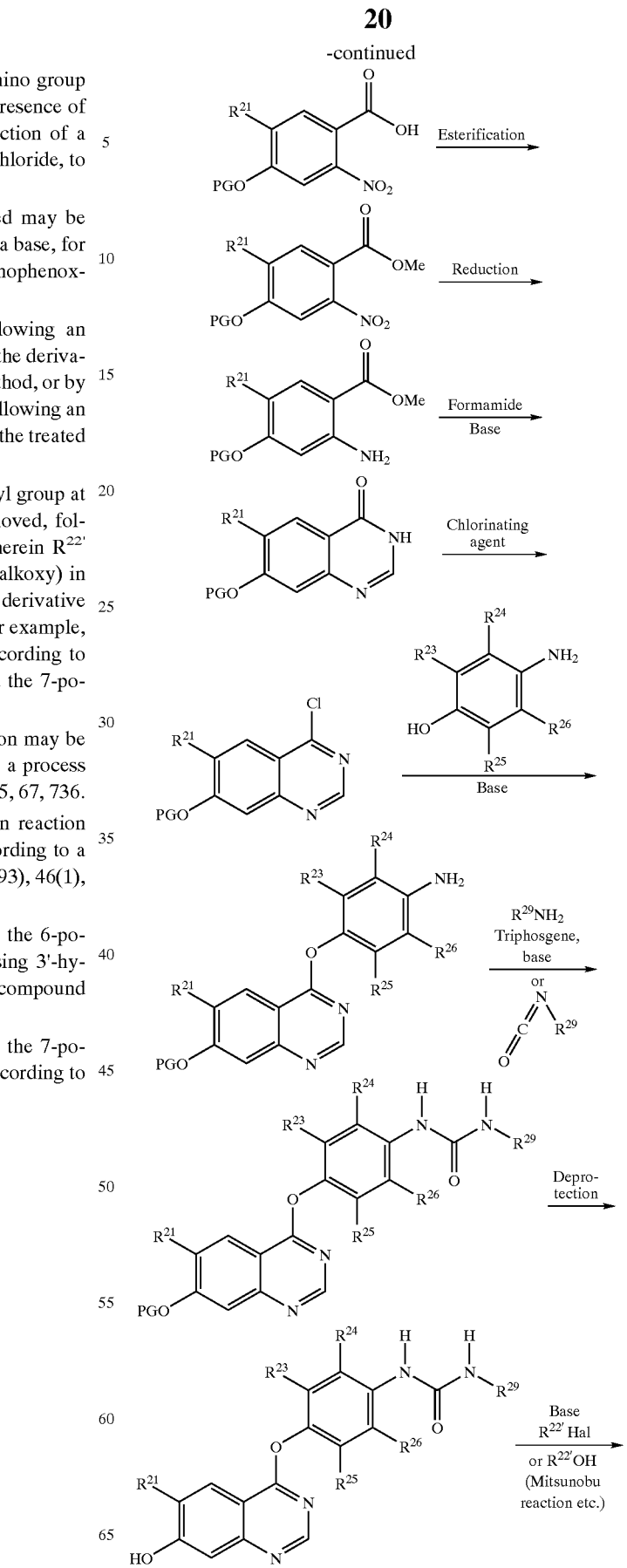

-continued

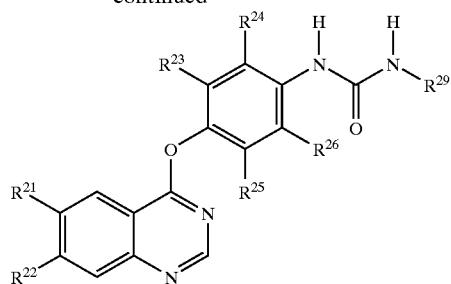

The 2-amino-benzoic ester derivative may be produced by esterifying a 2-nitro-benzoic acid derivative synthesized according to a method described, for example, in J. Med. Chem. 1977, 20, 146, for example, with dimethylsulfuric acid in the presence of a base, for example, potassium carbonate and then reducing the nitro group, for example, with iron/acetic acid.

Next, the compound thus obtained may be allowed to act on formamide in the presence of a base to form a 4-quinazolone ring, followed by action of a chlorinating agent, for example, phosphorus oxychloride, to produce a 4-chloroquinazoline derivative.

The 4-chloroquinazoline derivative thus obtained may be allowed to act on an aminophenol derivative in the presence of a base, for example, sodium hydride, to produce a 4-(aminophenoxy)quinazoline derivative.

The urea portion may be synthesized by allowing an isocyanate derivative (O=C=N—$R^{29}$) to act on the derivative thus obtained according to a conventional method, or by treating the derivative with triphosgene and then allowing an aromatic amine or alkylamine ($R^{29}NH_2$) to act on the treated derivative.

Next, the protective group (PG) for the hydroxyl group at the 7-position of the quinazoline ring may be removed, followed by action of an alkyl halide ($R^{22'}$ Hal wherein $R^{22'}$ represents an alkyl portion when $R^{22}$ represents alkoxy) in the presence of a base, or by action of an alcohol derivative ($R^{22'}$ OH) according to a conventional method, for example, Mitsunobu reaction, to produce a compound, according to the present invention, having an alkoxy group at the 7-position of the quinazoline ring.

The alkyl halide and the alcohol derivative used in the substitution reaction may be commercially available or produced according to a process described in the literature referred to in the description of scheme 3.

The derivative having a specific substituent at the 6-position of the quinazoline ring may be produced using 3-hydroxybenzaldehyde derivative as the starting compound according to scheme 4.

Use of Compounds/pharmaceutical Composition

The compounds according to the present invention have inhibitory activity against tumor proliferation in vivo (see Pharmacological Test Example 4).

Further, the compounds according to the present invention inhibit in vitro the activation of MAPK (mitogen-activated protein kinase) caused by stimulation of vascular endothelial cells with VEGF (vascular endothelial growth factor) (see Pharmacological Test Examples 1 and 2). Upon the stimulation of vascular endothelial cells with VEGF, MAPK is activated by a signal transmission system downstream of the receptor, and, consequently, an increase in phosphorylated MAPK is lo recognized (Abedi, H. and Zachary, I., J. Biol. Chem., 272, 15442–15451 (1997)). The activation of MAPK is known to play an important role in the growth of vascular endothelial cells in angiogenesis (Merenmies, J. et al., Cell Growth & Differ., 83–10 (1997); and Ferrara, N. and Davis-Smyth, T., Endocr. Rev., 18, 4–25 (1997)). Therefore, the compounds according to the present invention have angiogenesis inhibitory activity.

Angiogenesis at pathologic sites is deeply involved mainly in diseases, such as tumor, diabetic retinopathy, chronic rheumatism, psoriasis, atherosclerosis, and Kaposi's sarcoma, and metastasis of solid tumors (Forkman, J. Nature Med. 1: 27–31 (1995); Bicknell, R., Harris, A. L. Curr. Opin. Oncol. 8: 60–65 (1996)). Therefore, the compounds according to the present invention can be used in the treatment of diseases, such as tumor, diabetic retinopathy, chronic rheumatism, psoriasis, atherosclerosis, and Kaposi's sarcoma, and metastasis of solid tumors.

The compounds according to the present invention have no significant influence on cytomorphosis (see Pharmacological Test Example 3). Therefore, the compounds according to the present invention can be administered to living bodies with very excellent safety.

According to the present invention, there is provided a pharmaceutical composition comprising the compound according to the present invention. The pharmaceutical composition according to the present invention may be used in the treatment of diseases, such as tumor, diabetic retinopathy, chronic rheumatism, psoriasis, atherosclerosis, and Kaposi's sarcoma, and metastasis of solid tumors.

Further, according to the present invention, there is provided a method for treating a disease selected from the group consisting of tumor, diabetic retinopathy, chronic rheumatism, psoriasis, atherosclerosis, and Kaposi's sarcoma, comprising the step of administering the compound according to the present invention, together with a pharmaceutically acceptable carrier, to mammals.

The compounds according to the present invention can be administered to human and non-human animals orally or parenterally by administration routes, for example, intravenous administration, intramuscular administration, subcutaneous administration, rectal administration, or percutaneous administration. Therefore, the pharmaceutical composition comprising as an active ingredient the compound according to the present invention is formulated into suitable dosage forms according to the administration routes.

Specifically, oral preparations include tablets, capsules, powders, granules, and syrups, and parental preparations include injections, suppositories, tapes, and ointments.

These various preparations may be prepared by conventional methods, for example, with commonly used component, such as excipients, disintegrants, binders, lubricants, colorants, and diluents.

Excipients include, for example, lactose, glucose, corn starch, sorbit, and crystalline cellulose. Disintegrants include, for example, starch, sodium alginate, gelatin powder, calcium carbonate, calcium citrate, and dextrin. Binders include, for example, dimethylcellulose, polyvinyl alcohol, polyvinyl ether, methylcellulose, ethylcellulose, gum arabic, gelatin, hydroxypropylcellulose, and polyvinyl pyrrolidone. Lubricants include, for example, talc, magnesium stearate, polyethylene glycol, and hydrogenated vegetable oils.

In preparing injections, if necessary, for example, buffers, pH adjustors, stabilizers, tonicity agents, and preservatives may be added.

The content of the compound according to the present invention in the pharmaceutical composition according to the present invention may vary according to the dosage form. In general, however, the content is 0.5 to 50% by weight, preferably 1 to 20% by weight, based on the whole composition.

The dose may be appropriately determined in consideration of, for example, the age, weight, sex, difference in diseases, and severity of condition of patients, and the preparation may be administered, for example, in an amount of 0.1 to 100 mg/kg, preferably 1 to 50 mg/kg. This dose is administered at a time daily or divided doses of several times daily.

The compound according to the present invention may be administered in combination with other medicament(s). In this case, the compound according to the present invention may be administered simultaneously with or after or before the administration of other medicament(s). For example, when the object disease is malignant tumor, the compound according to the present invention can be allowed to act on target vascular endothelial cells to allow the tumor to regress, followed by the administration of a carcinostatic agent to effectively eliminate the tumor. The type, administration intervals and the like of the carcinostatic agent may be determined depending upon, for example, the type of cancer and the condition of patients. This treatment method is true of diseases other than the malignant tumor.

Furthermore, according to the present invention, there is provided a method for inhibiting the angiogenesis of target blood vessels, comprising the step of making the compound according to the present invention in contact with vascular endothelial cells of target blood vessels. Target blood vessels include blood vessels involved in feedings to tissues causative of diseases (for example, tumor tissues, retinopathy tissues, or rheumatism tissues). The compound according to the present invention may be brought into contact with the vascular endothelial cells, for example, by general administration (for example, intravenous administration or oral administration), local administration (for example, percutaneous administration or intraarticular administration), or drug targeting using a carrier (for example, liposome, lipid microsphere, or polymeric forms of drugs).

EXAMPLES

The present invention will be described with reference to the following examples, though it is not limited to these examples only.

Production Example 1

2-Chloro-4-[(6,7-dimethoxy-4-quinolyl)oxy]aniline

Sodium hydride (60 wt %, 0.72 g) was added to dimethyl sulfoxide (10 ml). The mixture was stirred at 50° C. for 30 min and was then cooled to room temperature. 4-Amino-3-chlorophenol hydrochloride (1.61 g) was added to the cooled mixture, and the mixture was stirred at room temperature for 10 min. Next, 4-chloro-6,7-dimethoxyquinoline (1.00 g) was added thereto, and the mixture was stirred at 100° C. overnight. Water was added to the reaction solution, followed by extraction with chloroform. The chloroform layer was then washed with a saturated aqueous sodium hydrogencarbonate solution and was dried over anhydrous sodium sulfate. The solvent was removed by distillation under the reduced pressure, and methanol was added to the residue. The precipitated crystal was collected by suction filtration to give 0.89 g (yield 60%) of the title compound.

$^1$H-NMR (CDCl$_3$, 400 MHz): δ 4.05 (s, 3H), 4.05 (s, 3H), 4.08 (s, 2H), 6.44 (d, J=5.4 Hz, 1H), 6.85 (d, J=8.5 Hz, 1H), 6.93–6.96 (m, 1H), 7.15 (d, J=2.7 Hz, 1H), 7.41 (s, 1H), 7.54 (6, 1H), 8.48 (d, J=5.1 Hz, 1H)

Production Example 2

4-[(6,7-Dimethoxy-4-quinolyl)oxy]-2,3-dimethylaniline

Sodium hydride (60 wt %, 0.72 g) was added to dimethyl sulfoxide (10 ml). The mixture was stirred at 50° C. for 30 min and was then cooled to room temperature. 4-Amino-2,3-dimethylphenol hydrochloride (1.55 g) was added to the cooled mixture, and the mixture was stirred at room temperature for 10 min. Next, 4-chloro-6,7-dimethoxyquinoline (1.00 g) was added thereto, and the mixture was stirred at 100° C. overnight. Water was added to the reaction solution, followed by extraction with chloroform. The chloroform layer was then washed with a saturated aqueous sodium hydrogencarbonate solution and was dried over anhydrous sodium sulfate. The solvent was removed by distillation under the reduced pressure, and methanol was added to the residue. The precipitated crystal was collected by suction filtration to give 0.94 g (yield 65%) of the title compound.

$^1$H-NMR (CDCl$_3$, 400 MHz): δ 2.07 (s, 3H), 2.15 (s, 3H), 3.62 (s, 2H), 4.05 (s, 3H), 4.07 (s, 3H), 6.25 (d, J=5.4 Hz, 1H), 6.64 (d, J=8.5 Hz, 1H), 6.83 (d, J=8.5 Hz, 1H), 7.42 (s, 1H), 7.64 (s, 1H), 8.42 (d, J=5.4 Hz, 1H)

Production Example 3

4-[(6,7-Dimethoxy-4-quinolyl)oxy]-2,5dimethylaniline

Sodium hydride (60 wt %, 0.36 g) was added to dimethyl sulfoxide (10 ml), and the mixture was stirred at 50° C. for 30 min and was then cooled to room temperature. 4-Amino-2,5-dimethylphenol (1.23 g) was added to the cooled mixture, and the mixture was stirred at room temperature for 10 min. Next, 4-chloro-6,7-dimethoxyquinoline (1.00 g) was added thereto, and the mixture was stirred at 100° C. overnight. Water was added to the reaction solution, followed by extraction with chloroform. The chloroform layer was then washed with a saturated aqueous sodium hydrogencarbonate solution and was dried over anhydrous sodium sulfate. The solvent was removed by distillation under the reduced pressure, and the residue was purified by chromatography on silica gel by development with chloroform/acetone (1/1) to give the title compound.

Production Example 4

3,5-Dichloro-4-[(6,7-dimethoxy-4 quinolyl)oxy]aniline

Sodium hydride (60 wt %, 0.36 g) was added to dimethyl sulfoxide (10 ml), and the mixture was stirred at 50° C. for 30 min and was then cooled to room temperature. 4-Amino-2,6-dichlorophenol (1.59 g) was added to the cooled mixture, and the mixture was stirred at room temperature for 10 min. Next, 4-chloro-6,7-dimethoxyquinoline (1.00 g) was added thereto, and the mixture was stirred at 100° C. overnight. Water was added to the reaction solution, followed by extraction with chloroform. The chloroform layer was then washed with a saturated aqueous sodium hydrogencarbonate solution and was dried over anhydrous sodium sulfate. The solvent was removed by distillation under the reduced pressure, and the residue was purified by chromatography on silica gel by development with chloroform/acetone (1/1) to give 0.35 g (yield 22%) of the title compound.

$^1$H-NMR (CDCl$_3$, 400 MHz): δ 3.84 (s, 2H), 4.05 (s, 3H), 4.08 (s, 3H), 6.28 (d, J=5.4 Hz, 1H), 6.74 (s, 2H), 7.43 (s, 1H), 7.64 (s, 1H), 8.48 (d, J=5.4 Hz, 1H).

Production Example 5

4-[(6,7-Dimethoxy-4-quinolyl)oxy]-2-nitroaniline

Sodium hydride (60 wt %, 0.54 g) was added to dimethyl sulfoxide (15 ml), and the mixture was stirred at 70° C. for 30 min and was then cooled to room temperature. 4-Amino-3-nitrophenol (2.07 g) was added to the cooled mixture, and the mixture was stirred at room temperature for 10 min. Next, 4-chloro-6,7-dimethoxyguinoline (1.50 g) was added thereto, and the mixture was stirred at 100° C. for 4 hr. Water was added to the reaction solution, followed by extraction with chloroform. The chloroform layer was then washed with a saturated aqueous sodium hydrogencarbonate solution and was dried over anhydrous sodium sulfate. The solvent was removed by distillation under the reduced pressure, and the residue was purified by chromatography on silica gel by development with chloroform/acetone (1/1) to give 0.53 g (yield 23%) of the title compound.

Production Example 6

1-[2-Amino-4-(benzyloxy)-5-methoxyphenyl]-1-ethanone 1-(4-Hydroxy-3-methoxyphenyl)-1-ethanone (20 g), potassium carbonate (18.3 g), tetra-n-butylammonium iodide (4.45 g), and benzyl bromide (17.3 ml) were dissolved in N,N-dimethylformamide (300 ml), and a reaction was allowed to proceed at 100° C. for one hr. The solvent was removed by distillation under the reduced pressure, and water was added to the residue, followed by extraction with ethyl acetate. The ethyl acetate layer was dried over sodium sulfate. Next, the solvent was removed by distillation under the reduced pressure. The residue and fuming nitric acid (12.47 ml) were dissolved in acetic acid (120 ml), and a reaction was allowed to proceed at room temperature for 2 hr. The reaction solution was neutralized at 0° C. by the addition of an aqueous sodium hydroxide solution, followed by extraction with chloroform. The chloroform layer was then dried over sodium sulfate. Next, the solvent was removed by distillation under the reduced pressure. The residue was dissolved in ethanol (1160 ml) and water (120 ml) with heating. Ammonium chloride (19.2 g) and zinc (101.7 g) were added thereto. The mixture was heated under reflux for 3 hr. The reaction solution was filtered through Celite, followed by washing with chloroform/methanol (3/1). The solvent was removed by distillation under the reduced pressure, and the residue was made alkaline with an aqueous sodium hydroxide solution, and the alkaline solution was extracted with chloroform. The chloroform layer was dried over sodium sulfate. The solvent was removed by distillation under the reduced pressure, and the residue was purified by chromatography on silica gel by development with chloroform/ethyl acetate (10/1) to give 24.95 g (yield 77%) of the title compound (3 steps).

$^1$H-NMR (CDCl$_3$, 400 MHz): δ 2.51 (s, 3H), 3.84 (s, 3H), 5.14 (s, 2H), 6.12 (s, 2H), 7.15–7.62 (m, 7H).

Production Example 7

7-(Benzyloxy)-6-methoxy-1,4-dihydro-4-quinolinone

1-[2-Amino-4-(benzyloxy)-5-methoxyphenyl]-1-ethanone (24.95 g) was dissolved in tetrahydrofuran (450 ml), and sodium methoxide (24.87 g) was added to the solution. The mixture was stirred at room temperature for one hr. Ethyl formate (37.07 ml) was then added thereto, and the mixture was stirred at room temperature for 2 hr. Water (150 ml) was then added thereto, and the mixture was stirred overnight. The reaction solution was adjusted to pH 4 by the addition of concentrated sulfuric acid at 0° C. Water was added thereto, and the mixture was extracted with chloroform. The chloroform layer was dried over sodium sulfate. The solvent was removed by distillation under the reduced pressure. The residue was purified by chromatography on silica gel by development with chloroform/methanol (10/1) to give 17.16 g (yield 66%) of the title compound.

$^1$H-NMR (DMSO-d$_6$, 400 MHz): δ 3.84 (s, 3H), 5.19 (s, 2H), 5.97 (d, J=7.1 Hz, 1H), 7.09 (s, 1H), 7.28–7.51 (m, 6H), 7.78 (d, J=7.3 Hz, 1H), 11.50–11.75 (br, 1H).

Production Example 8

7-(Benzyloxy)-4-chloro-6-methoxyquinoline

Phosphorus oxychloride (14.19 ml) was added to 7-(benzyloxy)-6-methoxy-1,4-dihydro-4-quinolinone (17.16 g), and the mixture was heated under reflux for one hr. The solvent was removed by distillation under the reduced pressure. The residue was dissolved in chloroform, and the solution was made alkaline by the addition of an aqueous sodium hydroxide solution, followed by extraction with chloroform. The chloroform layer was dried over sodium sulfate. The solvent was removed by distillation under the reduced pressure, and the residue was purified by chromatography on silica gel by development with chloroform/acetone (10/1) to give 3.82 g (yield 21%) of the title compound.

$^1$H-NMR (CDCl$_3$, 400 MHz): δ 4.06 (s, 3H), 5.32 (s, 2H), 7.30–7.55 (m, 8H), 8.56 (d, J=4.9 Hz, 1H).

Production Example 9

4-{[7-(Benzyloxy)-6-methoxy-4-quinolyl]oxy}-2,5-dimethylaniline

Sodium hydride (60 wt %, 1.17 g) was added to dimethyl sulfoxide (25 ml), and the mixture was stirred at 60° C. for 30 min and was then cooled to room temperature. Next, 4-amino-2,5-dimethylphenol (4.00 g) was added thereto, and the mixture was stirred at room temperature for 10 min. 7-(Benzyloxy)-4-chloro-6-methoxyquinoline (4.36 g) was then added thereto. The mixture was stirred for 22 hr before water was added to the reaction solution, followed by extraction with chloroform. The chloroform layer was then washed with a saturated aqueous sodium hydrogencarbonate solution and was dried over anhydrous sodium sulfate. The solvent was removed by distillation under the reduced pressure, and methanol was added to the residue to prepare a suspension. The precipitated crystal was collected by suction filtration to give 3.04 g (yield 52%) of the title compound.

$^1$H-NMR (CDCl$_3$, 400 MHz): δ 2.05 (s, 3H), 2.16 (s, 3H), 3.58 (s, 2H), 4.06 (s, 3H), 5.32 (s, 2H), 6.28 (d, J=5.1 Hz, 1H), 6.61 (s, 1H), 6.81 (s, 1H), 7.28–7.42 (m, 3H), 7.44 (s, 1H), 7.49–7.54 (m, 2H), 7.63 (s, 1H), 8.39 (d, J=5.1 Hz, 1H).

Mass Analysis, Found (ESI-MS, m/z): 401 (M$^+$+1).

Production Example 10

N-(4-{[7-(Benzyloxy)-6-methoxy-4-quinolyl]oxy}-2,5-dimethylphenyl)-N'-(2,4 difluorophenyl)urea 4-{[7-(Benzyloxy)-6-methoxy-4-quinolyl]oxy}-2,5-dimethylaniline (300 mg) was dissolved in chloroform (5 ml). 2,4-Difluorophenyl isocyanate (200 μl) was then added to the solution, and the mixture was stirred at 70° C. overnight. The reaction solution was purified by chromatography on silica gel by development with chloroform/acetone (75/25) to give 368 mg (yield 88%) of the title compound.

$^1$H-NMR (CDCl$_3$, 400 MHz): δ 2.17 (s, 3H), 2.26 (s, 3H), 4.06 (s, 3H), 5.33 (s, 2H), 6.29 (d, J=5.1 Hz, 1H), 6.42 (s, 1H), 6.76–6.93 (m, 3H), 6.70 (s, 3H), 7.30–7.54 (m, 7H), 7.60 (s, 1H), 8.04–8.12 (m, 1H), 8.44 (d, J=5.4 Hz, 1H).

Production Example 11

N-(4-{[7-(Benzyloxy)-6-methoxy-4-quinolyl]oxy}-2,5-dimethylphenyl)-N'-(2-methoxypheny)-urea 4-{[7-(Benzyloxy)-6-methoxy-4-quinolyl]oxy}-2,5-dimethylaniline (300 mg) was dissolved in chloroform (5 ml). 2-Methoxyphenyl isocyanate (0.24 ml) was then added to the solution, and the mixture was stirred at 70° C. overnight. The reaction solution was purified by chromatography on silica gel by development with chloroform/acetone (75/25) to give 365 mg (yield 89%) of the title compound. $^1$H-NMR (CDCl$_3$, 400 MHz): δ 2.17 (s, 3H), 2.28 (s, 3H), 3.83 (s, 3H), 4.07 (s, 3H), 5.33 (s, 2H), 6.26 (s, 3H), 6.29 (d, J=5.4 Hz, 1H), 6.86–7.06 (m, 4H), 7.12 (s, 1H), 7.30–7.41 (m, 3H), 7.46 (s, 1H), 7.50–7.56 (m, 3H), 7.61 (s, 1H), 8.11–8.16 (m, 1H), 8.43 (d, J=5.4 Hz, 1H)

Production Example 12

4-{[7-(Benzyloxy)-6-methoxy-4-quinolyl]oxy}-2-chloroaniline

Sodium hydride (60 wt %, 320 mg) was added to dimethyl sulfoxide (3.6 ml), and the mixture was stirred at 60° C. for 30 min and was then cooled to room temperature. Next, 4-amino-3-chlorophenol hydrochloride (720 mg) was added thereto, and the mixture was stirred at room temperature for 10 min. 7-(Benzyloxy)-4-chloro-6-methoxyquinoline (600 mg) was then added thereto, and the mixture was stirred at 105° C. for 22 hr. Water was added to the reaction solution, followed by extraction with chloroform. The chloroform layer was then washed with a saturated aqueous sodium hydrogencarbonate solution and was dried over anhydrous sodium sulfate. The solvent was removed by distillation under the reduced pressure, and methanol was added to the residue to prepare a suspension. The precipitated crystal was collected by suction filtration to give 533 mg (yield 66%) of the title compound.

$^1$H-NMR (CDCl$_3$, 400 MHz): δ 4.05 (s, 3H), 4.08 (s, 2H), 5.32 (s, 2H), 6.42 (d, J=5.1 Hz, 1H), 6.84 (d, J=8.5 Hz, 1H), 6.93 (dd, J=2.4 Hz, 8.1 Hz, 1H), 7.14 (d, J=2.4 Hz, 1H), 7.29–7.42 (m, 3H), 7.44 (s, 1H), 7.49–7.53 (m, 2H), 7.55 (s, 1H), 8.45 (d, J=5.3 Hz, 1H)

Mass analysis, found (ESI-MS, m/z): 497 (M$^+$+1).

Production Example 13

N-(4-{[7-(Benzyloxy)-6-methoxy-4-quinolyl]oxy}-2-chlororphenyl)-N'-(2,4-difluorophenyl)-urea 4-{[7-(Benzyloxy)-6-methoxy-4-quinolyl]oxy}-2-chloroaniline (260 mg) was dissolved in chloroform (10 ml). 2,4-Difluorophenyl isocyanate (198 mg) was then added to the solution, and the mixture was stirred at room temperature for 2 hr. The reaction solution was purified by chromatography on silica gel by development with chloroform/acetone (10/1) to give 337 mg (yield 94%) of the title compound.

$^1$H-NMR (CDCl$_3$, 400 MHz): δ 4.04 (s, 3H), 5.32 (s, 2H), 6.49 (d, J=5.1 Hz, 1H), 6.86–6.96 (m, 3H), 7.10–7.17 (m, 2H), 7.22–7.28 (m, 1H), 7.28–7.41 (m, 3H), 7.45–7.53 (ml 4H), 7.96–8.04 (m, 1H), 8.27 (d, J=9.0 Hz, 1H), 8.49 (d, J=5.4 Hz, 1H).

Mass Analysis, Found (ESI-MS, m/z): 562, 564 (M$^+$+1).

Production Example 14

N-{2-Chloro-4-[(7-hydroxy-6-methoxy-4-quinolyl)oxy]phenyl}-N'-(2,4-difluorophenyl)-urea N-(4-{[7-(Benzyloxy)-6-methoxy-4-quinolyl]oxy}-2-chlorophenyl)-N'-(2,4-difluorophenyl)urea (215 mg) was dissolved in dimethylformamide (11 ml). Palladium-carbon (215 mg) was added to the solution, and the mixture was stirred in a hydrogen atmosphere at room temperature overnight. Ethyl acetate (30 ml) was added to the reaction solution, and the mixture was then filtered through Celite. The solvent was removed by distillation under the reduced pressure to give 174 mg (yield 96%) of the title compound.

$^1$H-NMR (DMSO-d$_6$, 400 MHz): δ 3.94 (s, 3H), 6.47 (d, J=5.1 Hz, 1H), 7.01–7.11 (m, 1H), 7.18–7.36 (m, 3H), 7.44–7.52 (m, 2H), 7.95 (s, 1H), 7.98–8.13 (m, 1H), 8.23 (d, J=9.5 Hz, 1H), 6.50 (d, J=5.1 Hz, 1H), 8.81 (s, 1H), 9.31 (s, 1H).

Mass analysis, found (ESI-MS, m/z): 472 (M$^+$+1).

Production Example 15

4-{[7-(Benzyloxy)-6-methoxy-4-quinolyl]oxy}-2,3-dimethylaniline

Sodium hydride (60 wt %, 0.32 g) was added to dimethyl sulfoxide (6 ml), and the mixture was stirred at room temperature for 30 min. 4-Amino-2,3-dimethylphenol (1.10 g) was then added thereto, and the mixture was stirred at room temperature for 10 min. Next, 7-(benzyloxy)-4-chloro-6-methoxyquinoline (1.20 g) was added thereto, and the mixture was stirred at 110° C. for 6 hr. A saturated aqueous sodium hydrogencarbonate solution was added to the reaction solution, followed by extraction with chloroform. The chloroform layer was dried over anhydrous magnesium sulfate. The solvent was removed by distillation under the reduced pressure, and the residue was purified by chromatography on silica gel by development with chloroform/acetone (6/1) to give 0.78 g (yield 49%) of the title compound.

$^1$H-NMR (DMSO-d$_6$, 400 MHz): δ 1.87 (s, 3H), 1.96 (s, 3H), 3.97 (s, 3H), 4.78 (s, 2H), 5.23 (s, 2H), 6.12 (d, J=5.3 Hz, 1H), 6.54 (d, J=8.4 Hz, 1H), 6.69 (d, J=8.4 Hz, 1H), 7.27–7.51 (m, 7H), 8.31 (d, J=5.3 Hz, 1H).

Production Example 16

N-(4-{[7-Benzyloxy)-6-methoxy-4-quinolyl]oxy}-2,3-dimethylphenyl)-N'-(2,4-difluoro-phenyl)urea 4-{[7-(Benzyloxy)-6-methoxy-4-quinolyl]oxy}-2,3-dimethylaniline (260 mg) was dissolved in N,N-dimethylformamide (5 ml). 2,4-Difluorophenyl isocyanate (121 mg) was then added to the solution, and a reaction was allowed to proceed at room temperature overnight. Methanol was added to the reaction solution, and the solvent was removed by distillation under the reduced pressure. The residue was washed with methanol and was collected by filtration to give 219 mg (yield 61%) of the title compound.

$^1$H-NMR (DMSO-d$_6$, 400 MHz): δ 1.99 (s, 3H), 2.17 (s, 3H), 3.90 (s, 3H), 5.24 (s, 2H), 6.18 (d, J=5.1 Hz, 1H), 6.95–6.98 (m, 2H), 7.25–7.63 (m, 9H), 8.05–8.08 (m, 1H), 8.34–8.36 (m, 2H), 8.79 (s, 1H).

Production Example 17

7-(Benzyloxy)-4-(3-fluoro-4-nitrophenoxy)-6-methoxyquinoline 7-(Benzyloxy)-4-chloro-6-methoxyquinoline (300 mg) and 3-fluoro-4-nitrophenol (785 mg) were dissolved in chlorobenzene (3 ml), and the solution was stirred at 130° C. for 5 hr. Chloroform and an aqueous sodium hydroxide solution were added to the reaction solution, and the mixture was stirred for one hr. The reaction solution was extracted with chloroform, and the chloroform layer was dried over anhydrous magnesium sulfate. The solvent was removed by distillation under the reduced pressure. The residue was purified by thin-layer chromatography on silica gel by development with hexane/ethyl acetate (1/1) to give 197 mg (yield 47%) of the title compound.

$^1$H-NMR (DMSO-d$_6$, 400 MHz): δ 3.83 (s, 3H), 5.25 (s, 2H), 6.91 (d, J=5.1 Hz, 1H), 7.29–7.50 (m, 9H), 8.18–8.23 (m, 1H), 8.56 (d, J=5.1 Hz, 1H).

Production Example 18

4-(4-Amino-3-fluorophenoxy)-6-methoxy-7-quinolinol 7-(Benzyloxy)-4-(3-fluoro-4-nitrophenoxy)-6-methoxyquinoline (190 mg) was dissolved in N,N-dimethylformamide (5 ml) and triethylamine (1 ml). Palladium hydroxide (40 mg) was added to the solution, and the mixture was stirred in a hydrogen atmosphere at room temperature overnight. The solvent was removed by distillation under the reduced pressure. The residue was purified by thin-layer chromatography on silica gel by development with chloroform/methanol (20/1) to give 75 mg (yield 56%) of the title compound.

$^1$H-NMR (DMSO-d$_6$, 400 MHz): δ 3.87 (s, 3H), 5.11 (s, 2H), 6.29 (d, J=5.1 Hz, 1H), 6.77–6.80 (m, 2H), 6.93–6.99 (m, 1H), 7.19 (s, 1H), 7.40 (s, 1H), 8.31 (d, J=5.1 Hz, 1H), 10.03 (B, 1H).

Production Example 19

N-(2,4-Difluorophenyl)-N'-{-2-fluoro-4-[(7-hydroxy-6-methoxy-4-quinolyl)oxy]phenyl}-urea 4-(4-Amino-3-fluorophenoxy)-6-methoxy-7-quinolinol (70 mg) was dissolved in chloroform (1.5 ml) and N,N-dimethylformamide (1 ml). 2,4-Difluorophenyl isocyanate (43 mg) was then added to the solution, and a reaction was allowed to proceed at room temperature for 3 hr. Methanol was added to the reaction solution. The solvent was removed by distillation under the reduced pressure. The residue was purified by thin-layer chromatography on silica gel by development with chloroform/methanol (20/1) to quantitatively give the title compound.

$^1$H-NMR (DMSO-d$_6$, 400 MHz): δ 3.94 (s, 3H), 6.47 (d, J=5.1 Hz, 1H), 7.04–7.10 (m, 2H), 7.28–7.34 (m, 2H), 7.47 (s, 1H), 8.05–8.15 (m, 2H), 8.30 (s, 1H), 8.43 (d, J=5.1 Hz, 1H), 8.97–9.03 (m, 2H), 10.10 (s, 1H).

Production Example 20

4-Chloro-6-methoxy-7-quinolinol 7-(Benzyloxy)-4-chloro-6-methoxyquinoline (100 mg), thioanisole (300 µl), and methanesulfonic acid (25 µl) were dissolved in trifluoromethanesulfonic acid (1 ml). The solution was stirred at room temperature for 30 min. The solvent was removed by distillation under the reduced pressure. The residue was made neutral by the addition of an aqueous sodium hydroxide solution, and hexane was added thereto to prepare a suspension. The crystal was collected by suction filtration to give 53 mg (yield 75%) of the title compound.

$^1$H-NMR (DMSO-d$_6$, 400 MHz): δ 3.98 (s, 3H), 7.33 (s, 1H), 7.36 (s, 1H), 7.47 (d, J=4.9 Hz, 1H), 8.54 (d, J=4.9 Hz, 1H), 10.37 (br, 1H).

Production Example 21

4-Chloro-6-methoxy-7-(2-methoxyethoxy)quinoline

4-Chloro-6-methoxy-7-quinolinol (50 mg), potassium carbonate (40 mg), tetra-n-butylammonium iodide (9 mg), and 2-bromoethyl methyl ether (40 mg) were dissolved in N,N-dimethylformamide (10 ml). The solution was stirred at 70° C. overnight. The solvent was removed by distillation under the reduced pressure. A saturated aqueous sodium hydrogencarbonate solution was added to the residue, followed by extraction with chloroform. The chloroform layer was dried over sodium sulfate. The solvent was removed by distillation under the reduced pressure. The residue was purified by chromatography on silica gel by development with hexane/acetone/dichloromethane (6/2/1) to give 47 mg (yield 74%) of the title compound.

$^1$H-NMR (CDCl$_3$, 400 MHz): δ 3.49 (s, 3H), 3.88–3.90 (m, 2H), 4.04 (s, 3H), 4.32–4.35 (m, 2H), 7.35 (d, J=4.9 Hz, 1H), 7.40 (s, 1H), 7.43 (s, 1H), 8.57 (d, J=4.9 Hz, 1H).

Production Example 22

2-Chloro-4-{[(6-methoxy-7-(2-methoxyethoxy)-4-quinolyl]oxy}aniline

Sodium hydride (60 wt %, 153 mg) was added to dimethyl sulfoxide (2 ml). The mixture was stirred at 60° C. for 30 min and was then cooled to room temperature. 4-Amino-3-chlorophenol hydrochloride (343 mg) was added thereto, and the mixture was stirred at room temperature for 10 min. Next, a solution of 4-chloro-6-methoxy-7-(2-methoxyethoxy)quinoline (254 mg) in dimethyl sulfoxide (2 ml) was added to the reaction solution, and the mixture was stirred at 110° C. overnight. Water was added to the reaction solution, followed by extraction with chloroform. The chloroform layer was then washed with a saturated aqueous sodium hydrogencarbonate solution and was dried over anhydrous sodium sulfate. The solvent was removed by distillation under the reduced pressure. The residue was purified by chromatography on silica gel by development with chloroform/acetone (7/3) to give the title compound.

$^1$H-NMR (CDCl$_3$, 400 MHz): δ 3.49 (s, 3H), 3.89–3.91 (m, 2H), 4.02 (s, 3H), 4.09 (s, 2H), 4.33–4.35 (m, 2H), 6.43 (d, J=5.4 Hz, 1H), 6.85 (d, J=8.5 Hz, 1H), 6.93–6.96 (m, 1H), 7.15 (d, J=2.7 Hz, 1H), 7.41 (s, 1H), 7.52 (s, 1H), 8.47 (d, J=5.1 Hz, 1H)

Production Example 23

2-Chloro-4-[(6,7-dimethoxy-4-quinazolinyl)oxy]aniline

Sodium hydride (60 wt %, 5.80 g) was added to dimethyl sulfoxide (40 ml). The mixture was stirred at 60° C. for 30 min and was then cooled to room temperature. Next, 4-amino-3-chlorophenol hydrochloride (13.05 g) was added thereto. The mixture was stirred at room temperature for 10 min. 4-Chloro-6,7-dimethoxyquinazoline (8.14 g), which is a chloroquinazoline derivative synthesized by a conventional method as described, for example, in J. Am. Chem. Soc., 68, 1299 (1946) or J. Am. Chem. Soc., 68, 1305 (1946), was then added thereto. The mixture was stirred at 110° C. for 30 min. Water was then added to the reaction solution, followed by extraction with chloroform. The chloroform layer was then washed with a saturated aqueous sodium hydrogencarbonate solution and was dried over anhydrous sodium sulfate. The solvent was removed by distillation under the reduced pressure, and methanol was added to the residue to prepare a suspension. The precipitated crystal was collected by suction filtration to give 9.13 g (yield 76%) of the title compound.

$^1$H-NMR (CDCl$_3$, 400 MHz): δ 4.05–4.08 (m, 8H), 6.85 (d, J=8.5 Hz, 1H), 7.00 (dd, J=2.7 Hz, 8.8 Hz, 1H), 7.21 (d, J=2.7 Hz, 1H), 7.32 (s, 1H), 7.52 (s, 1H), 8.64 (s, 1H).

Mass analysis, found (ESI-MS, m/z): 332 (M$^+$+1).

Production Example 24

N-Benzyl-N-(2,4-difluorophenyl)amine

Magnesium sulfate (5.59 g) and a minor amount of acetic acid were added to a solution of 2,4-difluoroaniline (2.37 ml) and benzaldehyde (2.36 ml) in methanol (46 ml). The mixture was stirred at room temperature for 45 min. Sodium boron hydride (2.64 g) was added thereto under ice cooling, and the mixture was stirred at room temperature for one hr. The solvent was removed by distillation under the reduced pressure. Water and ethyl acetate were added to the residue. The mixture was stirred and was filtered through Celite. The organic layer was extracted with ethyl acetate and was dried over anhydrous sodium sulfate. The solvent was removed by distillation under the reduced pressure. The residue was purified by chromatography on silica gel by development with hexane/acetone (30/1) to give 3.04 g (yield 60%) of the title compound.

$^1$H-NMR (CDCl$_3$, 400 MHz): δ 4.34 (s, 2H), 6.56–6.82 (m, 3H), 7.25–7.38 (m, 5H).

Production Example 25

Methyl 4-(benzyloxy)-5-methoxy-2-nitrobenzoate

Commercially available methyl vanillate (50 g) and potassium carbonate (76 g) were dissolved in N,N-dimethylformamide (200 ml). Benzyl bromide (33 ml) was added dropwise to the solution over a period of 10 min. The mixture was stirred at room temperature overnight. Water (200 ml) was added thereto, followed by extraction with ethyl acetate. Saturated brine was then added to the organic layer, and the mixture was extracted with ethyl acetate. Sodium sulfate was added to the organic layer to dry the organic layer. Next, the organic layer was filtered, and the solvent was then removed by distillation under the reduced pressure. The residue was dried through a vacuum pump to give 68 g of a white solid subsequently, 100 ml of acetic acid and 200 ml of nitric acid were added under ice cooling. The mixture was stirred for 8 hr, and water was then added thereto. The resultant solid was then collected by filtration, was thoroughly washed with water, and was dried through a vacuum pump to give 74 g (yield 93%) of the title compound.

$^1$H-NMR (CDCl$_3$, 400 MHz): δ 3.90 (s, 3H), 3.98 (s, 3H), 5.21 (s, 2H), 7.08 (s, 1H), 7.31–7.45 (m, 5H), 7.51 (s, 1H).

Production Example 26

7-(Benzyloxy)-6-methoxy-3-dihydro-4-quinazoline

Methyl 4-(benzyloxy)-5-methoxy-2-nitrobenzoate (15.0 g) was dissolved in acetic acid (200 ml) at room temperature. Iron (powder) (13.2 g) was then added to the solution. The temperature of the mixture was raised to 90° C. and the mixture was then stirred for one hr. The resultant gray solid was filtered through Celite, followed by washing with acetic acid. Concentrated hydrochloric acid was added to the mother liquor. The solvent was then removed by distillation under the reduced pressure. This resulted in the precipitation of a solid. The solid was collected by filtration, was washed with ethyl acetate and ether, and was dried through a vacuum pump. Subsequently, chloroform and methanol were added to the solid to prepare a suspension, and a 10% aqueous sodium hydroxide solution was then added to dissolve the solid, followed by extraction with chloroform. After washing with water, the organic layer was dried over sodium sulfate. Next, the organic layer was filtered, and the solvent was then removed by distillation under the reduced pressure. The residue was dried through a vacuum pump to give 9.5 g (yield 70%) of a crude product of methyl 2-amino-4-(benzyloxy)-5-methoxybenzoate.

Methyl 2-amino-4-(benzyloxy)-5-methoxybenzoate (650 mg) was dissolved in N,N-dimethylformamide (15 ml) and methanol (3 ml). Formamide (0.46 ml) and sodium methoxide (373 mg) were added to the solution. The mixture was heated to 100° C. and was stirred overnight. The reaction solution was cooled to room temperature, and 10 ml of water was then added to the cooled reaction solution. The reaction solution was neutralized with a 1 M aqueous hydrochloric acid solution to precipitate a solid. The solid was collected by filtration, was washed with water and ether, and was then dried through a vacuum pump to give 566 mg (yield 87%) of the title compound.

$^1$H-NMR (DMSO-$d_6$, 400 MHz): δ 3.88 (s, 3H), 5.25 (s, 2H), 7.23 (s, 1H), 7.33–7.49 (m, 6H), 7.97 (s, 1H), 12.06 (br, 1H).

Production Example 27

7-(Benzyloxy)-4-chloro-6-methoxyquinazoline

Phosphorus oxychloride (515 ml) was added to 7-(benzyloxy)-6-methoxy-3,4-dihydro-4-quinazolinone (400 mg) and diisopropylethylamine (0.3 ml), and the mixture was refluxed for 20 min. The reaction solution was cooled to room temperature. A 10% aqueous sodium hydroxide solution was then added to the reaction solution, followed by extraction with chloroform. The organic layer was dried over sodium sulfate. The organic layer was filtered, and the solvent was then removed by distillation under the reduced pressure. The residue was dried through a vacuum pump to give 420 mg (yield 99%) of the title compound.

$^1$H-NMR (CDCl$_3$, 400 MHz): δ 4.08 (s, 3H), 5.34 (s, 2H), 7.35–7.51 (m, 7H), 8.86 (s, 1H).

Production Example 28

Methyl 5-(benzyloxy)-4-methoxy-2-nitrobenzoate

Commercially available methyl 3-hydroxy-4-methoxybenzoate (10 g) and potassium carbonate (23 g) were dissolved in N,N-dimethylformamide (50 ml). Benzyl bromide (6.5 ml) was added dropwise to the solution over a period of 10 min. The mixture was stirred at room temperature overnight. Water (200 ml) was added thereto, and the mixture was extracted with ethyl acetate. Saturated brine was then added to the organic layer, followed by extraction with ethyl acetate. Sodium sulfate was added to the organic layer to dry the organic layer. Next, the organic layer was filtered, and the solvent was then removed by distillation under the reduced pressure. The residue was dried through a vacuum pump to give 8.4 g of a white solid. Subsequently, 7.0 g of the solid was placed in a flask, and 100 ml of acetic acid and 200 ml of nitric acid were added thereto under ice cooling. The mixture was stirred for 8 hr, and water was then added thereto. The resultant solid was collected by filtration, was thoroughly washed with water, and was dried through a vacuum pump to give 7.9 g (yield 96%) of the title compound.

$^1$H-NMR (CDCl$_3$, 400 MHz): δ 3.89 (s, 3H), 3.96 (s, 3H), 5.21 (s, 2H), 7.15 (s, 1H), 7.34–7.45 (m, 6H).

Production Example 29

6-(Benzyloxy)-7-methoxy-3,4-dihydro-4-quinazolinone

Methyl 5-(benzyloxy)-4-methoxy-2-nitrobenzoate (15.8 g) was dissolved in acetic acid (200 ml) at room temperature. Iron (powder) (13.9 g) was then added to the solution. The mixture was heated to 90° C. and was stirred for one hr. The resultant gray solid was filtered through Celite and was washed with acetic acid. Concentrated hydrochloric acid was added to the mother liquor, and the solvent was then removed by distillation under the reduced pressure to precipitate a solid. The solid was collected by filtration, was washed with ethyl acetate and ether, and was dried through a vacuum pump. Subsequently, chloroform and methanol were added to the solid to prepare a suspension, and a 10% aqueous sodium hydroxide solution was then added to the suspension to dissolve the solid, followed by extraction with chloroform. The extract was washed with water, and the organic layer was then dried over sodium sulfate. Next, the organic layer was filtered, and the solvent was then removed by distillation under the reduced pressure. The residue was dried through a vacuum pump to give 10.4 g (yield 73%) of a crude product of methyl 2-amino-5-(benzyloxy)-4-methoxybenzoate.

Methyl 2-amino-5-(benzyloxy)-4-methoxybenzoate (5.0 g) was dissolved in N,N-dimethylformamide (150 ml) and methanol (30 ml). Formamide (3.5 ml) and sodium methoxide (2.8 g) were added to the solution. The mixture was heated to 100° C. and was then stirred overnight. The reaction solution was then cooled to room temperature, and 10 ml of water was then added. The reaction solution was neutralized with a 1 M aqueous hydrochloric acid solution to precipitate a solid. The solid was collected by filtration, was washed with water and ether, and was then dried through a vacuum pump to give 3.7 g (yield 76%) of the title compound. $^1$H-NMR (DMSO-d6, 400 MHz): δ 3.92 (s, 3H), 5.21 (s, 2H), 7.16 (s, 1H), 7.33–7.49 (m, 5H), 7.55 (s, 1H), 7.99 (s, 1H), 12.06 (br, 1H).

Production Example 30

6-(Benzyloxy)-4-chloro-7-methoxyquinazoline

Phosphorus oxychloride (3.1 ml) was added to 6-(benzyloxy)-7-methoxy-3,4-dihydro-4-quinazolinone (3.5 g) and diisopropylethylamine (11.5 ml). The mixture was refluxed for 20 min. The reaction solution was cooled to room temperature, and a 10% aqueous sodium hydroxide solution was then added to the cooled reaction solution, followed by extraction with chloroform. The organic layer was dried over sodium sulfate. The organic layer was filtered, and the solvent was then removed by distillation under the reduced pressure. The residue was dried through a vacuum pump to give 2.9 g (yield 72%) of the title compound.

$^1$H-NMR (CDCl$_4$, 400 MHz): δ 4.07 (s, 3H), 5.32 (s, 2H), 7.35–7.53 (m, 7H), 8.86 (s, 1H).

Production Example 31

4-{[7-(Benzyloxy)-6-methoxy-4-quinazolinyl]oxy}-2-chloroaniline 7-(Benzyloxy)-4-chloro-6-methoxyquinazoline (30.0 g) and tetrabutylammonium chloride (13.9 g) were dissolved in acetone (400 ml), and the solution was stirred at room temperature. A solution of 4-amino-3-chlorophenol hydrochloride (36.0 g) in a 20% aqueous sodium hydroxide solution (64 ml) was added thereto. The mixture was then heated under reflux for 3 hr. The reaction solution was cooled to room temperature, and chloroform and water were added to the cooled reaction solution, followed by extraction with chloroform. The extract was washed with a saturated aqueous sodium hydrogencarbonate solution and saturated brine and was then dried over anhydrous sodium sulfate. Next, sodium sulfate was removed, and the solvent was then removed by distillation. The residue was washed with methanol, and the washed solid was subjected to evaporation to dryness in vacuo through a vacuum pump to give 36.6 g (yield 90%) of the title compound.

$^1$H-NMR (DMSO-d$_6$, 400 MHz): δ 3.96 (s, 3H), 5.34 (s, 2H), 6.86 (d, J=8.8 Hz, 1H), 7.00 (dd, J=2.7 Hz, 8.8 Hz, 1H), 7.22 (d, J=2.7 Hz, 1H), 7.35–7.54 (m, 7H), 8.53 (s, 1H).

Production Example 32

N-(4-{[7-(Benzyloxy)-6-methoxy-4-quinazolinyl]oxy}-2-chlorophenyl)-N'-propylurea 4-{[7-(Benzyloxy)-6-methoxy-4-quinazolinyl]oxy}-2-chloroaniline (12.2 g) was dissolved in anhydrous chloroform. Triethylamine (8.4 ml) was then added to the solution, and the mixture was stirred at room temperature. Separately, triphosgene (4.5 g) was dissolved in anhydrous chloroform (12 ml), and the solution was added dropwise to the mixed solution. The mixture was stirred at room temperature for 20 min, and n-propylamine (4.9 ml) was then added thereto, followed by stirring at room temperature for additional one hr to precipitate a white solid. This solid was collected by filtration and was then washed with chloroform to give rib 9.4 g (yield 63%) of the title compound.

$^1$H-NMR (DMSO-d$_6$, 400 MHz): δ 0.91 (t, J=7.3 Hz, 3H), 1.44–1.50 (m, 2H), 3.06–3.09 (m, 2H), 3.98 (s, 3H), 5.35 (s, 2H), 6.97–7.01 (m, 1H), 7.23 (dd, J=2.7 Hz, 9.0 Hz, 1H), 7.37–7.57 (m, 9H), 8.20 (d, J=9.3 Hz, 1H), 8.55 (s, 1H).

Production Example 33

N-{2-Chloro-4-[(7-hydroxy6-methoxy-4-quinazolinyl)oxy]phenyl}-N'-propylurea

N-(4-{[7-(Benzyloxy)-6-methoxy-4-quinazolinyl]oxy}-2-chlorophenyl)-N'-propylurea (42.2 g) was dissolved in trifluoroacetic acid (200 ml). Methanesulfonic acid (11.1 ml) was then added to the solution, and the mixture was stirred at 100° C. for 4 hr. The reaction solution was cooled to room temperature, and trifluoroacetic acid was removed by distillation under the reduced pressure. Chloroform and methanol were added to the mixture as the residue, followed by extraction with a 10% aqueous sodium hydroxide solution three times. The aqueous layer was neutralized with concentrated hydrochloric acid to precipitate a solid. The solid was washed with water, methanol, and ether in that order, and was then dried in vacuo through a vacuum pump to give 20.7 g (yield 60%) of the title compound.

$^1$H-NMR (DMSO-d$_6$, 400 MHz): δ 0.91 (t, J=7.3 Hz, 3H), 1.42–1.49 (m, 2H), 3.06–3.17 (m, 2H), 3.84 (s, 3H), 6.65 (s, 1H), 7.03 (m, 1H), 7.14 (dd, J=2.7 Hz, 9.0 Hz, 1H), 7.20 (s, 1H), 7.35 (d, J=2.7 Hz, 1H), 8.05 (s, 1H), 8.14 (dd, J=2.7 Hz, 8.8 Hz, 1H), 8.19 (s, 1H).

Production Example 34

6,7-Dimethoxy-4-quinazolone

Formamide (150 ml) was added to methyl 2-amino-3,4-dimethoxybenzoate (20.0 g, 94.8 mmol). The mixture was heated at 160° C. for 8.5 hr. The reaction solution was cooled and was then filtered. The collected precipitate was washed with water (100 ml×2 times), and the washed precipitate was dried in vacuo to give 17.85 g (yield 91.5%) of the target compound.

$^1$H-NMR (DMSO-d$_6$, 400 MHz): δ 4.01 (s, 3H), 4.02 (s, 3H), 7.14 (s, 1H), 7.34 (s, 1H), 7.61 (s, 1H), 7.97 (s, 1H).

Production Example 35

4-Chloro-6,7-dimethoxyquinazoline

Sulfolane (250 ml) and phosphorus oxychloride (250 ml=412.5 g, 2.69 mol) were added to 6,7-dimethoxy-4-quinazolone (50.1 g, 0.24 mol), and the mixture was stirred at 120° C. for one hr. The reaction mixture was cooled to room temperature, and the excess phosphorus oxychloride was then removed by distillation under the reduced pressure. The residue was poured into ice water (1000 ml), and chloroform (1000 ml) was added thereto. The aqueous layer was adjusted to pH 6.5 by the addition of a 20% sodium hydroxide solution, followed by the separation of the organic layer from the aqueous layer. The separated organic layer was washed with water (1000 ml×six times), was dried over sodium sulfate, and was then concentrated under the reduced pressure. Tetrahydrofuran (470 ml) was added to the residue, and the mixture was refluxed. The reaction solution was cooled to −5° C. to −10° C. and was filtered and dried to give 38.5 g (yield 71.4%) of the target product.

$^1$H-NMR (DMSO-d$_6$, 400 MHz): δ 4.09 (s, 3H), 4.09 (s, 3H), 7.14 (s, 1H), 7.34 (s, 1H), 7.61 (s, 1H), 7.97 (s, 1H)

Production Example 36

4-Chloro-6,7dimethoxyquinazoline

Toluene (100 ml) and phosphorus oxychloride (7.4 g, 48.6 mmol) were added to 6,7-dimethoxy-4-quinazolone (10.0 g, 48.5 mmol), and the mixture was stirred at 120° C. for 6.5 hr. The reaction solution was cooled to room temperature, was then filtered, was washed with toluene (100 ml, 50 ml), and was dried to give 11.5 g (yield 91%) of the target product.

Production Example 37

4-(4'-Amino-3'-chloro)-phenoxy-6,7-dimethoxyquinazoline

Sodium hydroxide (8.5 g, 0.21 mol) and water (90 ml) were added to and dissolved in 4-amino-3-chlorophenol hydrochloride (14.6 g, 81 mmol). 4-Chloro-6,7-dimethoxyquinazoline (12 g, 53 mmol) and methyl ethyl ketone (225 ml) were added to the solution, and the mixture was refluxed for 2 hr. The reaction solution was cooled to about 50° C. and chloroform (500 ml) and water (500 ml)

were then added to the cooled reaction solution. The mixture was stirred for 10 min, and the organic layer was then separated from the aqueous layer. Chloroform (250 ml) was added to the aqueous layer, and the mixture was stirred for 10 min, followed by layer separation. The organic layer was concentrated under the reduced pressure. Methanol (50 ml) was added to the residue, and the mixture was stirred for 30 min. The reaction solution was then filtered and was dried to give 15.6 g (yield 85%) of the target product.

$^1$H-NMR (DMSO-$d_6$, 400 MHz): δ 3.95 (s, 3H), 3.97 (s, 3H), 5.33 (s, 2H), 6.85 (d, J=8.8 Hz, 1H), 6.98 (dd, J=2.8 Hz, J=8.8 Hz, 1H), 7.20 (d, J=2.8 Hz, 1H), 7.36 (s, 1H), 7.51 (s, 1H), 8.53 (s, 1H).

Production Example 38

4-(4'-Amino-3'-chloro)-phenoxy-6,7-dimethoxyquinazoline

A 20% aqueous sodium hydroxide solution (3.5 ml) and water (2 ml) were added to and dissolved in 4-amino-3-chlorophenol hydrochloride (1.3 g, 7.2 mmol). 4-Chloro-6,7-dimethoxyquinazoline (0.8 g, 3.6 mmol), chloroform (6 ml), and tetrabutylammonium bromide (0.58 g, 1.8 mmol) were added to the solution, and the mixture was refluxed for 2 hr. The reaction solution was cooled. Chloroform (10 ml) and water (10 ml) were then added to the cooled reaction solution, and the mixture was stirred for 10 min, followed by the separation of the organic layer from the aqueous layer. Chloroform (10 ml) was added to the separated aqueous layer, and the mixture was stirred for 10 min, followed by layer separation. The organic layer was concentrated under the reduced pressure. Methanol (2 ml) was added to the residue, and the mixture was stirred for 30 min. The reaction solution was then filtered and was dried to give 1.0 g (yield 83%) of the target product.

Example 1

N-(2,4-Difluorobenzyl)-N'-{4-[(6,7-dimethoxy-4-quinolyl)oxy]-2-fluorophenyl}urea 4-[(6,7-Dimethoxy-4-quinolyl)oxy]-2-fluoroaniline (100 mg) was dissolved in toluene (5.0 ml) and triethylamine (1.0 ml) with heating. A solution of triphosgene (103 mg) in dichloromethane (1.0 ml) was then added to the solution, and the mixture was heated under reflux for 3 min. Next, 2,4-difluorobenzylamine (54 mg) was added thereto, and the mixture was heated under reflux for additional 5 hr. A saturated aqueous sodium hydrogencarbonate solution was added to the reaction solution, followed by extraction with chloroform. The chloroform layer was dried over anhydrous sodium sulfate. The solvent was removed by distillation under the reduced pressure. The residue was purified by chromatography on silica gel by development with chloroform/acetone (2/1) to give 123 mg (yield 80%) of the title compound.

$^1$H-NMR (CDCl$_3$, 400 MHz): δ 4.02 (s, 3H), 4.03 (s, 3H), 4.47 (d, J=5.9 Hz, 2H), 5.78–5.90 (m, 1H), 6.46 (d, J=5.4 Hz, 1H), 6.74–6.99 (m, 4H), 7.03–7.14 (m, 1H), 7.3.5–7.44 (m, 2H), 7.50 (s, 1H), 8.16 (t, J=9.0 Hz, 1H), 8.47 (d, J=5.1 Hz, 1H).

Mass analysis, found (FD-MS, m/z): 483 (M$^+$).

Example 2

N-{4-[(6,7-Dimethoxy-4-quinolyl)oxy]-2-fluorophenyl}-N'-(2-fluoroethyl)urea

4-[(6,7-Dimethoxy-4-quinolyl)oxy]-2-fluoroaniline (100 mg) was dissolved in toluene (10 ml) and triethylamine (0.5 ml) with heating. A solution of triphosgene (47 mg) in dichloromethane (1.0 ml) was then added to the solution, and the mixture was heated under reflux for 5 min. Next, 2-fluoroethylamine hydrochloride (42 mg) was added thereto, and the mixture was heated under reflux for additional 8 hr. A saturated aqueous sodium hydrogencarbonate solution was added to the reaction solution, followed by extraction with ethyl acetate. The ethyl acetate layer was dried over anhydrous sodium sulfate. The solvent was removed by distillation under the reduced pressure. The residue was purified by chromatography on silica gel by development with chloroform/acetone (2/1) to give 93 mg (yield 72%) of the title compound.

$^1$H-NMR (DMSO-$d_6$, 400 MHz): δ 3.40 (m, 1H), 3.47 (m, 1H), 3.93 (s, 3H), 3.95 (s, 3H), 4.42 (t, J=4.9 Hz, 1H), 4.54 (t, J=4.9 Hz, 1H), 6.51 (d, J=5.4 Hz, 1H), 6.88 (m, 1H), 7.05 (m, 1H), 7.28 (dd, J=2.7 Hz, J=11.7 Hz, 1H), 7.40 (s, 1H), 7.49 (s, 1H), 8.21 (m, 1H), 8.47 (br, 1H), 8.48 (d, J=5.4 Hz, 1H).

Mass analysis, found (ESI-MS, m/z): 404 (M$^+$+1).

Example 3

N-{4-[(6,7-Dimethoxy-4-quinolyl)oxy]-2-fluorophanyl}-N'-(2-pyridylmethyl)urea

4-[(6,7-Dimethoxy-4-quinolyl)oxy]-2-fluoroaniline (100 mg) was dissolved in toluene (5 ml) and triethylamine (1 ml). A solution of triphosgene (104 mg) in dichloromethane was then added to the solution, and the mixture was refluxed for 5 min. Next, 2-(aminomethyl)pyridine (40 μl) was added thereto, and the mixture was heated under reflux for 2 hr. A saturated aqueous sodium hydrogencarbonate solution (1 ml) and chloroform (2 ml) were added to the reaction solution. The mixture was supported on diatomaceous earth, followed by extraction with chloroform. The solvent was removed by distillation under the reduced pressure. The residue was purified by chromatography on silica gel by development with chloroform/methanol (8/1) to give 126 mg (yield 88%) of the title compound.

$^1$H-NMR (CDCl$_3$, 400 MHz): δ 4.07 (s, 3H), 4.09 (s, 3H), 4.61 (d, J=5.4 Hz, 2H), 6.40–6.50 (br, 1H), 6.61 (d, J=5.9 Hz, 1H), 6.92–7.01 (m, 2H), 7.21–7.25 (m, 1H), 7.36 (d, J=7.8 Hz, 1H), 7.56 (s, 1H), 7.68–7.78 (m, 2H), 7.75 (s, 1H), 8.27–8.34 (m, 1H), 8.49 (d, J=6.1 Hz, 1H), 8.55 (d, J=4.1 Hz, 1H).

Mass analysis, found (FD-MS, m/z): 448 (M$^+$).

Example 4

N-Allyl-N'-{4-[(6,7-dimethoxy-4-quinoly-oxy]-2-fluorophenyl}urea

4-[(6,7-Dimethoxy-4-quinolyl)oxy]-2-fluoroaniline (100 mg) was dissolved in toluene (5 ml) and triethylamine (1 ml), and a solution of triphosgene (104 mg) in dichloromethane was then added to the solution. The mixture was heated under reflux for 5 min. Next, allylamine (22 mg) was added to the reaction solution, and the mixture was heated under reflux for additional 4 hr. A saturated aqueous sodium hydrogencarbonate solution (1 ml) and chloroform (2 ml) were added to the reaction solution, and the mixture was supported on diatomaceous earth, followed by extraction with chloroform. The solvent was removed by distillation under the reduced pressure. The residue was purified by chromatography on silica gel by development with chloroform/acetone (2/1) to give 125 mg (yield 98%) of the title compound.

$^1$H-NMR (CDCl$_3$, 400 MHz): δ 3.91–3.96 (m, 2H), 4.06 (s, 3H), 4.09 (s, 3H), 5.14–5.20 (m, 1H), 5.26–5.33 (m, 1H), 5.58–5.66 (br, 1H), 5.86–5.98 (m, 1H), 6.56 (d, J=5.9 Hz, 1H), 6.88–7.01 (m, 2H), 7.23 (s, 1H), 7.55 (so 1H), 7.66 (s, 1H), 8.26–8.33 (m, 1H), 8.47 (d, J=5.9 Hz, 1H).

Mass analysis, found (FD-MS, m/z): 397 (M$^+$).

Example 5

N-{4-[(6,7-Dimethoxy-4-quinolyl)oxy]-2-fluorophenyl}-N'-propylurea

4-[(6,7-Dimethoxy-4-quinolyl)oxy]-2-fluoroaniline (100 mg) was dissolved in toluene (10 ml). and triethylamine (2 ml), and a solution of triphosgene (104 mg) in dichloromethane was then added to the solution. The mixture was heated under reflux for 5 min. Next, propylamine (29 mg) was added, and the mixture was heated under reflux for 40 min. A saturated aqueous sodium hydrogencarbonate solution was added to the reaction solution, and the mixture was extracted with ethyl acetate. The ethyl acetate layer was then dried over anhydrous sodium sulfate. The solvent was removed by distillation under the reduced pressure. The residue was purified by thin-layer chromatography on silica gel by development with chloroform/methanol (10/1) to give 89 mg (yield 71%) of the title compound.

$^1$H-NMR (CDCl$_3$, 400 MHz): δ 0.97 (t, J=7.6 Hz, 3H), 1.55–1.64 (m, 2H), 3.24–3.29 (m, 2H), 4.05 (s, 3H), 4.06 (s, 3H), 5.11 (t, J=5.4 Hz, 1H), 6.51 (d, J=5.4 Hz, 1H), 6.74–6.76 (m, 1H), 6.91–6.99 (m, 2H), 7.48 (s, 1H), 7.52 (s, 1H), 8.18–8.23 (m, 1H), 8.49 (d, J=5.6 Hz, 1H).

Mass analysis, found (FD-MS, m/z): 399 (M$^+$).

Example 6

N-{4-[(6, 7-Dimethoxy-4-quinolyl)oxy]-2-fluorophenyl}-N'-(4-fluorobutyl)urea

4-[(6,7-Dimethoxy-4-quinolyl)oxy]-2-fluoroaniline (100 mg) was dissolved in toluene (6 ml) and triethylamine (1.0 ml) with heating, and a solution of triphosgene (104 mg) in dichloromethane (1.0 ml) was then added to the solution. The mixture was heated under reflux for 5 min. Next, 4-fluorobutylamine hydrochloride (55 mg) was added to the reaction solution, and the mixture was heated under reflux for additional 2 hr. A saturated aqueous sodium hydrogencarbonate solution was added to the reaction solution, followed by extraction with chloroform. The chloroform layer was dried over anhydrous sodium sulfate. The solvent was removed by distillation under the reduced pressure. The residue was purified by chromatography on silica gel by development with chloroform/acetone (2/1) to give 80 mg (yield 55%) of the title compound.

$^1$H-NMR (CDCl$_3$, 400 MHz): δ 1.66–1.87 (m, 4H), 3.33–3.40 (m, 2H), 4.04 (s, 3H), 4.05 (s, 3H), 4.44 (t, J=5.6 Hz, 1H), 4.56 (t, J=5.7 Hz, 1H), 4.90 (t, J=5.7 Hz, 1H), 6.48–6.52 (m, 2H), 6.93–7.02 (m, 2H), 7.42 (s, 1H), 7.51 (s, 1H), 8.15 (t, J=8.9 Hz, 1H), 8.50 (d, J=5.1 Hz, 1H).

Mass analysis, found (FD-MS, m/z): 431 (M$^-$).

Example 7

N-{4-[(6,7-Dimethoxy-4-quinolyl)oxy]-2-fluorophenyl}-N'-(2-propynyl)urea

4-[(6,7-Dimethoxy-4-quinolyl)oxy]-2-fluoroaniline (150 mg) was dissolved in chloroform (10 ml) and triethylamine (2 ml), and a solution of triphosgene (156 mg) in dichloromethane was added to the solution. The mixture was heated under reflux for 10 min. Next, propargylamine (53 mg) was added, and the mixture was heated under reflux for additional 30 min. A saturated aqueous sodium hydrogencarbonate solution was added to the reaction solution, and the mixture was extracted with chloroform. The chloroform layer was dried over anhydrous sodium sulfate. The solvent was removed by distillation under the reduced pressure. The residue was purified by chromatography on silica gel by development with chloroform/acetone (2/1) to give 164 mg (yield 87%) of the title compound.

$^1$H-NMR (DMSO-d$_6$, 400 MHz): δ 2.49–2.51 (m, 1H), 3.90–3.95 (m, 8H), 6.52 (d, J=5.1 Hz, 1H), 6.89–6.92 (m, 1H), 7.04–7.06 (m, 1H), 7.26–7.29 (m, 1H), 7.39 (s, 1H), 7.49 (s, 1H), 8.16–8.20 (m, 1H), 8.46–8.49 (m, 2H).

Example 8

N-{4-[(6,7-Dimethoxy-4-quinolyl)oxy]-2-fluorophenyl}-N'-ethylurea

4-[(6,7-Dimethoxy-4-quinolyl)oxy]-2-fluoroaniline (100 mg) was dissolved in toluene (8 ml) and triethylamine (1.0 ml) with heating, and a solution of triphosgene (47 mg) in toluene (1.0 ml) was then added to the solution. The mixture was heated under reflux for 5 min. Next, ethylamine hydrochloride (60 mg) was added to the reaction solution, and the mixture was heated under reflux for additional 5 hr. A saturated aqueous sodium hydrogencarbonate solution was added to the reaction solution, and the mixture was extracted with ethyl acetate. The ethyl acetate layer was dried over anhydrous sodium sulfate. The solvent was removed by distillation under the reduced pressure. The residue was purified by chromatography on silica gel by development with chloroform/acetone (2/1) to give 70 mg (yield 53%) of the title compound.

$^1$H-NMR (CDCl$_3$, 400 MHz): δ 1.21 (t, J=7.3 Hz, 3H), 3.34 (m, 2H), 4.06 (s, 3H), 4.08 (s, 3H), 5.64 (br, 1H), 6.55 (d, J=5.6 Hz, 1H), 6.89 (dd, J=2.7 Hz, J=11.2 Hz, 1H), 6.97 (m, 1H), 7.26 (br, 1H), 7.54 (s, 1H), 7.62 (s, 1H), 8.28 (t, J=9.0 Hz, 1H), 8.47 (d, J=5.6 Hz, 1H).

Mass analysis, found (ESI-MS, m/z): 386 (M$^+$1).

Example 9

N-Butyl-N'-{4-[(6,7-dimethoxy-4-quinolyl)oxy]-2-fluorophenyl}urea

4-[(6,7-Dimethoxy-4-quinolyl)oxy]-2-fluoroaniline (100 mg) was dissolved in toluene (8 ml) and triethylamine (1.0 ml) with heating, and a solution of triphosgene (47 mg) in toluene (1.0 ml) was then added to the solution. The mixture was heated under reflux for 5 min. Next, butylamine (80 mg) was added to the reaction solution, and the mixture was heated under reflux for additional 5 hr. A saturated aqueous sodium hydrogencarbonate solution was added to the reaction solution, and the mixture was extracted with ethyl acetate. The ethyl acetate layer was dried over anhydrous sodium sulfate. The solvent was removed by distillation under the reduced pressure. The residue was purified by chromatography on silica gel by development with chloroform/acetone (2/1) to give 117 mg (yield 81%) of the title compound.

$^1$H-NMR (CDCl$_3$, 400 MHz):δ 0.94 (t, J=7.3 Hz, 3H), 1.40 (m, 2H), 1.55 (m, 2H), 3.29 (dd, J=7.1 Hz, J=12.9 Hz, 2H), 4.06 (s, 3H), 4.09 (8, 3H), 5.72 (br, 1H), 6.56 (d, J=5.9 Hz, 1H), 6.88 (dd, J=2.7 Hz, J=11.2 Hz, 1H), 6.97 (d, J=9.0 Hz, 1H), 7.33 (s, 1H), 7.55 (s, 1H), 7.65 (s, 1H), 8.30 (t, J=9.0 Hz, 1H), 8.46 (d, J=5.9 Hz, 1H).

Mass analysis, found (ESI-MS, m/z): 414 (M$^+$1).

Example 10

N-(sec-Butyl)-N'-{4-[(6,7-dimethoxy-4-quinolyl) oxy]-2-fluorophenyl}urea

4-[(6,7-Dimethoxy-4-quinolyl)oxy]-2-fluoroaniline (100 mg) was dissolved in chloroform (5 ml) and triethylamine (1 ml), and a solution of triphosgene (104 mg) in dichloromethane was then added to the solution. The mixture was heated under reflux for 5 min. Next, sec-butylamine (48 μl) was added to the reaction solution. The mixture was heated under reflux for 10 min. The solvent was removed by distillation under the reduced pressure. The residue was purified by chromatography on silica gel by development with chloroform/acetone (8/2) to give 117 mg (yield 89%) of the title compound.

$^1$H-NMR (CDCl$_3$, 400 MHz): δ 0.95 (t, J=7.6 Hz, 3H), 1.18 (d, J=6.6 Hz, 3H), 1.47–1.55 (m, 2H), 3.79–3.89 (m, 1H), 4.04 (s, 6H), 5.28 (d, J=8.1 Hz, 1H), 6.48 (d, J=5.4 Hz, 1H), 6.89–6.98 (m, 2H), 7.08 (d, J=2.7 Hz, 1H), 7.42 (s, 1H), 7.51 (9, 1H), 8.20–8.24 (m, J=9.0 Hz, 1H), 8.48 (d, J=5.4.Hz, 1H).

Mass analysis, found (ESI-MS, m/z): 414 (M$^+$1).

Example 11

N-{4-[(6,7-Dimethoxy-4-quinolyl)oxy]-2-fluorophenyl}-N'-isobutylurea

4-[(6,7-Dimethoxy-4-quinolyl)oxy]-2-fluoroaniline (100 mg) was dissolved in chloroform (5 ml) and triethylamine (1 ml), and a solution of triphosgene (104 mg) in dichloromethane was then added to the solution. The mixture was heated under reflux for 5 min. Next, isobutylamine (50 μl) was added to the reaction solution, and the mixture was heated under reflux for 10 min. The reaction solution was purified by chromatography on silica gel by development with chloroform/acetone (4/1). Thus, the title compound was quantitatively obtained.

$^1$H-NMR (CDCl$_3$, 400 MHz): δ 0.94 (d, J=6.6 Hz, 6H), 1.77–1.84 (m, 1H), 3.10–3.13 (m, 2H), 4.03 (s, 3H), 4.03 (s, 3H), 5.58 (t, J=5.4 Hz, 1H), 6.47 (d, J=5.4 Hz, H), 6.88–6.97 (m, 2H), 7.18 (s, 1H), 7.41 (s, 1H), 7.50 (s, 1H), 8.18–8.23 (m, 1H), 8.48 (d, J=5.1 Hz, 1H).

Mass analysis, found (ESI-MS, m/z): 414 (M$^+$1).

Example 12

N-{4-[(6,7-Dimethoxy-4-quinolyl)oxy]-2-fluorophenyl}-N'-(1,2-dimethylpropyl)urea 4-[(6, 7-Dimethoxy-4-quinolyl)oxy]-2-fluoroaniline (100 mg) was dissolved in chloroform (5 ml) and triethylamine (1 ml), and a solution of triphosgene (47 mg) in dichloromethane was then added to the solution. The mixture was stirred at room temperature for 30 min. Next, 1,2-dimethylpropylamine (55 l) was added to the reaction solution, and the mixture was stirred at room temperature for 10 min. The solvent was removed by distillation under the reduced pressure. The residue was purified by chromatography on silica gel by development with chloroform/acetone (2/1) to give 89 mg (yield 65%) of the title compound.

$^1$H-NMR (CDCl$_3$, 400 MHz): δ 0.93 (d, J=2.2 Hz, 3H), 0.95 (d, J=2.4 Hz, 3H), 1.14 (d, J=6.8 Hz, 3H), 1.72–1.80 (m, 1H), 3.76–3.84 (m, 1H), 4.04 (s, 3H), 4.05 (s, 3H), 4.91 (d, J=8.5 Hz, 1H), 6.48 (d, J=5.4 Hz, 1H), 6.74 (d, J=2.9 Hz, 1H), 6.91–6.98 (m, 2H), 7.42 (s, 1H), 7.51 (s, 1H), 8.18–8.23 (m, 1H), 8.49 (d, J=5.4 Hz, 1H).

Mass analysis, found (ESI-MS, m/z): 428 (M$^+$1).

Example 13

N-{2-Chloro-4-[(6,7-dimethoxy-4-quinolyl)oxy] phenyl}-N-propylurea

2-Chloro-4-[(6,7-dimethoxy-4-quinolyl)oxy]aniline (100 mg) was dissolved in chloroform (7.5 ml) and triethylamine (1 ml), and a solution of triphosgene (99 mg) in chloroform was then added to the solution. The mixture was heated under reflux for 5 min. Next, n-propylamine (21 mg) was added to the reaction solution, and the mixture was heated under reflux for additional 2 hr. A saturated aqueous sodium hydrogencarbonate solution was added to the reaction solution, and the mixture was supported on diatomaceous earth, followed by extraction with chloroform. The solvent was removed by distillation under the reduced pressure. The residue was purified by chromatography on silica gel by development with chloroform/methanol (8/1). Thus, the title compound was quantitatively obtained.

$^1$H-NMR (CDCl$_3$, 400 MHz): δ 0.99 (t, J=7.3 Hz, 3H), 1.58–1.65 (m, 2H), 3.24–3.31 (m, 2H), 4.04 (6, 3H), 4.05 (s, 3H), 4.94 (t, J=5.9 Hz, 1H), 6.48 (d, J=5.1 Hz, 1H), 6.77 (s, 1H), 7.11 (dd, J=2.7 Hz, 9.0 Hz, 1H), 7.21 (d, J=2.7 Hz, 1H), 7.43 (s, 1H), 7.52 (s, 1H), 8.27 (d, J=9.0 Hz, 1H), 8.50 (d, J=5.1 Hz, 1H).

Mass analysis, found (FD-MS, m/z): 415, 417 (M$^+$).

Example 14

N-{2-Chloro-4-[(6,7-dimethoxy-4-quinolyl)oxy] phenyl}-N'-(4-fluoro-2-methylphenyl)urea 2-Chloro-4-[(6,7-dimethoxy-4-quinolyl)oxy]aniline (122 mg) was dissolved in chloroform (10 ml) and triethylamine (1 ml), and a solution of triphosgene (110 mg) in dichloromethane was then added to the solution. The mixture was stirred at room temperature for 30 min. Next, 4-fluoro-2-methylaniline (126 µl) was added to the reaction solution, and the mixture was stirred at room temperature for 2 hr. Methanol was added to the reaction solution, and the solvent was removed by distillation under the reduced pressure. The residue was purified by chromatography on silica gel by development with chloroform/acetone (2/1) to give 142 mg (yield 79%) of the title compound.

$^1$H-NMR (CDCl$_3$, 400 MHz): δ 2.37 (s, 3H), 4.04 (s, 3H), 4.04 (s, 3H), 6.31 (s, 1H), 6.47 (d, J=5.1 Hz, 1H), 6.97–7.06 (m, 3H), 7.11–7.14 (m, 1H), 7.19 (d, J=2.7 Hz, 1H), 7.41–7.44 (m, 2H), 7.50 (s, 1H), 8.35 (d, J=9.0 Hz, 1H), 8.50 (d, J=5.4 Hz, 1H).

Mass analysis, found (ESI-MS, m/z): 482, 484 (M$^+$+1).

Example 15

N-(5-Bromo-6-methyl-2-pyridyl)-N'-{2-chloro-4-[(6,7-dimethoxy-4-quinolyl)oxy]phenyl}urea 2-Chloro-4-[(6,7-dimethoxy-4-quinolyl)oxy]aniline (122 mg) was dissolved in chloroform (10 ml) and triethylamine (1 ml), and a solution of triphosgene (110 mg) in dichloromethane was then added to the solution. The mixture was stirred at room temperature for 30 min. Next, 6-amino-3-bromo-2-methylpyridine (208 mg) was added to the reaction solution, and the mixture was stirred at room temperature for 2 hr. Methanol was added to the reaction solution, and the solvent was removed by distillation under the reduced pressure. The residue was purified by chromatography on silica gel by development with chloroform/acetone (2/1) to give 155 mg (yield 77%) of the title compound.

$^1$H-NMR (CDCl$_3$, 400 MHz): δ 2.69 (s, 3H), 4.06 (s, 6H), 6.53 (d, J=5.4 Hz, 1H), 6.56 (d, J=8.5 Hz, 1H), 7.14–7.17 (m, 1H), 7.30 (d, J=2.7 Hz, 1H), 7.44 (s, 1H), 7.53 (s, 1H), 7.75 (d, J=8.5 Hz, 1H), 7.93 (s, 1H), 8.49 (d, J=9.0 Hz, 1H), 8.52 (d, J=5.4 Hz, 1H), 11.92 (s, 1H).

Mass analysis, found (ESI-MS, m/z): 543, 545, 547 (M$^+$+1).

Example 16

N-{2-chloro-4-[(6,7-dimethoxy-4-quinolyl)oxy]phenyl}-N'-(5-chloro-2-pyridyl)urea 2-Chloro-4-[(6,7-dimethoxy-4-quinolyl)oxy]aniline (122 mg) was dissolved in chloroform (10 ml) and triethylamine (1 ml), and a solution of triphosgene (110 mg) in dichloromethane was then added to the solution. The mixture was stirred at room temperature for 30 min. Next, 2-amino-5-chloropyridine (143 mg) was added to the reaction solution, and the mixture was stirred at room temperature for 2 hr. Methanol was added to the reaction solution, and the solvent was removed by distillation under the reduced pressure. The residue was purified by chromatography on silica gel by development with chloroform/acetone (2/1) to give 148 mg (yield 82%) of the title compound.

$^1$H-NMR (CDCl$_3$, 400 MHz): δ 4.06 (8, 3H), 4.06 (6, 3H), 6.53 (d, J=5.1 Hz, 1H), 6.95 (d, J=8.8 Hz, 1H), 7.14–7.17 (m, 1H), 7.31 (d, J=2.7 Hz, 1H), 7.44 (s, 1H), 7.53 (s, 1H), 7.64–7.67 (m, 1H), 8.28 (d, J=2.7 Hz, 1H), 8.50–8.53 (m, 2H), 8.92 (s, 1H), 12.11 (brs, 1H).

Mass analysis, found (ESI-MS, m/z): 485, 487, 489 (M$^+$1).

Example 17

N-(5-Bromo-2-pyridyl)-N'-{2-chloro-4-[(6,7-dimethoxy-4-quinolyl)oxy]phenyl}urea

2-Chloro-4-[(6,7-dimethoxy-4-quinolyl)oxy]aniline (122 mg) was dissolved in chloroform (10 ml) and triethylamine (1 ml), and a solution of triphosgene (110 mg) in dichloromethane was then added to the solution. The mixture was stirred at room temperature for 30 min. Next, 2-amino-5-bromopyridine (192 mg) was added to the reaction solution, and the mixture was stirred at room temperature for 2 hr. Methanol was added to the reaction solution, and the solvent was removed by distillation under the reduced pressure. The residue was purified by chromatography on silica gel by development with chloroform/acetone (2/1) to give 108 mg (yield 55%) of the title compound.

$^1$H-NMR (CDCl$_3$, 400 MHz): δ 4.06 (s, 3H), 4.06 (s, 3H), 6.53 (d, J=5.1 Hz, 1H), 6.80 (d, J=8.8 Hz, 1H), 7.14–7.18 (m, 1H), 7.30 (d, J=2.7 Hz, 1H), 7.45 (s, 1H), 7.53 (s, 1H), 7.77–7.80 (m, 1H), 8.15 (s, 1H), 8.39 (d, J=2.4 Hz, 1H), 8.50 (d, J=9.0 Hz, 1H), 8.52 (d, J=5.4 Hz, 1H), 12.09 (brs, 1H).

Mass analysis, found (ESI-MS, m/z): 529, 531, 533 (M$^+$1).

Example 18

N-{2-Chloro-4-[(6,7-dimethoxy-4-quinolyl) oxy]phenyl}-N'-(2-methoxyphenyl)urea

2-Chloro-4-[(6,7-dimethoxy-4-quinolyl)oxy]aniline (100 mg) was dissolved in chloroform(10 ml), and 2-methoxyphenyl isocyanate (54 mg) was added to the solution. The mixture was stirred at 600° C. overnight. Methanol was added to the reaction solution, and the solvent was removed by distillation under the reduced pressure. The residue was purified by chromatography on silica gel by development with chloroform/acetone (6/4) to give 111 mg (yield 77%) of the title compound.

$^1$H-NMR (CDCl$_3$, 400 MHz): δ 3.85 (s, 3H), 4.04 (s, 3H), 4.05 (s, 3H), 6.50 (d, J=5.1 Hz, 1H), 6.89–6.93 (m, 1H), 6.98–7.03 (m, 1H), 7.05–7.10 (m, 1H), 7.14 (dd, J=2.7 Hz, 9.0 Hz, 1H), 7.23 (d, J=2.7 Hz, 1H), 7.35 (s, 1H), 7.36 (s, 1H), 7.44 (s, 1H), 7.52 (6, 1H), 8.05–8.07 (m, 1H), 8.34 (d, J=9.0 Hz, 1H), 8.52 (d, J=5.4 Hz, 1H).

Mass analysis, found (ESI-MS, m/z): 480, 482 (M$^+$1).

Example 19

N-{2-Chloro-4-[(6,7-dimethoxy-4-quinolyl)oxy]phenyl}-N'-(2-methyl)phenyl) urea

2-Chloro-4-[(6,7-dimethoxy-4-quinolyl)oxy]aniline (122 mg) was dissolved in chloroform (10 ml), and o-toluyl isocyanate (59 mg) was added to the solution. The mixture was stirred at room temperature overnight. Methanol was added to the reaction solution, and the solvent was removed by distillation under the reduced pressure. The residue was dissolved in a minor amount of chloroform, and a large amount of ether was added to the solution to precipitate a crystal. The crystal was collected by filtration to give 59 mg (yield 34%) of the title compound.

$^1$H-NMR (CDCl$_3$, 400 MHz): δ 2.38 (s, 3H), 4.04 (s, 3H), 4.05 (s, 3H), 6.22 (s, 1H), 6.47 (d, J=5.1 Hz, 1H), 7.01 (s,

1H), 7.11–7.14 (m, 1H), 7.18 (d, J=2.7 Hz, 1H), 7.25–7.35 (m, 3H), 7.42 (s, 1H), 7.46 (d, J=6.8 Hz, 1H), 7.50 (s, 1H), 8.37 (d, J=8.8 Hz, 1H), 8.50 (d, J=5.1 Hz, 1H).

Mass analysis, found (ESI-MS, m/z): 464, 466 (M$^+$1).

Example 20

N-{2-Chloro-4-[(6,7-dimethoxy-4-quinolyl)oxy]phenyl}-N'-(5-methyl-2-pyridyl)urea 2-Chloro-4-[(6,7-dimethoxy-4-quinolyl)oxy]aniline (122 mg) was dissolved in chloroform (10 ml) and triethylamine (1 ml), and a solution of triphosgene (110 mg) in dichloromethane was then added to the solution. The mixture was stirred at room temperature for 30 min. Next, 2-amino-5-picoline (120 mg) was added to the reaction solution, and the mixture was stirred at room temperature for 2 hr. Methanol was added to the reaction solution, and the solvent was removed by distillation under the reduced pressure. The residue was purified by chromatography on silica gel by development with chloroform/acetone (2/1) to give 119 mg (yield 69%) of the title compound.

$^1$H-NMR (CDCl$_3$, 400 MHz): δ 2.31 (s, 3H), 4.06 (s, 6H), 6.53 (d, J=5.4 Hz, 1H), 6.76 (d, J=8.3 Hz, 1H), 7.13–7.16 (m, 1H), 7.29 (d, J=2.7 Hz, 1H), 7.43 (s, 1H), 7.49–7.52 (m, 1H), 7.54 (s, 1H), 8.00 (s, 1H), 8.14 (9, 1H), 8.52 (d, J=5.1 Hz, 1H), 8.55 (d, J=9.0 Hz, 1H), 12.57 (brs, 1H).

Mass analysis, found (ESI-MS, m/z): 465, 467 (M$^+$1).

Example 21

N-{2-Chloro-4-[(6,7-dimethoxy-4-quinolyl)oxy]phenyl}-N'-(6-methyl-2-pyridyl)urea 2-Chloro-4-[(6,7-dimethoxy-4-quinolyl)oxy]aniline (122 mg) was dissolved in chloroform (10 ml) and triethylamine (1 ml), and a solution of triphosgene (110 mg) in dichloromethane was then added to the solution. The mixture was stirred at room temperature for 30 min. Next, 6-amino-2-picoline (120 mg) was added to the reaction solution, and the mixture was stirred at room temperature for 2 hr. Methanol was added to the reaction solution, and the solvent was removed by distillation under the reduced pressure. The residue was purified by chromatography on silica gel by development with chloroform/acetone (2/1) to give 73 mg (yield 42%) of the title compound.

$^1$H-NMR (CDCl$_3$, 400 MHz): δ 2.57 (s, 3H), 4.06 (s, 6H), 6.54 (d, J=5.4 Hz, 1H), 6.66 (d, J=8.1 Hz, 1H), 6.83 (d, J=7.6 Hz, 1H), 7.15–7.18 (m, 1H), 7.30 (d, J=2.7 Hz, 1H), 7.44 (6, 1H), 7.54–7.59 (m, 2H), 8.36 (s, 1H), 8.52 (d, J=5.1 Hz, 1H), 8.57 (d, J=9.0 Hz, 1H), 12.45 (s, 1H).

Mass analysis, found (ESI-MS, m/z): 465, 467 (M$^+$1).

Example 22

N-{2-Chloro-4-[(6,7-dimethoxy-4-quinolyl)oxy]phenyl}-N'-(4-methoxyphenyl)urea hydrochloride 2-Chloro-4-[(6,7-dimethoxy-4-quinolyl)oxy]aniline (100 mg) was dissolved in chloroform (4 ml), and 4-methoxyphenyl isocyanate (60 μl) was then added to the solution. A reaction was then allowed to proceed at room temperature overnight. The solvent was removed by distillation under the reduced pressure. The residue was dissolved in a minor amount of chloroform, and a large amount of ether was added thereto. The resultant precipitate was collected by suction filtration to give 90 mg, (yield 67%) of N-2-chloro-4-[(6,7-dimethoxy-4-quinolyl)oxy]phenyl-N'-(4-methoxy-phenyl)urea. This product was suspended in 4 ml of methanol, and a hydrochloric acid-methanol solution was added to the suspension. The mixture was stirred at room temperature for 4 hr. and the solvent was then removed by distillation to give the title compound.

$^1$H-NMR (DMSO-d$_6$, 400 MHz): δ 3.73 (s, 3H), 4.03 (s, 3H), 4.05 (s, 3H), 6.90 (d, J=9.3 Hz, 2H), 6.97 (d, J=6.6 Hz, 1H), 7.37–7.41 (m, 3H), 7.62 (s, 1H), 7.67 (d, J=2.7 Hz, 1H), 8.39 (d, J=9.0 Hz, 1H), 8.49 (s, 1H), 8.82 (d, J=6.6 Hz, 1H), 9.49 (s, 1H).

Example 23

N-{2-Chloro-4-[(6,7-dimethoxy-4-quinolyl)oxy]phenyl}-N'-(1-naphthyl)urea

2-Chloro-4-[(6,7-dimethoxy-4-quinolyl)oxy]aniline (122 mg) was dissolved in chloroform (10 ml), and 1-naphthyl isocyanate (75 mg) was added to the solution. The mixture was stirred at room temperature overnight. Methanol was added to the reaction solution, and the solvent was removed by distillation under the reduced pressure. The residue was dissolved in a minor amount of chloroform, and a large amount of ether was added to the solution to precipitate a crystal. The crystal was collected by filtration to give 105 mg (yield 57%) of the title compound.

$^1$H-NMR (CDCl$_3$, 400 MHz): δ 4.03 (s, 3H), 4.04 (s, 3H), 6.44 (d, J=5.4 Hz, 1H), 6.72 (s, 1H), 7.10–7.13 (m, 3H), 7.41 (s, 1H), 7.48 (s, 1H), 7.55–7.69 (m, 4H), 7.88–7.96 (m, 2H), 8.15 (d, J=7.6 Hz, 1H), 8.38–8.40 (m, 1H), 8.48 (d, J=5.1 Hz, 1H).

Mass analysis, found (ESI-MS, m/z): 500, 502 (M$^+$1).

Example 24

N-(2,4-Difluorophenyl)-N'-{4-[(6,7-dimethoxy4quinoly)oxy]-2,3-dimethylphenyl}urea 4-[(6,7-Dimethoxy-4-quinolyl)oxy]-2,3-dimethyl-aniline (710 mg) was dissolved in chloroform (7 ml), and 2,4-difluorophenyl isocyanate (310 μl) was then added to the solution. The mixture was heated under reflux for one hr, and a large amount of ether was added to the reaction solution. The resultant precipitate was collected by suction filtration to give 735 mg (yield 70%) of the title compound.

$^1$H-NMR (CDCl$_3$, 400 MHz): δ 2.14 (s, 3H), 2.27 (s, 3H), 4.04 (s, 3H), 4.06 (s, 3H), 6.27 (d, J=5.4 Hz, 1H), 6.78–6.89 (m, 2H), 6.95 (s, 1H), 7.03 (d, J=8.5 Hz, 1H), 7.10 (s, 1H), 7.40–7.45 (m, 2H), 7.61 (s, 1H), 8.03–8.12 (m, 1H), 8.46 (d, J=5.4 Hz, 1H).

Mass analysis, found (FAB-MS, m/z): 480 (M$^+$1).

Example 25

N-{4-[(6,7-Dimethoxy-4-quinolyl)oxy]-2,3-dimethylphenyl}-N'-(4-fluoro-2-methylphenyl)urea 4-[(6,7-Dimethoxy-4-quinolyl)oxy]-2,3-dimethyl-aniline (120 mg) was dissolved in chloroform (10 ml) and triethylamine (1 ml), and a solution of triphosgene (110 mg) in dichloromethane was then added to the solution. The mixture was stirred at room temperature for 30 min. Next, 4-fluoro-2-methylaniline (126 µl) was added to the reaction solution, and the mixture was stirred at room temperature for 2 hr. Methanol was added to the reaction solution, and the solvent was removed by distillation under the reduced pressure. The residue was purified by chromatography on silica gel by development with chloroform/methanol (91/9) to give 160 mg (yield 91%) of the title compound.

$^1$H-NMR (CDCl$_3$, 400 MHz): δ 2.12 (s, 3H), 2.22 (s, 3H), 2.25 (s, 3H), 4.05 (s, 3H), 4.06 (s, 3H), 6.24 (d, J=5.1 Hz, 1H), 6.33 (s, 1H), 6.42 (s, 1H), 6.94–7.03 (m, 3H), 7.43 (s, 1H), 7.46–7.55 (m, 2H), 7.60 (s, 1H), 8.43 (d, J=5.1 Hz, 1H).

Mass analysis, found (ESI-MS, m/z): 476 (M$^+$1).

Example 26

N-{4-[(6,7-Dimethoxy-4-quinolyl)oxy]-2,3-dimethylphenyl}-N'-(3-fluoro-2-methoxyphenyl)urea 4-[(6,7-Dimethoxy-4-quinolyl)oxy]-2,3-dimethylaniline (120 mg) was dissolved in chloroform (10 ml) and triethylamine (1 ml), and a solution of triphosgene (110 mg) in dichloromethane was then added to the solution. The mixture was stirred at room temperature for 30 min. Next, 3-fluoro-o-anisidine (132 µl) was added to the reaction solution, and the mixture was stirred at room temperature for 2 hr. Methanol was added to the reaction solution, and the solvent was removed by distillation under the reduced pressure. The residue was purified by chromatography on silica gel by development with chloroform/methanol (91/9) to give 23 mg (yield 13%) of the title compound.

$^1$H-NMR (CDCl$_3$, 400 MHz): δ 2.15 (s, 3H), 2.32 (s, 3H), 3.84 (d, J=1.7 Hz, 3H), 4.05 (s, 3H), 4.08 (8, 3H), 6.28 (d, J=5.4 Hz, 1H), 6.72–6.77 (m, 1H), 6.96–7.09 (m, 3H), 7.43 (d, J=8.5 Hz, 1H), 7.46 (s, 1H), 7.60 (s, 1H), 7.62 (s, 1H), 8.02–8.05 (m, 1H), 8.46 (d, J=5.4 Hz, 1H).

Mass analysis, found (ESI-MS, m/z): 492 (M$^+$1).

Example 27

N-(5-Bromo-6-methyl-2-pyridyl)-N'-{4-[(6,7-dimethoxy-4-quinolyl)oxy]-2,3-dimethylphenyl}urea 4-[(6,7-Dimethoxy-4-quinolyl)oxy]-2,3-dimethyl-aniline (120 mg) was dissolved in chloroform (10 ml) and triethylamine (1 ml), and a solution of triphosgene (110 mg) in dichloromethane was then added to the solution. The mixture was stirred at room temperature for 30 min. Next, 6-amino-3-bromo-2-methylpyridine (208 mg) was added to the reaction solution, and the mixture was stirred at room temperature for 2 hr. Methanol was added to the reaction solution, and the solvent was removed by distillation under the reduced pressure. The residue was purified by chromatography on silica gel by development with chloroform/methanol (91/9) to give 103 mg (yield 52%) of the title compound.

$^1$H-NMR (CDCl$_3$, 400 MHz): δ 2.16 (s, 3H), 2.42 (s, 3H), 2.65 (s, 3H), 4.06 (s, 3H), 4.08 (s, 3H), 6.32 (d, J=5.1 Hz, 1H), 6.64 (d, J=8.8 Hz, 1H), 7.04 (d, J=8.8 Hz, 1H), 7.44 (s, 1H), 7.64 (s, 1H), 7.74 (d, J=8.8 Hz, 1H), 7.91 (d, J=8.8 Hz, 1H), 8.29 (s, 1H), 8.45 (d, J=5.4 Hz, 1H), 11.30 (brs, 1H).

Mass analysis, found (ESI-MS, m/z): 537, 539 (M$^+$1).

Example 28

N-(5-Chloro-2-pyridyl)-N'-{4-[(6,7-dimethoxy-4-quinolyl)oxy]-2,3-dimethylphenyl}urea 4-[(6,7-Dimethoxy-4-quinolyl)oxy]-2,3-dimethyl-aniline (3.00 g) was dissolved in chloroform (150 ml) and triethylamine (6 ml), and a solution of triphosgene (2.74 g) in dichloromethane was then added to the solution. The mixture was stirred at room temperature for 30 min. Next, 2-amino-5-chloropyridine (2.38 g) was added to the reaction solution, and the mixture was then stirred at room temperature for additional 2 hr. A saturated aqueous sodium hydrogencarbonate solution was added to the reaction solution, and the mixture was extracted with chloroform. The chloroform layer was dried over anhydrous sodium sulfate. The solvent was removed by distillation under the reduced pressure, and the residue was purified by chromatography on silica gel by development with chloroform/methanol (20/1) to give 3.4 g (yield 77%) of the title compound.

$^1$H-NMR (CDCl$_3$, 400 MHz): δ 2.16 (s, 3H), 2.38 (s, 3H), 4.06 (s, 3H), 4.08 (s, 3H), 6.31 (d, J=5.4 Hz, 1H), 6.89 (d, J=8.8 Hz, 1H), 7.04 (d, J=8.8 Hz, 1H), 7.44 (s, 1H), 7.62–7.68 (m, 2H), 7.90 (d, J=8.8 Hz, 1H), 8.23 (d, J=2.4 Hz, 1H), 8.45 (d, J=5.4 Hz, 1H), 8.50 (s, 1H), 11.23 (brs, 1H).

Mass analysis, found (ESI-MS, m/z): 479, 481 (M$^+$1).

Example 29

N-(5-Bromo-2-pyridyl)-N'-{4-[(6,7-dimethoxy-4-quinolyl)oxy]-2,3-dimethylphenyl}urea 4-[(6,7-Dimethoxy-4-quinolyl)oxy]-2,3-dimethyl-aniline (120 mg) was dissolved in chloroform (10 ml) and triethylamine (1 ml), and a solution of triphosgene (110 mg) in dichloromethane was then added to the solution. The mixture was stirred at room temperature for 30 min. Next, 2-amino-5-bromopyridine (192 mg) was added to the reaction solution, and the mixture was stirred at room temperature for 2 hr. Methanol was added to the reaction solution, and the solvent was removed by distillation under the reduced pressure. The residue was purified by chromatography on silica gel by development with chloroform/methanol (91/9). The solvent was removed by distillation, and a crystal was precipitated from a minor amount of methanol and a large amount of ether. The crystal was collected by filtration to give 80 mg (yield 41%) of the title compound.

$^1$H-NMR (CDCl$_3$, 400 MHz): δ 2.16 (s, 3H), 2.38 (s, 3H), 4.06 (s, 3H), 4.08 (8, 3H), 6.31 (d, J=5.1 Hz, 1H), 6.96 (d, J=8.5 Hz, 1H), 7.03,(d, J=8.8 Hz, 1H), 7.45 (s, 1H), 7.64 (s, 1H), 7.75–7.77 (m, 1H), 7.89 (d, J=8.8 Hz, 1H), 8.31 (d, J=2.4 Hz, 1H), 8.45 (d, J=5.4 Hz, 1H), 8.81 (s, 1H), 11.17 (brs, 1H).

Mass analysis, found (ESI-MS, m/z): 523, 525 (M$^+$1).

Example 30

N-{4-[(6,7-Dimethoxy-4-quinolyl)oxyl-2,3-dimethylphenyl}-N'-(2methoxyphenyl)urea 4-[(6,7-Dimethoxy-4-quinolyl)oxy]-2,3-dimethyl-aniline (120 mg) was dissolved in chloroform (10 ml), and 2-methoxyphenyl isocyanate (60 µl) was added to the solution. The mixture was stirred at room temperature overnight. Methanol was added to the reaction solution, and the solvent was removed by distillation under the reduced pressure. The residue was dissolved in a minor amount of chloroform, and a large amount of ether was added thereto to precipitate a crystal which was then collected by filtration to give 131 mg (yield 75%) of the title compound.

$^1$H-NMR (CDCl$_3$, 400 MHz): δ 2.16 (s, 3H), 2.32 (s, 3H), 3.81 (s, 3H), 4.06 (s, 3H), 4.08 (s, 3H), 6.25 (s, 1H), 6.26 (d, J=5.4 Hz, 1H), 6.85–6.87 (m, 1H), 6.97–7.07 (m, 4H), 7.41 (d, J=8.5 Hz, 1H), 7.44 (s, 1H), 7.62 (s, 1H), 8.15–8.17 (m, 1H), 8.45 (d, J=5.4 Hz, 1H).

Mass analysis, found (ESI-MS, m/z): 474 (M$^+$1).

Example 31

N-{4-[(6,7-Dimethoxy-4-quinolyl)oxy]-2,3-dimethylphenyl}-N'-(2-methylphenyl)urea 4-[(6,7-Dimethoxy-4-quinolyl)oxy]-2,3-dimethyl-aniline (120 mg) was dissolved in chloroform (10 ml), and o-toluyl isocyanate (55 µl) was added to the solution. The mixture was stirred at room temperature overnight. Methanol was added to the reaction solution, and the solvent was removed by distillation under the reduced pressure. The residue was dissolved in a minor amount of chloroform, and a large amount of ether was added to the solution to precipitate a crystal which was then collected by filtration to give 130 mg (yield 70%) of the title compound.

$^1$H-NMR (CDCl$_3$, 400 MHz): δ 2.12 (s, 3H), 2.22 (s, 3H), 2.26 (s, 3H), 4.05 (s, 3H), 4.07 (s, 3H), 6.23–6.28 (m, 3H), 7.02 (d, J=8.5 Hz, 1H), 7.14–7.17 (m, 1H), 7.24–7.29 (m, $^2$H), 7.43 (s, 1H), 7.49 (d, J=8.5 Hz, 1H), 7.60 (s, 1H), 7.63 (d, J=7.3 Hz, 1H), 8.43 (d, J=5.4 Hz, 1H).

Mass analysis, found (ESI-MS, m/2): 458 (M$^+$+1).

Example 32

N-(4-Chloro-2-(6,7-methylphenyl)-N'-{4-[(6,7-dimethoxy-4-quinolyl)oxy]-2,3-dimethylphenyl}urea 4-6,7-Dimethoxy-4-quinolyl)oxy]-2,3-dimethyl-aniline (120 mg) was dissolved in chloroform (10 ml) and triethylamine (1 ml), and a solution of triphosgene (110 mg) in dichloromethane was then added to the solution. The mixture was stirred at room temperature for 30 min. Next, 4-chloro-2-methylaniline (130 µl) was added to the reaction solution, and the mixture was stirred at room temperature for 2 hr. Methanol was added to the reaction solution, and the solvent was removed by distillation under the reduced pressure. The residue was purified by chromatography on silica gel by development with chloroform/methanol (91/9) to give 136 mg (yield 75%) of the title compound.

$^1$H-NMR (CDCl$_3$, 400 MHz): δ 2.14 (s, 3H), 2.18 (s, 3H), 2.27 (s, 3H), 4.05 (s, 3H), 4.07 (s, 3H), 6.24 (d, J=5.4 Hz, 1H), 6.33 (s, 1H), 6.40 (s, 1H), 7.03 (d, J=8.5 Hz, 1H), 7.19–7.21 (m, 2H), 7.42–7.44 (m, 2H), 7.60 (s, 1H), 7.65 (d, J=9.0 Hz, 1H), 8.44 (d, J=5.1 Hz, 1H).

Mass analysis, found (ESI-MS, m/z): 492, 494 (M$^+$1).

Example 33

N-{4-[(6,7-Dimethoxy-4-quinolyl)oxy]-2,3-dimethylphenyl}-N'-(2pyridyl)urea

4-[(6,7-Dimethoxy-4-quinolyl)oxy]-2,3-dimethyl-aniline (120 mg) was dissolved in chloroform (10 ml) and triethylamine (1 ml), and a solution of triphosgene (110 mg) in dichloromethane was then added to the solution. The mixture was stirred at room temperature for 30 min. Next, 2-aminopyridine (104 mg) was added to the reaction solution, and the mixture was heated under reflux overnight. Methanol was added to the reaction solution, and the solvent was removed by distillation under the reduced pressure. The residue was purified by chromatography on silica gel by development with chloroform/methanol (91/9) to give 72 mg (yield 44%) of the title compound.

$^1$H-NMR (CDCl$_3$, 400 MHz): δ 2.16 (s, 3H), 2.41 (s, 3H), 4.06 (s, 3H), 4.08 (s, 3H), 6.32 (d, J=5.4 Hz, 1H), 6.92–6.98 (m, 2H), 7.04 (d, J=8.8 Hz, 1H), 7.44 g (s, 1H), 7.65 (8, 1H), 7.67–7.69 (m, 1H), 7.97 (d, J=8.8 Hz, 1H), 8.25–8.27 (m, 1H), 8.45 (d, J=5.1 Hz, 1H), 8.72 (6, 1H), 11.77 (br, 1H).

Mass analysis, found (ESI-MS, m/z): 445 (M$^+$1).

Example 34

N-{4-[(6,7-Dimethoxy-4-quinolyl)oxy ]-2,3-dimethylphenyl}-N'-(5-methyl2-pyridyl)urea 4-[(6,7-Dimethoxy-4-quinolyl)oxy]-2,3-dimethyl-aniline (120 mg) was dissolved in chloroform (10 ml) and triethylamine (1 ml), and a solution of triphosgene (110 mg) in dichloromethane was then added to the solution. The mixture was stirred at room temperature for 30 min. Next, 2-amino-5-picoline (120 mg) was added to the reaction solution, and the mixture was stirred at room temperature for 2 hr. Methanol was added to the reaction solution, and the solvent was removed by distillation under the reduced pressure. The residue was purified by chromatography on silica gel by development with chloroform/methanol (91/9) to give 122 mg (yield 72%) of the title compound.

$^1$H-NMR (CDCl$_3$, 400 MHz): δ 2.15 (s, 3H), 2.28 (s, 3H), 2.39 (s, 3H), 4.04 (s, 3H), 4.07 (s, 3H), 6.32 (d, J=5.4 Hz, 1H), 6.90 (d, J=8.3 Hz, 1H), 7.02 (d, J=8.8 Hz, 1H), 7.43 (s, 1H), 7.45–7.48 (m, 1H), 7.64 (s, 1H), 7.99 (d, J=8.8 Hz, 1H), 8.06 (d, J=1.5 Hz, 1H), 8.44 (d, J=5.4 Hz, 1H), 9.23 (s, 1H), 11.77 (br, 1H).

Mass analysis, found (FD-MS, m/z): 458 (M$^+$).

Example 35

N-{4-[(6,7-Dimethoxy-4-quinoly)oxy ]-2,3-dimethylphenyl}-N'-(6-methyl-2-pyridyl)urea 4-[(6,7-Dimethoxy-4-quinolyl)oxy]-2,3-dimethyl-aniline (120 mg) was dissolved in chloroform (10 ml) and triethylamine (1 ml), and a solution of triphosgene (110 mg) in dichloromethane was then added to the solution. The mixture was stirred at room temperature for 30 min. Next, 6-amino-2-picoline (120 mg) was added to the reaction solution, and the mixture was heated under reflux overnight. Methanol was added to the reaction solution, and the solvent was removed by distillation under the reduced pressure. The residue was purified by chromatography on silica gel by development with chloroform/acetone (40/60) to give 64 mg (yield 38%) of the title compound.

$^1$H-NMR (CDCl$_3$, 400 MHz): δ 2.16 (s, 3H), 2.44 (s, 3H), 2.54 (s, 3H), 4.06 (s, 3H), 4.08 (s, 3H), 6.32 (d, J=5.4 Hz, 1H), 6.61 (d, J=8.3 Hz, 1H), 6.82 (d, J=7.6 Hz, 1H), 7.04 (d, J=8.8 Hz, 1H), 7.44 (s, 1H), 7.53–7.57 (m, 1H), 7.65 (8, 1H), 7.79 (s, 1H), 7.99 (d, J=8.8 Hz, 1H), 8.44 (d, J=5.1 Hz, 1H), 11.76 (br, 1H).

Mass analysis, found (FD-MS, m/z): 458 (M⁺).

Example 36

N-{4-[6,7-Dimethoxy-4-quinolyl)oxy]-2,3-dimethylphenyl}-N'-(4-methoxyphenyl)urea 4-[(6,7-Dimethoxy-4-quinolyl)oxy]-2,3-dimethyl-aniline (100 mg) was dissolved in chloroform (4 ml), and 4-methoxyphenyl isocyanate (60 µl) was then added to the solution. The mixture was allowed to react at room temperature overnight, and the solvent was removed by distillation under the reduced pressure. The residue was dissolved in a minor amount of chloroform, and a large amount of ether was added to the solution. The resultant precipitate was then collected by suction filtration to give 115 mg (yield 78%) of the title compound.

¹H-NMR (CDCl₃, 400 MHz): δ 2.02 (s, 3H), 2.30 (s, 3H), 3.76 (s, 3H), 4.06 (s, 3H), 4.12 (s, 3H), 6.46 (d, J=6.3 Hz, 1H), 6.78 (d, J=9.0 Hz, 2H), 6.91 (d, J=8.8 Hz, 1H), 7.39 (d, J=9.0 Hz, 2H), 7.67 (s, 1H), 7.69 (d, J=8.8 Hz, 1H), 7.92 (s, 1H), 8.20–8.23 (m, 1H).

Mass analysis, found (ESI-MS, m/z): 474 (M⁺1).

Example 37

N-(2,4-Difluorophenyl)-N'-4-[(6,7-dimethoxy-4-quinolyl)oxy]-2,5-dimethylphenyl}urea 4-[(6,7-Dimethoxy-4-quinolyl)oxy]-2,5-dimethyl-aniline (200 mg) was dissolved in chloroform (15 ml), and 2,4-difluorophenyl isocyanate (88 µl) was then added to the solution. The mixture was heated under reflux for one hr. The reaction solution was purified by chromatography on silica gel by development with chloroform/acetone (4/1) to give 287 mg (yield 97%) of the title compound.

¹H-NMR (CDCl₃, 400 MHz): δ 2.17 (s, 3H), 2.26 (s, 3H), 4.05 (s, 3H), 4.06 (s, 3H), 6.31 (d, J=5.4 Hz, 1H), 6.57 (s, 1H), 6.81–6.95 (m, 3H), 7.00 (s, 1H), 7.43 (s, 1H), 7.55 (s, 1H), 7.59 (s, 1H), 8.05–8.13 (m, 1H), 8.47 (d, J=5.4 Hz, 1H).

Mass analysis, found (FD-MS, m/z): 479 (M⁺).

Example 38

N-{4-[(6,7-Dimethoxy-4-quinolyl)oxy]-2,5-dimethylphenyl}-N'-propylurea

4-[(6,7-Dimethoxy-4-quinolyl)oxy]-2,5-dimethyl-aniline (150 mg) was dissolved in chloroform (13 ml) and triethylamine (1.5 ml), and a solution of triphosgene (151 mg) in chloroform was then added to the solution. The mixture was heated under reflux for 5 min. Next, n-propylamine (33 mg) was added to the reaction solution, and the mixture was heated under reflux for additional 2 hr. A saturated aqueous sodium hydrogencarbonate solution was added to the reaction solution, and the mixture was supported on diatomaceous earth, followed by extraction with chloroform. The solvent was removed by distillation under the reduced pressure. The residue was purified by chromatography on silica gel by development with chloroform/acetone (4/1) to give 178 mg (yield 95%) of the title compound.

¹H-NMR (CDCl₃, 400 MHz): δ 0.94 (t, J=7.3 Hz, 3H), 1.51–1.65 (m, 2H), 2.15 (s, 3H), 2.26 (s, 3H), 3.21—3.28 (m, 2H), 4.05 (s, 3H), 4.06 (s, 3H), 4.63–4.69 (m, 1H), 5.97 (s, 1H), 6.31 (d, J=5.1 Hz, 1H), 6.98 (s, 1H), 7.43 (s, 2H), 7.58 (s, 1H), 8.46 (d, J=5.4 Hz, 1H).

Mass analysis, found (FD-MS, m/z): 409 (M⁺).

Example 39

N-(4-Chloro-2-methylphenyl)-N'-{4-[(6,7-dimethoxy-4-quinolyl)oxy]-2,5-dimethylphenyl}urea 4-[(6,7-Dimethoxy-4-quinolyl)oxy]-2,5-dimethyl-aniline (100 mg) was dissolved in chloroform (10 ml) and triethylamine (1 ml), and a solution of triphosgene (92 mg) in dichloromethane was then added to the solution. The mixture was stirred at room temperature for 30 min. Next, 4-chloro-2-methylaniline (44 µl) was added to the reaction solution, and the mixture was stirred at room temperature overnight. A saturated aqueous sodium hydrogencarbonate solution was added to the reaction solution, followed by extraction with chloroform. The chloroform layer was dried over sodium sulfate. The solvent was removed by distillation under the reduced pressure. The residue was dissolved in a minor amount of chloroform, and a large amount of ether was added to the solution to precipitate a crystal which was then collected by filtration to give 118 mg (yield 78%) of the title compound.

¹H-NMR (CDCl₃, 400 MHz): δ 2.16 (s, 3H), 2.21 (s, 3H), 2.23 (s, 3H), 4.05 (s, 3H), 4.06 (s, 3H), 6.28 (d, J=5.4 Hz, 1H), 6.30 (s, 1H), 6.32 (s, 1H), 6.98 (s, 1H), 7.22–7.23 (m, 2H), 7.43 (s, 1H), 7.58 (s, 1H), 7.59–7.63 (m, 2H), 8.45 (d, J=5.1 Hz, 1H).

Mass analysis, found (ESI-MS, m/z): 492, 494 (M⁺1).

Example 40

N-{4-[(6,7-Dimethoxy-4-quinolyl)oxy ]-2.5-dimethylphenyl}-N'-(4fluoro-2methylphenyl)urea 4-[(6,7-Dimethoxy-4-quinolyl)oxy]-2,5-dimethyl-aniline (100 mg) was dissolved in chloroform (10 ml) and triethylamine (1 ml), and a solution of triphosgene (92 mg) in dichloromethane was then added to the solution. The mixture was stirred at room temperature for 30 min. Next, 4-fluoro-2-methylaniline (42 µl) was added to the reaction solution, and the mixture was stirred at room temperature overnight. A saturated aqueous sodium hydrogencarbonate solution was added to the reaction solution, and the mixture was extracted with chloroform. The chloroform layer was dried over sodium sulfate. The solvent was removed by distillation under the reduced pressure. The residue was dissolved in a minor amount of to chloroform, and a large amount of ether was added to the solution to precipitate a crystal which was then collected by filtration to give 108 mg (yield 74%) of the title compound.

¹H-NMR (CDCl₃, 400 MHz): δ 2.15 (s, 6H), 2.30 (s, 3H), 4.05 (s, 3H), 4.06 (s, 3H), 6.24 (s, 2H), 6.28 (d, J=5.1 Hz, 1H), 6.94 (8, 1H), 6.96–7.00 (m, 2H), 7.42 (s, 1H), 7.49–7.52 (m, 1H), 7.58 (s, 1H), 7.64 (s, 1H), 8.44 (d, J=5.1 Hz, 1H)

Mass analysis, found (ESI-MS, m/z): 476 (M⁺1) dimethylphenyl}-N'-(3-fluoro-2-methoxyphenyl)urea 4-[(6,7-Dimethoxy-4-quinolyl)oxy]-2,5-dimethyl-aniline (100 mg) was dissolved in chloroform (10 ml) and triethylamine (1 ml), and a solution of triphosgene (92 mg) in dichloromethane was then added to the solution. The mixture was stirred at room temperature for 30 min. Next, 3-fluoro-o-anisidine (44 μl) was added to the reaction solution, and the mixture was stirred at room temperature overnight. A saturated aqueous sodium hydrogencarbonate solution was added to the reaction solution, and the mixture was extracted with chloroform. The chloroform layer was dried over sodium sulfate. The solvent was removed by distillation under the reduced pressure. The residue was purified by chromatography on silica gel by development with chloroform/acetone (2/1) to give 126 mg (yield 83%) of the title compound.

$^1$H-NMR (CDCl$_3$, 400 MHz): δ 2.16 (s, 3H), 2.27 (s, 3H), 3.83 (d, J=1.7 Hz, 3H), 4.04 (s, 3H), 4.07 (s, 3H), 6.31 (d, J=5.1 Hz, 1H), 6.74–6.79 (m, 1H), 6.97–7.03 (m, 3H), 7.44 (s, 1H), 7.57 (s, 1H), 7.60 (s, 1H), 7.66 (s, 1H), 8.02–8.04 (m, 1H), 8.48 (d, J=5.1 Hz, 1H).

Mass analysis, found (ESI-MS, m/z): 492 (M$^+$1).

Example 42

N-{4-[(6,7Dimethoxy-4-qiunolyl)oxy]-2,5-dimethylphenyl}-N'-(2-methylphenyl)urea

4-[(6,7-Dimethoxy-4-quinolyl)oxy]-2,5-dimethyl-aniline (100 mg) was dissolved in chloroform (10 ml), and o-toluyl isocyanate (46 μl) was added to the solution. The mixture was stirred at room temperature overnight. Methanol was added to the reaction solution, and the solvent was removed by distillation under the reduced pressure. The residue was purified by chromatography on silica gel by development with chloroform/acetone (2/1) to give 111 mg (yield 79%) of the title compound.

$^1$H-NMR (CDCl$_3$, 400 MHz): δ 2.12 (s, 1H), 2.26 (s, 3H), 4.03 (s, 3H), 4.05 (s, 3H), 6.27 (d, J=5.1 Hz, 1H), 6.77 (s, 1H), 6.81 (s, 1H), 6.91 (8, 1H), 7.11–7.15 (m, 1H), 7.22 (s, 1H), 7.24 (s, 1H), 7.42 (s, 1H), 7.59 (s, 1H), 7.63 (d, J=7.8 Hz, 1H), 7.68 (s, 1H), 8.43 (d, J=5.4 Hz, 1H).

Mass analysis, found (ESI-MS, m/z): 458 (M$^+$1).

Example 43

N-{4-[(6,7-Dimethoxy-4-quinolyl)oxy]-2,5-dimethylphenyl}-N'-(2-methoxyphenyl)urea 4-[(6,7-Dimethoxy-4-quinolyl)oxy]-2,5-dimethyl-aniline (100 mg) was dissolved in chloroform (10 ml), and 2-methoxyphenyl isocyanate (49 μl) was added to the solution. The mixture was heated under reflux overnight. Methanol was added to the reaction solution. The solvent was removed by distillation under the reduced pressure. The residue was purified by chromatography on silica gel by development with chloroform/acetone (2/1) to quantitatively give the title compound.

$^1$H-NMR (CDCl$_3$, 400 MHz): δ 2.14 (s, 3H), 2.24 (s, 3H), 3.75 (s, 3H), 4.03 (s, 3H), 4.07 (s, 3H), 6.31 (d, J=5.1 Hz, 1H), 6.84–6.87 (m, 1H), 6.95–7.03 (m, 3H), 7.06 (s, 1H), 7.44 (s, 1H), 7.56 (s, 1H), 7.61 (s, 1H), 7.63 (s, 1H), 8.17–8.20 (m, 1H), 8.46 (d, J=5.1 Hz, 1H).

Mass analysis, found (ESI-MS, m/z): 474 (M$^+$+1).

Example 44

N-(5-Bromo-6-methyl-2-pyridyl)-N'-{4-[(6,7-dimethoxy-4-quinolyl) oxy]-2,5-dimethylphenyl}urea 4-[(6,7-Dimethoxy-4-quinolyl)oxy]-2,5-dimethyl-aniline (100 mg) was dissolved in chloroform (10 ml) and triethylamine (1 ml), and a solution of triphosgene (92 mg) in dichloromethane was then added to the solution. The mixture was stirred at room temperature for 30 min. Next, 6-amino-3-bromo-2-methylpyridine (69 mg) was added to the reaction solution, and the mixture was stirred at room temperature overnight. A saturated aqueous sodium hydrogencarbonate solution was added to the reaction solution, and the mixture was extracted with chloroform. The chloroform layer was dried over sodium sulfate. The solvent was removed by distillation under the reduced pressure. The residue was dissolved in a minor amount of chloroform, and a larger amount of ether was added to the solution to precipitate a crystal which was then collected by filtration to give 80 mg (yield 48%) of the title compound.

$^1$H-NMR (CDCl$_3$, 400 MHz): δ 2.18 (s, 3H), 2.42 (s, 3H), 2.65 (s, 3H), 4.06 (s, 3H), 4.08 (s, 3H), 6.34 (d, J=5.4 Hz, 1H), 6.57 (d, J=8.5 Hz, 1H), 6.98 (s, 1H), 7.43 (s, 1H), 7.62 (s, 1H), 7.70 (s, 1H), 7.74 (d, J=8.5 Hz, 1H), 8.05 (s, 1H), 8.46 (d, J=5.4 Hz, 1H), 11.17 (br, 1H).

Mass analysis, found (ESI-MS, m/z): 537, 539 (M$^+$1).

Example 45

N-(2,6-Dimethoxy-3-pyridyl)-N'-{4-[(6,7-dimethoxy-4-quinolyl)oxy]-2,5-dimethylphenyl}urea 4-[(6,7-Dimethoxy-4-quinolyl)oxy]-2,5-dimethyl-aniline (100 mg) was dissolved in chloroform (10 ml) and triethylamine (1 ml), and a solution of triphosgene (92 mg) in dichloromethane was then added to the solution. The mixture was stirred at room temperature for 30 min. Next, 3-amino-2,6-dimethoxypyridine (70 mg) was added to the reaction solution, and the mixture was stirred at room temperature overnight. A saturated aqueous sodium hydrogencarbonate solution was added to the reaction solution, and the mixture was extracted with chloroform. The chloroform layer was dried over sodium sulfate. The solvent was removed by distillation under the reduced pressure. The residue was dissolved in a minor amount of chloroform, and a large amount of ether was added to the solution to precipitate a crystal which was then collected by filtration to give 124 mg (yield 79%) of the title compound.

$^1$H-NMR (CDCl$_3$, 400 MHz): δ 2.17 (s, 3H), 2.27 (s, 3H), 3.89 (s, 3H), 3.95 (s, 3H), 4.06 (s, 3H), 4.07 (s, 3H), 6.31 (d, J=5.1 Hz, 1H), 6.34 (d, J=8.5 Hz, 1H), 6.36 (s, 1H), 6.74 (s, 1H), 6.99 (s, 1H), 7.44 (s, 1H), 7.57 (s, 1H), 7.60 (s, 1H), 8.20 (d, J=8.3 Hz, 1R), 8.46 (d, J=5.1 Hz, 1H).

Mass analysis, found (ESI-MS, m/z): 505 (M$^+$1).

Example 46

N-{4-[(6,7-Dimethoxy-4-quinolyl)oxy]-2,5-dimethylphenyl}-N'-(4methoxyphenyl)urea 4-[(6,7-Dimethoxy-4-quinolyl)oxy]-2,5-dimethyl-aniline (100 mg) was dissolved in chloroform (4 ml), and 4-methoxyphenyl isocyanate (60 μl) was then added to the solution. The mixture was allowed to react at room temperature overnight. The solvent was removed by distillation under the reduced pressure. The residue was dissolved in a minor amount of chloroform, and a large amount of ether was added to the solution. The resultant precipitate was collected by suction filtration to give 110 mg (yield 74%) of the title compound.

¹H-NMR (CDCl₃, 400 MHz): δ 2.07 (s, 3H), 2.26 (s, 3H), 3.76 (s, 3H), 4.03 (s, 3H), 4.08 (s, 3H), 6.39 (d, J=6.1 Hz, 1H), 6.80 (d, J=9.0 Hz, 2H), 6.87 (s, 1H), 7.36 (d, J=9.0 Hz, 2H), 7.55 (br, 1H), 7.62 (.s, 1H), 7.67 (s, 1H), 7.80 (s, 1H), 8.19 (br, 1H), 8.27 (d, J=6.1 Hz, 1H).

Mass analysis, found (ESI-MS, m/z): 474 (M⁺1).

Example 47

N-{4[(6,7-Dimethoxy-4-quinolyl)oxy]-2-nitrolphenyl}-N'-propylurea

4-[(6,7-Dimethoxy-4-quinolyl)oxy]-2-nitroaniline (150 mg) was dissolved in chloroform (10 ml) and triethylamine (1.5 ml), and a solution of triphosgene (144 mg) in chloroform was then added to the solution. The mixture was heated under reflux for 5 min. Next, n-propylamine (31 mg) was added. The mixture was heated under reflux for additional 2 hr. A saturated aqueous sodium hydrogencarbonate solution was added to the reaction solution, and the mixture was supported on diatomaceous earth, followed by extraction with chloroform. The solvent was removed by distillation under the reduced pressure. The residue was purified by chromatography on silica gel by development with chloroform/acetone (4/1) to give 160 mg (yield 86%) of the title compound.

¹H-NMR (CDCl₃, 400 MHz): δ 1.01 (t, J=7.5 Hz, 3H), 1.59–1.69 (m, 2H), 3.27–3.34 (m, 2H), 4.05 (s, 3H), 4.06 (s, 3H), 4.95–5.01 (br, 1H), 6.47 (d, J=5.4 Hz, 1H), 7.43–7.51 (m, 3H), 8.04 (d, J=2.7 Hz, 1H), 8.53 (d, J=5.4 Hz, 1H), 8.81 (d, J=9.3 Hz, 1H), 9.74–9.79 (br, 1H).

Mass analysis, found (FD-MS, m/z): 426 (M⁺).

Example 48

N(2,4-Difluorophenyl)-N'-{4-[(6,7-dimethoxy-4-quinolyl)oxyl-2-nitrophenyl}urea

4-[(6,7-Dimethoxy-4-quinolyl)oxyl-2-nitroaniline (100 mg) was dissolved in chloroform (10 ml) and triethylamine (1 ml), and a solution of triphosgene (96 mg) in chloroform was then added to the solution. The mixture was heated under reflux for 5 min. Next, 2,4-difluoroaniline (45 mg) was added to the reaction solution, and the mixture was further heated under reflux overnight. A saturated aqueous sodium hydrogencarbonate solution was added to the reaction solution, and the mixture was supported on diatomaceous earth, followed by extraction with chloroform. The solvent was removed by distillation under the reduced pressure. The residue was purified by thin-layer chromatography on silica gel by development with chloroform/acetone (3/1) to give 81 mg (yield 56%) of the title compound.

¹H-NMR (CDCl₃, 400 MHz): δ 4.05 (s, 3H), 4.06 (s, 3H), 6.50 (d, J=5.1 Hz, 1H), 6.91–6.98 (m, 3H), 7.45 (s, 1H), 7.49 (s, 1H), 7.50–7.54 (m, 1H), 7.88–7.97 (m, 1H), 8.05 (d, J=2.9 Hz, 1H), 8.54 (d, J=5.1 Hz, 1H), 8.77 (d, J=9.3 Hz, 1H), 9.98 (s, 1H).

Mass analysis, found (FD-MS, m/z): 496 (M⁺).

Example 49

N-{3,5-Dichloro-4-[(6,7-dimethoxy-4-quinolyl)oxy]phenyl}-N'-(2,4-difluorophenyl)urea 3,5-Dichloro-4-[(6,7-dimethoxy-4-quinolyl)oxy]-aniline (53 mg) was dissolved in chloroform (5 ml), and 2,4-difluorophenyl isocyanate (34 µl) was added to the solution. The mixture was heated under reflux overnight. The solvent was removed by distillation under the reduced pressure. The residue was purified by chromatography on silica gel by development with chloroform/acetone (2/1) to give 56 mg (yield 74%) of the title compound.

¹H-NMR (CDCl₃, 400 MHz): δ 4.05 (s, 3H), 4.09 (s, 3H), 6.26 (d, J=5.4 Hz, 1H), 6.86–6.93 (m, 2H), 7.05 (s, 1H), 7.44 (s, 1H), 7.46 (s, 1H), 7.60 (s, 2H), 7.64 (s, 1H), 8.01–8.05 (m, 1H), 8.48 (d, J=5.4 Hz, 1H).

Mass analysis, found (FAB-MS, m/z): 520, 522, 524 (M⁺1).

Example 50

N-(2,4-Difluorophenyl)-N'-(2-fluoro-4-{[6-methoxy-7-(2-morpholinoethoxy)-4-quinolyl]oxy}phenyl)-urea N-(2,4-Difluorophenyl)-N'-{2-fluoro-4-[(7-hydroxy-6-methoxy-4-quinolyl)oxy]phenyl}urea (20 mg), potassium carbonate (7 mg), tetra-n-butylammonium iodide (2 mg), and N-(2-chloroethyl)morpholine hydrochloride (10 mg) were dissolved in N,N-dimethylformamide (1 ml), and the solution was stirred at 70° C. overnight. A saturated aqueous sodium hydrogencarbonate solution was added to the reaction solution, and the mixture was extracted with chloroform. The chloroform layer was dried over anhydrous magnesium sulfate. The solvent was removed by distillation under the reduced pressure. The residue was purified by thin-layer chromatography on silica gel by development with chloroform/methanol (30/1) to give 14 mg (yield 57%) of the title compound.

¹H-NMR (CDCl₃, 400 MHz): δ 2.57 (t, J=4.4 Hz, 4H), 2.88 (m, 2H), 3.69 (t, J=4.4 Hz, 4H), 3.94 (s, 3H), 4.26 (t, J=5.9 Hz, 2H), 6.43 (d, J=5.1 Hz, 1H), 6.77–6.95 (m, 4H), 7.35 (s, 1H), 7.43 (s, 1H), 7.96–8.02 (m, 1H), 8.13–8.17 (m, 1H), 8.44 (d, J=5.1 Hz, 1H).

Example 51

N-(2-Chloro-4-{[6-methoxy-7-(2-morpholinoethoxy)-4-quinolyl]oxy}phenyl,)-N'-(2,4-difluorophenyl)urea N-{2-Chloro-4-[(7-hydroxy-6-methoxy-4-quinolyl)-oxy]phenyl}-N'-(2,4-difluorophenyl)urea (174 mg) was dissolved in N,N-dimethylformamide (9 ml), and potassium carbonate (64 mg), tetra-n-butylammonium iodide (14 mg), and N-(2-chloroethyl)morpholine hydrochloride (86 mg) were then added to the solution. The mixture was stirred at 70° C. for 17 hr, and a saturated aqueous sodium hydrogencarbonate solution was then added to the reaction solution, followed by extraction with chloroform. The chloroform layer was dried over anhydrous sodium sulfate. The solvent was removed by distillation under the reduced pressure. The residue was purified by chromatography on silica gel by development with chloroform/methanol (20/1) to give 75 mg (yield 35%) of the title compound.

¹H-NMR (CDCl₃, 400 MHz): δ 2.60–2.67 (m, 4H), 2.95 (t, J=6.0 Hz, 2H), 3.71–3.79 (m, 4H), 4.01 (s, 3H), 4.33 (t, J=6.0 Hz, 2H), 6.50 (d, J=5.1 Hz, 1H), 6.85–6.97 (m, 2H), 7.09–7.17 (m, 2H), 7.22–7.27 (m, 2H), 7.42 (s, 1H), 7.50 (s,

1H), 7.97–8.01 (m, 1H), 8.28 (d, J=9.0 Hz, 1H), 8.51 (d, J=5.1 Hz, 1H).

Mass analysis, found (ESI-MS, m/z): 585, 587 (M+1).

Example 52

N-(2,4-Difluorophenyl)-N'-(4-{]6-methoxy-(7-(2-morpholinoethoxy)-4-quinolyl]oxy}-2,5-dimethyl-phenyl)urea N-(4-{[7-(Benzyloxy)-6-methoxy-4-quinolyl]oxy}-2,5-dimethylphenyl)-N'-(2,4-difluorophenyl)urea (366 mg) was dissolved in N,N-dimethylformamide (6 ml), and palladium hydroxide (366 mg) was added to the solution. The mixture was stirred in a hydrogen atmosphere at room temperature overnight. The solvent was removed by distillation under the reduced pressure. The residue was dissolved in chloroform and methanol. The reaction solution was filtered through Celite. Next, the solvent was removed by distillation under the reduced pressure. The residue (213 mg), potassium carbonate (109 mg), tetra-n-butylammonium iodide (12 mg), and N-(2-chloroethyl)morpholine hydrochloride (74 mg) were dissolved in N,N-dimethylformamide (5 ml), and the solution was stirred at 70° C. overnight. The solvent was removed by distillation under the reduced pressure. Water was added to the residue, and the mixture was extracted with chloroform. The chloroform layer was dried over sodium sulfate. The solvent was removed by distillation under the reduced pressure. The residue was purified by thin-layer chromatography on silica gel by development with chloroform/methanol (10/1) to give 106 mg (yield 55%) of the title compound.

$^1$H-NMR (CDCl$_3$, 400 MHz): δ 2.17 (s, 3H), 2.27 (s, 3H), 2.64 (t, J=4.6 Hz, 4H), 2.96 (t, J=6.0 Hz, 2H), 3.76 (t, J=4.6 Hz, 4H), 4.03 (s, 3H), 4.34 (t, J=6.0 Hz, 2H), 6.31 (d, J=5.4 Hz, 1H), 6.47 (s, 1H), 6.81–6.92 (m, 3H), 7.00 (s, 1H), 7.43 (s, 1H), 7.54 (s, 1H), 7.58 (s, 1H), 8.05–8.12 (m, 1H), 8.47 (d, J=5.4 Hz, 1H).

Example 53

N-(4-{[6-Methoxy-7-(2-morpholinoethoxy)-4-quinolyl]oxy}-2,5-dimethylphenyl)-N'-(2-methoxyphenyl)-urea N-(4-{[7-(Benzyloxy)-6-methoxy-4-quinolyl]oxy}-2,5-dimethylphenyl)-N'-(2-methoxyphenyl)urea (363 mg) was dissolved in N,N-dimethylformamide (6 ml), and palladium hydroxide (363 mg) was added to the solution. The mixture was stirred in a hydrogen atmosphere at room by temperature overnight. The solvent was removed by distillation under the reduced pressure. The residue was dissolved in chloroform and methanol, and the solution was filtered through Celite. Next, the solvent was removed by distillation under the reduced pressure. The residue (191 mg), potassium carbonate (219 mg), tetra-n-butylammonium iodide (12 mg), and N-(2-chloroethyl)morpholine hydrochloride (148 mg) were dissolved in N,N-dimethylformamide (5 ml). The solution was stirred at 70° C. overnight. The solvent was removed by distillation under the reduced pressure. Water was added to the residue, and the mixture was extracted with chloroform. The chloroform layer was dried over sodium sulfate. The solvent was removed by distillation under the reduced pressure. The residue was purified by thin-layer chromatography on silica gel by development with chloroform/methanol (10/1) to give 101 mg (yield 55%) of the title compound.

$^1$H-NMR (CDCl, 400 MHz): δ 2.17 (s, 3H), 2.28 (s, 3H), 2.64 (t, J=4.5 Hz, 4H), 2.96 (t, J=5.9 Hz, 2H), 3.76 (t, J=4.6 Hz, 4H), 3.83 (s, 3H), 4.04 (s, 3H), 4.34 (t, J=6.0 Hz, 2H), 6.30 (d, J=5.4 Hz, 2H), 6.86–6.90 (m, 1H), 6.96–7.06 (m, 3H), 7.16 (s, 1H), 7.43 (s, 1H), 7.57 (s, 1H), 7.59 (s, 1H), 8.11–8.16 (m, 1H), 8.46 (d, J=5.4 Hz, 1H).

Example 54

N-(2-Chloro-4-{[6-methoxy-7-2-methoxyethoxy)-4-quinolyl]oxy}phenyl)-N,-(2,4-difluorophenyl)urea Sodium hydride (60 wt %, 153 mg) was added to dimethyl sulfoxide (2 ml), and the mixture was stirred at 60° C. for 30 min and was then cooled to room temperature. 4-Amino-3-chlorophenol hydrochloride (343 mg) was added to the reaction solution, and the mixture was stirred at room temperature for 10 min. Next, a solution of 4-chloro-6-methoxy-7-(2-methoxyethoxy)-quinoline (254 mg) in dimethyl sulfoxide (2 ml) was added to the reaction solution. The mixture was stirred at 110° C. overnight. Water was added to the reaction solution, followed by extraction with chloroform. The chloroform layer was then washed with a saturated aqueous sodium hydrogencarbonate solution and was dried over anhydrous sodium sulfate. The solvent was removed by distillation under the reduced pressure. The residue was purified by chromatography on silica gel by development with chloroform/acetone (7/3) to give 332 mg of a mixture containing 2-chloro-4-{[(6-methoxy-7-(2-methoxyethoxy)-4-quinolyl]oxy}aniline as a major product. A 83 mg portion of the mixture was dissolved in chloroform (5 ml), and 2,4-difluorophenyl isocyanate (32 μl) was added to the solution. The mixture was heated under reflux overnight. The solvent was removed by distillation under the reduced pressure. The residue was purified by chromatography on silica gel by development with chloroform/acetone (2/1) to give 50 mg of the title compound. 1H-NMR (DMSO-d$_6$, 400 MHz): δ 3.75–3.77 (m, 2H), 3.94 (s, 3H), 4.27–4.29 (m, 2H), 6.55 (d, J=5.1 Hz, 1H), 7.04–7.09 (m, 1H), 7.25–7.36 (m, 2H), 7.42 (s, 1H), 7.50 (s, 1H), 7.51 (s, 1H), 8.09–8.15 (m, 1H), 8.24 (d, J=9.0 Hz, 1H), 8.49 (d, J=5.4 Hz, 1H), 8.82 (s, 1H), 9.31 (s, 1H).

Example 55

N-(2-Chloro-4-{]6-methoxy-7-(2-methoxyethoxy)-4-quinolyl]oxy}phenyl)N'-(2-methoxyphenyl )urea Sodium hydride (60 wt %, 153 mg) was added to dimethyl sulfoxide (2 ml), and the mixture was stirred at 60° C. for 30 min and was then cooled to room temperature. 4-Amino-3-chlorophenol hydrochloride (343 mg) was added to the reaction solution, and the mixture was stirred at room temperature for 10 min. Next, a solution of 4-chloro-6-methoxy-7-(2-methoxyethoxy)quinoline (254 mg) in dimethyl sulfoxide (2 ml) was added to the reaction solution, and the mixture was stirred at 110° C. overnight. Water was added to the reaction solution, followed by extraction with chloroform. The chloroform layer was then washed with a saturated aqueous sodium hydrogencarbonate solution and was then dried over anhydrous sodium sulfate. The solvent was removed by distillation under the reduced pressure. The residue was purified by chromatography on silica gel by development with chloroform/acetone (7/3) to give 332 mg of a mixture containing 2-chloro-4-{[(6-methoxy-7-(2-methoxyethoxy)-4-quinolyl]oxy}aniline as a main product. A 83 mg portion of the mixture was dissolved in chloroform (5 ml), and 2-methoxyphenyl isocyanate (35 µl) was added to the solution. The mixture was heated under reflux overnight. The solvent was removed by distillation under the reduced pressure. The residue was purified by chromatography on silica gel by development with chloroform/acetone (2/1) to give 31 mg of the title compound.

$^1$H-NMR (DMSO-$d_6$, 400 MHz): δ 3.75–3.77 (m, 2H), 3.90 (s, 3H), 3.94 (s, 3H), 4.27–4.29 (m, 2H), 6.55 (d, J=5.1 Hz, 1H), 6.89–7.05 (m, 3H), 7.24–7.27 (m, 1H), 7.42 (s, 1H), 7.48 (d, J=2.7 Hz, 1H), 7.50 (s, 1H), 8.08–8.11 (m, 1H), 8.18–8.22 (m, 1H), 8.49 (d, J=5.4 Hz, 1H), 8.99–9.03 (m, 2H).

Example 56

N-(2,4-Difluorophenyl)-N'-(4-{[6-methoxy-7-(2-methoxyethoxy)-4-quinolyl]oxy}-2,3-dimethylphenyl) urea N-(4-{[7-(Benzyloxy)-6-methoxy-4-quinolyl]oxy}-2,3-dimethylphenyl)-N'-(2,4-difluorophenyl)urea (213 mg) was dissolved in N,N-dimethylformamide (5 ml) and triethylamine (1 ml), and palladium hydroxide (40 mg) was added to the solution. The mixture was stirred in a hydrogen atmosphere at room temperature overnight. The reaction solution was filtered through Celite and was then washed with chloroform/methanol. The solvent was removed by distillation under the reduced pressure. A 90 mg portion of the residue (184 mg) was dissolved in N,N-dimethylformamide (1.5 ml), and potassium carbonate (32 mg), tetra-n-butylammonium iodide (7 mg), and 2-bromoethyl methyl ether (32 mg) were added to the solution. The mixture was stirred at 70° C. overnight. A saturated aqueous sodium hydrogencarbonate solution was added to the reaction solution, and the mixture was extracted with chloroform. The chloroform layer was dried over anhydrous magnesium sulfate. The solvent was removed by distillation under the reduced pressure. The residue was purified by thin-layer chromatography on silica gel by development with chloroform/acetone (2/1) to give 110 mg of the title compound.

$^1$H-NMR (DMSO-$d_6$, 400 MHz): δ 1.97 (s, 3H), 2.17 (s, 3H), 3.31 (s, 3H), 3.70 (t, J=4.4 Hz, 2H), 3.90 (s, 3H), 4.21 (t, J=4.4 Hz, 2H), 6.18 (d, J=5.1 Hz, 1H), 6.95–6.98 (m, 2H), 7.22–7.31 (m, 1H), 7.34 (s, 1H), 7.51 (s, 1H), 7.62 (d, J=8.8 Hz, 1H), 8.03–8.10 (m, 1H), 8.36 (d, J=5.1 Hz, 1H), 8.38 (s, 1H), 8.79 (s, 1H).

Example 57

N-(4-{[6-Methoxy-7-(2-methoxyethoxy)-4quinolyl]oxy}-2,3-dimethylphenyl)-N'-(2-methoxyphenyl)-urea N-(4-{[7-(Benzyloxy)-6-methoxy-4-quinolyl]oxy}-2,3-dimethylphenyl)-N'-(2-methoxyphenyl)urea (161 mg) was dissolved in N,N-dimethylformamide (4 ml) and triethylamine (1 ml), and palladium hydroxide (32 mg) was added to the solution. The mixture was stirred in a hydrogen atmosphere at room temperature overnight. The reaction solution was filtered through Celite and was washed with chloroform/methanol. The solvent was removed by distillation under the reduced pressure. A 110 mg portion of the residue (223 mg) was dissolved in N,N-dimethylformamide (1.5 ml), and potassium carbonate (23 mg), tetra-n-butylammonium iodide (5 mg), and 2-bromoethyl methyl ether (23 mg) were added to the solution. The mixture was stirred at 70° C. overnight. A saturated aqueous sodium hydrogencarbonate solution was added to the reaction solution, and the mixture was extracted with chloroform. The chloroform layer was dried over anhydrous magnesium sulfate. The solvent was removed by distillation under the reduced pressure. The residue was purified by thin-layer chromatography on silica gel by development with chloroform/acetone (2/1) to give 89 mg of the title compound.

$^1$H-NMR (DMSO-$d_6$, 400 MHz): δ 2.00 (s, 3H), 2.17 (s, 3H), 3.70 (t, J=4.2 Hz, 2H), 3.83 (s, 3H), 3.90 (s, 3H), 4.22 (t, J=4.2 Hz, 2H), 6.19 (d, J=5.1 Hz, 1H), 6.81–6.88 (m, 2H), 6.94–6.97 (m, 2H), 7.34 (s, 1H), 7.51 (s, 1H), 7.58 (d, J=8.8 Hz, 1H), 8.07 (d, J=8.8 Hz, 1H), 8.36 (d, J=5.1 Hz, 1H), 8.48 (s, 1H), 8.58 (s, 1H).

Example 58

N-(2,4-Difluorophenyl)-N'-(4-{[6-methoxy-7-(2-methoxyethoxy-4-quinolyl]oxy}-2,5-dimethylphenyl)urea N-(4-{[7-(Benzyloxy)-6-methoxy-4-quinolyl]oxy}-2,5-dimethylphenyl)-N'-(2,4-difluorophenyl)urea (366 mg) was dissolved in N,N-dimethylformamide (6 ml), and palladium hydroxide (366 mg) was added to the solution. The mixture was stirred in a hydrogen atmosphere at room temperature overnight. The solvent was removed by distillation under the reduced pressure. The residue was dissolved in chloroform and methanol, and the solution was filtered through Celite. Next, the solvent was removed by distillation under the reduced pressure. The residue (213 mg), potassium carbonate (109 mg), tetra-n-butylammonium iodide (12 mg), and 2-bromoethyl methyl ether (40 µl) were dissolved in N,N-dimethylformamide (5 ml), and the solution was stirred at 70° C. overnight. The solvent was removed by distillation under the reduced pressure. Water was added to the residue, and the mixture was extracted with chloroform. The chloroform layer was dried over sodium sulfate. The solvent was removed by distillation under the reduced pressure. The residue was purified by thin-layer chromatography on silica gel by development with chloroform/methanol (10/1) to give 124 mg (yield 73%) of to the title compound.

$^1$H-NMR (CDCl$_3$, 400 MHz): δ 2.17 (s, 3H), 2.26 (s, 3H), 3.49 (s, 3H), 3.90 (t, J=4.8 Hz, 2H), 4.03 (s, 3H), 4.34 (t, J=4.8 Hz, 2H), 6.30 (d, J=5.1 Hz, 1H), 6.57 (s, 1H), 6.81–6.95 (m, 3H), 7.00 (s, 1H), 7.43 (s, 3H), 7.55 (s, 1H), 7.57 (s, 1H), 8.05–8.14 (m, 1H), 8.46 (d, J=5.4 Hz, 1H).

Mass analysis, found (ESI-MS, m/z): 524 (M$^+$1).

Example 59

N-(4-{[6-Methoxy-7-(2-methoxyethoxy)-4-quinolyl]oxy}-2,5-dimethylphenyl)-N'-(2-methoxyphenyl-urea N-(4-{[7-(Benzyloxy)-6-methoxy-4-quinolyl]oxy}-2,5-dimethylphenyl)-N'-(2-methoxyphenyl)urea (363 mg) was dissolved in N,N-dimethylformamide (6 ml), and palladium hydroxide (363 mg) was added to the solution. The mixture was stirred in a hydrogen atmosphere at room temperature overnight. The solvent was removed by distillation under the reduced pressure, and the residue was dissolved in chloroform and methanol. The solution was filtered through Celite. Next, the solvent was removed by distillation under the reduced pressure. The residue (191 mg), potassium carbonate (110 mg), tetra-n-butylammonium iodide (12 mg), and 2-bromoethyl methyl ether (80 mg) were dissolved in N,N-dimethylformamide (5 ml), and the solution was stirred at 70° C. overnight. The solvent was removed by distillation under the reduced pressure. Water was added to the residue, and the mixture was extracted with chloroform. The chloroform layer was dried over sodium sulfate. The solvent was removed by distillation under the reduced pressure. The residue was purified by thin-layer chromatography on silica gel by development with chloroform/methanol (10/1) to give 128 mg (yield 76%) of the title compound.

$^1$H-NMR (CDCl$_3$, 400 MHz): δ 2.17 (s, 3H), 2.28 (s, 3H), 3.49 (s, 3H), 3.83 (s, 3H), 3.90 (t, J=4.8 Hz, 2H), 4.04 (s, 3H), 4.35 (t, J=4.9 Hz, 2H), 6.30 (d, J=5.4 Hz, 1H), 6.33 (s, 1H), 6.86–6.90 (m, 1H), 6.96–7.06 (m, 3H), 7.17 (s, 1H), 7.43 (s, 1H), 7.56 (s, 1H), 7.58 (s, 1H), 8.12–8.17 (m, 1H), 8.45 (d, J=5.1 Hz, 1H).

Mass analysis, found (ESI-MS, m/z): 518 (M$^+$1).

Example 60

N-(4-{[7-(Benzyloxy)-6-methoxy-4-quinolyl]oxy}-2,3-dimethylphenyl)-N'-(2-methoxyphenyl)-urea 4-{[7-(Benzyloxy)-6-methoxy-4-quinolyl]oxy}-2,3-dimethylaniline (260 mg) was dissolved in N,N-dimethylformamide (5 ml), and 2-methoxyphenyl isocyanate (116 mg) was then added to the solution. The mixture was allowed to react at room temperature overnight. A saturated aqueous sodium hydrogencarbonate solution was added to the reaction solution, and the mixture was extracted with chloroform. The chloroform layer was dried over anhydrous magnesium sulfate. The solvent was removed by distillation under the reduced pressure. The residue was purified by thin-layer chromatography on silica gel by development with chloroform/acetone (211) to give 169 mg (yield 47%) of the title compound.

$^1$H-NMR (DMSO-d$_6$, 400 MHz): δ 1.99 (s, 3H), 2.02 (s, 3H), 3.83 (s, 3H), 3.90 (s, 3H), 5.25 (s, 2H), 6.18 (d, J=5.3 Hz, 1H), 6.81–6.87 (m, 2H), 6.95 (d, J=6.1 Hz, 1H), 7.29–7.59 (m, 7H), 8.07 (d, J=6.1 Hz, 1H), 8.35 (d, J=5.3 Hz, 1H), 8.48 (s, 1H), 8.58 (s, 1H).

Example 61

N-{2-Chloro-4-[(6,7-dimethoxy-4-quinazolinyl)oxy] phenyl}-N'-(2,4-difluorophenyl)urea 2-Chloro-4-[(6,7-dimethoxy-4-quinazolinyl)oxy]-aniline (214 mg) was dissolved in chloroform (5 ml), and 2,4-difluorophenyl isocyanate (180 μl) was then added to the solution. The mixture was allowed to react at 70° C. for 4 hr, and a large amount of ether was added to the reaction solution. The resultant precipitate was collected by suction filtration to give 146 mg (yield 46%) of the title compound.

$^1$H-NMR (DMSO-d$_6$, 400 MHz): δ 3.98 (s, 3H), 3.99 (s, 3H), 7.03–7.10 (m, 1H), 7.28–7.37 (m, 2H), 7.40 (s, 1H), 7.56 (s, 2H), 8.08–8.21 (m, 2H), 8.57 (s, 1H), 8.80 (s, 1H), 9.30 (s, 1H).

Mass analysis, found (ESI-MS, m/z): 487, 489 (M$^+$1).

Example 62

N-{2-Chloro-4-[(6,7-dimethoxy-4-quinazolinyl)oxy] phenyl}-N'-propylurea

2-Chloro-4-[(6,7-dimethoxy-4-quinazolinyl)oxy]-aniline (5.13 g) was dissolved in chloroform (100 ml) and triethylamine (50 ml), and a solution of triphosgene (4.59 g) in chloroform (3 ml) was then added to the solution. The mixture was stirred for 30 min. Next, n-propylamine (2.74 g) was added to the reaction solution, and the mixture was stirred for additional 2 hr. A saturated aqueous sodium hydrogencarbonate solution was added to the reaction solution, and the mixture was extracted with chloroform. The chloroform layer was dried over anhydrous sodium sulfate. The solvent was removed by distillation under the reduced pressure. The residue was purified by chromatography on silica gel by development with chloroform/methanol (50/1) to give 4.14 g (yield 64%) of the title compound.

$^1$H-NMR (DMSO-d$_6$, 400 MHz): δ 0.91 (t, J=7.3 Hz, 3H), 1.41–1.53 (m, 2H), 3.05–3.12 (m, 2H), 3.97 (s, 3H), 3.99 (s, 3H), 6.99 (t, J=5.4 Hz, 1H), 7.22 (dd, J=2.7 Hz, 9.0 Hz, 1H), 7.38 (s, 1H), 7.46 (d, J=2.9 Hz, 1H), 7.54 (s, 1H), 8.04 (s, 1H), 8.20 (d, J=9.3 Hz, 1H), 8.55 (s, 1H).

Mass analysis, found (ESI-MS, m/z); 417 (M$^+$1).

Example 63

N-{4-[(6,7-Dimethoxy-4-quinazolinyl)oxy]-phenyl}-N'-ethylurea

4-[(6,7-Dimethoxy-4-quinazolinyl)oxy]aniline (50 mg) was dissolved in chloroform (3 ml) and triethylamine (0.2 ml), and a solution of triphosgene (50 mg) in chloroform was then added to the solution. The mixture was stirred at room temperature for 30 min. Next, ethylamine hydrochloride (69 mg) was added to the reaction solution, and the mixture was further stirred at room temperature overnight. Methanol was added to the reaction solution, and the solution was purified by HPLC by development with chloroform/methanol to give 10 mg (yield 16%) of the title compound.

$^1$H-NMR (DMSO-d$_6$, 400 MHz): δ 1.07 (t, J=7.3 Hz, 3H), 3.11–3.14 (m, 2H), 3.97 (s, 3H), 3.99 (s, 3H), 6.10 (t, J=5.4 Hz, 1H), 7.14 (d, J=9.0 Hz, 2H), 7.37 (s, 1H), 7.46 (d, J=9.0 Hz, 2H), 7.55 (s, 1H), 8.49 (br, 1H), 8.53 (s, 1H).

Mass analysis, found (ESI-MS, m/z): 369 (M$^+$1).

Example 64

N-{4-[(6,7-Dimethoxy-4-quinazolinyl)oxy]-phenyl}-N'-propylurea

4-[(6,7-Dimethoxy-4-quinazolinyl)oxy]aniline (50 mg) was dissolved in chloroform (3 ml) and triethylamine (0.2 ml), and a solution of triphosgene (50 mg) in chloroform was then added to the solution. The mixture was stirred at room temperature for 30 min. Next, propylamine (21 μl) was added to the reaction solution, and the mixture was further stirred at room temperature overnight. Methanol was added to the reaction solution, and the solution was purified by HPLC by development with chloroform/methanol to give 30 mg (yield 47%) of the title compound.

$^1$H-NMR (DMSO-d$_6$, 400 MHz): δ 0.89 (t, J=7.6 Hz, 3H), 1.41–1.50 (m, 2H), 3.04–3.08 (m, 2H), 3.97 (s, 3H), 3.99 (s, 3H), 6.15 (t, J=5.9 Hz, 1H), 7.15 (d, J=8.8 Hz, 2H), 7.37 (s, 1H), 7.46 (d, J=9.0 Hz, 2H), 7.55 (s, 1H), 8.48 (br, 1H), 8.53 (s, 1H).

Mass analysis, found (ESI-MS, m/z): 383 (M$^+$1).

Example 65

N-Butyl-N'-{4-[(6,7-dimethoxy-4-quinazolinyl)oxy]phenyl}urea

4-[(6,7-Dimethoxy-4-quinazolinyl)oxy]aniline (50 mg) was dissolved in chloroform (3 ml) and triethylamine (0.2 ml), and a solution of triphosgene (50 mg) in chloroform was then added to the solution. The mixture was stirred at room temperature for 30 min. Next, butylamine (22 μl) was added to the reaction solution, and the mixture was further stirred at room temperature overnight. Methanol was added to the reaction solution, and the mixture was purified by HPLC by development with chloroform/methanol to give 29 mg (yield 43%) of the title compound.

$^1$H-NMR (DMSO-d$_6$, 400 MHz): δ 0.91 (t, J=7.3 Hz, 3H), 1.28–1.47 (m, 4H), 3.07–3.12 (m, 2H), 3.97 (s, 3H), 3.99 (s, 3H), 6.12 (t, J=5.6 Hz, 1H), 7.15 (d, J=8.8 Hz, 2H), 7.37 (s, 1H), 7.46 (d, J=9.0 Hz, 2H), 7.55 (s, 1H), 8.47 (br, 1H), 8.53 (s, 1H).

Mass analysis, found (ESI-MS, m/z): 397 (M$^+$1).

Example 66

N-{4-[(6,7-Dimethoxy-4-quinazolinyl)oxy]-phenyl}-N'-pentylurea

4-[(6,7-Dimethoxy-4-quinazolinyl)oxy]aniline (50 mg) was dissolved in chloroform (3 ml) and triethylamine (0.2 ml), and a solutioin of triphosgene (50 mg) in chloroform was then added to the solution. The mixture was stirred at room temperature for 30 min. Next, amylamine (26 μl) was added to the reaction solution, and the mixture was stirred at room temperature overnight. Methanol was added to the reaction solution, and the mixture was purified by HPLC by development with chloroform/methanol to give 21 mg (yield 30%) of the title compound. $^1$H-NMR (DMSO-d$_6$, 400 MHz): δ 0.89 (t, J=7.1 Hz, 3H), 1.27–1.47 (m, 4H), 1.41–1.48 (m, 2H), 3.06–3.11 (m, 2H), 3.97 (s, 3H), 3.99 (s, 3H), 6.13 (t, J=5.6 Hz, 1H), 7.15 (d, J=9.0 Hz, 2H), 7.37 (s, 1H), 7.46 (d, J=8.8 Hz, 2H), 7.55 (s, 1H), 8.47 (br, 1H), 8.53 (s, 1H).

Mass analysis, found (ESI-MS, m/z): 411 (M$^+$1).

Example 67

N-(sec-Butyl)-N'-{4-[(6,7-dimethoxy-4-quinazolinyl)oxy]phenyl}urea

4-[(6,7-Dimethoxy-4-quinazolinyl)oxy]aniline (50 mg) was dissolved in chloroform (3 ml) and triethylamine (0.2 ml), and a solution of triphosgene (50 mg) in chloroform was then added to the solution. The mixture was stirred at room temperature for 30 min. Next, sec-butylamine (23 μl) was added, and the mixture was stirred at room temperature overnight. Methanol was added to the reaction solution, and the mixture was purified by HPLC by development with chloroform/methanol to give 33 mg (yield 49%) of the title compound.

$^1$H-NMR (DMSO-d$_6$, 400 MHz): δ 0.88 (t, J=7.3 Hz, 3H), 1.08 (d, J=6.6 Hz, 3H), 1.40–1.47 (m, 2H), 3.58–3.64 (m, 1H), 3.97 (s, 3H), 3.99 (s, 3H), 5.98 (t, J=8.1 Hz, 1H), 7.15 (d, J=9.0 Hz, 2H), 7.37 (s, 1H), 7.46 (d, J=9.0 Hz, 2H), 7.55 (s, 1H), 8.38 (s, 1H), 8.53 (s, 1H).

Mass analysis, found (ESI-MS, m/z): 397 (M$^+$1).

Example 68

N-Allyl-N'-{4-[(6,7-Dimethoxy-4-quinazolinyl)oxy]phenyl}urea

4-[(6,7-Dimethoxy-4-quinazolinyl)oxy]aniline (50 mg) was dissolved in chloroform (3 ml) and triethylamine (0.2 ml), and a solution of triphosgene (50 mg) in chloroform was then added to the solution. The mixture was stirred at room temperature for 30 min. Next, allylamine hydrochloride (31 mg) was added to the reaction solution, and the mixture was stirred at room temperature overnight. Methanol was added to the reaction solution, and the mixture was purified by HPLC by development with chloroform/methanol to give 21 mg (yield 33%) of the title compound.

$^1$H-NMR (DMSO-d$_6$, 400 MHZ): δ 3.73–3.76 (m, 2H), 3.97 (s, 3H), 3.99 (s, 3H), 5.07–5.21 (m, 2H), 5.84–5.92 (m, 1H), 6.28 (t, J=5.6 Hz, 1H), 7.16 (d, J=9.0 Hz, 2H), 7.38 (s, 1H), 7.47 (d, J=9.0 Hz, 2H), 7.55 (s, 1H), 8.53 (s, 1H), 8.59 (s, 1H).

Mass analysis, found (ESI-MS, m/z): 381 (M$^+$1).

Example 69

N-{4-[(6,7-Dimethoxy-4-quinazolinyl)-oxy]phenyl}-N'-(2-propynyl)urea

4-[(6,7-Dimethoxy-4-quinazolinyl)oxy]aniline (50 mg) was dissolved in chloroform (3 ml) and triethylamine (0.2 ml), and a solution of triphosgene (50 mg) in chloroform was then added to the solution. The mixture was stirred at room temperature for 30 min. Next, propargylamine hydrochloride (31 mg) was added to the reaction solution, and the mixture was stirred at room temperature overnight. Methanol was added to the reaction solution, and the mixture was purified by HPLC by development with chloroform/methanol to give 26 mg (yield 41%) of the title compound.

$^1$H-NMR (DMSO-d$_6$, 400 MHz): δ 3.11–3.12 (m, 1H), 3.89–3.90 (m, 2H), 3.97 (s, 3H), 3.99 (s, 3H), 6.49 (t, J=5.9 Hz, 1H), 7.17 (d, J=9.0 Hz, 2H), 7.38 (s, 1H), 7.48 (d, J=8.8 Hz, 2H), 7.55 (s, 1H), 8.53 (s, 1H), 8.68 (s, 1H).

Mass analysis, found (ESI-MS, m/z): 379 (M$^+$1).

Example 70

N-(2,4-Difluorobenzyl)-N'-{4-[(6,7-dimethoxy-4-quinazolinyl)oxy]phenyl}urea

4-[(6,7-Dimethoxy-4-quinazolinyl)oxy]aniline (50 mg) was dissolved in chloroform (3 ml) and triethylamine (0.2 ml), and a solution of triphosgene (50 mg) in chloroform was then added to the solution. The mixture was stirred at room temperature for 30 min. Next, 2,4-difluorobenzylamine (22 μl) was added to the reaction solution, and the mixture was stirred at room temperature overnight. Methanol was added to the reaction solution, and the mixture was purified by HPLC by development with chloroform/methanol to give 32 mg (yield 41%) of the title compound.

$^1$H-NMR (DMSO-d$_6$, 400 MHz): δ 3.97 (s, 3H), 3.98 (s, 3H), 4.32–4.33 (m, 2H), 6.66 (t, J=5.9 Hz, 1H), 7.06–7.10 (m, 1H), 7.16 (d, J=8.8 Hz, 2H), 7.19–7.24 (m, 1H), 7.37 (s, 1H), 7.40–7.44 (m, 1H), 7.48 (d, J=9.0 Hz, 2H), 7.55 (s, 1H), 8.52 (s, 1H), 8.69 (s, 1H).

Mass analysis, found (ESI-MS, m/z): 467 (M$^+$1).

Example 71

N-{4-[(6,7-Dimethoxy-4-quinazolinyl)oxy]-phenyl}-N'-(2-pyridylmethyl)urea

4-[(6,7-Dimethoxy-4-quinazolinyl)oxy]aniline (50 mg) was dissolved in chloroform (3 ml) and triethylamine (0.2 ml), and a solution of triphosgene (50 mg) in chloroform was then added to the solution. The mixture was stirred at room temperature for 30 min. Next, 2,4-difluorobenzylamine (31 μl) was added to the reaction solution, and the mixture was stirred at room temperature overnight. Methanol was added to the reaction solution, and the mixture was purified by HPLC by development with chloroform/methanol to give 31 mg (yield 43%) of the title compound.

$^1$H-NMR (DMSO-d$_6$, 400 MHz): δ 3.42 (s, 2H), 3.98 (s, 3H), 3.99 (s, 3H), 7.16–7.19 (m, 2H), 7.22–7.27 (m, 3H), 7.38 (s, 1H), 7.57 (s, 1H), 7.67 (d, J=8.8 Hz, 2H), 7.88–7.92 (m, 1H), 8.46–8.48 (m, 1H), 8.54 (s, 1H), 8.87 (s, 1H), 12.19 (s, 1H).

Mass analysis, found (FD-MS, m/z): 431 (M$^+$).

Example 72

N-(2,4-Difluorophenyl)-N'-{4-[(6,7-dimethoxy-4-quinazolinyl)oxy]phenyl}urea

4-[(6,7-Dimethoxy-4-quinazolinyl)oxy]aniline (50 mg) was dissolved in chloroform (3 ml), and 2,4-difluorophenyl isocyanate (24 μl) was then added to the solution. The mixture was heated under reflux overnight. The precipitated crystal was collected by filtration and was washed to give 55 mg (yield 72%) of the title compound. $^1$H-NMR (DMSO-d$_6$, 400 MHz): δ 3.98 (s, 3H), 3.99 (s, 3H), 7.04–7.08 (m, 2H), 7.24 (d, J=8.8 Hz, 2H), 7.29–7.35 (m, 1H), 7.38 (s, 1H), 7.54 (d, J=9.0 Hz, 2H), 7.56 (s, 1H), 8.06–8.14 (m, 1H), 8.51–8.54 (m, 1H), 8.54 (s, 1H), 9.11–9.12 (m, 1H).

Mass analysis, found (ESI-MS, m/z): 453 (M$^+$1).

Example 73

N-{4-[(6,7-Dimethoxy-4-quinazolinyl)ox]-phenyl}-N'-(4-fluorophenyl)urea

4-[(6,7-Dimethoxy-4-quinazolinyl)oxy]aniline (50 mg) was dissolved in chloroform (3 ml), and p-fluorophenyl isocyanate (23 μl) was then added to the solution. The mixture was heated under reflux overnight. Methanol was added to the reaction solution, and the mixture was purified by HPLC by development with chloroform/methanol to give 26 mg (yield 36%) of the title compound.

$^1$H-NMR (DMSO-d$_6$, 400 MHz): δ 3.98 (s, 3H), 3.99 (s, 3H), 7.11–7.15 (m, 2H), 7.22 (d, J=8.8 Hz, 2H), 7.38 (s, 1H), 7.46–7.50 (m, 2H), 7.54 (d, J=9.0 Hz, 2H), 7.56 (s, 1H), 8.54 (s, 1H), 8.72 (s, 1H), 8.75 (s, 1H).

Mass analysis, found (ESI-MS, m/z): 435 (M$^+$1).

Example 74

N-{4-[(6,7Dimethoxy-4-quinazolinyl)ox]-phenyl}-N'-(2-methylphenyl)urea

4-[(6,7-Dimethoxy-4-quinazolinyl)oxy]aniline (50 mg) was dissolved in chloroform (3 ml), and o-toluyl isocyanate (25 μl) was then added to the solution. The mixture was heated under reflux overnight. Methanol was added to the reaction solution, and the mixture was purified by HPLC by development with chloroform/methanol to give 30 mg (yield 41%) of the title compound.

$^1$H-NMR (DMSO-d$_6$, 400 MHz): δ 2.26 (s, 3H), 3.98 (s, 3H), 3.99 (s, 3H), 6.93–6.98 (m, 1H), 7.13–7.19 (m, 2H), 7.22 (d, J=8.8 Hz, 2H), 7.38 (s, 1H), 7.54–7.56 (m, 3H), 7.83–7.86 (m, 1H), 7.93 (s, 1H), 8.54 (s, 1H), 9.10–9.11 (m, 1H).

Mass analysis, found (ESI-MS, m/z): 431 (M$^+$+1).

Example 75

N-{4[(6,7-Dimethoxy-4-quinazolinyl)oxy]-phenyl}-N'-(2-methoxyphenyl)urea

4-[(6,7-Dimethoxy-4-quinazolinyl)oxy]aniline (50 mg) was dissolved in chloroform (3 ml), and 2-methoxyphenyl isocyanate (27 l) was then added to the solution. The mixture was heated under reflux overnight. Methanol was added to the reaction solution, and the mixture was purified by HPLC by development with chloroform/methanol to give 34 mg (yield 45%) of the title compound.

$^1$H-NMR (DMSO-d$_6$, 400 MHz): δ 3.89 (s, 3H), 3.98 (s, 3H), 3.99 (s, 3H), 6.89–7.05 (m, 3H), 7.22 (d, J=8.8 Hz, 2H), 7.38 (s, 1H), 7.54 (d, J=8.8 Hz, 2H), 7.56 (s, 1H), 8.13–8.15 (m, 1H), 8.23–8.24 (m, 1H), 8.54 (s, 1H), 9.40–9.41 (m, 1H).

Mass analysis, found (ESI-MS, m/z): 447 (M$^+$1).

Example 76

N-{2-Chloro-4-[(6,7-dimethoxy-4-quinazolinyl)oxy]phenyl}-N'-ethylurea

2-Chloro-4-[(6,7-dimethoxy-4-quinazolinyl)oxy]-aniline (200 mg) was dissolved in chloroform (5 ml) and triethylamine (1 ml), and a solution of triphosgene (179 mg) in chloroform was then added to the solution. The mixture was stirred at room temperature for 30 min. Next, ethylamine hydrochloride (246 mg) was added to the reaction solution, and the mixture was stirred at room temperature overnight. A saturated aqueous sodium hydrogencarbonate solution was added to the reaction solution, and the mixture was extracted with chloroform. The chloroform layer was dried over anhydrous sodium sulfate. The solvent was removed by distillation under the reduced pressure. The residue was purified by HPLC by development with chloroform/methanol to give 159 mg (yield 65%) of the title compound.

$^1$H-NMR (DMSO-d$_6$, 400 MHz): δ 1.08 (t, J=7.1 Hz, 3H), 3.11–3.16 (m, 2H), 3.97 (s, 3H), 3.99 (s, 3H), 6.96 (t, J=5.6 Hz, 1H), 7.23 (dd, J=2.7 Hz, 9.0 Hz, 1H), 7.39 (s, 1H), 7.47 (d, J=2.7 Hz, 1H), 7.55 (s, 1H), 8.02 (s, 1H), 8.20 (d, J=9.3 HZ, 1H), 8.56 (s, 1H).

Mass analysis, found (ESI-MS, m/z): 403 (M$^+$1).

Example 77

N-Butyl-N'-{2-chloro-4-[(6,7-dimethoxy-4-quinazolinyl)oxy]phenyl}urea

2-Chloro-4-[(6,7-dimethoxy-4-quinazolinyl)oxy]-aniline (50 mg) was dissolved in chloroform (5 ml) and triethylamine (1 ml), and a solution of triphosgene (45 mg) in chloroform was then added to the solution. The mixture was stirred at room temperature for 30 min. Next, butylamine (22 μl) was added to the reaction solution, and the mixture was stirred at room temperature for additional 30 min. A saturated aqueous sodium hydrogencarbonate solution was added to the reaction solution, and the mixture was extracted with chloroform. The chloroform layer was dried over anhydrous sodium sulfate. The solvent was removed by distillation under the reduced pressure. The residue was purified by HPLC by development with chloroform/methanol to give 30 mg (yield 46%) of the title compound.

$^1$H-NMR (DMSO-d$_6$, 400 MHz): δ 0.91 (t, J=7.3 Hz, 3H), 1.31–1.46 (m, 4H), 3.09–3.14 (m, 2H), 3.97 (s, 3H), 3.99 (s, 3H), 6.96 (t, J=5.6 Hz, 1H), 7.23 (dd, J=2.7 Hz, 9.0 Hz, 1H), 7.39 (s, 1H), 7.47 (d, J=2.7 Hz, 1H), 7.55 (s, 1H), 8.03 (s, 1H), 8.20 (d, J 9.0 Hz, 1H), 8.56 (s, 1H).

Mass analysis, found (ESI-MS, m/z): 431 (M$^+$1).

Example 78

N-{2-Chloro-4-[(6,7-dimethoxy-4-quinazolinyl)oxy]phenyl}-N'-pentylurea

2-Chloro-4-[(6,7-dimethoxy-4-quinazolinyl)oxy]-aniline (50 mg) was dissolved in chloroform (5 ml) and triethylamine (1 ml), and a solution of triphosgene (45 mg) in chloroform was then added to the solution. The mixture was stirred at room temperature for 30 min. Next, amylamine (26 μl) was added to the reaction solution, and the mixture was stirred at room temperature for additional 30 min. A saturated aqueous sodium hydrogencarbonate solution was added to the reaction solution, and the mixture was extracted with chloroform. The chloroform layer was dried over anhydrous sodium sulfate. The solvent was removed by distillation under the reduced pressure. The residue was purified by HPLC by development with chloroform/methanol to give 33 mg (yield 49%) of the title compound.

$^1$H-NMR (DMSO-d$_6$, 400 MHz): δ 0.90 (t, J=7.1 Hz, 3H), 1.24–1.34 (m, 4H), 1.43–1.48 (m, 2H), 3.08–3.14 (m, 2H), 3.97 (s, 3H), 3.99 (s, 3H), 6.97 (t, J=5.1 Hz, 1H), 7.23 (dd, J=2.7 Hz, 9.0 Hz, 1H), 7.39 (s, 1H), 7.47 (d, J=2.8 Hz, 1H), 7.55 (s, 1H), 8.03 (s, 1H), 8.20 (d, J=9.0 Hz, 1H), 8.56 (s, 1H).

Mass analysis, found (ESI-MS, m/z): 445 (M$^+$1).

Example 79

N-(sec-Butyl)-N'-{2-chloro-4-[(6,7-dimethoxy-4-quinazolinyl)oxy]phenyl}urea

2-Chloro-4-[(6,7-dimethoxy-4-quinazolinyl)oxy]-aniline (50 mg) was dissolved in chloroform (5 ml) and triethylamine (1 ml), and a solution of triphosgene (45 mg) in chloroform was then added to the solution. The mixture was stirred at room temperature for 30 min. Next, sec-butylamine (23 1l) was added to the reaction solution, and the mixture was stirred at room temperature for additional 30 min. A saturated aqueous sodium hydrogencarbonate solution was added to the reaction solution, and the mixture was extracted with chloroform. The chloroform layer was dried over anhydrous sodium sulfate. The solvent was removed by distillation under the reduced pressure. The residue was purified by HPLC by development with chloroform/methanol to give 34 mg (yield 52%) of the title compound.

$^1$H-NMR (DMSO-d$_6$, 400 MHz): δ 0.89 (t, J=7.6 Hz, 3H), 1.09 (d, J=6.6 Hz, 3H), 1.43–1.46 (m, 2H), 3.58–3.66 (m, 1H), 3.97 (s, 3H), 3.99 (s, 3H), 6.88 (d, J=7.6 Hz, 1H), 7.22 (dd, J=2.4 Hz, 9.3 Hz, 1H), 7.39 (s, 1H), 7.47 (d, J=2.7 Hz, 1H), 7.55 (s, 1H), 7.98 (s, 1H), 8.23 (d, J=9.0 Hz, 1H), 8.55–8.56 (m, 1H).

Mass analysis, found (ESI-MS, m/z): 431 (M$^+$1).

Example 80

N-Allyl-N'-{2-chloro-4-[(6,7-dimethoxy-4-quinazolinyl)oxy]phenyl}urea

2-Chloro-4-[(6,7-dimethoxy-4-quinazolinyl)oxy]-aniline (50 mg) was dissolved in chloroform (5 ml) and triethylamine (1 ml), and a solution of triphosgene (45 mg) in chloroform was then added to the solution. The mixture was stirred at room temperature for 30 min. Next, allylamine hydrochloride (21 mg) was added to the reaction solution, and the mixture was stirred at room temperature for additional 30 min. A saturated aqueous sodium hydrogencarbonate solution was added to the reaction solution, and the mixture was extracted with chloroform. The chloroform layer was dried over anhydrous sodium sulfate. The solvent was removed by distillation under the reduced pressure. The residue was purified by HPLC by development with chloroform/methanol to give 45 mg (yield 72%) of the title compound.

$^1$H-NMR (DMSO-d$_6$, 400 MHz): δ 3.76–3.79 (m, 2H), 3.97 (s, 3H), 3.99 (s, 3H), 5.10–5.24 (m, 2H), 5.85–5.94 (m, 1H), 7.11 (t, J=5.4 Hz, 1H), 7.24 (dd, J=2.7 Hz, 9.0 Hz, 1H), 7.39 (s, 1H), 7.49 (d, J=2.7 Hz,1H), 7.55 (s, 1H), 8.14 (s, 1H), 8.19 (d, J=9.0 Hz, 1H), 8.56 (s, 1H).

Mass analysis, found (ESI-MS, m/z): 415 (M$^+$1).

Example 81

N-{2-Chloro-4-[(6,7-dimethoxy-4-quinazolinyl)oxy]phenyl}-N'-(2-propynyl)urea

2-Chloro-4-[(6,7-dimethoxy-4-quinazolinyl)oxy)-aniline (50 mg) was dissolved in chloroform (5 ml) and triethylamine (1 ml), and a solution of triphosgene (45 mg) in chloroform was then added to the solution. The mixture was stirred at room temperature for 30 min. Next, propargylamine hydrochloride (21 mg) was added to the reaction solution, and the mixture was stirred at room temperature for additional 30 min. The precipitated crystal was collected by filtration and was washed to give 38 mg (yield 61%) of the title compound.

¹H-NMR (DMSO-d₆, 400 MHz): δ 3.16–3.17 (m, 1H), 3.93–3.95 (m, 2H), 3.97 (s, 3H), 3.99 (s, 3H), 7.25 (dd, J=2.7 Hz, 9.0 Hz, 1H), 7.30 (t, J=5.6 Hz, 1H), 7.39 (s, 1H), 7.50 (d, J=2.7 Hz, 1H), 7.55 (6, 1H), 8.16 (d, J=9.3 Hz, 1H), 8.18 (s, 1H), 8.56 (s, 1H).

Mass analysis, found (ESI-MS, m/z): 413 (M⁺+1).

Example 82

N-{2-Chloro-4-[(6,7-dimethoxy-4-quinazolinyl)oxy] phenyl}-N'-(2,4-difluorobenzyl)urea 2-Chloro-4-[(6,7-dimethoxy-4-quinazolinyl)oxy]-aniline (50 mg) was dissolved in chloroform (5 ml) and triethylamine (1 ml), and a solution of triphosgene (45 mg) in chloroform was then added to the solution. The mixture was stirred at room temperature for 30 min. Next, 2,4-difluorobenzylamine (22 μl) was added to the reaction solution, and the mixture was stirred at room 10 temperature for additional 30 min. The precipitated crystal was collected by filtration and was washed to give 48 mg (yield 64%) of the title compound.

¹H-NMR (DMSO-d₆, 400 MHz): δ 3.97 (s, 3H), 3.99 (s, 3H), 4.33–4.36 (m, 2H), 7.08–7.12 (m, 1H), 7.22–7.28 (m, 2H), 7.39 (s, 1H), 7.42–7.46 (m, 1H), 7.49 (d, J=2.7 Hz, 1H), 7.54 (s, 1H), 8.18–8.20 (m, 2H), 8.56 (5, 1H).

Mass analysis, found (ESI-MS, m/z): 501 (M⁺+1).

Example 83

N-{2-Chloro-4-[(6,7-dimethoxy-4-quinazolinyl)oxy] phenyl}-N'-(2pyridylethyl)urea 2-Chloro-4-[(6,7-dimethoxy-4-quinazolinyl)oxy]-aniline (50 mg) was dissolved in chloroform (5 ml) and triethylamine (1 ml), and a solution of triphosgene (45 mg) in chloroform was then added to the solution. The mixture was stirred at room temperature for 30 min. Next, 2-(methylamino)pyridine (19 μl) was added to the reaction solution, and the mixture was stirred at 60° C. for additional one hr. A saturated aqueous sodium hydrogencarbonate solution was added to the reaction solution, and the mixture was extracted with chloroform. The chloroform layer was dried over anhydrous sodium sulfate. The solvent was removed by distillation under the reduced pressure. The residue was purified by HPLC by development with chloroform/methanol to give 26 mg (yield 37%) of the title compound.

¹H-NMR (CDCl₃, 400 MHz): δ 3.51 (s, 2H), 4.07 (s, 3H), 4.07 (s, 3H), 7.03–7.10 (m, 2H), 7.19 (dd, J=2.7 Hz, 9.0 Hz, 1H), 7.35 (s, 1H), 7.36 (d, J=2.7 Hz, 1H), 7.54 (6, 1H), 7.76–7.81 (m, 1H), 8.38–8.43 (m, 1H), 8.56 (d, J=9.0 Hz, 1H), 8.64 (s, 1H), 13.53 (s, 1H).

Mass analysis, found (ESI-MS, m/z): 466 (M⁺+1).

Example 85

N-{2-Chloro-4-[(6,7-dimethoxy-4-quinazolinyl)oxy] phenyl}-N'-(4-fluorophenyl)urea 2-Chloro-4-[(6,7-dimethoxy-4-quinazolinyl)oxy]-aniline (50 mg) was dissolved in chloroform (5 ml), and p-fluorophenyl isocyanate (21 μl) was then added to the solution. The mixture was stirred at 60° C. for one hr. The precipitated crystal was collected by filtration and was washed to give 57 mg (yield 81%) of the title compound.

¹H-NMR (DMSO-d, 400 MHz): δ 3.98 (6, 3H), 3.99 (s, 3H), 7.13–7.17 (m, 2H), 7.30 (dd, J=2.4 Hz, 8.8 Hz, 1H), 7.40 (s, 1H), 7.48–7.51 (m, 2H), 7.55–7.56 (m, 2H), 8.21 (d, J=9.0 Hz, 1H), 8.31 (s, 1H), 8.57 (s, 1H).

Mass analysis, found (ESI-MS, m/z): 469 (M⁺+1).

Example 86

N-{2-Chloro-4-[(6,7-dimethoxy-4-quinazolinyl)oxy] phenyl}-N'-(2methoxyphenyl)urea 2-Chloro-4-[(6,7-dimethoxy-4-quinazolinyl)oxy]-aniline (50 mg) was dissolved in chloroform (5 ml), and 2-methoxyphenyl isocyanate (24 μl) was then added to the solution. The mixture was stirred at 60 C for one hr. Methanol was added to the reaction solution, and the mixture was purified by HPLC by development with chloroform/methanol to give 39 mg (yield 54%) of the title compound.

¹H-NMR (DMSO-d₆, 400 MHz): δ 3.90 (s, 3H), 3.98 (s, 3H), 3.99 (s, 3H), 6.89–7.05 (m, 3H), 7.29 (dd, J=2.7 Hz, 9.0 Hz, 1H), 7.40 (s, 1H), 7.54 (d, J=2.7 Hz, 1H), 7.56 (s, 1H), 8.09–8.16 (m, 2H), 8.58 (s, 1H), 8.96–9.02 (m, 2H).

Mass analysis, found (ESI-MS, m/z): 418 (M⁺+1).

Example 87

N-{2-Chloro-4-[(6,7-dimethoxy-4-quinazoliny)oxy] phenyl}-N'-(5-chloro-2-]pyridyl)urea 2-Chloro-4-[(6,7-dimethoxy-4-quinazolinyl)oxy]-aniline (50 mg) was dissolved in chloroform (5 ml) and triethylamine (1 ml), and a solution of triphosgene (45 mg) in chloroform was then added to the solution. The mixture was stirred at room temperature for 30 min. Next, 2-amino-5-chloropyridine (23 mg) was added to the reaction solution, and the mixture was stirred at 60° C. for additional one hr. A saturated aqueous sodium hydrogencarbonate solution was added to the reaction solution, and the mixture was extracted with chloroform. The chloroform layer was dried over anhydrous sodium sulfate. The solvent was removed by distillation under the reduced pressure. The residue was purified by HPLC by development with chloroform/methanol to give 39 mg (yield 53%) of the title compound.

¹H-NMR (DMSO-d₆, 400 MHz): δ 3.98 (s, 3H), 4.00 (s, 3H), 7.33 (dd, J=2.7 Hz, 9.3 Hz, 1H), 7.40 (s, 1H), 7.43–7.48 (m, 1H), 7.56 (s, 1H), 7.60 (d, J=2.7 Hz, 1H), 7.91 (dd, J=2.7 Hz, 9.0 Hz, 1H), 8.35 (d, J=8.8 Hz, 1H), 8.40 (d, J 2.4 Hz, 1H), 8.58 (s, 1H), 10.17 (s, 1H).

Mass analysis, found (ESI-MS, m/z): 486 (M⁺+1).

Example 88

N-{4-[(6,7-Dimethoxy-4-quinazolinyl)oxy]-2-fluorophenyl}-N'-propylurea

4-[(6,7-Dimethoxy-4-quinazolinyl)oxy]-2-fluoro-aniline (50 mg) was dissolved in chloroform (3 ml) and triethylamine (0.3 ml), and a solution of triphosgene (47 mg) in chloroform was then added to the solution. The mixture was stirred at room temperature for 30 min. Next, propylamine (20 μl) was added to the reaction solution, and the mixture was further stirred at room temperature overnight. Methanol was added to the reaction solution, and the mixture was purified by HPLC by development with chloroform/methanol to give 9 mg (yield 14%) of the title compound.

$^1$H-NMR (DMSO-d$_6$, 400 MHz): δ 0.90 (t, J=7.6 Hz, 3H), 1.43–1.49 (m, 2H), 3.05–3.10 (m, 2H), 3.97 (s, 3H), 3.99 (s, 3H), 6.61 (t, J=5.6 Hz, 1H), 7.05–7.07 (m, 1H), 7.27–7.31 (m, 1H), 7.38 (s, 1H), 7.54 (s, 1H), 8.14–8.19 (m, 1H), 8.28–8.29 (m, 1H), 8.55 (s, 1H).

Mass analysis, found (ESI-MS, m/z): 401 (M$^+$+1).

Example 89

N-Butyl-N'-{4-[(6,7-dimethoxy-4-quinazolinyl)oxy]-2-fluorophenyl}urea

4-[(6,7-Dimethoxy-4-quinazolinyl)oxy]-2-fluoro-aniline (50 mg) was dissolved in chloroform (3 ml) and triethylamine (0.3 ml), and a solution of triphosgene (47 mg) in chloroform was then added to the solution. The mixture was stirred at room temperature for 30 min. Next, butylamine (24 μl) was added, and the mixture was further stirred at room temperature overnight. Methanol was added to the reaction solution, and the mixture was purified by HPLC by development with chloroform/methanol to give 25 mg (yield 38%) of the title compound.

$^1$H-NMR (DMSO-d$_6$, 400 MHz): δ 0.91 (t, J=7.3 Hz, 3H), 1.30–1.47 (m, 4H), 3.09–3.13 (m, 2H), 3.97 (s, 3H), 3.99 (s, 3H), 6.58 (t, J=5.6 Hz, 1H), 7.04–7.07 (m, 1H), 7.28–7.31 (m, 1H), 7.38 (s, 1H), 7.54 (s, 1H), 8.14–8.19 (m, 1H), 8.26–8.28 (m, 1H), 8.55 (s, 1H).

Mass analysis, found (ESI-MS, m/z): 415 (M$^+$+1 ).

Example 90

N-(sec-Butyl )-N'-{4-(6,7-dimethoxy-4-quinazolinyl)oxy]-2-fluorophenyl}urea

4-[(6,7-Dimethoxy-4-quinazolinyl)oxy]-2-fluoro-aniline (50 mg) was dissolved in chloroform (3 ml) and triethylamine (0.3 ml), and a solution of triphosgene (47 mg) in chloroform was then added to the solution. The mixture was stirred at room temperature for 30 min. Next, sec-butylamine (25 μl) was added to the reaction solution, and the mixture was further stirred at room temperature overnight. Methanol was added to the reaction solution, and the mixture was purified by HPLC by development with chloroform/methanol to give 12 mg (yield 18%) of the title compound.

$^1$H-NMR (DMSO-d$_6$, 400 MHz): δ 0.89 (t, J=7.6 Hz, 3H), 1.08 (d, J=6.6 Hz, 3H), 1.39–1.48 (m, 2H), 3.58–3.64 (m, 1H), 3.97 (9, 3H), 3.99 (s, 3H), 6.51 (d, J=7.6 Hz, 1H), 7.04–7.08 (m, 1H), 7.30 (dd, J=2.4 Hz, 11.7 Hz, 1H), 7.39 (s, 1H), 7.54 (s, 1H), 8.16–8.22 (m, 2H), 8.56 (s, 1H).

Mass analysis, found (ESI-MS, m/z): 415 (M$^+$+1).

Example 91

N-Allyl-N'-{4-[(6,7-dimethoxy-4-quinazolinyl)oxy]-2-fluorophenyl}urea

4-[(6,7-Dimethoxy-4-quinazolinyl)oxy]-2-fluoro-aniline (50 mg) was dissolved in chloroform (3 ml) and triethylamine (0.3 ml), and a solution of triphosgene (47 mg) in chloroform was then added to the solution. The mixture was stirred at room temperature for 30 min. Next, allylamine hydrochloride (30 mg) was added to the Be reaction solution, and the mixture was further stirred at room temperature overnight. Methanol was added to the reaction solution, and the mixture was purified by HPLC by development with chloroform/methanol to give 18 mg (yield 28%) of the title compound.

$^1$H-NMR (DMSO-d, 400 MHz): δ 3.75–3.79 (m, 2H), 3.97 (s, 3H), 3.99 (s, 3H), 5.08–5.22 (m, 2H), 5.84–5.94 (m, 1H), 6.72 (t, J=5.9 Hz, 1H), 7.06–7.08 (m, 1H), 7.30–7.33 (m, 1H), 7.39 (s, 1H), 7.54 (s, 1H), 8.13–8.18 (m, 1H), 8.40 (s, 1H), 8.56 (s, 1H).

Mass analysis, found (ESI-MS, m/z): 399 (M$^+$+1).

Example 92.

N-{4-[(6,7-Dimethoxy-4-quinazolinyl)oxy]-2-fluorophenyl}-N'-(2 propynyl)urea

4-[(6,7-Dimethoxy-4-quinazolinyl)oxy]-2-fluoro-aniline (50 mg) was dissolved in chloroform (3 ml) and triethylamine (0.3 ml), and a solution of triphosgene (47 mg) in chloroform was then added to the solution. The mixture was stirred at room temperature for 30 min. Next, propargylamine hydrochloride (29 mg) was added to the reaction solution, and the mixture was further stirred at room temperature overnight. A saturated aqueous sodium hydrogencarbonate solution was added to the reaction solution, and the mixture was extracted with chloroform. The chloroform layer was dried over anhydrous sodium sulfate. The solvent was removed by distillation under the reduced pressure. The residue was washed with chloroform to give 21 mg (yield 33%) of the title compound.

$^1$H-NMR. (DMSO-d, 400 MHz): δ 3.15 (t, J=2.4 Hz, 1H), 3.91–3.94 (m, 2H), 3.97 (s, 3H), 3.99 (s, 3H), 7.07–7.11 (m, 1H), 7.33 (dd, J=2.4 Hz, 11.7 Hz, 1H), 7.39 (s, 1H), 7.54 (s, 1H), 8.09–8.15 (m, 1H), 8.47–8.48 (m, 1H), 8.56 (s, 1H).

Mass analysis, found (ESI-MS, m/z): 397 (M$^+$+1).

Example 93

N-(2,4-Difluorobenzyl)-N'-{4-[(6,7-dimethoxy-4-quinazolinyl)oxy]-2fluorophenyl}urea 4-[(6,7-Dimethoxy-4-quinazolinyl)oxy]-2-fluoro-aniline (50 mg) was dissolved in chloroform (3 ml) and triethylamine (0.3 ml), and a solution of triphosgene (47 mg) in chloroform was then added to the solution. The mixture was stirred at room temperature for 30 min. Next, 2,4-difluorobenzylamine (28 μl) was added to the reaction solution, and the mixture was further stirred at room temperature overnight. The precipitated crystal was collected by filtration and was washed to give 20 mg (yield 26%) of the title compound.

$^1$H-NMR (DMSO-d$_6$, 400 MHz): δ 3.97 (s, 3H), 3.99 (s, 3H), 4.34 (d, J=5.8 Hz, 2H), 7.07–7.11 (m, 3H), 7.21–7.27 (m, 1H), 7.30–7.33 (m, 1H), 7.39 (s, 1H), 7.41–7.47 (m, 1H), 7.54 (s, 1H), 8.12–8.16 (m, 1H), 8.46–8.47 (m, 1H), 8.55 (s, 1H).

Mass analysis, found (FD-MS, m/z): 484 (M$^+$).

Example 94

N-(2,4-Difluorophenyl)-N'-{4-[(6,7-dimethoxy4quinazolinyl)oxy]-2fluorophenyl}urea dimethoxy4quinazolinyl)oxy]2fluorophenyl}urea 4-[(6,7-Dimethoxy-4-quinazolinyl)oxy]-2-fluoro-aniline (50 mg) was dissolved in chloroform (3 ml), and 2,4- difluorophenyl isocyanate (29 μl) was then added to the solution. The mixture was stirred at 60° C. overnight. The precipitated crystal was collected by filtration and was washed to give 50 mg (yield 67%) of the title compound.

$^1$H-NMR (DMSO-d$_6$, 400 MHz): δ 3.98 (s, 3H), 3.99 (s, 3H), 7.04–7.08 (m, 1H), 7.13–7.15 (m, 1H), 7.29–7.40 (m, 3H), 7.55 (s, 1H), 8.10–8.23 (m, 2H), 8.57 (s, 1H), 8.97–9.04 (m, 2H).

Mass analysis, found (ESI-MS, m/z); 471 (M$^+$+1).

Example 95

N-{4-[(6,7-Dimethoxy-4-quinazolinyl)oxy]-2-fluorophenyl}-N'-(2methylphenyl)urea

4-[(6,7-Dimethoxy-4-quinazolinyl)oxy]-2-fluoro-aniline (50 mg) was dissolved in chloroform (3 ml) and o-toluyl isocyanate (30 μl) was then added to the solution. The mixture was stirred at 60° C. overnight. Methanol was added to the reaction solution, and the mixture was purified by HPLC by development with chloroform/methanol to give 17 mg (yield 24%) of the title compound.

$^1$H-NMR (DMSO-d$_6$, 400 MHz): δ

2.27 (s, 3H), 3.98 (s, 3H), 3.99 (s, 3H), 6.95–6.98 (m, 1H), 7.12–7.20 (m, 3H), 7.36–7.39 (m, 2H), 7.55 (6, 1H), 7.86 (d, J=7.8 Hz, 1H), 8.21–8.26 (m, 1H), 8.35 (s, 1H), 8.57 (s, 1H), 9.00–9.02 (m, 1H).

Mass analysis, found (ESI-MS, m/z): 449 (M$^+$+1).

Example 96

N-{4-[(6,7-Dimethoxy-4-quinazolinyl)oxy]-2-fluorophenyl}-N'-(2-methoxyphenyl)urea 4-[(6,7-Dimethoxy-4-quinazolinyl)oxy]-2-fluoro-aniline (50 mg) was dissolved in chloroform (3 ml), and 2-methoxyphenyl isocyanate (32 μl) was then added to the solution. The mixture was stirred at 60° C. overnight. Methanol was added to the reaction solution, and the mixture was purified by HPLC by development with chloroform/methanol to give 22 mg (yield 30%) of the title compound.

$^1$H-NMR (DMSO-d$_6$, 400 MHz): δ 3.89 (s, 3H), 3.98 (s, 3H), 3.99 (s, 3H), 6.88–7.04 (ml 3H), 7.11–7.14 (m, 1H), 7.35–7.39 (m, 1H), 7.40 (s, 1H), 7.56 (s, 1H), 8.12–8.15 (m, 1H), 8.19–8.25 (ml 1H), 8.57 (s, 1H), 8.75–8.78 (m, 1H), 9.26–9.29 (m, 1H).

Mass analysis, found (ESI-MS, m/z): 465 (M$^+$+1).

Example 97

N-{4-[(6,7-Dimethoxy-4-quinazolinyl)oxy]-3-methylphenyl}-N'-propylurea

4-[(6,7-Dimethoxy-4-quinazolinyl)oxy]-3-methyl-aniline (50 mg) was dissolved in chloroform (3 ml) and triethylamine (0.2 ml), and a solution of triphosgene (48 mg) in chloroform was then added to the solution. The mixture was stirred at room temperature for 30 min. Next, propylamine (20 μl) was added to the reaction solution, and the mixture was further stirred at room temperature overnight. Methanol was added to the reaction solution, and the mixture was purified by HPLC by development with chloroform/methanol to give 30 mg (yield 47%) of the title compound.

$^1$H-NMR (DMSO-d$_6$, 400 MHz): δ 0.89 (t, J=7.5 Hz, 3H), 1.41–1.50 (m, 2H), 2.03 (s, 3H), 3.03–3.08 (m, 2H), 3.98 (s, 3H), 3.99 (s, 3H), 6.13 (t, J=5.4 Hz, 1H), 7.04 (d, J=8.5 Hz, 1H), 7.28 (dd, J=2.4 Hz, 8.5 Hz, 1H), 7.36 (d, J=2.4 Hz, 1H), 7.38 (s, 1H), 7.58 (s, 1H), 8.39 (s, 1H), 8.50 (s, 1H).

Mass analysis, found (ESI-MS, m/z): 397 (M$^+$+1).

Example 98

N-Butyl-N'-{4-[(6,7-dimethoxy-4-quinazolinyl)oxy]-3-methylphenyl}urea

4-[(6,7-Dimethoxy-4-quinazolinyl)oxy]-3-methyl-aniline (50 mg) was dissolved in chloroform (3 ml) and triethylamine (0.2 ml), and a solution of triphosgene (48 mg) in chloroform was then added to the solution. The mixture was stirred at room temperature for 30 min. Next, butylamine (24 μl) was added to the reaction solution, and the mixture was further stirred at room temperature overnight. Methanol was added to the reaction solution, and the mixture was purified by HPLC by development with chloroform/methanol to give 31 mg (yield 47%) of the title compound.

$^1$H-NMR (DMSO-d$_6$, 400 MHz): δ 0.91 (t, J=7.3 Hz, 3H), 1.29–1.46 (m, 4H), 2.03 (s, 3H), 3.07–3.12 (m, 2H), 3.98 (s, 3H), 3.99 (s, 3H), 6.11 (t, J=5.6 Hz, 1H), 7.05 (d, J=8.8 Hz, 1H), 7.27 (dd, J=2.3 Hz, 8.5 Hz, 1H), 7.36 (d, J=2.4 Hz, 1H), 7.38 (s, 1H), 7.58 (s, 1H), 8.39 (s, 1H), 8.51 (s, 1H).

Mass analysis, found (ESI-MS, m/z): 411 (M$^+$+1).

Example 99

N-(2,4-Difluorophenyl)-N'-{4-[(6,7-dimethoxy-4-quinazolinyl)oxy]-3-methylphenyl}urea 4-[(6,7-Dimethoxy-4-quinazolinyl)oxy]-3-methyl-aniline (50 mg) was dissolved in chloroform (3 ml), and 2,4-difluorophenyl isocyanate (23 μl) was then added to the solution. The mixture was heated under reflux overnight. The precipitated crystal was collected by filtration and was washed to give 59 mg (yield 79%) of the title compound.

$^1$H-NMR (DMSO-d$_6$, 400 MHz): δ 2.07 (s, 3H), 3.99 (s, 3H), 3.99 (s, 3H), 7.03–7.08 (m, 1H), 7.14 (d, J=8.5 Hz, 1H), 7.29–7.37 (m, 2H), 7.39 (s, 1H), 7.43 (d, J=2.4 Hz, 1H), 7.60 (s, 1H), 8.07–8.14 (m, 1H), 8.52 (s, 1H), 9.03–9.05 (m, 1H).

Mass analysis, found (ESI-MS, m/z): 467 (M$^+$+1).

Example 100

N-{4-[(6,7-Dimethoxy-4-quinazolinyl)oxy]-3-methylphenyl}-N'-(4-fluorophenyl)urea 4-[(6,7-Dimethoxy-4-quinazolinyl)oxy]-3-methyl-aniline (50 mg) was dissolved in chloroform (3 ml), and p-fluorophenyl isocyanate (22 μl) was then added to the solution. The mixture was heated under reflux overnight. The precipitated crystal was collected by filtration and was washed to give 42 mg (yield 58%) of the title compound.

$^1$H-NMR (DMSO-d$_6$, 400 MHz): δ 2.07 (s, 3H), 3.98 (s, 3H), 3.99 (s, 3H), 7.10–7.14 (m, 3H), 7.35 (dd, J=2.4 Hz, 8.5 Hz, 1H), 7.39 (s, 1H), 7.43 (d, J=2.4 Hz, 1H), 7.46–7.49 (m, 2H), 7.59 (s, 1H), 8.51 (s, 1H), 8.66 (s, 1H), 8.70 (s, 1H).

Mass analysis, found (ESI-MS, m/z): 449 (M$^+$+1).

Example 101

N-{4-[(6,7Dimethoxy-4-quinazolinyl)oxy ]-3-methylphenyl{-N'- (2-methoxyphenyl)urea 4-[(6,7-Dimethoxy-4-quinazolinyl)oxy]-3-methyl-aniline (50 mg) was dissolved in chloroform (3 ml), and 2-methoxyphenyl isocyanate (26 μl) was then added to the solution. The mixture was heated under reflux overnight. Methanol was added to the reaction solution, and the mixture was purified by HPLC by development with chloroform/methanol to give 41 mg (yield 55%) of the title compound.

$^1$H-NMR (DMSO-$d_6$, 400 MHz): δ 2.07 (s, 3H), 3.89 (s, 3H), 3.99 (s, 3H), 3.99 (9, 3H), 6.88–6.97 (m, 2H), 7.01–7.03 (m, 1H), 7.12 (d, J=8.5 Hz, 1H), 7.35 (dd, J=2.4 Hz, 8.5 Hz, 1H), 7.39 (s, 1H), 7.44 (d, J=2.4 Hz, 1H), 7.60 (s, 1H), 8.13–8.15 (m, 1H), 8.23 (s, 1H), 8.52 (s, 1H), 9.33 (s, 1H).

Mass analysis, found (ESI-MS, m/z): 461 (M$^+$+1).

Example 102

N-{4-[(6,7-Dimethoxy-4-quinazolinyl)oxy]-2-methylphenyl}-N'-propylurea

4-[(6,7-Dimethoxy-4-quinazolinyl)oxy]-2-methyl-aniline (50 mg) was dissolved in chloroform (3 ml) and triethylamine (0.2 ml), and a solution of triphosgene (48 mg) in chloroform was then added to the solution. The mixture was stirred at room temperature for 30 min. Next, propylamine (20 1l) was added to the reaction solution, and the mixture was further stirred at room temperature overnight. Methanol was added to the reaction solution, and the mixture was purified by HPLC by development with chloroform/methanol to give 30 mg (yield 47%) of the title compound.

$^1$H-NMR (DMSO-$d_6$, 400 MHz): δ 0.90 (t, J=7.3 Hz, 3H), 1.42–1.51 (m, 2H), 2.21 (s, 3H), 3.04–3.09 (m, 2H), 3.97 (s, 3H), 3.99 (s, 3H), 6.53 (t, J=5.6 Hz, 1H), 7.02 (dd, J=2.7 Hz, 8.8 Hz, 1H), 7.08 (d, J=2.7 Hz, 1H), 7.37 (s, 1H), 7.54 (s, 1H), 7.65 (s, 1H), 7.85 (d, J=8.8 Hz, 1H), 8.53 (s, 1H).

Mass analysis, found (ESI-MS, m/z): 397 (M$^+$+1).

Example 103

N-Butyl-N'-{4-[(6,7-dimethoxy-4-quinazolinyl)oxy]2methylphenyl}urea

4-[(6,7-Dimethoxy-4-quinazolinyl)oxy]-2-methyl-aniline (50 mg) was dissolved in chloroform (3 ml) and triethylamine (0.2 ml), and a solution of triphosgene (48 mg) in chloroform was then added to the solution. The mixture was stirred at room temperature for 30 min. Next, butylamine (24 μl) was added to the reaction solution, and the mixture was further stirred at room temperature overnight. Methanol was added to the reaction solution, and the mixture was purified by HPLC by development with chloroform/methanol to give 37 mg (yield 56%) of the title compound.

$^1$H-NMR (DMSO-$d_6$, 400 MHz): δ 0.92 (t, J=7.1 Hz, 3H), 1.31–1.48 (m, 4H), 2.21 (s, 3H), 3.08–3.13 (m, 2H), 3.97 (s, 3H), 3.99 (s, 3H), 6.50 (t, J=5.4 Hz, 1H), 7.02 (dd, J=2.7 Hz, 8.8 Hz, 1H), 7.08 (d, J=2.7 Hz, 1H), 7.37 (s, 1H), 7.54 (s, 1H), 7.64 (s, 1H), 7.86 (d, J=8.8 Hz, 1H), 8.53 (s, 1H).

Mass analysis, found (ESI-MS, m/z): 411 (M$^+$+1).

Example 104

N-(2,4-Difluorophenyl)-N'-{4-[(6,7-dimethoxy-4-quinazolinyl)oxy]-2-methylphenyl}urea 4-[(6,7-Dimethoxy-4-quinazolinyl)oxy]-2-methyl-aniline (50 mg) was dissolved in chloroform (3 ml), and 2,4-difluorophenyl isocyanate (23 μl) was then added to the solution. The mixture was heated under reflux overnight. The precipitated crystal was collected by filtration and was washed to quantitatively give the title compound.

$^1$H-NMR (DMSO-$d_6$, 400 MHz): δ 2.29 (s, 3H), 3.98 (s, 3H), 3.99 (s, 3H), 7.03–7.11 (m, 2H), 7.16 (d, J=2.7 Hz, 1H), 7.29–7.35 (m, 1H), 7.38 (s, 1H), 7.55 (s, 1H), 7.87–7.90 (m, 1H), 8.13–8.19 (m, 1H), 8.36–8.39 (m, 1H), 8.55 (s, 1H), 8.92–8.95 (m, 1H).

Mass analysis, found (ESI-MS, m/z): 467 (M$^+$+1).

Example 105

N-{4-[(6,7-Dimethoxy-4-(quinazolinyl)oxy]-2-methylphenyl}-N'-(4-fluorophenyl)urea 4-[(6,7-Dimethoxy-4-quinazolinyl)oxy]-2-methyl-aniline (50 mg) was dissolved in chloroform (3 ml), and p-fluorophenyl isocyanate (22 μl) was then added to the solution. The mixture was heated under reflux overnight. The precipitated crystal was collected by filtration and was washed to quantitatively give the title compound.

$^1$H-NMR (DMSO-$d_6$, 400 MHz): δ 2.28 (s, 3H), 3.98 (s, 3H), 3.99 (s, 3H), 7.08–7.15 (m, 4H), 7.38 (s, 1H), 7.47–7.50 (m, 2H), 7.55 (8, 1H), 7.84–7.88 (m, 1H), 7.98 (s, 1H), 8.55 (s, 1H), 9.03–9.05 (m, 1H).

Mass analysis, found (ESI-MS, m/z): 449 (M$^+$+1).

Example 106

N-{4-[(6,7-Dimethoxy-4-quinazolinyl)oxy]-$^2$-methylphenyl}-N'-(2-methoxyphenyl)urea 4-[(6,7-Dimethoxy-4-quinazolinyl)oxy]-2-methyl-aniline (50 mg) was dissolved in chloroform (3 ml), and 2-methoxyphenyl isocyanate (26 μl) was then added to the solution. The mixture was heated under reflux overnight. The precipitated crystal was collected by filtration and was washed to give 70 mg (yield 95%) of the title compound.

$^1$H-NMR (DMSO-$d_5$, 400 MHz): δ 2.29 (s, 3H), 3.90 (s, 3H), 3.98 (s, 3H), 3.99 (s, 3H), 6.87–6.97 (m, 2H), 7.02–7.04 (m, 1H), 7.08 (dd, J=2.9 Hz, 8.8 Hz, 1H), 7.14 (d, J=2.7 Hz, 1H), 7.38 (s, 1H), 7.55 (s, 1H), 7.84 (d, J=8.8 Hz, 1H), 8.13–8.15 (m, 1H), 8.55 (s, 1H), 8.58 (s, 1H), 8.61–8.62 (m, 1H).

Mass analysis, found (ESI-MS, m/z): 461 (M$^+$+1).

Example 107

N-{4-4-[(6,7-Dimethoxy-4-quinazolinyl]-2-nitrophenyl}-N'-propylurea

4-[(6,7-Dimethoxy-4-quinazolinyl)oxy]-2-nitro-aniline (50 mg) was dissolved in chloroform (10 ml) and triethylamine (0.2 ml), and a solution of triphosgene (43 mg) in chloroform was then added to the solution. The mixture was stirred at room temperature for 30 min. Next, propylamine (18 μl) was added to the reaction solution, and the mixture was further stirred at room temperature overnight. Methanol was added to the reaction solution, and the mixture was purified by HPLC by development with chloroform/methanol to give 24 mg (yield 38%) of the title compound.

$^1$H-NMR (DMSO-$d_6$, 400 MHz): δ 0.91 (t, J=7.6 Hz, 3H), 1.45–1.51 (m, 2H), 3.06–3.09 (m, 2H), 3.98 (s, 3H), 4.00 (s,

3H), 7.40 (s, 1H), 7.52 (br, 1H), 7.58 (s, 1H), 7.67–7.70 (m, 1H), 8.04–8.06 (m, 1H), 8.38–8.41 (m, 1H), 8.57 (s, 1H), 9.35 (s, 1H).

Mass analysis, found (ESI-MS, m/z): 428 (M$^+$+1).

Example 108

N-Butyl-N'-{4-[(6,7-dimethoxy-4-quinazolinyl)oxy]-2-nitrophenyl}urea

4-[(6,7-Dimethoxy-4-quinazolinyl)oxy]-2-nitro-aniline (50 mg) was dissolved in chloroform (10 ml) and triethylamine (0.2 ml), and a solution of triphosgene (43 mg) in chloroform was then added to the solution. The mixture was stirred at room temperature for 30 min. Next, butylamine (22 μl) was added to the reaction solution, and the mixture was further stirred at room temperature overnight. Methanol was added to the reaction solution, and the mixture was purified by HPLC by development with chloroform/methanol to give 15 mg (yield 23%) of the title compound.

$^1$H-NMR (DMSO-d$_6$, 400 MHz): δ 0.91 (t, J=7.3 Hz, 3H), 1.30–1.49 (m, 4H), 3.10–3.15 (m, 2H), 3.98 (s, 3H), 4.00 (s, 3H), 7.40 (s, 1H), 7.51 (br, 1H), 7.57 (s, 1H), 7.68 (dd, J=2.9 Hz, 9.3 Hz, 1H), 8.05 (d, J=2.9 Hz, 1H), 8.40 (d, J=9.2 Hz, 1H), 8.57 (s, 1H), 9.35 (s, 1H).

Mass analysis, found (ESI-MS, m/z): 442 (M$^+$+1).

Example 109

N-{2-Chloro-4-[(6,7-dimethoxy-4-quinazolinyl)oxy]phenyl}-N-methoxymethyl-N'-propylurea N-{2-Chloro-4-[(6,7-dimethoxy-4-quinazolinyl)oxy]phenyl}-N'-propylurea (100 mg) was dissolved in anhydrous tetrahydrofuran (30 ml), and sodium hydride (60 wt %, 88 mg) was added to the solution. The mixture was stirred at room temperature for 15 min. Next, chloromethyl methyl ether (67 μl) was added to the reaction solution, and the mixture was stirred at room temperature for additional 30 min. The solvent was removed by distillation under the reduced pressure, and water was added to the residue. The mixture was extracted with chloroform. The chloroform layer was dried over anhydrous sodium sulfate. The solvent was removed by distillation under the reduced pressure. The residue was purified by HPLC by development with chloroform/methanol to give 18 mg (yield 18%) of the title compound.

$^1$H-NMR (DMSO-d$_6$, 400 MHz): δ 0.89 (t, J=7.6 Hz, 3H), 1.46–1.55 (m, 2H), 3.20 (br, 2H), 3.48 (s, 3H), 4.07 (s, 3H), 4.08 (s, 3H), 4.54 (br, 2H), 7.29 (dd, J=2.7 Hz, 8.5 Hz, 1H), 7.37 (s, 1H), 7.47 (d, J=8.8 Hz, 1H), 7.50 (s, 1H), 7.50 (d, J=2.7 Hz, 1H), 8.66 (s, 1H).

Mass analysis, found (ESI-MS, m/z): 461 (K+$^+$+1).

Example 110

N-Acetyl-N-{2-chloro-4-[(6,7-dimethoxy-4-quinazolinyl)oxy]phenyl-N'-propylurea

N-{2-Chloro-4-[(6,7-dimethoxy-4-quinazolinyl)oxy]phenyl}-N'-propylurea (100 mg) was dissolved in anhydrous tetrahydrofuran (30 ml), and sodium hydride (60 wt %, 88 mg) was added to the solution. The mixture was stirred at room temperature for 15 min. Next, acetyl chloride (63 μl) was added to the reaction solution, and the mixture was stirred at room temperature for additional 2 hr. The solvent was removed by distillation under the reduced pressure, and water was added to the residue. The mixture was extracted with chloroform. The chloroform layer was dried over anhydrous sodium sulfate. The solvent was removed by distillation under the reduced pressure. The residue was purified by HPLC by development with chloroform/acetone to give 27 mg (yield 26%) of the title compound.

$^1$H-NMR (DMSO-d$_6$, 400 MHz): δ 0.98 (t, J=7.3 Hz, 3H), 1.59–1.68 (m, 2H), 2.04 (s, 3H), 3.27–3.36 (m, 2H), 4.07 (s, 3H), 4.08 (s, 3H), 7.31–7.33 (m, 1H), 7.35 (s, 1H), 7.41 (d, J=9.0 Hz, 1H), 7.50–7.51 (m, 2H), 8.63 (s, 1H), 9.08 (br, 1H).

Mass analysis, found (ESI-MS, m/z): 459 (M$^+$+1).

Example 111

N'-{2-Chloro-4-[(6,7-dimethoxy-4-quinazolinyl)oxy]phenyl}-N-methyl-N-propylurea

2-Chloro-4-[(6,7-dimethoxy-4-quinazolinyl)oxy]-aniline (56 mg) was dissolved in chloroform (4 ml) and triethylamine (0.3 ml), and a solution of triphosgene (50 mg) in chloroform was then added to the solution. The mixture was stirred at room temperature for 30 min. Next, N-methylpropylamine (26 μl) was added to the reaction solution, and the mixture was stirred at room temperature for additional one hr. Methanol was added to the reaction solution, and the mixture was purified by HPLC by development with chloroform/methanol. The solvent was removed by distillation, and the resultant crystal was washed with hexane to give 42 mg (yield 58%) of the title compound.

$^1$H-NMR (DMSO-d$_6$, 400 MHz): δ 0.99 (t, J=7.3 Hz, 3H), 1.64–1.74 (m, 2H), 3.08 (s, 3H), 3.34 (t, J=7.6 Hz, 2H), 4.07 (s, 3H), 4.08 (s, 3H), 7.00 (s, 1H), 7.17 (dd, J=2.7 Hz, 9.3 Hz, 1H), 7.31 (d, J=2.7 Hz, 1H), 7.38 (s, 1H), 7.53 (s, 1H), 8.41 (d, J=9.0 Hz, 1H), 8.64 (s, 1H).

Mass analysis, found (ESI-MS, m/z): 431 (M$^+$+1).

Example 112

N'-{2-Chloro-4-[(6,7-dimethoxy-4-quinazolinyl)oxy]phenyl}-N-ethyl-N-propylurea

2-Chloro-4-[(6,7-dimethoxy-4-quinazolinyl)oxy]-aniline (80 mg) was dissolved in chloroform (3 ml) and triethylamine (0.3 ml), and a solution of triphosgene (72 mg) in chloroform was then added to the solution. The mixture was stirred at room temperature for 15 min. Next, N-ethylpropylamine (44 μl) was added to the reaction solution, and the mixture was stirred at room temperature for additional 30 min. Methanol was added to the reaction solution, and the mixture was purified by HPLC by development with chloroform/methanol. The solvent was removed by distillation. The resultant crystal was washed with hexane to give 40 mg (yield 37%) of the title compound.

$^1$H-NMR (DMSO-d, 400 MHz): δ 1.00 (t, J=7.3 Hz,3H), 1.28 (t, J=7.1 Hz, 3H), 1.69–1.74 (m, 2H), 3.32 (t, J=7.6 Hz, 2H), 3.43 (q, J=7.1 Hz, 2H), 4.07 (s, 3H), 4.07 (s, 3H), 7.02

(s, 1H), 7.17 (dd, J=2.9 Hz, 9.2 Hz, 1H), 7.31 (d, J=2.7 Hz, 1H), 7.36 (s, 1H), 7.53 (s, 1H), 8.42 (d, J=9.0 Hz, 1H), 8.63 (s, 1H).

Mass analysis, found (ESI-MS, m/z): 445 (M$^+$+1).

Example 113

N'-{2-Chloro-4-[(6,7-dimethoxy-4-quinazolinyl)oxy]phenyl}-N,N-dipropylurea

2-Chloro-4-[(6,7-dimethoxy-4-quinazolinyl)oxy]-aniline (100 mg) was dissolved in chloroform (3 ml) and triethylamine (0.3 ml), and a solution of triphosgene (90 mg) in chloroform was then added to the solution. The mixture was stirred at room temperature for 15 min. Next, dipropylamine (62 μl) was added to the reaction solution, and the mixture was stirred at room temperature for additional 30 min. Methanol was added to the reaction solution, and the mixture was purified by HPLC by development with chloroform/methanol. The solvent was removed by distillation, and the resultant crystal was washed with hexane to give 48 mg (yield 35%) of the title compound.

$^1$H-NMR (DMSO-d$_6$, 400 MHz): δ 0.99 (t, J=7.3 Hz, 6H), 1.66–1.76 (m, 4H), 3.32 (t, J=7.8 Hz, 4H), 4.07 (s, 3H), 4.07 (s, 3H), 7.03 (s, 1H), 7.16 (dd, J=2.7 Hz, 9.3 Hz, 1H), 7.31 (d, J=2.7 Hz, 1H), 7.34 (s, 1H), 7.52 (s, 1H), 8.43 (d, J=9.0 Hz, 1H), 8.63 (s, 1H).

Mass analysis, found (ESI-MS, m/z): 459 (M$^+$+1).

Example 114

N-Butyl-N'-4-{chloro-4-[(6,7-dimethoxy-4-quinazoliny)oxy]phenyl}-N-methylurea

2-Chloro-4-[(6,7-dimethoxy-4-quinazolinyl)oxy]-aniline (80 mg) was dissolved in chloroform (3 ml) and triethylamine (0.3 ml), and a solution of triphosgene (72 mg) in chloroform was then added to the solution. The mixture was stirred at room temperature for 15 min. Next, N-methylbutylamine (43 μl) was added to the reaction solution, and the mixture was stirred at room temperature for additional 30 min. Methanol was added to the reaction solution, and the mixture was purified by HPLC by development with chloroform/methanol. The solvent was removed by distillation, and the resultant crystal was washed with hexane to give 26 mg (yield 24%) of the title compound.

$^1$H-NMR (DMSO-d$_6$, 400 MHz): δ 0.99 (t, J=7.3 Hz, 3H), 1.38–1.43 (m, 2H), 1.62–1.66 (m, 2H), 3.07 (s, 3H), 3.40 (t, J=7.3 Hz, 2H), 4.07 (s, 3H), 4.07 (s, 3H), 7.00 (s, 1H), 7.17 (dd, J=2.7 Hz, 9.3 Hz, 1H), 7.31 (d, J=2.7 Hz, 1H), 7.36 (s, 1H), 7.53 (s, 1H), 8.41 (d, J=9.3 Hz, 1H), 8.63 (s, 1H).

Mass analysis, found (ESI-MS, m/z): 445 (M$^+$+1).

Example 115

N'-{2-Chloro-4-[(6,7-dimethoxy-4-quinazolinyl)oxy]phenyl}-N-(4-chlorophenyl)-N-methylurea 2-Chloro-4-[(6,7-dimethoxy-4-quinazolinyl)oxy]-aniline (80 mg) was dissolved in chloroform (3 ml) and triethylamine (0.3 ml), and a solution of triphosgene (72 mg) in chloroform was then added to the solution. The mixture was stirred at room temperature for 15 min. Next, 4-chloro-N-methylaniline (35 μl) was added to the reaction solution, and the mixture was heated under reflux for additional 30 min. Methanol was added to the reaction solution, and the mixture was purified by HPLC by development with chloroform/methanol, and the solvent was removed by distillation. The resultant crystal was washed with ether to give 83 mg (yield 69%) of the title compound.

$^1$H-NMR (DMSO-d$_6$, 400 MHz): δ 3.36 (s, 3H), 4.06 (s, 3H), 4.07 (s, 3H), 6.89 (s, 1H), 7.17 (dd, J=2.7 Hz, 9.0 Hz, 1H), 7.23 (d, J=2.7 Hz, 1H), 7.33–7.35 (m, 3H), 7.48–7.50 (m, 3H), 8.41 (d, J=9.0 HZ, 1H), 8.61 (s, 1H).

Mass analysis, found (ESI-MS, m/z): 499 (M$^+$+1).

Example 116

N'-{2-Chloro-4-[(6,7-dimethoxy-4-quinazolinyl)oxy]phenyl}-N,N-diethylurea

2-Chloro-4-[(6,7-dimethoxy-4-quinazolinyl)oxy]-aniline (50 mg) was dissolved in chloroform (2 ml) and triethylamine (0.5 ml), and a solution of triphosgene (48 mg) in chloroform was then added to the solution. The mixture was stirred at room temperature for 30 min. Next, diethylamine (0.5 ml) was added to the reaction solution, and the mixture was further stirred at room temperature overnight. Methanol was added to the reaction solution, and the mixture was purified by HPLC by development with chloroform/methanol to give 37 mg (yield 93%) of the title compound.

$^1$H-NMR (CDCl$_3$, 400 MHz): δ 1.30 (t, J=7.1 Hz, 6H), 3.44 (q, J=7.1 Hz, 4H), 4.12 (s, 3H), 4.20 (s, 3H), 7.16 (dd, J=2.7 Hz, 9.0 Hz, 1H), 7.27 (s, 1H), 7.31 (d, J=2.7 Hz, 1H), 7.59 (s, 1B), 8.15 (s, 1H), 8.48 (d, J=9.0 Hz, 1H), 8.81 (s, 1H).

Mass analysis, found (ESI-MS, m/z): 431 (M$^+$+1).

Example 117

N-{2-Chloro-4-r (6,7-dimethoxy-4-quinazolinyl)oxy]phenyl}-N'-methylurea

2-Chloro-4-[(6,7-dimethoxy-4-quinazolinyl)oxy]-aniline (50 mg) was dissolved in chloroform (2 ml) and triethylamine (0.5 ml), and a solution of triphosgene (48 mg) in chloroform was then added to the solution. The mixture was stirred at room temperature for 30 min. Next, the reaction solution was cooled to −78° C., and methylamine hydrochloride (130 mg) was added to the cooled reaction solution. The temperature of the mixture was spontaneously raised, and the mixture was further stirred at room temperature overnight. Methanol was added to the reaction solution, and the mixture was purified by HPLC by development with chloroform/methanol to give 41 mg (yield 70%) of the title compound.

$^1$H-NMR (DMSO-d6, 400 MHz): δ 2.68 (d, J=4.4 Hz, 3H), 3.97 (s, 3H), 3.99 (s, 3H), 6.86–6.88 (m, 1H), 7.21 (dd, J=2.7 Hz, 9.0 Hz, 1H), 7.37 (s, 1H), 7.43 (d, J=2.7 Hz, 1H), 7.53 (s, 1H), 8.07 (s, 1H), 8.17 (d, J=9.0 Hz, 1H), 8.54 (s, 1H).

Mass analysis, found (ESI-MS, m/z): 389 (M$^+$+1).

Example 118

N'-{2-Chloro-4-[(6,7-dimethoxy-4-quinazolinyl)oxy]phenyl}-N,N-dimethylurea

2-Chloro-4-[(6,7-dimethoxy-4-quinazolinyl)oxy]-aniline (50 mg) was dissolved in chloroform (2 ml) and triethylamine (0.5 ml), and a solution of triphosgene (48 mg) in chloroform was then added to the solution. The mixture was stirred at room temperature for 30 min. Next, the reaction solution was cooled to −78° C. and dimethylamine hydrochloride (250 mg) was added to the cooled reaction solution. The temperature of the mixture was spontaneously raised, and the mixture was further stirred at room temperature overnight. Methanol was added to the reaction solution, and the mixture was purified by HPLC by development with chloroform/methanol to give 33 mg (yield 53%) of the title compound.

$^1$H-NMR (CDCl$_3$, 400 MHz): δ 3.11 (s, 6H), 4.12 (s, 3H), 4.20 (s, 3H), 7.05 (s, 1H), 7.17 (dd, J=2.4 Hz, 9.3 Hz, 1H), 7.31 (d, J=2.4 Hz, 1H), 7.59 (s, 1H), 8.15 (s, 1H), 8.46 (d, J=9.3 Hz, 1H), 8.82 (s, 1H).

Mass analysis, found (ESI-MS, m/z): 403 (M$^+$+1).

Example 119

N-(2-Chloro-4-{[6-methoxy-7-(3-morpholinopropoxy)-4-quinazolinyl]oxy}phenyl)-N'-propyl-urea N-{2-Chloro-4-[(7-hydroxy-6-methoxy-4-quinazolinyl)oxy]phenyl}-N'-propylurea (75 mg), potassium carbonate (51 mg), and 1,3-dibromopropane (76 μl) was dissolved in N,N-dimethylformamide (4 ml), and the solution was stirred at room temperature for 3 hr. The solvent was removed by distillation under the reduced pressure. Water was added to the residue, and the mixture was extracted with chloroform. The organic layer was dried over anhydrous sodium sulfate. The solvent was removed by distillation under the reduced pressure. The residue was washed with ether to give 74 mg (yield 78%) of N-(4-{[7-(3-bromopropoxy)-6-methoxy-4-quinazolinyl ]-oxy}-2-chlorophenyl)-N'-propylurea as an intermediate. The intermediate (74 mg), potassium carbonate (51 mg), and morpholine (130 μl ) were dissolved in N,N-dimethylformamide (4 ml), and the solution was stirred at room temperature overnight. The solvent was removed by distillation under the reduced pressure. A saturated aqueous sodium hydrogencarbonate solution was added to the residue, and the mixture was extracted with chloroform. The organic layer was dried over anhydrous sodium sulfate. The solvent was removed by distillation under the reduced pressure. The residue was purified by chromatography on silica gel by development with chloroform/methanol to give 49 mg (yield 63%) of the title compound.

$^1$H-NMR (CDCl$_3$, 400 MHz): δ 0.89 (t, J=7.44 Hz, 3H), 1.41–1.50 (m, 2H), 1.97 (t, J=6.83 Hz, 1H), 2.33–2.49 (m, 4H), 3.04–3.09 (m, 2H), 3.32–3.38 (m, 4H), 3.52–3.68 (m, 3H), 4.03 (s, 3H), 4.23–4.29 (m, 1H), 4.32 (t, J=5.89 Hz, 1H), 6.98 (t, J=5.49 Hz, 1H), 7.21 (dd, J=2.68, 9.03 Hz, 1H), 7.36 (s, 1H), 7.46 (d, J=2.68 Hz, 1H), 7.53 (d, J=7.81 Hz, 1H), 8.03 (s, 1H), 8.18 (d, J=9.27 Hz, 1H), 8.54 (d, J=4.39 Hz, 1H).

Mass analysis, found (ESI-MS, m/z): 529 (M$^+$).

Example 120

N-(2-Chloro4-[6-methoxy-7-(2-morpholinoethoxy)-4-quinazolinyl]oxy}phenyl)-N'-propyl-urea N-{2-Chloro-4-[(7-hydroxy-6-methoxy-4-quinazolinyl)oxy]phenyl}-N'-propylurea (72 mg), potassium carbonate (30 mg), and 1,2-dibromoethane (62 μl) were dissolved in N,N-dimethylformamide (4 ml), and the solution was stirred at room temperature for 3 hr. The solvent was removed by distillation under the reduced pressure. Water was added to the residue, and the mixture was extracted with chloroform. The organic layer was dried over anhydrous sodium sulfate. The solvent was removed by distillation under the reduced pressure. The residue was washed with ether to give 40 mg (yield 45%) of N-(4-{[7-(2-bromoethoxy)-6-methoxy-4-quinazolinyl ]-oxy}-2-chlorophenyl)-N'-propylurea as an intermediate. The intermediate (45 mg), potassium carbonate (30 mg), and morpholine (80 μl) were dissolved in N,N-dimethylformamide (2 ml), and the solution was stirred at room temperature overnight. The solvent was removed by distillation under the reduced pressure. A saturated aqueous sodium hydrogencarbonate solution was added to the residue, and the mixture was extracted with chloroform. The organic layer was dried over anhydrous sodium sulfate, and the solvent was removed by distillation under the reduced pressure. The residue was purified by chromatography on silica gel by development with chloroform/methanol to give 42 mg (yield 56%) of the title compound.

$^1$H-NMR (CDCl$_3$, 400 MHz): δ 0.89 (t, J=7.32 Hz, 3H), 1.43–1.49 (m, 2H), 2.32–2.38 (m, 2H), 2.66 (bs, 1H), 2.79 (t, J=5.86 Hz, 1H), 3.04–3.09 (m, 2H), 3.29–3.36 (m, 4H), 3.53 (m, 1H), 3.57–3.59 (m, 2H), 3.96 (s, 3H), 4.31 (t, J=5.85 Hz, 1H), 6.98 (m, 1H), 7.21–7.23 (m, 1H), 7.41 (s, 1H), 7.46–7.47 (m, 1H), 7.55 (d, J=12.69 Hz, 1H), 8.03 (s, 1H), 8.19 (d, J=9.27 Hz, 1H), 8.55 (d, J=5.37 Hz, 1H).

Mass analysis, found (ESI-MS, m/z): 517 (M$^+$+1).

Example 121

N-(2-Chloro-4-{[7-(3-hydroxypropoxy)-6-methoxy4-quinazolinyl]oxy}phenyl)-N'-propylurea N-{2-Chloro-4-[(7-hydroxy-6-methoxy-4-quinazolinyl)oxy]phenyl}-N'-propylurea (55 mg), potassium carbonate (20 mg), and 3-bromo-1-propanol (62 μl) were dissolved in N,N-dimethylformamide (4 ml), and the solution was stirred at room temperature for 3 hr. The solvent was removed by distillation under the reduced pressure. Water was added to the residue, and the mixture was extracted with chloroform. The organic layer was dried over anhydrous sodium sulfate, and the solvent was removed by distillation under the reduced pressure. The residue was purified by chromatography on silica gel by development with chloroform/methanol to give 25 mg (yield 40%) of the title compound.

$^1$H-NMR (CDCl$_3$, 400 MHz): δ 0.91 (t, J=7.44 Hz, 3H), 1.24 (bs, 1H), 1.43–1.52 (m, 2H), 1.97 (t, J=6.22 Hz, 2H), 3.06–3.11 (m, 2H), 3.56–3.71 (m, 2H), 3.97 (s, 3H), 4.27 (m, 2H), 6.99 (t, J=5.62 Hz, 1H), 7.23 (dd, J=2.68, 9.03 Hz, 1H), 7.38 (d, J=9.03 Hz, 1H), 7.47 (d, J=2.68 Hz, 1H), 7.54 (s, 1H), 8.05 (s, 1H), 8.20 (d, J=9.03 Hz, 1H), 8.55 (s, 1H).

Mass analysis, found (ESI-MS, m/z): 461 (M$^+$+1).

Example 122

N-(2-Chloro-4-{[7-(2-hydroxyethoxy)-6-methoxy-4-quinazolinyl]oxy}phenyl)-N'-propylurea N-{2-Chloro-4-[(7-hydroxy-6-methoxy-4-quinazolinyl)oxy]phenyl}-N'-propylurea (50 mg), potassium carbonate (30 mg), and ethylenebromohydrin (44 μl) were dissolved in N,N-dimethylformamide (4 ml), and the solution was stirred at room temperature for 3 hr. The solvent was removed by distillation under the reduced pressure. Water was added to the residue, and the mixture was extracted with chloroform. The organic layer was dried over anhydrous sodium sulfate. The solvent was removed by distillation under the reduced pressure. The residue was purified by chromatography on silica gel by development with chloroform/methanol to give 12 mg (yield 22%) of the title compound.

$^1$H-NMR (CDCl$_3$, 400 MHz): δ 0.91 (t, J=7.44 Hz, 3H), 1.42–1.49 (m, 2H), 3.06–3.11 (m, 2H), 3.80–3.83 (m, 2H), 3.98 (s, 3H), 4.22 (t, J=4.64 Hz, 2H), 4.98 (t, J=5.37 Hz, 1H), 6.99 (t, J=5.37 Hz, 1H), 7.33 (dd, J=2.69 Hz, 9.03 Hz, 1H), 7.39 (s, 1H), 7.48 (d, J=2.68 Hz, 1H), 7.55 (s, 1H), 8.05 (s, 1H), 8.19 (d, J=9.27 Hz, 1H), 8.55 (s, 1H).

Mass analysis, found (ESI-MS, m/z): 447 (M$^+$+1).

Example 123

N-(2-Chloro-4-{[6-methoxy-7-(4 pyridylmethoxy)-4-quinazolinyl]oxy}phenyl)-N'-propylurea A starting compound (N-{2-chloro-4-[(7-hydroxy-6-methoxy-4-quinazolinyl)oxy]phenyl}-N'-propylurea, 80 mg), potassium carbonate (138 mg), and 4-chloromethylpyridine hydrochloride (41 mg), were dissolved in N,N-dimethylformamide (1 ml), and the solution was stirred at 80° C., for 3 hr. Water was added to the reaction mixture, followed by extraction with chloroform-propanol (3/1). The organic layer was dried over anhydrous sodium sulfate, and the solvent was removed by distillation under the reduced pressure. The residue was purified by HPLC to give 65 mg (yield 66%) of the title compound.

$^1$H-NMR (CDCl$_3$, 400 MHz): δ 0.96 (t, J=7.6 Hz, 3H), 1.53–1.64 (m, 2H), 3.25 (dd, J=7.3 Hz, 12.9 Hz, 2H), 4.07 (s, 3H), 5.32 (s, 2H), 6.66 (s, 1H), 7.14 (dd, J=2.7 Hz, 9.0 Hz, 1H), 7.27 (s, 1H), 7.29 (d, J=2.7 Hz, 1H), 7.41 (d, J=5.9 Hz, 2H), 7.54 (s, 1H), 8.24 (d, J=9.0 Hz, 1H), 8.59 (s, 1H), 8.63 (d, J=6.1 Hz, 2H).

Mass analysis, found (ESI-MS, m/z): 494 (M$^+$+1).

Example 124

N-[2-Chloro-4-({6-methoxy-7-[(5-morpholinopentyl)oxy]-4-quinazolinyl}oxy)phenyl]-N'-propylurea N-{2-Chloro-4-[(7-hydroxy-6-methoxy-4-quinazolinyl) oxy]phenyl}-N'-propylurea (70 mg), potassium carbonate (30 mg), and pentamethylene bromide (80 μl) were dissolved in N,N-dimethylformamide (5 ml), and the solution was stirred at room temperature for 3 hr. The solvent was removed by distillation under the reduced pressure. Water was added to the residue, and the mixture was extracted with chloroform. The organic layer was dried over anhydrous sodium sulfate, and the solvent was removed by distillation under the reduced pressure. The residue was washed with ether to give 43 mg (yield 46%) of N-[4-({7-(5-bromopentyl)oxy}-6-methoxy-4-quinazolinyl)oxy]-2-chlorophenyl]-N'-propylurea as an intermediate. The intermediate (43 mg), potassium carbonate (30 mg), and morpholine (70 μl) were dissolved in N,N-dimethylformamide (4 ml), and the solution was stirred at room temperature overnight. The solvent was removed by distillation under the reduced pressure. A saturated aqueous sodium hydrogencarbonate solution was added to the residue, and the mixture was extracted with chloroform. The organic layer was dried over anhydrous sodium sulfate, and the solvent was removed by distillation under the reduced pressure. The residue was purified by chromatography on silica gel by development with chloroform/methanol to give 30 mg (yield 68%) of the title compound.

$^1$H-NMR (CDCl$_3$, 400 MHz): δ 1.71 (t, J=7.32 Hz, 3H), 2.28 (t, J=7.20 Hz, 2H), 2.63 (m, 2H), 3.08–3.14 (m, 5H), 3.29–3.30 (m, 5H), 3.47 (bs, 1H), 3.73 (m, 1H), 3.86–3.90 (m, 2H), 4.36 (t, J=4.65 Hz, 3H), 4.46 (t, J=4.76 Hz, 1H), 4.77 (s, 1H), 4.99 (t, J=6.34 Hz, 2H), 7.80 (m, 1H), 8.02 (dd, J=2.68 Hz, 9.27 Hz, 1H), 8.18 (s, 1H), 8.27 (d, J=2.68 Hz, 1H), 8.34 (s, 1H), 8.85 (s, 1H), 9.00 (d, J=9.03 Hz, 1H), 9.35 (s, 1H).

Mass analysis, found (ESI-MS, m/z): 559 (M$^+$+1).

Example 125

N-{2-Chloro-4-[(6-methoxy-7-{[5-(1H-1,2,3-triazol-1-yl) pentyl]oxy}-4-quinazolinyl)oxy]phenyl}-N'-propylurea Triazole (0.41 ml), 1-bromo-5-chloropentane (1.0 ml), tetrabutylammonium iodide (10 mg), and a 3 M aqueous sodium hydroxide solution (1 ml) were dissolved in acetone (10 ml), and the solution was stirred at 50° C. for 18 hr. Water was added to the reaction mixture, and the mixture was extracted with chloroform. The organic layer was dried over anhydrous sodium sulfate. The solvent was removed by distillation under the reduced pressure. The residue was purified by chromatography by development with chloroform to give an intermediate (390 mg).

A starting compound (N-{2-chloro-4-[(7-hydroxy-6-methoxy-4-quinazolinyl)oxy]phenyl}-N'-propylurea, 80 mg), potassium carbonate (138 mg), and the above intermediate (52 mg) were dissolved in N,N-dimethylformamide (1 ml), and the solution was stirred at 120° C. for 5 hr. Water was added to the reaction mixture, and the mixture was extracted with chloroform-propanol (3/1). The organic layer was dried over anhydrous sodium sulfate. The solvent was removed by distillation under the reduced pressure. The residue was purified by HPLC to give 41 mg (yield 38%) of the title compound.

$^1$H-NMR (CDCl$_3$, 400 MHz): δ 0.96 (t, J=7.6 Hz, 3H), 1.50–1.65 (m, 4H), 1.90–2.08 (m, 4H), 3.24 (dd, J=7.1 Hz, 12.9 Hz, 2H), 4.01 (s, 3H), 4.17 (t, J=6.6 Hz, 2H), 4.44 (t, J=7.3 Hz, 2H), 4.88–4.94 (m, 1H), 6.32 (s, 1H), 7.14 (dd, J 2.7 Hz, 9.0 Hz, 1H), 7.25 (s, 1H), 7.29 (d, J=2.7 Hz, 1H), 7.48 (s, 1H), 7.55 (s, 1H), 7.70 (s, 1H), 8.23 (d, J=9.0 Hz, 1H), 8.55 (s, 1H).

Mass analysis, found (ESI-MS, m/z): 540 (M$^{30}$ +1 ).

Example 126

N'-(2-Chloro-4-{[6-methoxy-7-(4-pyridylmethoxy)-4quinazolinyl]oxy}phenyl)-N,N-diethyl-area A starting compound (N'-{2-chloro-4-[(7-hydroxy-6-methoxy-4-quinazolinyl)oxy]phenyl}-N,N-diethylurea, 83 mg), potassium carbonate (138 mg), and 4-chloromethylpyridine hydrochloride (49 mg) were dissolved in N,N-dimethylformamide (1 ml), and the solution was stirred at room temperature for 18 hr. Water was added to the reaction mixture, and the mixture was extracted with chloroform-propanol (3/1). The organic layer was dried over anhydrous sodium sulfate. The solvent was removed by distillation under the reduced pressure. The residue was purified by HPLC to give 57 mg (yield 56%) of the title compound.

$^1$H-NMR (CDCl$_3$, 400 MHz): δ 1.26 (t, J=7.3 Hz, 6H), 3.41 (q, J=7.1 Hz, 4H), 4.08 (s, 3H), 5.32 (s, 2H), 6.98 (s, 1H), 7.14 (dd, J=2.7 Hz, 9.0 Hz, 1H), 7.27 (s, 1H), 7.29 (d, J=2.7 Hz, 1H), 7.41 (d, J=5.9 Hz, 2H), 7.55 (s, 1H), 8.37 (d, J=9.0 Hz, 1H), 8.58 (s, 1H), 8.63 (d, J=5.9 Hz, 2H).

Mass analysis, found (ESI-MS, m/z): 508 (M$^+$+1).

Example 127

N-(2-Chloro-4-{[6-methoxy-7-(4-morpholinobutoxy)-4-quinazolinyl]oxy}phenyl)-N'-propylurea N-{2-Chloro-4-[(7-hydroxy-6-methoxy-4-quinazolinyl)oxy]phenyl}-N'-propylurea (70 mg), potassium carbonate (30 mg), and pentamethylene bromide (80 μl) were dissolved in N,N-dimethylformamide (5 ml), and the solution was stirred at room temperature for 3 hr. The solvent was removed by distillation under the reduced pressure. Water was added to the residue, and the mixture was extracted with chloroform. The organic layer was dried over anhydrous sodium sulfate. The solvent was removed by distillation under the reduced pressure. The residue was washed with ether to give 43 mg (yield 46%) of N-(4-{[7-(4-bromobutoxy)-6-methoxy-4-quinazolinyl]-oxy}-2-chlorophenyl)-N'-propylurea as an intermediate. The intermediate (43 mg), potassium carbonate (30 mg), and morpholine (40 μl) were dissolved in N,N-dimethylformamide (4 ml), and the solution was stirred at room temperature overnight. The solvent was removed by distillation under the reduced pressure. A saturated aqueous sodium hydrogencarbonate solution was added to the residue, and the mixture was extracted with chloroform. The organic layer was dried over anhydrous sodium sulfate. The solvent was removed by distillation under the reduced pressure. The residue was purified by chromatography on silica gel by development with chloroform/methanol to give 23 mg (yield 53%) of the title compound.

$^1$H-NMR (CDCl$_3$, 400 MHz): δ 0.99 (t, J=7.32 Hz, 3H), 1.56–1.62 (m, 13H), 2.00–2.08 (m, 2H), 3.26–3.28 (m, 2H), 4.04 (s, 3H), 4.24 (m, 2H), 4.72–4.77 (m, 1H), 6.65 (s, 1H), 6.99 (s, 1H), 7.19–7.26 (m, 1H), 7.30 (s, 1H), 7.32–7.34 (m, 1H), 7.51 (s, 1H), 8.25 (d, J=9.03 Hz, 1H), 8.61 (s, 1H).

Mass analysis, found (ESI-MS, m/z): 545 (M$^+$+1).

Example 128

N-[2-Chloro-4-({6-methoxy-7-[2-(4-methylpiperazino)ethoxy]-4-quinazolinyl}oxy)penyl]-N'-propylurea N-{2-Chloro-4-[(7-hydroxy-6-methoxy-4-quinazolinyl)oxy]phenyl}-N'-propylurea (60 mg), potassium carbonate (30 mg), and 1,2-dibromoethane (70 μl) were dissolved in N,N-dimethylformamide (4 ml), and the solution was stirred at room temperature for 3 hr. The solvent was removed by distillation under the reduced pressure. Water was added to the residue, and the mixture was extracted with chloroform. The organic layer was dried over anhydrous sodium sulfate. The solvent was removed by distillation under the reduced pressure. The residue was washed with ether to give 46 mg (yield 62%) of N-(4-{[7-(2-bromoethoxy)-6-methoxy-4-quinazolinyl]-oxy}-2-chlorophenyl)-N'-propylurea as an intermediate. The intermediate (46 mg), potassium carbonate (20 mg), and N-methylpiperazine (50 μl) were dissolved in N,N-dimethylformamide (3 ml), and the solution was stirred at room temperature overnight. The solvent was removed by distillation under the reduced pressure. A saturated aqueous sodium hydrogencarbonate solution was added to the residue, and the mixture was extracted with chloroform. The organic layer was dried over anhydrous sodium sulfate. The solvent was removed by distillation under the reduced pressure. The residue was purified by chromatography on silica gel by development with chloroform/methanol to give 24 mg (yield 50%) of the title compound.

$^1$H-NMR (CDCl$_3$, 400 MHz): δ 0.99 (t, J=7.32 Hz, 3H), 1.61–1.64 (m, 2H), 2.75 (m, 2H), 3.00–3.16 (m, 4H), 3.25–3.16 (m, 4H), 3.25–3.29 (m, 2H), 4.02 (s, 3H), 4.27–4.35 (m, 2H), 4.78–4.83 (m, 2H), 5.33 (s, 3H), 6.69 (s, 1H), 7.17 (dd, J=2.68 Hz, 9.03 Hz, 1H), 7.31 (s, 1H), 7.49 (s, 1H), 8.26 (d, J=9.27 Hz, 1H), 8.59 (s, 1H).

Mass analysis, found (ESI-MS, m/z): 530 (M$^+$+1).

Example 129

N-{2-chloro-4-[(7-{2-[(2-hydroxyethyl)-(methyl)amino]ethoxy}-6-methoxy-4-quinazolinyl)oxy]-phenyl}-N'-propylurea N-{2-Chloro-4-[(7-hydroxy-6-methoxy-4-quinazolinyl)oxy]phenyl}-N'-propylurea (65 mg), potassium carbonate (30 mg), and 1,2-dibromoethane (30 μl) were dissolved in N,N-dimethylformamide (4 ml), and the solution was stirred at room temperature for 3 hr. The solvent was removed by distillation under the reduced pressure. Water was added to the residue, and the mixture was extracted with chloroform. The organic layer was dried over anhydrous sodium sulfate. The solvent was removed by distillation under the reduced pressure. The residue was washed with ether to give 36 mg (yield 45%) of N-(4-{[7-(2-bromoethoxy)-6-methoxy-4-quinazolinyl]-oxy}-2-chlorophenyl)-N'-propylurea as an intermediate. The intermediate (36 mg), potassium carbonate (30 mg), and N-methylethanolamine (30 μl) were dissolved in N,N-dimethylformamide (3 ml), and the solution was stirred at room temperature overnight. The solvent was removed by distillation under, the reduced pressure. A saturated aqueous sodium hydrogencarbonate solution was added to the residue, and the mixture was extracted with chloroform. The organic layer was dried over anhydrous sodium sulfate. The solvent was removed by distillation under the reduced pressure. The residue was purified by chromatography on silica gel by development with chloroform/methanol to give 21 mg (yield 55%) of the title compound.

¹H-NMR (CDCl₃, 400 MHz): δ 0.98 (t, J=7.32 Hz, 3H), 1.59 (m, 2H), 1.94 (bs, 1H), 3.23 (m, 2H), 4.03 (s, 3H), 4.07–4.15 (m, 4H), 4.76 (m, 4H), 5.35 (s, 3H), 7.10–7.17 (m, 1H), 7.28 (s, 3H), 7.40 (s, 1H), 7.54 (s, 1H), 8.37 (d, J=9.03 Hz, 1H), 8.64 (s, 1H).

Mass analysis, found (ESI-MS, m/z): 504 (M⁺+1).

Example 130

N-[2-Chloro-4-({6-methoxy-7-[3-(4-methylpiperazino)propoxy]-4-quinazolinyl}oxy)phenyl]-N'-propylurea N-{2-Chloro-4-[(7-hydroxy-6-methoxy-4-quinazolinyl)oxy]phenyl}-N'-propylurea (75 mg), potassium carbonate (30 mg), and 1,3-dibromopropane (75 μl) were dissolved in N,N-dimethylformamide (4 ml), and the solution was stirred at room temperature for 3 hr. The solvent was removed by distillation under the reduced pressure. Water was added to the residue, and the mixture was extracted with chloroform. The organic layer was dried over anhydrous sodium sulfate. The solvent was removed by distillation under the reduced pressure. The residue was washed with ether to give 50 mg (yield 52%) of N-(4-{[7-(3-bromopropoxy)-6-methoxy-4-quinazolinyl]-oxy}-2-chlorophenyl)-N'-propylurea as an intermediate. The intermediate (30 mg), potassium carbonate (20 mg), and N-methylpiperazine (40 μl) were dissolved in N,N-dimethylformamide (3 ml), and the solution was stirred at room temperature overnight. The solvent was removed by distillation under the reduced pressure. A saturated aqueous sodium hydrogencarbonate solution was added to the residue, and the mixture was extracted with chloroform. The organic layer was dried over anhydrous sodium sulfate, and the solvent was removed by distillation under the reduced pressure. The residue was purified by chromatography on silica gel by development with chloroform/methanol to give 20 mg (yield 63%) of the title compound.

¹H-NMR (CDCl₃, 400 MHz): δ 0.99 (t, J=7.32 Hz, 3H), 1.58–1.62 (m, 2H), 2.25–2.50 (m, 3H), 2.70–2.85 (m, 3H), 2.92–2.98 (m, 3H), 3.25 (m, 2H), 4.04 (s, 3H), 4.25 (m, 2H), 4.83 (m, 3H), 5.34 (s, 3H), 6.70 (s, 1H), 7.21 (dd, J=2.68, 9.03 Hz, 1H), 7.26 (s, 2H), 7.31 (s, 1H), 7.49 (s, 1H), 8.18 (d, J=9.27 Hz, 1H), 8.59 (s, 1H).

Mass analysis, found (ESI-MS, m/z): 544 (M⁺+1).

Example 131

N'-[2-Chloro-4-({6-methoxy-7-[2-(1H-1,2,3-triazol-1-yl)ethoxy]-4-quinazolinyl}oxy)phenyl]-N,N-diethylurea A starting compound (N'-{2-chloro-4-[(7-hydroxy-6-methoxy-4-quinazolinyl)oxy]phenyl}-N,N-diethylurea, 83 mg), potassium carbonate (138 mg), and 2-(1H-1,2,3-triazol-1-yl) ethyl 4-methyl-l-benzenesulfonate (59 mg) were dissolved in N,N-dimethylformamide (1 ml), and the solution was stirred at 80° C. for 18 hr. Water was added to the reaction mixture, and the mixture was extracted with chloroform-propanol (3/1). The organic layer was dried over anhydrous sodium sulfate. The solvent was removed by distillation under the reduced pressure. The residue was washed with ether to give an intermediate. Triphosgene (90 mg) was added to a solution of the intermediate and triethylamine (0.027 ml) in chloroform (1 ml) at 0° C. and the mixture was stirred for 30 min. The reaction mixture was cooled to 0° C. and diethylamine (0.044 ml) was then added dropwise to the cooled reaction mixture. The temperature of the mixture was raised to room temperature over a period of 2 hr. A saturated aqueous sodium hydrogencarbonate solution was added to the reaction mixture, followed by extraction with chloroform-propanol (3/1). The organic layer was dried over anhydrous sodium sulfate. The solvent was removed by distillation under the reduced pressure. The residue was purified by HPLC to give 30 mg (yield 29%) of the title compound.

¹H-NMR (CDCl₃, 400 MHz): δ 1.26 (t, J=7.1 Hz, 6H), 3.41 (q, J=7.1 Hz, 4H), 4.03 (s, 3H), 4.53 (t, J=4.9 Hz, 2H), 4.94 (t, J=5.1 Hz, 2H), 6.98 (s, 1H), 7.13 (dd, J=2.7 Hz, 9.0 Hz, 1H), 7.26 (s, 1H), 7.73 (s, 1H), 7.94 (s, 1H), 8.38 (d, J=9.0 Hz, 1H), 8.60 (s, 1H).

Example 132

3-{[4-(3-Chloro-4-{[(diethylamino-carbonyl]amino}phenoxy)-6-methoxy-7-quinazolinyl]oxy}-propyl -N,N-diethylcarbamate A starting compound (N'-{2-chloro-4-[(7-hydroxy-6-methoxy-4-quinazolinyl)oxy]phenyl}-N,N-diethylurea, 83 mg), potassium carbonate (138 mg), and 3-bromo-1-propanol (0.027 ml) were dissolved in N,N-dimethylformamide (1 ml), and the solution was stirred at 80° C. for 18 hr. Water was added to the reaction mixture, and the mixture was extracted with chloroform-propanol (3/1). The organic layer was dried over anhydrous sodium sulfate. The solvent was removed by distillation under the reduced pressure. The residue was washed with ether to give an intermediate. Triphosgene (90 mg) was added to a solution of the intermediate and triethylamine (0.027 ml) in chloroform (1 ml) at 0° C. and the mixture was stirred for 30 min. The reaction mixture was cooled to 0° C. and diethylamine (0.044 ml) was then added dropwise to the cooled reaction mixture. The temperature of the mixture was raised to room temperature over a period of 2 hr. A saturated aqueous sodium hydrogencarbonate solution was added to the reaction mixture, and the mixture was extracted with chloroform-propanol (3/1). The organic layer was dried over anhydrous sodium sulfate. The solvent was removed by distillation under the reduced pressure. The residue was purified by HPLC to give 19 mg (yield 17%) of the title compound.

¹H-NMR (CDCl₃, 400 MHz): δ 1.04 (t, J=7.1 Hz, 6H), 1.22 (t, J=7.3 Hz, 6H), 3.09 (q, J=7.1 Hz, 4H), 3.36 (q, J=7.1 Hz, 4H), 3.75 (t, J=6.3 Hz, 2H), 3.97 (s, 3H), 4.29 (t, J=6.1 Hz, 2H), 6.93 (s, 1H), 7.10 (dd, J=2.7 Hz, 9.0 Hz, 1H), 7.24 (d, J=2.7 Hz, 1H), 7.27 (s, 1H), 7.45 (s, 1H), 8.33 (d, J=9.3 Hz, 1H), 8.55 (s, 1H).

Example 133

N-[2-Chloro-4-({6-methoxy-7-[3-(4-pyridylthio)propoxy]-4-quinazolinyl}oxy)phenyl]-N'-propylurea A starting compound (N-(4-{[7-(3-bromopropoxy)-6-methoxy-4-quinazolinyl]oxy}-2-chlorophenyl)-N'-propylurea, 80 mg), potassium carbonate (138 mg), and 4-mercaptopyridine (22 mg) were dissolved in N,N-dimethylformamide (1 ml), and the solution was stirred at room temperature for 3 hr. Water was added to the reaction mixture, and the mixture was extracted with chloroform-propanol (3/1). The organic layer was dried over anhydrous sodium sulfate. The solvent was removed by distillation under the reduced pressure. The residue was washed with ether to give 60 mg (yield 72%) of the title compound.

$^1$H-NMR (CDCl$_3$, 400 MHz): δ 0.91 (t, J=7.6 Hz, 3H), 1.50–1.60 (m, 2H), 2.24–2.32 (m, 2H), 3.11–3.24 (m, 4H), 3.99 (s, 3H), 4.25 (t, J=5.9 Hz, 2H), 4.70–4.80 (m, 1H), 6.62 (s, 1H), 7.11 (dd, J=2.7 Hz, 9.0 Hz, 1H), 7.11–7.16 (m, 2H), 7.23 (s, 1H), 7.25 (d, J=2.7 Hz, 1H), 7.45 (s, 1H), 8.19 (d, J=9.0 Hz, 1H), 8.30–8.34 (m, 2H), 8.55 (s, 1H).

Mass analysis, found (ESI-MS, m/z): 554 (M$^+$+1).

Example 134

N-{2-Chloro-4-[(6-methoxy-7-{3-[(1-methyl-1H-1,2,3,4-tetrazol-5-yl)thio]propoxy}-4-quinazolinyl)–oxy]phenyl}-N'-propylurea A starting compound (N-(4-{[7-(3-bromopropoxy)-6-methoxy-4-quinazolinyl]oxy}-2-chlorophenyl)-N'-propyl-urea, 80 mg), potassium carbonate (138 mg), and 5-mercapto-1-tetrazole (23 mg) were dissolved in N,N-dimethylformamide (1 ml), and the solution was stirred at room temperature for 3 hr. Water was added to the reaction mixture, and the mixture was extracted with chloroform-propanol (3/1). The organic layer was dried over anhydrous sodium sulfate, and the solvent was removed by distillation under the reduced pressure. The residue was washed with ether to give 71 mg (yield 85%) of the title compound.

$^1$H-NMR (CDCl$_3$, 400 MHz): δ 0.91 (t, J=7.3 Hz, 3H), 1.51–1.56 (m, 2H), 2.39–2.48 (m, 2H), 3.17–3.23 (m, 2H), 3.56 (t, J=7.1 Hz, 2H), 3.86 (s, 3H), 3.97 (s, 3H), 4.27 (t, J=5.9 Hz, 2H), 4.75–4.82 (m, 1H), 6.63 (s, 1H), 7.10 (dd, J=2.7 Hz, 9.0 Hz, 1H), 7.24 (d, J=3.7 Hz, 1H), 7.44 (s, 1H), 8.19 (d, J=9.0 Hz, 1H), 8.55 (s, 1H).

Mass analysis, found (ESI-MS, m/z): 559 (M$^+$+1).

Example 135

N-(2-Chloro-4-{[6-methoxy-7-(3-piperidino-propoxy)-4-quinazolinyl]oxy}phenyl)-N'-propylurea N-{2-Chloro-4-[(7-hydroxy-6-methoxy-4-quinazolinyl)oxy]phenyl}-N'-propylurea (500 mg), potassium carbonate (857 mg), and 1,3-dibromopropane (0.5 ml) were dissolved in N,N-dimethylformamide (5 ml), and the solution was stirred at room temperature for 3 hr. The solvent was removed by distillation under the reduced pressure. Water was added to the residue, and the mixture was extracted with chloroform/2-propanol (4/1). The organic layer was dried over anhydrous sodium sulfate. The solvent was removed by distillation under the reduced pressure. The residue was washed with ether to give 451 mg (yield 71%) of N-(4-{[7-(3-bromopropoxy)-6-methoxy-4-quinazolinyl]oxy}-2-chlorophenyl}-N'-propyl-urea. N-(4-{[7-(3-Bromopropoxy)-6-methoxy-4-quinazolinyl]oxy}-2-chlorophenyl}-N'-propylurea (70 mg), potassium carbonate (54 mg), and piperidine (39 µl) were dissolved in N,N-dimethylformamide (2 ml), and the solution was stirred at room temperature overnight. The solvent was removed by distillation under the reduced pressure. A saturated aqueous sodium hydrogencarbonate solution was added to the residue, and the mixture was extracted with chloroform. The organic layer was dried over anhydrous sodium sulfate. The solvent was removed by distillation under the reduced pressure. The residue was purified by chromatography on silica gel by development with chloroform/methanol (20/1) to give 35 mg (yield 50%) of the title compound.

$^1$H-NMR (CDCl$_3$, 400 MHz): δ 0.98 (t, J=7.6 Hz, 3H), 1.46 (br, 2H), 1.54–1.66 (m, 8H), 2.15 (br, 2H), 2.44 (br, 2H), 2.55 (br, 2H), 3.20–3.30 (m, 2H), 4.04 (s, 3H), 4.27 (t, J=6.6 Hz, 2H), 4.77 (t, J=5.9 Hz, 1H), 6.65 (s, 1H), 7, 17 (dd, J=2.7 Hz, 9.0 Hz, 1H), 7.32 (d, J=2.7 Hz, 1H), 7.33 (s, 1H), 7.49 (s, 1H), 8.24 (d, J=9.0 Hz, 1H), 8.61 (s, 1H).

Example 136

N-[2-Chloro-4-({7-methoxy-6-[2-(4-methylpiperazino)ethoxy]-4-quinazolinyl}oxy)phenyl]N'-propylurea N-{2-Chloro-4-[(6-hydroxy-7-methoxy-4-quinazolinyl)oxy]phenyl}-N'-propylurea (500 mg), potassium carbonate (857 mg), and 1,3-dibromopropane (0.5 ml) were dissolved in N,N-dimethylformamide (5 ml), and the solution was stirred at room temperature for 3 hr. The solvent was removed by distillation under the reduced pressure. Water was added to the residue, and the mixture was extracted with chloroform/2-propanol (4/1). The organic layer was dried over anhydrous sodium kp sulfate. The solvent was removed by distillation under the reduced pressure. The residue was washed with ether to give 451 mg (yield 71%) of N-(4-{[6-(2-bromoethoxy)-7-methoxy-4-quinazolinyl]oxy}-2-chlorophenyl}-N'-propyl-urea. N-(4-{[6-(2-Bromoethoxy)-7-methoxy-4-quinazolinyl]oxy}-2-chlorophenyl}-N'-propylurea (50 mg), (3 potassium carbonate (40 mg), and N-methylpiperazine (50 µl) were dissolved in N,N-dimethylformamide (1 ml), and the solution was stirred at room temperature overnight. The solvent was removed by distillation under the reduced pressure. A saturated aqueous sodium hydrogencarbonate solution was added to the residue, and the mixture was extracted with chloroform. The organic layer was dried over anhydrous sodium sulfate. The solvent was removed by distillation under the reduced pressure. The residue was purified by chromatography on silica gel by development with chloroform/methanol to give 20 mg (yield 44%) of the title compound.

$^1$H-NMR (CDCl$_3$, 400 MHz): δ 0.98 (t, J=7.3 Hz, 3H), 1.56–1.65 (m, 2H), 1.77 (br, 4H), 2.31 (s, 3H), 2.53 (br, 2H), 2.71 (br, 2H), 2.97 (t, J=6.1 Hz, 3H), 3.24–3.29 (m, 2H), 4.04 (s, 3H), 4.32 (t, J=6.1 Hz, 2H), 4.83 (br, 1H), 6.69 (s, 1H), 7.16 (dd, J=2.7 Hz, 9.0 Hz, 1H), 7.30 (s, 1H), 7.31 (s, 1H), 7.55 (s, 1H), 8.25 (d, J=9.0 Hz, 1H), 8.62 (s, 1H).

Mass analysis, found (ESI-MS, m/z): 529 (M$^+$+1).

Example 137

N-[2-Chloro-4-({7-methoxy-6-[3-(4methyl-piperazino)propoxy]-4-quinazolinyl}oxy)phenyl]-N'-propylurea N-{2-Chloro-4-[(6-hydroxy-7-methoxy-4-quinazolinyl)oxy]phenyl}-N'-propylurea (500 mg), potassium carbonate (857 mg), and 1,3-dibromopropane (0.5 ml) were dissolved in N,N-dimethylformamide (5 ml), and the solution was stirred at room temperature for 3 hr. The solvent was removed by distillation under the reduced pressure. Water was added to the residue, and the mixture was extracted with chloroform/2-propanol (4/1). The organic layer was dried over anhydrous sodium sulfate. The solvent was removed by distillation under the reduced pressure. The residue was washed with ether to give 451 mg (yield 71%) of N-(4-{[6-(3-bromopropoxy)-7-methoxy-4-quinazolinyl]oxy}-2-chlorophenyl}-N'-propylurea. N-(4-{[6-(3-Bromopropoxy)-7-methoxy-4-quinazolinyl]oxy}-2-chlorophenyl}-N'-propylurea (50 mg), potassium carbonate (40 mg), and N-methylpiperazine (50 µl) were dissolved in N,N-dimethylformamide (1 ml), and the solution was stirred at room temperature overnight. The solvent was removed by distillation under the reduced pressure. A saturated aqueous sodium hydrogencarbonate solution was added to the residue, and the mixture was extracted with chloroform. The organic layer was dried over anhydrous sodium sulfate. The solvent was removed by distillation under the reduced pressure. The residue was purified by chromatography on silica gel by development with chloroform/methanol to give 20 mg (yield 44%) of the title compound.

$^1$H-NMR (CDCl$_3$, 400 MHz): δ 0.98 (t, J=7.6 Hz, 3H), 1.58–1.64 (m, 2H), 1.71 (br, 4H), 2.31 (s, 3H), 2.53 (br, 2H), 2.71 (br, 2H), 2.11–2.17 (m, 2H), 2.30 (s, 3H), 2.59–2.62 (m, 2H), 3.24–3.29 (m, 2H), 4.04 (s, 3H), 4.26 (t, J=6.6 Hz, 2H), 4.80 (br, 1H), 6.67 (s, 1H), 7.17 (dd, J=2.7 Hz, 9.0 Hz, 1H), 7.31 (s, 1H), 7.31 (s, 1H), 7.52 (s, 1H), 8.25 (d, J=9.0 Hz, 1H), 8.61 (s, 1H).

Mass analysis, found (ESI-MS, m/z): 543 (M$^+$+1).

Example 138

N-(2-Chloro-4-{[7-methoxy-6-(2-pyridyl-methoxy)-4-quinazolinyl]oxy}phenyl)-N'-propylurea A starting compound (N-{2-chloro-4-[(6-hydroxy-7-methoxy-4-quinazolinyl)oxy]phenyl}-N'-propylurea, 80 mg), potassium carbonate (138 mg), and 2-(chloromethyl)pyridine hydrochloride (41 mg) were dissolved in N,N-dimethylformamide (1 ml), and the solution was stirred at 120° C. for 3 hr. Water was added to the reaction mixture, and the mixture was extracted with chloroform-propanol (3/1). The organic layer was dried over anhydrous sodium sulfate, and the solvent was removed by distillation under the reduced pressure. The residue was washed with ethyl acetate to give 54 mg (yield 55%) of the title compound.

$^1$H-NMR (CDCl$_3$, 400 MHz): δ 0.91 (t, J=7.6 Hz, 3H), 1.51–1.58 (m, 2H), 3.17–3.22 (m, 2H), 4.02 (s, 3H), 4.69 (br, 1H), 5.36 (s, 2H), 6.57 (s, 1H), 7.08 (dd, J=2.7 Hz, 9.0 Hz, 1H), 7.21–7.29 (m, 2H), 7.53–7.55 (m, 2H), 7.66–7.71 (m, 1H), 8.15 (d, J=9.0 Hz, 1H), 8.55–8.57 (m, 2H).

Mass analysis, found (ESI-MS, m/z): 494 (M$^+$+1).

Example 139

N-(2Chloro-4-{[7-methoxy-6-(3-morpholino-propoxy)4-quinazolinyl]oxy}phenyl)-N'-propylurea A starting compound (N-(4-{[6-(3-propoxy)-7-methoxy-4-quinazolinyl]oxy}-2-chlorophenyl)-N'-propyl-urea, 54 mg), potassium carbonate (138 mg), and morpholine (0.017 ml) were dissolved in N,N-dimethylformamide (1 ml), and the solution was stirred at 120° C. for 3 hr. Water was added to the reaction mixture, and the mixture was extracted with chloroform-propanol (3/1). The organic layer was dried over anhydrous sodium sulfate. The solvent was removed by distillation under the reduced pressure. The residue was washed with ethyl acetate to give 42 mg (yield 77%) of the title compound.

$^1$H-NMR (CDCl$_3$, 400 MHz): δ 0.91 (t, J=7.6 Hz, 3H), 1.47–1.59 (m, 4H), 1.88–2.00 (m, 2H), 2.35–2.48 (m, 4H), 3.20 (dd, J=7.3 Hz, 12.9 Hz, 2H), 3.62–3.74 (m, 4H), 3.97 (s, 3H), 4.15 (t, J=6.3 Hz, 2H), 4.74–4.80 (m, 1H), 6.63 (s, 1H), 7.09 (dd, J=2.7 Hz, 9.0 Hz, 1H), 7.24 (d, J=2.7 Hz 1H), 7.42 (s, 1H), 8.18 (d, J=9.0 Hz, 1H), 8.54 (s, 1H).

Mass analysis, found (ESI-MS, m/z): 530 (M$^+$+1).

Example 140

N-{2-Chloro-4-[(6-{3-(2-hydroxyethyl)-(methyl)amino]propoxy}-7-methoxy-4-quinazolinyl)oxy]-phenyl}-N'-propylurea A starting compound (N-(4-{[6-(3-bromopropoxy)-7-methoxy-4-quinazolinyl]oxy}-2-chlorophenyl)-N'-propylurea, 51 mg), potassium carbonate (68 mg), and 2-(methylamino)ethanol (15 mg) were dissolved in N,N-dimethylformamide (1 ml), and the solution was stirred at 80° C. for 3 hr. Water was added to the reaction mixture, and the mixture was extracted with chloroform-propanol (3/1). The organic layer was dried over anhydrous sodium sulfate, and the solvent was removed by distillation under the reduced pressure. The residue was purified by HPLC by development with chloroform/methanol to give 25 mg (yield 48%) of the title compound.

$^1$H-NMR (CDCl$_3$, 400 MHz): δ 0.95 (t, J=7.6 Hz, 3H), 1.53–1.62 (m, 2H), 2.08–2.15 (m, 2H), 2.30 (s, 3H), 2.58 (t, J=5.4 Hz, 2H), 2.68 (t, J=7.1 Hz, 2H), 3.21–3.26 (m, 2H), 3.60 (t, J=5.4 Hz, 2H), 4.02 (s, 3H), 4.23 (t, J=6.3 Hz, 2H), 5.06 (t, J=5.6 Hz, 1 Hz), 6.79 (s, 1H), 7.13 (dd, J=2.7 Hz, 9.0 Hz, 1H), 7.27–7.28 (m, 2H), 7.48 (s, 1H), 8.21 (d, J=9.0 Hz, 1H), 8.58 (s, 1H).

Example 141

N-(2-Chloro-4-{[6-methoxy-7-(2-pyridyl-methoxy)-4-quinolyl]oxy}phenyl)-N'-propylurea A starting compound (N-{2-chloro-4-[(7-hydroxy-6-methoxy-4-quinolyl)oxy]phenyl)-N'-propylurea, 80 mg), potassium carbonate (138 mg), and 2-chloromethylpyridine hydrochloride (41 mg) were dissolved in N,N-dimethylformamide (1 ml), and the solution was stirred at 80° C. for 3 hr. Water was added to the reaction mixture, and the mixture was extracted with chloroform-propanol (3/1). The organic layer was dried over anhydrous sodium sulfate. The solvent was removed by distillation under the reduced pressure. The residue was purified by HPLC to give 81 mg (yield 82%) of the title compound.

$^1$H-NMR (CDCl$_3$, 400 MHz): δ 0.97 (t, J=7.6 Hz, 3H), 1.54–1.65 (m, 2H), 3.25 (dd, J=7.1 Hz, 12.9 Hz, 2H), 4.05 (s, 3H), 4.75–4.82 (m, 1H), 5.42 (s, 2H), 6.46 (d, J=5.4 Hz, 1H), 6.67 (s, 1H), 7.08 (dd, J=2.9 Hz, 9.0 Hz, 1H), 7.19 (d,

J=2.7 Hz, 1H), 7.44 (s, 1H), 7.53 (s, 1H), 7.56 (d, J=7.8 Hz, 1H), 7.69 (dt, J=2.0 Hz, 7.8 Hz, 1H), 8.25 (d, J=9.0 Hz, 1H), 8.46 (d, J=5.1 Hz, 1H), 8.61 (d, J=4.6 Hz, 1H).

Mass analysis, found (ESI-MS, m/z): 493 (M$^+$+1).

Example 142

N-(2-chloro-4-{[6-methoxy-7-(3-pyridyl-methoxy)-4-quinolyl]oxy}phenyl)-N'-propylurea A starting compound (N-{2-chloro-4-[(7-hydroxy-6-methoxy-4-quinolyl) oxy]phenyl}-N'-propylurea, 80 mg), potassium carbonate (138 mg), and 3-chloromethylpyridine hydrochloride (41 mg) were dissolved in N,N-dimethylformamide (1 ml), and the solution was stirred at 80° C. for 3 hr. Water was added to the reaction mixture, and the mixture was extracted with chloroform-propanol (3/1). The organic layer was dried over anhydrous sodium sulfate, and the solvent was removed by distillation under the reduced pressure. The residue was purified by HPLC to give 70 mg (yield 71%) of the title compound.

$^1$H-NMR (CDCl$_3$, 400 MHz): δ 0.97 (t, J=7.3 Hz, 3H), 1.54–1.65 (m, 2H), 3.25 (dd, J=7.3 Hz, 12.9 Hz, 2H), 4.02 (s, 3H), 4.82–4.90 (m, 1H), 5.30 (s, 2H), 6.47 (d, J=5.4 Hz, 1H), 6.72 (6, 1H), 7.09 (dd, J=2.7 Hz, 9.0 Hz, 1H), 7.19 (d, J=2.7 Hz, 1H), 7.32 (dd, J=4.9 Hz, 7.8 Hz, 1H), 7.47 (s, 1H), 7.52 (s, 1H), 7.84 (d, J=7.8 Hz, 1H), 8.26 (d, J=9.3 Hz, 1H), 8.47 (d, J=5.4 Hz, 1H), 8.58 (d, J=3.2 Hz, 1H), 8.75 (s, 1H).

Mass analysis, found (ESI-MS, m/z): 493 (M$^+$+1).

Example 143

N-(2-Chloro-4-{[6-methoxy-7-(4-pyridyl-methoxy)-4-quinolyl]oxy}phenyl)-N'-propylurea A starting compound (N-{2-chloro-4-[(7-hydroxy-6-methoxy-4-quinolyl) oxy]phenyl}-N'-propylurea, 80 mg), potassium carbonate (138 mg), and 4-chloromethylpyridine hydrochloride (41 mg) were dissolved in N,N-hr dimethylformamide (1 ml), and the solution was stirred at 80° C. for 3 hr. Water was added to the reaction mixture, and the mixture was extracted with chloroform-propanol (3/1). The organic layer was dried over anhydrous sodium sulfate, and the solvent was removed by distillation under the reduced pressure. The residue was purified by HPLC to give 71 mg (yield 71%) of the title compound.

$^1$H-NMR (CDCl$_3$, 400 MHz): δ 0.97 (t, J=7.6 Hz, 3H), 1.54–1.65 (m, 2H), 3.25 (dd, J=7.1 Hz, 12.9 Hz, 2H), 4.05 (s, 3H), 4.86–4.92 (m, 1H), 5.32 (s, 2H), 6.48 (d, J=4.7 Hz, 1H), 6.73 (s, 1H), 7.08 (dd, J=2.7 Hz, 9.0 Hz, 1H), 7.19 (d, J=2.9 Hz, 1H), 7.38 (s, 1H), 7.41 (d, J=6.1 Hz, 2H), 7.54 (s, 1H), 8.26 (d, J=9.0 Hz, 1H), 8.46 (d, J=5.4 Hz, 1H), 8.61 (d, J=6.1 Hz, 2H).

Mass analysis, found (ESI-MS, m/z): 493 (M$^+$+1).

Example 144

N-(2-Chloro-4-{[6-methoxy-7-(2-morpholinoethoxy)-4-quinolyl]oxy}phenyl)-N'-propylurea A starting compound (N-{2-chloro-4-[(7-hydroxy-6-methoxy-4-quinolyl)oxy]phenyl}-N'-propylurea, 100 mg), potassium carbonate (172 mg), and 1,2-dibromoethane (0.086 ml) were dissolved in N,N-dimethylformamide (1 ml), and the solution was stirred at room temperature for 3 hr. Water was added to the reaction mixture, and the mixture was extracted with chloroform-propanol (3/1). The organic layer was dried over anhydrous sodium sulfate, and the solvent was removed by distillation under the reduced pressure. The residue was washed with ether to give an intermediate (N-(4-{[7-(2-bromoethoxy)-6-methoxy-4-quinolyl]oxy}-2-chlorophenyl)-N'-propylurea). The intermediate, potassium carbonate (138 mg), and morpholine (0.17 ml) were dissolved in N,N-dimethylformamide (1 ml), and the solution was stirred at 80° C for 2 hr. Water was added to the reaction mixture, and the mixture was extracted with chloroform-propanol (3/1). The organic layer was dried over anhydrous sodium sulfate, and the solvent was removed by distillation under the reduced pressure. The residue was purified by chromatography on silica gel by development with chloroform/methanol to give 70 mg (yield 54%) of the title compound.

$^1$H-NMR (CDCl$_3$, 400 MHz): δ 0.91 (t, J=7.6 Hz, 3H), 1.50–1.59 (m, 2H), 2.57 (t, J=4.6 Hz, 4H), 2.88 (t, J=5.9 Hz, 2H), 3.18–3.23 (m, 2H), 3.68 (t, J=4.6 Hz, 4H), 3.94 (s, 3H), 4.26 (t, J=5.9 Hz, 2H), 4.98 (t, J=5.3 Hz, 2H), 6.41 (d, J=5.3 Hz, 1H), 6.74 (br, 1H), 7.03 (dd, J=2.7 Hz, 9.0 Hz, 1H), 7.14 (d, J=2.7 Hz, 1H), 7.34 (s, 1H), 7.43 (s, 1H), 8.42 (d, J=5.1 Hz, 1H).

Mass analysis, found (ESI-MS, m/z): 515 (M$^+$+1).

Example 145

N-[2-Chloro-4-({6-methoxy-7-[2-(1H-1,2,3-triazol-1-yl)ethoxy]-4-quinalyl}oxy)phenyl]-N'-propylurea A starting compound (N-{2-chloro-4-[(7-hydroxy-6-methoxy-4-quinolyl)oxy]phenyl}-N'-propylurea, 80 mg), potassium carbonate (138 mg), and 2-(1H-1,2,3-triazol-1-yl)ethyl 4-methyl-1-benzenesulfonate (59 mg) were dissolved in N,N-dimethylformamide (1 ml), and the solution was stirred at 120° C. for 5 hr. Water was added to the reaction mixture, and the mixture was extracted with chloroform-propanol (3/1). The organic layer was dried over anhydrous sodium sulfate, and the solvent was removed by distillation under the reduced pressure. The residue was purified by HPLC by development with chloroform-methanol to give 92 mg (yield 92%) of the title compound.

$^1$H-NMR (CDCl$_3$, 400 MHz): δ 0.97 (t, J=7.6 Hz, 3H), 1.57–1.63 (m, 2H), 3.23–3.28 (m, 2H), 4.01 (s, 3H), 4.52 (t, J=5.1 Hz, 2H), 4.81 (br, 1H), 4.93 (t, J=5.1 Hz, 2H), 6.47 (d, J=5.4 Hz, 1H), 6.69 (s, 1H), 7.08 (dd, J=2.7 Hz, 9.0 Hz, 1H), 7.18 (d, J=2.7 Hz, 1H), 7.37 (s, 1H), 7.51 (s, 1H), 7.72 (d, J=1.0 Hz, 1H), 7.97 (d, J=1.0 Hz, 1H), 8.26 (d, J=9.0 Hz, 1H), 8.48 (d, J=5.4 Hz, 1H).

Mass analysis, found (ESI-MS, m/z): 497 (M$^+$+1).

Example 146

N-[2-Chloro-4-({7-[2-(1H-1imidazolyl- ethoxy]-6-methoxy4-quinolyl}oxy)phenyl]-N'-propylurea A starting compound (N-{2-chloro-4-[(7-hydroxy-6-methoxy-4-quinolyl)oxy]phenyl}-N'-propylurea, 80 mg), potassium carbonate (138 mg), and 2-(1H-1-imidazolyl) ethyl 4-methyl-1-benzenesulfonate (59 mg) were dissolved in N,N-dimethylformamide (1 ml), and the solution was stirred at 120° C. for 5 hr. Water was added to the reaction mixture, and the mixture was extracted with chloroform-propanol (3/1). The organic layer was dried over anhydrous sodium sulfate. The solvent was removed by distillation under the reduced pressure, and the residue was purified by HPLC by development with chloroform/methanol to give 81 mg (yield 82%) of the title compound.

$^1$H-NMR (CDCl$_3$, 400 MHz): δ 0.96 (t, J=7.6 Hz, 3H), 1.50–1.65 (m, 2H), 1.90–2.08 (m, 2H), 3.24 (dd, J=7.1 Hz, 12.9 Hz, 2H), 4.01 (s, 3H), 4.17 (t, J=6.6 Hz, 2H), 4.44 (t, J=7.3 Hz, 2H), 4.88–4.94 (m, 1H), 6.32 (s, 1H), 7.14 (dd, J=2.7 Hz, 9.0 Hz, 1H), 7.25 (s, 1H), 7.29 (d, J=2.7 Hz, 1H), 7.48 (s, 1H), 7.55 (s, 1H), 7.70 (s, 1H), 8.23 (d, J=9.0 Hz, 1H), 8.58 (s, 1H).

Mass analysis, found (ESI-MS, m/z): 496 (M$^+$+1).

Example 147

N-(2-Chloro-4-{[7-(3-hydroxypropoxy -6-methoxy-4-quinolyl]oxy}phenyl)-N'-propylurea A starting compound (N-{2-chloro-4-[(7-hydroxy-6-methoxy-4-quinolyl)oxy]phenyl}-N'-propylurea, 80 mg), potassium carbonate (138 mg), and 3-bromo-1-propanol (0.027 ml) were dissolved in N,N-dimethylformamide (1 ml), and the solution was stirred at room temperature for 18 hr. Water was added to the reaction mixture, and the mixture was extracted with chloroform-propanol (3/1). The organic layer was dried over anhydrous sodium sulfate, and the solvent was removed by distillation under the reduced pressure. The residue was purified by HPLC by development with chloroform/methanol to give 94 mg (yield 100%) of the title compound.

$^1$H-NMR (CDCl$_3$, 400 MHz): a 0.92 (t, J=7.6 Hz, 3H), 1.45–1.62 (m, 2H), 2.09–2.18 (m, 2H), 3.21 (dd, J=7.1 Hz, 12.9 Hz, 2H), 3.87 (t, J=5.6 Hz, 2H), 3.94 (s, 3H), 4.31 (t, J=6.1 Hz, 2H), 4.81–4.87 (m, 1H), 6.42 (d, J=5.1 Hz, 1H), 6.69 (s, 1H), 7.03 (dd, J=2.7 Hz, 9.0 Hz, 1H), 7.14 (d, J=2.7 Hz, 1H), 7.36 (s, 1H), 7.43 (s, 1H), 8.20 (d, J=9.0 Hz, 1H), 8.42 (d, J=5.4 Hz, 1H).

Example 148

N-[2-Chloro-4-(}6-methoxy-7-[2-(4-methyl-piperazno)ethoxy]-4-quinolyl}oxy)phenyl]-N'-propylurea A starting compound (N-(4-{[7-(2-bromoethoxy)-6-methoxy-4-quinolyl]oxy}-2-chlorophenyl)-N'-propylurea, 50 mg), potassium carbonate (138 mg), and 1-methylpiperazine (0.055 ml) were dissolved in N,N-dimethylformamide (1 ml), and the solution was stirred at room temperature for 18 hr. Water was added to the reaction mixture, and the mixture was extracted with chloroform-propanol (3/1). The organic layer was dried over anhydrous sodium sulfate, and the solvent was removed by distillation under the reduced pressure. The residue was washed with ether to give 54 mg (yield 100%) of the title compound.

$^1$H-NMR (CDCl$_3$, 400 MHz): δ 0.92 (t, J=7.3 Hz, 3H), 1.49–1.62 (m, 2H), 2.24 (8, 3H), 2.35–2.70 (m, 2H), 2.90 (t, J=4.6 Hz, 2H), 3.21 (dd, J=7.3 Hz, 12.9 Hz, 2H), 3.94 (s, 3H), 4.26 (t, J=6.1 Hz, 2H), 4.75–4.85 (m, 1H), 6.41 (d, J=5.1 Hz, 1H), 6.67 (s, 1H), 7.04 (dd, J=2.7 Hz, 9.0 Hz, 1H), 7.14 (d, J=2.7 Hz, 1H), 7.34 (s, 1H), 7.42 (s, 1H), 8.19 (d, J=9.0 Hz, 1H), 8.42 (d, J=5.1 Hz, 1H).

Mass analysis, found (ESI-MS, m/z): 528 (M$^+$+1).

Example 149

N-(2-Chloro-4-{[7-(2-hydroxyethoxy)-6-methoxy-4-quinolyl]oxy}phenyl)-N'-propylurea A starting compound (N-{2-chloro-4-[(7-hydroxy-6-methoxy-4-quinolyl)oxy]phenyl}-N'-propylurea, 80 mg), potassium carbonate (138 mg), and 2-bromoethanol (0.621 ml) were dissolved in N,N-dimethylformamide (1 ml), and the solution was stirred at room temperature for 18 hr. Water was added to the reaction mixture, and the mixture was extracted with chloroform-propanol (3/1). The organic layer was dried over anhydrous sodium sulfate, and the solvent was removed by distillation under the reduced pressure. The residue was purified by HPLC by development with chloroform/methanol to give 80 mg (yield 90%) of the title compound.

$^1$H-NMR (CDCl$_3$, 400 MHz): δ 0.96 (t, J=7.6 Hz, 3H), 1.54–1.65 (m, 2H), 3.25 (dd, J=7.1 Hz, 12.9 Hz, 2H), 3.99 (s, 3H), 4.07 (t, J=4.4 Hz, 2H), 4.28 (t, J=4.6 Hz, 2H), 6.46 (d, J=5.4 Hz, 1H), 6.77 (d, J=8.3 Hz, 1H), 7.08 (s, 1H), 7.08 (dd, J=2.7 Hz, 9.0 Hz, 1H), 7.42 (s, 1H), 7.49 (s, 1H), 8.25 (d, J=9.0 Hz, 1H), 8.48 (d, J=2.9 Hz, 1H).

Example 150

N-{2-Chloro-4-[(7-{2-[(2-hydroxyethyl)-(methyl)amino]ethoxy}-6-methoxy-4-quinolyl)oxy]phenyl}-N'-propylurea A starting compound (N-(4-{[7-(2-bromoethoxy)-6-methoxy-4-quinolyl]oxy}-2-chlorophenyl)-N'-propylurea, 50 mg), potassium carbonate (138 mg), and 2-(methylamino)ethanol (0.040 ml) were dissolved in N,N-dimethylformamide (1 ml), and the solution was stirred at room temperature for 18 hr. Water was added to the reaction mixture, and the mixture was extracted with chloroform-propanol (3/1). The organic layer was dried over anhydrous sodium sulfate, and the solvent was removed by distillation under the reduced pressure. The residue was washed with ether to give 53 mg (yield 106%) of the title compound.

$^1$H-NMR (CDCl$_3$, 400 MHz): δ 0.97 (t, J=7.6 Hz, 3H), 1.54–1.65 (m, 2H), 2.42 (s, 3H), 2.69 (t, J=5.1 Hz, 2H), 3.00 (t, J=5.6 Hz, 2H), 3.26 (dd, J=7.1 Hz, 12.7 Hz, 2H), 3.64 (t, J=5.1 Hz, 2H), 3.99 (s, 3H), 4.26 (t, J=5.6 Hz, 2H), 4.66–4.69 (m, 1H), 6.46 (d, J=5.1 Hz; 1H), 6.70 (s, 1H), 7.09 (dd, J=2.7 Hz, 9.0 Hz, 1H), 7.19 (d, J=2.7 Hz, 1H), 7.39 (s, 1H), 7.47 (s, 1H), 8.24 (d, J=9.0 Hz, 1H), 8.47 (d, J=5.1 Hz, 1H).

Mass analysis, found (ESI-MS, m/z): 503 (M$^+$+1).

Example 151

N-(2-Chloro-4-{[6-methoxy-7-(3-morpholinoproxy) 4-quinolyl]oxy}phenyl)-N'-propylurea A starting compound (N-(4-{[7-(3-bromopropoxy)-6-methoxy-4-quinolyl]oxy}-2-chlorophenyl)-N'-propylurea, 52 mg), potassium carbonate (138 mg), and morpholine (0.044 ml) were dissolved in N,N-dimethylformamide (1 ml), and the solution was stirred at room temperature for 18 hr. Water was added to the reaction mixture, and the mixture was extracted with chloroform-propanol (3/1). The organic layer was dried over anhydrous sodium sulfate, and the solvent was removed by distillation under the reduced pressure. The residue was washed with ether to give 23 mg (yield 44%) of the title compound.

$^1$H-NMR (CDCl$_3$, 400 MHz): δ 0.92 (t, J=7.6 Hz, 3H), 1.49–1.60 (m, 2H), 2.02–2.11 (m, 2H), 2.40–2.47 (m, 4H), 2.52 (t, J=7.1 Hz, 2H), 3.21 (dd, J=7.1 Hz, 12.9 Hz, 2H), 3.62–3.69 (m, 4H), 3.95 (s, 3H), 4.20 (t, J=6.6 Hz, 2H), 4.70–4.78 (m, 1H), 6.41 (d, J=5.1 Hz, 1H), 6.64 (s, 1H), 7.04 (dd, J=2.7 Hz, 9.0 Hz, 1H), 7.15 (d, J=2.7 Hz, 1H), 7.37 (s, 1H), 7.43 (s, 1H), 8.20 (d, J=9.0 Hz, 1H), 8.42 (d, J=5.4 Hz, 1H).

Example 152

N-[2-Chloro-4-(6-methoxy-7-{[3-(4-methyl-piperazno)propoxy]4quinolyl}oxy)phenyl]-N'-propylurea A starting compound (N-(4-{[7-(3-bromopropoxy)-6-methoxy-4-quinolyl]oxy}-2-chlorophenyl)-N'-propylurea, 52 mg), potassium carbonate (138 mg), and 1-methylpiperazine (0.055 ml) were dissolved in N,N-dimethylformamide (1 ml), and the solution was stirred at room temperature for 18 hr. Water was added to the reaction mixture, and the mixture was extracted with chloroform-propanol (3/1). The organic layer was dried over anhydrous sodium sulfate, and the solvent was removed by distillation under the reduced pressure. The residue was washed with ether to give 41 mg (yield 76%) of the title compound.

$^1$H-NMR (CDCl$_3$, 400 MHz): δ 0.92 (t, J=7.6 Hz, 3H), 1.49–1.64 (m, 2H), 2.02–2.10 (m, 2H), 2.23 (s, 3H), 2.30–2.56 (m, 8H), 2.52 (t, J=7.3 Hz, 2H), 3.20 (dd, J=7.1 Hz, 12.9 Hz, 2H), 3.94 (s, 3H), 4.19 (t, J=6.8 Hz, 2H), 4.83–4.92 (m, 1H), 6.40 (d, J=5.1 Hz, 1H), 6.69 (s, 1H), 7.03 (dd, J=2.9 Hz, 9.3 Hz, 1H), 7.14 (d, J=2.7 Hz, 1H), 7.35 (s, 1H), 7.42 (s, 1H), 8.19 (d, J=9.0 Hz, 1H), 8.42 (d, J=5.4 Hz, 1H).

Mass analysis, found (ESI-MS, m/z): 542 (M$^+$+1).

Example 153

N-[2-Chloro-4-(6-methoxy-7-{[3-(1H-1,2,3-triazol-1-yl)propoxy]-4-quinolyl}oxy)phenyl]-N'-propylurea Triazole (0.41 ml), 1-bromo-3-chloropropane (0.79 ml), tetrabutylammonium iodide (10 mg), and a 3 M aqueous sodium hydroxide solution (1 ml) were dissolved in acetone (10 ml), and the solution was stirred at 50° C. for 18 hr. Water was added to the reaction mixture, and the mixture was extracted with chloroform. The organic layer was dried over anhydrous sodium sulfate, and the solvent was removed by distillation under the reduced pressure. The residue was purified by chromatography by development with chloroform to give an intermeidate (327 mg).

A starting compound (N-{2-chloro-4-[(7-hydroxy-6-methoxy-4-quinolyl)oxy]phenyl}-N'-propylurea, 80 mg), potassium carbonate (138 mg), and the intermediate (43 mg) were dissolved in N,N-dimethylformamide (1 ml), and the solution was stirred at 80° C. for 3 hr. Water was added to the reaction mixture, and the mixture was extracted with chloroform-propanol (3/1). The organic layer was dried over anhydrous sodium sulfate, and the solvent was removed by distillation under the reduced pressure. The residue was purified by HPLC by development with chloroform/methanol to give 54 mg (yield 52%) of the title compound.

$^1$H-NMR (CDCl$_3$, 400 MHz): δ 0.97 (t, J=7.6 Hz, 3H), 1.54–1.65 (m, 2H), 2.49–2.58 (m, 2H), 3.26 (dd, J=7.1 Hz, 13.2 Hz, 2H), 4.01 (s, 3H), 4.15 (t, J=5.9 Hz, 2H), 4.69 (t, J=6.6 Hz, 2H), 4.90–5.00 (m, 1H), 6.46 (d, J=5.1 Hz, 1H), 6.77 (s, 1H), 7.08 (dd, J=2.7 Hz, 9.0 Hz, 1H), 7.19 (d, J=2.7 Hz, 1H), 7.36 (s, 1H), 7.51 (s, 1H), 7.61 (s, 1H), 7.67 (s, 1H), 8.26 (d, J=9.0 Hz, 1H), 8.47 (d, J=5.4 Hz, 1H).

Mass analysis, found (ESI-MS, m/z): 511 (M$^+$+1).

Example 154

N-[2-Chloro-4-({7-[3-(1H-1-imidazolyl-propoxy]-6-methoxy-4- quinolyl}oxy)phenyl]-N'-propylurea Imidazole (680 mg), 1-bromo-3-chloropropane (0.79 ml), tetrabutylammonium iodide (10 mg), and a 3 M aqueous sodium hydroxide solution (1 ml) were dissolved in acetone (10 ml), and the solution was stirred at 50° C. for 18 hr. Water was added to the reaction mixture, and the mixture was extracted with chloroform. The organic layer was dried over anhydrous sodium sulfate, and the solvent was removed by distillation under the reduced pressure. The residue was purified by chromatography by development with chloroform to give an intermediate (1-(3-chloropropyl)-1H-imidazole, 525 mg).

A starting compound (N-{2-chloro-4-[(7-hydroxy-6-methoxy-4-quinolyl)oxy]phenyl}-N'-propylurea, 80 mg), potassium carbonate (138 mg), and the intermediate (42 mg) were dissolved in N,N-dimethylformamide (1 ml), and the solution was stirred at 80° C. for 3 hr. Water was added to the reaction mixture, and the mixture was extracted with chloroform-propanol (3/1). The organic layer was dried over anhydrous sodium sulfate, and the solvent was removed by distillation under the reduced pressure. The residue was purified by HPLC by development with chloroform/methanol to give 23 mg (yield 23%) of the title compound.

$^1$H-NMR (CDCl$_3$, 400 MHz): δ 0.91 (t, J=7.3 Hz, 3H), 1.48–1.60 (m, 2H), 2.27–2.36 (m, 2H), 3.20 (dd, J=6.8 Hz, 12.9 Hz, 2H), 3.97 (s, 3H), 4.06 (t, J=5.9 Hz, 2H), 4.21 (t, J=6.8 Hz, 2H), 6.39 (d, J=5.4 Hz, 1H), 6.90 (s, 1H), 6.98–7.04 (m, 2H), 7.12 (d, J=2.7 Hz, 1H), 7.30 (s, 1H), 7.44–7.48 (m, 2H), 8.22 (d, J=9.0 Hz, 1H), 8.41 (d, J=5.4 Hz, 1H).

Example 155

N-{2-Chloro-4-[(7-{2[di(hydroxyethyl)-amino]ethoxy}-6-methoxy-4-quinolyl)oxy]phenyl}-N'-propylurea A starting compound (N-(4-{[7-(2-bromoethoxy)-6-methoxy-4-quinolyl]oxy}-2-chlorophenyl)-N'-propylurea, 50 mg), potassium carbonate (138 mg), and 1-methylpiperazine (0.055 ml) were dissolved in N,N-dimethylformamide (1 ml), and the mixture was stirred at room temperature for 18 hr. Water was added to the reaction mixture, and the mixture was extracted with chloroform-propanol (3/1). The organic layer was dried over anhydrous sodium sulfate, and the solvent was removed by distillation under the reduced pressure. The residue was washed with ether to give 46 mg (yield 92%) of the title compound.

$^1$H-NMR (CDCl$_3$, 400 MHz): δ 0.92 (t, J=7.3 Hz, 3H), 1.50–1.60 (m, 2H), 2.74 (t, J=4.9 Hz, 4H), 3.04 (t, J=4.9 Hz, 2H), 3.15–3.24 (m, 2H), 3.60 (t, J=5.1 Hz, 4H), 3.94 (s, 3H), 4.17 (t, J=5.0 Hz, 2H), 6.41 (d, J=5.4 Hz, 1H), 6.75 (s, 1H), 7.04 (dd, J=2.4 Hz, 8.8 Hz, 1H), 7.14 (d, J=2.7 Hz, 1H), 7.38 (s, 1H), 7.43 (s, 1H), 8.19 (d, J=9.0 Hz, 1H), 8.42 (d, J=5.4 Hz, 1H).

Example 156

N-{2-Chloro-4-[(7-{3-[di(2-hydroxyethyl)-amino] propoxy}-6-methoxy-4-quinolyl)oxy]phenyl}-N'-propylurea A starting compound (N-(4-{[7-(3-bromopropoxy)-6-methoxy-4-quinolyl]oxy}-2-chlorophenyl)-N'-propylurea, 52 mg), potassium carbonate (138 mg), and diethanolamine (53 mg) were dissolved in N,N-dimethylformamide (1 ml), and the solution was stirred at room temperature for 18 hr. Water was added to the reaction mixture, and the mixture was extracted with chloroform-propanol (3/1). The organic layer was dried over anhydrous sodium sulfate, and the solvent was removed by distillation under the reduced pressure. The residue was washed with ether to give 41 mg (yield 82%) of the title compound.

$^1$H-NMR (CDCl$_3$, 400 MHz): δ 0.89 (t, J=7.3 Hz, 3H), 1.46–1.56 (m, 2H), 1.97–2.05 (m, 2H), 2.63 (t, J=5.1 Hz, 4H), 2.69 (t, J=6.1 Hz, 2H), 3.19 (dd, J=7.1 Hz, 13.2 Hz, 2H), 3.60 (t, J=4.9 Hz, 4H), 3.94 (s, 3H), 4.32 (t, J=5.9 Hz, 2H), 5.27–5.35 (m, 1H), 6.37 (d, J=5.4 Hz, 1H), 6.94 (s, 1H), 7.01 (dd, J=2.9 Hz, 9.0 Hz, 1H), 7.10 (d, J=2.7 Hz, 1H), 7.42 (s, 1H), 7.53 (s, 1H), 8.19 (d, J=9.0 Hz, 1H), 8.35 (d, J=5.4 Hz, 1H).

Mass analysis, found (ESI-MS, m/z): 547 (M$^+$+1).

Example 157

N-{2-Chloro-4-[(7-{3-[(2-hydroxy-ethyl)(methyl) amino]propoxy}-6-methoxy-4-quinolyl)oxy]-phenyl}-N'-propylurea A starting compound (N-(4-{[7-(3-bromopropoxy)-6-methoxy-4-quinolyl]oxy}-2-chlorophenyl)-N'-propylurea, 52 mg), potassium carbonate (138 mg), and 2-(methylamino)ethanol (0.040 ml) were dissolved in N,N-dimethylformamide (1 ml), and the solution was stirred at room temperature for 18 hr. Water was added to the reaction mixture, and the mixture was extracted with chloroform-propanol (3/1). The organic layer was dried over anhydrous sodium sulfate, and the solvent was removed by distillation under the reduced pressure. The residue was washed with ether to give 51 mg (yield 98%) of the title compound.

$^1$H-NMR (CDCl$_3$, 400 MHz): δ 0.91 (t, J=7.6 Hz, 3H), 1.45–1.59 (m, 2H), 2.05 (t, J=6.8 Hz, 2H), 2.24 (s, 3H), 2.51 (t, J=5.1 Hz, 2H), 2.59 (t, J=7.1 Hz, 2H), 3.20 (dd, J=6.8 Hz, 12.9 Hz, 2H), 3.57 (t, J=5.4 Hz, 2H), 3.95 (s, 3H), 4.22 (t, J=6.3 Hz, 2H), 5.00–5.08 (m, 1H), 6.40 (d, J=5.1 Hz, 1H), 6.79 (s, 1H), 7.03 (dd, J=2.7 Hz, 9.0 Hz, 1H), 7.13 (d, J=2.7 Hz, 1H), 7.426 (s, 1H), 7.433 (s, 1H), 8.19 (d, J=9.0 Hz, 1H), 8.40 (d, J=5.4 Hz, 1H).

Mass analysis, found (ESI-MS, m/z): 517 (M$^+$+1).

Example 158

N-[2-Chloro-4-({6-methoxy-7-[4-(1H-1,2,3-triazol-1-yl) butoxy]-4-quinolyl}oxy)phenyl]-N'-propylurea Triazole (0.41 ml), 1-bromo-4-chlorobutane (0.93 ml), tetrabutylammonium iodide (10 mg), and a 3 M aqueous sodium hydroxide solution (1 ml) were dissolved in acetone (10 ml), and the solution was stirred at 50° C. for 18 hr. Water was added to the reaction mixture, and the mixture was extracted with chloroform. The organic layer was dried over anhydrous sodium sulfate, and the solvent was removed by distillation under the reduced pressure. The residue was purified by chromatography by development with chloroform to give an intermediate (1-(4-chlorobutyl)-1H-1,2,3-triazole, 314 mg).

A starting compound (N-{2-chloro-4-[(7-hydroxy-6-methoxy-4-quinolyl)oxy]phenyl}-N'-propylurea, 80 mg), potassium carbonate (138 mg), and the intermediate (48 mg) were dissolved in N,N-dimethylformamide (1 ml), and the solution was stirred at 80° C. for 3 hr. Water was added to the reaction mixture, and the mixture was extracted with chloroform-propanol (3/1). The organic layer was dried over anhydrous sodium sulfate, and the solvent was removed by distillation under the reduced pressure. The residue was purified by HPLC by development with chloroform/methanol to give 42 mg (yield 40%) of the title compound.

$^1$H-NMR (CDCl$_1$ 400 MHz): δ 0.96 (t, J=7.3 Hz, 3H), 1.54–1.65 (m, 2H), 1.88–1.98 (m, 2H), 2.14–2.24 (m, 2H), 3.26 (dd, J=6.6 Hz, 13.2 Hz, 2H), 3.99 (s, 3H), 4.20 (t, J=5.9 Hz, 2H), 4.55 (t, J=7.1 Hz, 2H), 5.00–5.06 (m, 1H), 6.46 (d, J=5.4 Hz, 1H), 6.80 (s, 1H), 7.08 (dd, J=2.7 Hz, 9.0 Hz, 1H), 7.19 (d, J=2.7 Hz, 1H), 7.37 (s, 1H), 7.49 (s, 1H), 7.68–7.72 (m, 2H), 8.26 (d, J=9.0 Hz, 1H), 8.47 (d, J=5.1 Hz, 1H).

Mass analysis, found (ESI-MS, m/z): 525 (M$^+$+1).

Example 159

N-{2-Chloro-4-[(6-methoxy-7-{[5-(1H-1H-1,2,3-triazol-1-yl) pentyl]oxy}-4-quinolyl)oxy]phenyl}-N'-propylurea Triazole (0.41 ml), 1-bromo-5-chloropentane (1.0 ml), tetrabutylammonium iodide (10 mg), and a 3 M aqueous sodium hydroxide solution (1 ml) were dissolved in acetone (10 ml), and the solution was stirred at 50° C. for 18 hr. Water was added to the reaction mixture, and the mixture was extracted with chloroform. The organic layer was dried over anhydrous sodium sulfate, and the solvent was removed by distillation under the reduced pressure. The residue was purified by chromatography by development with chloroform to give an intermediate (1-(5-chloropentyl-1H-1,2,3-triazole, 390 mg).

A starting compound (N-{2-chloro-4-[(7-hydroxy-6-methoxy-4-quinolyl)oxy]phenyl}-N'-propylurea, 80 mg), potassium carbonate (138 mg), and the intermediate (51 mg) were dissolved in N,N-dimethylformamide (1 ml), and the solution was stirred at 80° C. for 3 hr. Water was added to the reaction mixture, and the mixture was extracted with chloroform-propanol (3/1). The organic layer was dried over anhydrous sodium sulfate, and the solvent was removed by distillation under the reduced pressure. The residue was purified by HPLC by development with chloroform/methanol to give 33 mg (yield 31%) of the title compound.

$^1$H-NMR (CDCl$_3$, 400 MHz): δ 0.92 (t, J=7.6 Hz, 3H), 1.47–1.59 (m, 2H), 1.85–2.03 (m, 4H), 3.21 (dd, J=6.6 Hz, 13.2 Hz, 2H), 3.94 (s, 3H), 4.11 (t, J=6.3 Hz, 2H), 4.38 (t, J=7.1 Hz, 2H), 4.86–4.94 (m, 1H), 6.41 (d, J=5.4 Hz, 1H), 6.71 (s, 1H), 7.03 (dd, J=2.4 Hz, 9.0 Hz, 1H), 7.14 (d, J=2.7 Hz, 1H), 7.31 (s, 1H), 7.43 (s, 1H), 7.51 (s, 1H), 7.64 (s, 1H), 8.20 (d, J=9.0 Hz, 1H), 8.41 (d, J=5.4 Hz, 1H).

Mass analysis, found (ESI-MS, m/z): 539 (M$^+$+1).

Example 160

N-2-Chloro-4-({7-[4-(1H-1-imidazoly-butoxyl-6-methoxy-4-quinolyl}oxy)phenyl]-N'-propylurea Imidazole (680 mg), 1-bromo-4-chlorobutane (0.93 ml), tetrabutylammonium iodide (10 mg), and a 3 M aqueous sodium hydroxide solution (1 ml) were dissolved in acetone (10 ml), and the solution was stirred at 50° C. for 18 hr. Water was added to the reaction mixture, and the mixture was extracted with chloroform. The organic layer was dried over anhydrous sodium sulfate, and the solvent was removed by distillation under the reduced pressure. The residue was purified by chromatography by development with chloroform to give an intermediate (1-(4-chlorobutyl)-1H-imidazole, 756 mg).

A starting compound (N-{2-chloro-4-[(7-hydroxy-6-methoxy-4-quinolyl)oxy]phenyl}-N'-propylurea, 80 mg), potassium carbonate (138 mg), and the intermediate (48 mg) were dissolved in N,N-dimethylformamide (1 ml), and the solution was stirred at 80° C. for 3 hr. Water was added to the reaction mixture, and the mixture was extracted with chloroform-propanol (3/1). The organic layer was dried over anhydrous sodium sulfate, and the solvent was removed by distillation under the reduced pressure. The residue was purified by HPLC by development with chloroform/methanol to give 29 mg (yield 28%) of the title compound.

$^1$H-NMR (CDCl$_3$, 400 MHz): δ 0.96 (t, J=7.3 Hz, 3H), 1.54–1.65 (m, 2H), 1.83–1.95 (m, 2H), 1.98–2.08 (m, 2H), 3.25 (dd, J=6.8 Hz, 12.7 Hz, 2H), 4.00 (s, 3H), 4.10 (t, J=7.1 Hz, 2H), 4.20 (t, J=6.1 Hz, 2H), 5.08–5.16 (m, 1H), 6.46 (d, J=5.1 Hz, 1H), 6.83 (s, 1H), 6.97 (s, 1H), 7.06 (s, 1H), 7.08 (dd, J=2.9 Hz, 9.3 Hz, 1H), 7.18 (d, J=2.7 Hz, 1H), 7.37 (s, 1H), 7.49 (s, 1H), 7.58 (s, 1H), 8.26 (d, J=9.0 Hz, 1H), 8.46 (d, J=5.4 Hz, 1H).

Example 161

N-(2-Chloro-4-{[6-methoxy-7-(4-pyridyl-methoxy)-4-quinazolinyl]oxy}phenyl)-N'-(2,4-difluorophenyl) urea A starting compound (N'-{2-chloro -4-[(7-hydroxy-6-methoxy-4-quinazolinyl)oxy]phenyl}-N'-(2,4-difluorophenyl)urea, 80 mg), potassium carbonate (138 mg), and 4-chloromethylpyridine hydrochloride (41 mg) were dissolved in N,N-dimethylformamide (1 ml), and the solution was stirred at room temperature for 18 hr. Water was added to the reaction mixture, and the mixture was extracted with chloroform-propanol (3/1). The organic layer was dried over anhydrous sodium sulfate, and the solvent was removed by distillation under the reduced pressure. The residue was washed with ether to give 50 mg (yield 52%) of the title compound.

$^1$H-NMR (CDCl$_3$, 400 MHz): δ 4.03 (s, 3H), 5.46 (s, 2H), 7.03–7.11 (m, 1H), 7.28–7.38 (m, 1H), 7.47 (s, 1H), 7.50 (d, J=5.9 Hz, 2H), 7.56 (d, J=2.7 Hz, 1H), 7.61 (s, 1H), 7.95 (s, 1H), 8.09–8.18 (m, 1H), 8.19 (d, J=9.0 Hz, 1H), 8.57 (s, 1H), 8.63 (d, J=5.9 Hz, 2H), 8.81 (s, 1H), 9.30 (s, 1H).

Example 162

N-(2-Chloro-4-{[6-methoxy-7-(2-morpholino-ethoxy)-4-quinazolinyl]oxy}phenyl)-N'-(2,4-difluorophenyl)urea A starting compound (N'-{2-chloro-4-[(7-hydroxy-6-methoxy-4-quinazolinyl)oxy]phenyl}-N'-(2,4-difluoro-phenyl)urea, 100 mg), potassium carbonate (857 mg), and 1,2-dibromoethane (0.085 ml) were dissolved in N,N-dimethylformamide (1 ml), and the solution was stirred at room temperature for 18 hr. Water was added to the reaction mixture, and the mixture was extracted with chloroform-propanol (3/1). The organic layer was dried over anhydrous sodium sulfate, and the solvent was removed by distillation under the reduced pressure. The residue was washed with ether to give an intermediate (N-(4-{[7-(2-bromoethoxy)-6-methoxy-4-quinazolinyl]oxy}-2-chlorophenyl)-N'-(2,4-difluorophenyl)urea). The intermediate, potassium carbonate (138 mg), and morpholine (0.05 ml) were dissolved in N,N-dimethylformamide (1 ml), and the solution was stirred at room temperature for 18 hr. Water was added to the reaction mixture, and the mixture was extracted with chloroform-propanol (3/1). The organic layer was dried over anhydrous sodium sulfate, and the solvent was removed by distillation under the reduced pressure. The residue was purified by HPLC by development with chloroform/methanol to give 57 mg (yield 46%) of the to title compound.

$^1$H-NMR (CDCl$_3$, 400 MHz): δ 2.54–2.63 (m, 4H), 2.85–2.94 (m, 2H), 3.66–3.73 (m, 4H), 3.97 (s, 3H), 4.25–4.32 (m, 2H), 6.77–6.88 (m, 2H), 7.09 (s, 1H), 7.14 (dd, J=2.7 Hz, 9.0 Hz, 1H), 7.257 (s, 1H), 7.264 (s, 1H), 7.44 (s, 1H), 7.90–7.99 (m, 1H), 8.22 (d, J=9.0 Hz, 1H), 8.56 (s, 1H).

Mass analysis, found (ESI-MS, m/z): 586 (M$^+$+1).

Example 163

N-(2-Chloro-4-{[6-methoxy-7-(3-morpholino-propoxy)-4-quinazolinyl]oxy}phenyl)-N'-(2,4-difluoro-phenyl)urea A starting compound (N-(4-{[7-(3-bromopropoxy)-6-methoxy-4-quinazolinyl]oxy}-2-chlorophenyl)-N'-(2,4-difluorophenyl)urea, 59 mg), potassium carbonate (857 mg), and morpholine (0.043 ml) were dissolved in N,N-dimethylformamide (1 ml), and the solution was stirred at room temperature for 18 hr. Water was added to the reaction mixture, and the mixture was extracted with chloroform-propanol (3/1). The organic layer was dried over anhydrous sodium sulfate, and the solvent was removed by distillation under the reduced pressure. The residue was washed with ether to give 53 mg (yield 89%) of the title compound.

$^1$H-NMR (CDCl$_3$, 400 MHz): δ 2.06–2.16 (m, 2H), 2.43–2.57 (m, 4H), 2.56 (t, J=6.8 Hz, 2H), 3.68–3.75 (m, 4H), 4.03 (s, 3H), 4.27 (t, J=6.6 Hz, 2H), 6.79–6.91 (m, 2H), 7.14 (s, 1H), 7.19 (dd, J=2.7 Hz, 9.0 Hz, 1H), 7.28 (s, 1H), 7.29 (d, J=9.0 Hz, 1H), 7.33 (s, 1H), 7.49 (s, 1H), 8.26 (d, J=9.0 Hz, 1H), 8.61 (s, 1H).

Mass analysis, found (ESI-MS, m/z): 600 (M$^+$+1).

Example 164

N-[2-Chloro-4-({6-methoxy-7-[3-(4-methyl-piperazino)propoxy]-4-quinazolinyl}oxy)phenyl]-N'-(2,4-difluorophenyl)urea A starting compound (N-(4-{[7-(3-bromopropoxy)-6-methoxy-4-quinazolinyl]oxy}-2-chlorophenyl)-N'-(2,4-difluorophenyl)urea, 59 mg), potassium carbonate (138 mg), and 1-methylpiperazine (0.055 ml) were dissolved in N,N-dimethylformamide (1 ml), and the solution was stirred at room temperature for 18 hr. Water was added to the reaction mixture, and the mixture was extracted with chloroform-propanol (3/1). The organic layer was dried over anhydrous sodium sulfate, and the solvent was removed by distillation under the reduced pressure. The residue was washed with ether to give 58 mg (yield 95%) of the title compound.

$^1$H-NMR (CDCl$_3$, 400 MHz): δ 2.01–2.12 (m, 2H), 2.23 (s, 3H), 2.23–2.80 (m, 8H), 2.51 (t, J=7.1 Hz, 2H), 3.97 (s, 3H), 4.20 (t, J=7.2 Hz, 2H), 6.73–6.87 (m, 2H), 7.13 (dd, J=2.7 Hz, 9.0 Hz, 1H), 7.24 (d, J=2.7 Hz, 1H), 7.27 (s, 1H), 7.30 (s, 1H), 7.44 (s, 1H), 7.91–8.00 (m, 2H), 8.21 (d, J=9.0 Hz, 1H), 8.56 (s, 1H).

Example 165

N-{2-Chloro-4-[(7-{3-[(2-hydroxyethyl)-(methyl)amino]propoxy}-6-methoxy-4-quinazolinyl)oxy]-phenyl}-N'-(2,4-difluorophenyl)urea A starting compound (N-(4-{[7-(3-bromopropoxy)-6-methoxy-4-quinazolinyl]oxy}-2-chlorophenyl)-N'-(2,4-difluorophenyl)urea, 59 mg), potassium carbonate (138 mg), and 2-(methylamino)ethanol (0.040 ml) were dissolved in N,N-dimethylformamide (1 ml), and the solution was stirred at room temperature for 18 hr. Water was added to the reaction mixture, and the mixture was extracted with chloroform-propanol (3/1). The organic layer was dried over anhydrous sodium sulfate, and the solvent was removed by distillation under the reduced pressure. The residue was washed with ether to give 58 mg (yield 100%) of the title compound.

$^1$H-NMR (CDCl$_3$, 400 MHz): δ 2.06–2.16 (m, 2H), 2.30 (s, 3H), 2.57 (t, J=5.1 Hz, 2H), 2.65 (t, J=6.8 Hz, 1H), 3.63 (t, J=5.4 Hz, 2H), 4.02 (s, 3H), 4.28 (t, J=6.1 Hz, 2H), 6.79–6.91 (m, 2H), 7.18 (dd, J=2.7 Hz, 9.0 Hz, 1H), 7.28 (d, J=2.7 Hz, 1H), 7.37 (s, 1H), 7.48 (s, 1H), 7.96–8.06 (m, 2H), 8.26 (d, J=9.0 Hz, 1H), 8.59 (s, 1H).

Mass analysis, found (ESI-MS, m/z): 588 (M$^+$+1).

Example 166

N-[2-Chloro-4-{6-methoxy-7-[2-(4-methyl-piperazino) ethoxy]-4-quinolyl})oxy)phenyl]-N'-(2, 4-difluorophenyl)urea A starting compound (N-(4-{[7-(2-bromoethoxy)-6-methoxy-4-quinolyl]oxy}-2-chlorophenyl)-N'-(2,4-difluorophenyl)urea, 50 mg), potassium carbonate (138 mg), and 1-methylpiperazine (0.055 ml) were dissolved in N,N-dimethylformamide (1 ml), and the solution was stirred at room temperature for 18 hr. Water was added to the reaction mixture, and the mixture was extracted with chloroform-propanol (3/1). The organic layer was dried over anhydrous sodium sulfate, and the solvent was removed by distillation under the reduced pressure. The residue was washed with ether to give 48 mg (yield 93%) of the title compound.

$^1$H-NMR (CDCl$_3$, 400 MHz): δ 2.31 (s, 3H), 2.40–2.75 (m, 8H), 2.95 (t, J=6.1 Hz, 2H), 3.99 (s, 3H), 4.31 (t, J=5.9 Hz, 2H), 6.48 (d, J=5.1 Hz, 1H), 6.85–6.96 (m, 3H), 7.12 (dd, J=2.7 Hz, 9.0 Hz, 1H), 7.15 (s, 1H), 7.22 (d, J=2.7 Hz, 1H), 7.40 (s, 1H), 7.47 (s, 1H), 7.94–8.03 (m, 1H), 8.25 (d, J=9.0 Hz, 1H), 8.49 (d, J=5.1 Hz, 1H).

Example 167

N-{2-Chloro-4-[(7-{2-[(2-hydroxyethyl)-(methyl)amino]ethoxy}-6-methoxy-4-quinolyl)oxy]phenyl}-N'-(2,4difluorophenyl)urea A starting compound (N-(4-{[7-(2-bromoethoxy)-6-methoxy-4-quinolyl]oxy}-2-chlorophenyl)-N'-(2,4-difluorophenyl)urea, 50 mg), potassium carbonate (138 mg), and 2-(methylamino)ethanol (0.040 ml) were dissolved in N,N-dimethylformamide (1 ml), and the solution was stirred at room temperature for 18 hr. Water was added to the reaction mixture, and the mixture was extracted with chloroform-propanol (3/1). The organic layer was dried over anhydrous sodium sulfate, and the solvent was removed by distillation under the reduced pressure. The residue was washed with ether to give 48 mg (yield 97%) of the title compound.

$^1$H-NMR (CDCl$_3$, 400 MHz): δ 2.44 (s, 3H), 2.71 (t, J=4.9 Hz, 2H), 3.02 (t, J=5.6 Hz, 4H), 3.66 (t, J=5.1 Hz, 2H), 3.97 (s, 3H), 4.27 (t, J=5.6 Hz, 2H), 6.46 (d, J=5.4 Hz, 1H), 6.80–6.93 (m, 2H), 7.11 (dd, J=2.7 Hz, 9.0 Hz, 1H), 7.19 (d, J=2.7 Hz, 1H), 7.45 (s, 1H), 7.96–8.04 (m, 1H), 8.25 (d, J=9.0 Hz, 1H), 8.48 (d, J=5.1 Hz, 1H).

Example 168

N-(2-chloro-4-{[6-methoxy-7-(3-morpholino-propoxy)-4-quinolyl]oxy}phenyl)-N'-(2,4-difluorophenyl)urea A starting compound (N-(4-{[7-(3-bromopropoxy)-6-methoxy-4-quinolyl]oxy}-2-chlorophenyl)-N'-(2,4-difluorophenyl)urea, 50 mg), potassium carbonate (138 mg), and morpholine (0.044 ml) were dissolved in N,N-dimethylformamide (1 ml), and the solution was stirred at room temperature for 18 hr. Water was added to the reaction mixture, and the mixture was extracted with chloroform-propanol (3/1). The organic layer was dried over anhydrous sodium sulfate, and the solvent was removed by distillation under the reduced pressure. The residue was washed with ether to give 32 mg (yield 64%) of the title compound.

$^1$H-NMR (CDCl, 400 MHz): δ 2.06–2.16 (m, 2H), 2.43–2.51 (m, 4H), 2.56 (t, J=7.3 Hz, 2H), 3.68–3.74 (m, 4H), 4.00 (s, 3H), 4.25 (t, J=6.6 Hz, 2H), 6.47 (d, J=5.1 Hz, 1H), 6.84–6.93 (m, 2H), 7.06 (8, 1H), 7.12 (dd, J=2.7 Hz, 9.0 Hz, 1H), 7.22 (d, J=2.9 Hz, 1H), 7.42 (s, 1H), 7.47 (s, 1H), 7.95–8.04 (m, 1H), 8.25 (d, J=9.0 Hz, 1H), 8.48 (d, J=5.4 Hz, 1H).

Example 169

N-(2-Chloro4-{[6-methoxy-7-(3-pyridyl-methoxy)-4-quinolyl]oxy}phenyl)-N'-(2,4-difluorophenyl)-urea N-{2-Chloro-4-[(7-hydroxy-6-methoxy-4-quinolyl)-oxy]phenyl}-N'-(2,4-difluorophenyl)urea (55 mg), potassium carbonate (31 mg), and 3-picolyl chloride hydrochloride (22 mg) were dissolved in N,N-dimethylformamide (1 ml), and the solution was stirred at 80° C. for one hr. The solvent was removed by distillation under the reduced pressure. A saturated aqueous sodium hydrogencarbonate solution was added to the residue, and the mixture was extracted with chloroform. The chloroform layer was dried over anhydrous sodium sulfate. The solvent was removed by distillation under the reduced pressure. The residue was washed with ether to give 30 mg (yield 48%) of the title compound.

$^1$H-NMR (CDCl$_3$, 400 MHz): δ 4.03 (s, 3H), 5.31 (s, 2H), 6.49 (d, J=5.4 Hz, 1H), 6.77–6.88 (m, 2H), 7.10–7.16 (m, 2H), 7.31–7.35 (m, 1H), 7.48 (s, 1H), 7.54 (s, 1H), 7.86 (d, J=7.8 Hz, 1H), 7.96 (s, 1H), 8.03–8.10 (m, 1H), 8.32 (d, J=9.0 Hz, 1H), 8.42 (s, 1H), 8.49 (d, J=5.4 Hz, 1H), 8.59 (d, J=3.9 Hz, 1H), 8.77 (s, 1H).

Example 170

N-[2-Chloro-4-({6-methoxy-7-[2-(1H-1,2,3- triazol-1-yl)ethoxy]-4-quinolyl}oxy)phenyl]-N'-42,4-difluorophenyl)urea N-{2-Chloro-4-[(7-hydroxy-6-methoxy-4-quinolyl)-oxy]phenyl}-N'-(2,4-difluorophenyl) urea (55 mg), potassium carbonate (31 mg), and 2-(1H-1,2,3-triazol-1-yl)ethyl 4-methyl-1-benzenesulfonate (36 mg) were dissolved in N,N-dimethylformamide (1 ml), and the solution was stirred at 80° C. for one hr. The solvent was removed by distillation under the reduced pressure. A saturated aqueous sodium hydrogencarbonate solution was added to the residue, and the mixture was extracted with chloroform. The chloroform layer was dried over anhydrous sodium sulfate. The solvent was removed by distillation under the reduced pressure. The residue was washed with ether to give 46 mg (yield 72%) of the title compound.

$^1$H-NMR (CDCl$_3$, 400 MHz): δ 4.02 (s, 3H), 4.53 (d, J=4.9 Hz, 2H), 4.95 (d, J=5.1 Hz, 2H), 6.47 (d, J=15 5.1 Hz, 1H), 6.83–6.92 (m, 2H), 7.11 (dd, J=2.7 Hz, 9.0 Hz, 1H), 7.16 (d, J=2.7 Hz, 1H), 7.39 (6, 1H), 7.52 (s, 1H), 7.58 (s, 1H), 7.70 (s, 1H), 7.76 (s, 1H), 8.00 (s, 1H), 8.01–8.07 (m, 1H), 8.29 (d, J=9.0 Hz, 1H), 8.49 (d, J=5.4 Hz, 1H).

Example 171

N-(2-Methoxy-4-{[6-methoxy-7-(3-morpholino-propoxy)-4-quinazolinyl]oxy}phenyl)-N'-propylurea N-4-[(7-Hydroxy-6-methoxy-4-quinazolinyl)oxy]-2-methoxyphenyl}-N'-propylurea (100 mg), potassium carbonate (138 mg), and 1,3-dibromopropane (56 mg) were dissolved in N,N-dimethylformamide (5 ml), and the solution was stirred at room temperature for 3 hr. The solvent was removed by distillation under the reduced pressure. Water was added to the residue, and the mixture was extracted with chloroform/2-propanol (4/1). The organic layer was dried over anhydrous sodium sulfate, and the solvent was removed by distillation under the reduced pressure. The residue was washed with ether to give 53 mg (yield 41%) of N-(4-[7-(3-bromopropoxy)-6-methoxy-4-quinazolinyl]oxy-2-methoxy-phenyl}-N'-propylurea. N-(4-{[6-(3-Bromopropoxy)-7-methoxy-4-quinazolinyl]oxy}-2-chlorophenyl}-N'-propylurea (50 mg), potassium carbonate (60 mg), and N-methylpiperazine (100 μl) were dissolved in N,N-dimethylformamide (2 ml), and the solution was stirred at room temperature for 16 hr. The solvent was removed by distillation under the reduced pressure. A saturated aqueous sodium hydrogencarbonate solution was added to the residue, and the mixture was extracted with chloroform. The organic layer was dried over anhydrous sodium sulfate, and the solvent was removed by distillation under the reduced pressure. The residue was purified by chromatography on silica gel by development with chloroform/methanol to give 22 mg (yield 42%) of the title compound.

$^1$H-NMR (CDCl$_3$, 400 MHz): δ 0.97 (t, J=7.6 Hz, 3H), 1.56–1.60 (m, 2H), 2.14 (br, 2H), 2.50 (br, 4H), 2.58 (br, 2H), 3.23–3.26 (m, 2H), 3.74 (br, 4H), 3.87 (s, 3H), 4.04 (s, 3H), 4.27–4.31 (m, 2H), 4.62–4.64 (m, 1H), 6.65 (s, 1H), 6.79–6.85 (m, 2H), 7.33 (s, 1H), 7.53 (s, 1H), 8.10 (d, J=8.5 Hz, 1H), 8.62 (s, 1H).

Mass analysis, found (ESI-MS, m/z): 526 (M$^+$+1).

Example 172

N-(2,4-Difluorophenyl)-N'-(2-methoxy-4-{[6-methoxy-7-(3-morpholinopropoxy)-4-quinazoliny]oxy}-phenyl)urea N-(2,4-Difluorophenyl)-N'-4-[(7-hydroxy-6-methoxy-4-quinazolinyl) oxy]-2-methoxyphenylurea (375 mg), potassium carbonate (442 mg), and 1,3-dibromopropane (242 mg) were dissolved in N,N-dimethylformamide (5 ml), and the solution was stirred at room temperature for 3 hr. The solvent was removed by distillation under the reduced pressure. Water was added to the residue, followed by extraction with ethyl acetate. The organic layer was dried over anhydrous sodium sulfate, and the solvent was removed by distillation under the reduced pressure. The residue was washed with ether to give 210 mg (yield 45%) of N-{4-[7-(3-bromopropoxy)-6-methoxy-4-quinazolinyl]oxy-2-methoxyphenyl}-N'-(2,4-difluorophenyl)urea. N-(4-{(6-(3-Bromopropoxy)-7-methoxy-4-quinazolinyl]oxy}-2-chlorophenyl}-N'-propylurea (130 mg), triethylamine (0.5 ml), and morpholine (0.5 ml) were dissolved in N,N-dimethylformamide (4 ml), and the solution was stirred at room temperature for 18 hr. The solvent was removed by distillation under the reduced pressure. A saturated aqueous sodium hydrogencarbonate solution was added to the residue, and the mixture was extracted with chloroform. The organic layer was dried over anhydrous sodium sulfate, and the solvent was removed by distillation under the reduced pressure. The residue was purified by chromatography on silica gel by development with chloroform/methanol to give 81 mg (yield 62%) of the title compound.

$^1$H-NMR (CDCl$_3$, 400 MHz): δ 1.97–2.00 (m, 2H), 2.39 (br, 4H), 2.49–2.51 (m, 2H), 3.58–3.60 (m, 4H), 3.88 (s, 3H), 3.98 (s, 3H), 4.25 (t, J=6.3 Hz, 2H), 4.27–4.31 (m, 2H), 4.62–4.64 (m, 1H), 6.84 (dd, J=2.7 Hz, 8.8 Hz, 1H), 7.03–7.07 (m, 2H), 7.28–7.34 (m, 1H), 7.38 (s, 1H), 7.55 (s, 1H), 8.11–8.17 (m, 2H), 8.55 (s,1H), 8.74 (s, 1H), 9.18 (s, 1H).

Mass analysis, found (ESI-MS, m/z): 596 (M⁺+1).

Example 173

N-(2Methoxy-4-{[6-methoxy-7-(3-morpholino-propoxy)-4-quinolyl]oxy}phenyl)-N'-propylurea A starting compound (N-{4-[(7-hydroxy-6-methoxy-4-quinolyl)oxy]-2-methoxyphenyl}-N'-propylurea, 80 mg), potassium carbonate (138 mg), and 1,3-dibromopropane (0.10 ml) were dissolved in N,N-dimethylformamide (1 ml), and the solution was stirred at room temperature for 18 hr. Water was added to the reaction mixture, and the mixture was extracted with chloroform-propanol (3/1). The organic layer was dried over anhydrous sodium sulfate, and the solvent was removed by distillation under the reduced pressure. The residue was washed with ether to give an intermediate. The intermediate, potassium carbonate (138 mg), and morpholine (0.040 ml) were dissolved in N,N-dimethylformamide (1 ml), and the solution was stirred at room temperature for 18 hr. Water was added to the reaction mixture, and the mixture was extracted with chloroform-propanol (3/1). The organic layer was dried over anhydrous sodium sulfate, and the solvent was removed by distillation under the reduced pressure. The residue was purified by chromatography on silica gel by development with chloroform/methanol to give 74 mg (yield 71%) of the title compound.

$^1$H-NMR (CDCl$_3$, 400 MHz): δ 0.95 (t, J=7.6 Hz, 3H), 1.52–1.69 (m, 2H), 2.06–2.15 (m, 2H), 2.43–2.49 (m, 4H), 2.55 (t, J=7.3 Hz, 2H), 3.23 (dd, J=6.1 Hz, 12.9 Hz, 2H), 3.67–3.72 (m, 4H), 3.81 (s, 3H), 4.00 (s, 3H), 4.24 (t, J=6.8 Hz, 2H), 6.44 (d, J=5.1 Hz, 1H), 6.68 (d, J=2.4 Hz, 1H), 6.76 (dd, J=2.4 Hz, 8.8 Hz, 1H), 7.40 (s, 1H), 7.53 (s, 1H), 8.12 (d, J=8.8 Hz, 1H), 8.44 (d, J=5.1 Hz, 1H).

Example 174

N-(2-Methoxy-4-{[6-methoxy-7-(4-pyridylmethoxy)-4quinolyl]oxy}phenyl)-N'-propylurea A starting compound (N-{4-[(7-hydroxy-6-methoxy-4-quinolyl)oxy]-2-methoxyphenyl}-N'-propylurea, 80 mg), potassium carbonate (138 mg), and 4-chloromethylpyridine hydrochloride (48 mg) were dissolved in N,N-dimethylformamide (1 ml), and the solution was stirred at room temperature for 18 hr. Water was added to the reaction mixture, and the mixture was extracted with chloroform-propanol (3/1). The organic layer was dried over anhydrous sodium sulfate, and the solvent was removed by distillation under the reduced pressure. The residue was purified by HPLC by development with chloroform/methanol to give 65 mg (yield 67%) of the title compound.

$^1$H-NMR (CDCl$_3$, 400 MHz): δ 0.95 (t, J=7.3 Hz, 3H), 1.52–1.69 (m, 2H), 3.24 (dd, J=7.3 Hz, 12.9 Hz, 2H), 3.82 (s, 3H), 4.06 (s, 3H), 4.63–4.69 (m, 1H), 5.32 (s, 2H), 6.46 (d, J=5.4 Hz, 1H), 6.68 (d, J=2.7 Hz, 1H), 6.77 (dd, J=2.4 Hz, 8.5 Hz, 1H), 7.37 (s, 1H), 7.42 (d, J=6.1 Hz, 2H), 7.59 (s, 1H), 8.14 (d, J=8.5 Hz, 1H), 8.43 (d, J=5.4 Hz, 1H), 8.61 (d, J=6.1 Hz, 2H).

Example 175

N-Ethyl-N'-(4-{[6-methoxy-7-(2morpholino-ethoxy)-4-quinolyl]oxy}-2,5-dimethylphenyl)urea A starting compound (N-ethyl-N'-{4-[(7-hydroxy-6-methoxy-4-quinolyl)oxy]-2,5-dimethylphenyl}urea, 76 mg), potassium carbonate (138 mg), and 1,2-dibromoethane (0.085 ml) were dissolved in N,N-dimethylformamide (1 ml), and the solution was stirred at room temperature for 18 hr. Water was added to the reaction mixture, and the mixture was extracted with chloroform-propanol (3/1). The organic layer was dried over anhydrous sodium sulfate, and the solvent was removed by distillation under the reduced pressure. The residue was washed with ether to give an intermediate (N-(4-{[7-(2-bromoethoxy)-6-methoxy-4-quinolyl]oxy}-2,5-dimethylphenyl)-N'-ethylurea). The intermediate, potassium carbonate (138 mg), and morpholine (0.044 ml) were dissolved in N,N-dimethylformamide (1 ml), and the solution was stirred at room temperature for 18 hr. Water was added to the reaction mixture, and the mixture was extracted with chloroform-propanol (3/1). The organic layer was dried over anhydrous sodium sulfate, and the solvent was removed by distillation under the reduced pressure. The residue was purified by HPLC by development with chloroform/methanol to give 72 mg (yield 73%) of the title compound.

$^1$H-NMR (CDCl$_3$, 400 MHz): δ 1.10 (t, J=7.3 Hz, 3H), 2.07 (s, 3H), 2.16 (s, 3H), 2.53–2.59 (m, 4H), 2.88 (t, J=5.9 Hz, 2H), 3.20–3.30 (m, 2H), 3.66–3.71 (m, 4H), 3.96 (6, 3H), 4.26 (t, J=5.9 Hz, 2H), 4.73–4.82 (m, 1H), 6.16 (s, 1H), 6.23 (d, J=5.4 Hz, 1H), 6.88 (s, 1H), 7.35 (s, 1H), 7.40 (s, 1H), 7.50 (s, 1H), 8.38 (d, J=5.1 Hz, 1H).

Example 176

N-[4-({6-Methoxy-7-[3-(4-methylpiperazino-propoxy]-4-quinolyl}oxy)-2.5-dimethylphenyl]-N'-propylurea A starting compound (N-{4-[(7-hydroxy-6-methoxy-4-quinolyl)oxy]-2,5-dimethylphenyl}-N'-propylurea, 80 mg), potassium carbonate (138 mg), and 1,3-dibromopropane (0.10 ml) were dissolved in N,N-dimethylformamide (1 ml), and the solution was stirred at room temperature for 18 hr. Water was added to the reaction mixture, and the mixture was extracted with chloroform-propanol (3/1). The organic layer was dried over anhydrous sodium sulfate, and the solvent was removed by distillation under the reduced pressure. The residue was washed with ether to give an intermediate (N-(4-{[7-(3-bromopropoxy)-6-methoxy-4-quinolyl]oxy}-2,5-dimethylphenyl)-N'-propylurea). The intermediate, potassium carbonate (138 mg), and 1-methylpiperazine (0.055 ml) were dissolved in N,N-dimethylformamide (1 ml), and the mixture was stirred at room temperature for 18 hr. Water was added to the reaction mixture, and the mixture was extracted with chloroform-propanol (3/1). The organic layer was dried over anhydrous sodium sulfate, and the solvent was removed by distillation under the reduced pressure. The residue was washed with ether to give 33 mg (yield 31%) of the title compound.

$^1$H-NMR (CDCl$_3$, 400 MHz): δ 0.91 (t, J=7.6 Hz, 3H), 1.50–1.58 (m, 2H), 2.07–2.20 (m, 2H), 2.12 (s, 3H), 2.23 (s, 3H), 2.28 (s, 3H), 2.33–2.70 (m, 10H), 3.21 (dd, J=7.3 Hz, 13.4 Hz, 2H), 4.00 (s, 3H), 4.24 (t, J=6.6 Hz, 2H), 4.64–4.76 (m, 1H), 5.95–6.05 (m, 1H), 6.27 (d, J=5.1 Hz, 1H), 6.95 (s, 1H), 7.39–7.43 (m, 2H), 7.54 (s, 1H), 8.42 (d, J=5.1 Hz, 1H).

Mass analysis, found (ESI-MS, m/z): 536 (M⁺+1).

Example 177

N-(2,4-Difluorophenyl)-N'-[4-({6-methoxy-7-[2-(1H-1,2,3-triazol-1-yl)ethoxy]-4-quinolyl}oxy)-2,5-dimethylphenyl]urea A starting compound (N-(2,4-difluorophenyl)-N'-{4-[(7-hydroxy-6-methoxy-4-quinolyl)oxy]-2,5-dimethylphenyl}urea, 93 mg), potassium carbonate (138 mg), and 2-(1H-1,2,3-triazol-1-yl)ethyl 4-methyl-1-benzenesulfonate (52 mg) were dissolved in N,N-dimethylformamide (1 ml), and the solution was stirred at 80° C. for 5 hr. Water was added to the reaction mixture, and the mixture was extracted with chloroform-propanol (3/1). The organic layer was dried over anhydrous sodium sulfate, and the solvent was removed by distillation under the reduced pressure. The residue was purified by HPLC by development with chloroform/methanol to give 33 mg (yield 30%) of the title compound.

$^1$H-NMR (CDCl$_3$, 400 MHz): δ 2.10 (s, 3H), 2.19 (s, 3H), 4.01 (s, 3H), 4.51 (t, J=4.9 Hz, 2H), 4.93 (t, J=5.4 Hz, 2H), 4.94 (s, 1H), 6.28 (d, J=5.1 Hz, 1H), 6.75–6.88 (m, 2H), 6.90 (s, 1H), 7.36 (s, 1H), 7.58 (s, 1H), 7.60 (s, 1H), 7.73 (s, 1H), 7.99 (s, 1H), 8.08 (dd, J=9.3 Hz, 15.1 Hz, 1H), 8.41 (d, J=5.1 Hz, 1H).

Example 178

N'-(2-Chloro-4-{[6-methoxy-7-(2-morpholinoethoxy)-4quinazolinyl]oxy}phenyl)-N,N-dimethylurea A starting compound (N'-{2-chloro-4-[(7-hydroxy-6-methoxy-4-quinazolinyl)oxy]phenyl}-N,N-dimethylurea, 80 mg), potassium carbonate (138 mg), and 1,2-dibromoethane (0.085 ml) were dissolved in N,N-dimethylformamide (1 ml), and the solution was stirred at room temperature for 18 hr. Water was added to the reaction mixture, and the mixture was extracted with chloroform-propanol (3/1). The organic layer was dried over anhydrous sodium sulfate, and the solvent was removed by distillation under the reduced pressure. The residue was washed with ether to give an intermediate (N'-(4-{[7-(2-bromoethoxy)-6-methoxy-4-quinazolinyl]oxy}-2-chlorophenyl)-N,N-dimethylurea). The intermediate, potassium carbonate (138 mg), and morpholine (0.043 ml) were dissolved in N,N-dimethylformamide (1 ml), and the solution was stirred at room temperature overnight. Water was added to the reaction mixture, and the mixture was extracted with chloroform-propanol (3/1). The organic layer was dried over anhydrous sodium sulfate, and the solvent was removed by distillation under the reduced pressure. The residue was purified by HPLC by development with chloroform/methanol to give 72 mg (yield 72%) of the title compound.

$^1$H-NMR (CDCl$_3$, 400 MHz): δ 2.58–2.66 (m, 4H), 2.90–2.98 (m, 2H), 3.08 (s, 6H), 3.70–3.79 (m, 4H), 4.02 (s, 3H), 4.29–4.37 (m, 2H), 6.97 (s, 1H), 7.15 (dd, J=2.7 Hz, 9.0 Hz, 1H), 7.24–7.26 (m, 1H), 7.29 (s, 1H), 7.49 (s, 1H), 8.36 (d, J=9.3 Hz, 1H), 8.60 (s, 1H).

Mass analysis, found (ESI-MS, m/z): 502 (M$^+$+1).

Example 179

N'-(2-Chloro-4-{[6-methoxy-7-(4-morpholinobutoxy)-4-quinazolinyl]oxy}phenyl)-N,N-dimethylurea A starting compound (N'-{2-chloro-4-[(7-hydroxy-6-methoxy-4-quinazolinyl) oxy]phenyl}-N,N-dimethylurea, 80 mg), potassium carbonate (138 mg), and 1,4-dibromobutane (0.12 ml) were dissolved in N,N-dimethylformamide (1 ml), and the solution was stirred at room temperature for 18 hr. Water was added to the reaction mixture, and the mixture was extracted with chloroform-propanol (3/1). The organic layer was dried over anhydrous sodium sulfate, and the solvent was removed by distillation under the reduced pressure. The residue was washed with ether to give an intermediate (N'-(4-{[7-(4-bromobutoxy)-6-methoxy-4-quinazolinyl]oxy}-2-chloro-phenyl)-N,N-dimethylurea). The intermediate, potassium carbonate (138 mg), and morpholine (0.043 ml) were dissolved in N,N-dimethylformamide (1 ml), and the solution was stirred at room temperature overnight. Water was added to the reaction mixture, and the mixture was extracted with chloroform-propanol (3/1). The organic layer was dried over anhydrous sodium sulfate, and the solvent was removed by distillation under the reduced pressure. The residue was purified by HPLC by development with chloroform/methanol to give 47 mg (yield 44%) of the title compound.

$^1$H-NMR (CDCl$_3$, 400 MHz): δ 1.67–1.77 (m, 2H), 1.93–2.03 (m, 2H), 2.39–2.50 (m, 4H), 3.67 (s, 6H), 3.64–3.75 (m, 4H), 4.02 (s, 3H), 4.21 (t, J=6.6 Hz, 2H), 6.97 (s, 1H), 7.16 (dd, J=2.7 Hz, 9.3 Hz, 1H), 7.26 (s, 1H), 7.28 (s, 1H), 7.29 (d, J=2.7 Hz, 1H), 7.48 (s, 1H), 8.36 (d, J=9.3 Hz, 1H), 8.59 (S, 1H).

Example 180

N'-(2-Chloro-4-{[6-methoxy-7(4-pyridyl-methoxy)-4quinazolinyl]oxy}phenyl)-N,N-dimethylurea A starting compound (N'-{2-chloro-4-[(7-hydroxy-6-methoxy-4-quinazolinyl)oxy]phenyl}-N,N-dimethylurea, 50 mg), potassium carbonate (138 mg), and 4-chloromethylpyridine hydrochloride (49 mg) were dissolved in N,N-dimethylformamide (1 ml), and the solution was stirred at room temperature for 18 hr. Water was added to the reaction mixture, and the mixture was extracted with chloroform-propanol (3/1). The organic layer was dried over anhydrous sodium sulfate, and the solvent was removed by distillation under the reduced pressure. The residue was purified by HPLC by development with chloroform/methanol to give 37 mg (yield 60%) of the title compound.

$^1$H-NMR (CDCl$_3$, 400 MHz): δ 3.07 (s, 6H), 4.07 (s, 3H), 5.32 (s, 2H), 6.97 (s, 1H), 7.15 (dd, J=2.7 Hz, 9.0 Hz, 1H), 7.26 (s, 1H), 7.29 (d, J=2.7 Hz, 1H), 7.41 (d, J=6.1 Hz, 1H), 7.55 (s, 1H), 8.37 (d, J=9.0 Hz, 1H), 8.58 (s, 1H), 8.63 (d, J=6.1 Hz, 1H).

Mass analysis, found (ESI-MS, m/z): 480 (M$^+$+1).

Example 181

Methyl 2-{[4-(3-chloro-4-{[(dimethylamino)carbonyl]amino}phenoxy)6-methoxy-7quinazolinyl]oxy}acetate A starting compound (N'-{2-chloro-4-[(7-hydroxy-6-methoxy-4-quinazolinyl)oxy]phenyl}-N,N-dimethylurea, 50 mg), potassium carbonate (138 mg), and bromoethyl acetate (49 mg) were dissolved in N,N-dimethylformamide (1 ml), and the solution was stirred at room temperature for 18 hr. Water was added to the reaction mixture, and the mixture was extracted with chloroform-propanol (3/1). The organic layer was dried over anhydrous sodium sulfate, and the solvent was removed by distillation under the reduced pressure. The residue was purified by HPLC by development with chloroform/methanol to give 37 mg (yield 60%) of the title compound.

$^1$H-NMR (CDCl$_3$, 400 MHz): δ 3.07 (s, 6H), 3.82 (s, 3H), 4.06 (s, 3H), 4.87 (s, 2H), 6.97 (s, 1H), 7.14 (dd, J=2.7 Hz, 9.0 Hz, 1H), 7.18 (s, 1H), 7.29 (d, J=2.7 Hz, 1H), 7.54 (s, 1H), 8.36 (d, J=9.0 Hz, 1H), 8.60 (s, 1H).

Example 182

N'-[2-Chloro-4-({6-methoxy-7-[3-(4-methylpiperazino) propoxy]-4-quinazolinyl}oxy) phenyl]-N,N-dimethylurea A starting compound (N'-{2-chloro-4-[(7-hydroxy-6-methoxy-4-quinazolinyl)oxy]phenyl}-N,N-dimethylurea, 400 mg), potassium carbonate (966 mg), and 1,3-dibromopropane (0.51 ml) were dissolved in N,N-dimethylformamide (5 ml), and the solution was stirred at room temperature for 18 hr. Water was added to the to reaction mixture, and the mixture was extracted with chloroform-propanol (3/1). The organic layer was dried over anhydrous sodium sulfate, and the solvent was removed by distillation under the reduced pressure. The residue was washed with ether to give 398 mg (yield 78%) of an intermediate (N'-(4-{[7-(3-bromopropoxy)-6-methoxy-4-quinazolinyl]oxy}-2-chlorophenyl)-N,N-dimethylurea). The intermediate (51 mg), potassium carbonate (138 mg), and 1-methylpiperazine (0.055 ml) were dissolved in N,N-dimethylformamide (1 ml), and the solution was stirred at room temperature for 18 hr. Water was added to the reaction mixture, and the mixture was extracted with chloroform-propanol (3/1). The organic layer was dried over anhydrous sodium sulfate, and the solvent was removed by distillation under the reduced pressure. The residue was washed with ether to give 46 mg (yield 85%) of the title compound.

$^1$H-NMR (CDCl$_3$, 400 MHz): δ 2.06–2.16 (m, 2H), 2.29 (s, 3H), 2.30–2.60 (m, 10H), 3.07 (s, 6H), 4.02 (s, 3H), 4.25 (t, J=6.8 Hz, 2H), 6.96 (s, 1H), 7.15 (dd, J=2.7Hz, 9.0 Hz, 1H), 7.29 (d, J=2.7 Hz, 1H), 7.30 (s, 1H), 7.48 (s, 1H), 8.36 (d, J=9.0 Hz, 1H), 8.59 (s, 1H).

Mass analysis, found (ESI-MS, m/z): 529 (M$^+$+1).

Example 183

N'-{2-Chloro-4-[(7-{3-[(2-hydroxyethyl)-methyl) amino]propoxy}-6-methoxy-4-quinazolinyl)oxy]-phenyl}-N,N-dimethylurea A starting compound (N'-{2-chloro-4-[(7-hydroxy-6-methoxy-4-quinazolinyl) oxy]phenyl}-N,N-dimethylurea, 400 mg), potassium carbonate (966 mg), and 1,3-dibromopropane (0.51 ml) were dissolved in N,N-dimethylformamide (5 ml), and the mixture was stirred at room temperature for 18 hr. Water was added to the reaction mixture, and the mixture was extracted with chloroform-propanol (3/1). The organic layer was dried over anhydrous sodium sulfate, and the solvent was removed by distillation under the reduced pressure. The residue was washed with ether to give 398 mg (yield 78%) of an intermediate (N'-(4-{[7-(3-bromopropoxy)-6-methoxy-4-quinazolinyl]oxy}-2-chlorophenyl)-N,N-dimethylurea). The intermediate (51 mg), potassium carbonate (138 mg), and 2-(methylamino) ethanol (0.040 ml) were dissolved in N,N-dimethylformamide (1 ml). The mixture was stirred at room temperature for 18 hr. Water was added to the reaction mixture, and the mixture was extracted with chloroform-propanol (3/1). The organic layer was dried over anhydrous sodium sulfate, and the solvent was removed by distillation under the reduced pressure. The residue was washed with ether to give 49 mg (yield 97%) of the title compound.

$^1$H-NMR (CDCl$_{5, 400}$ MHz): δ 2.01–2.11 (m, 2H), 2.25 (s, 3H), 2.52 (t, J=5.1 Hz, 2H), 2.61 (t, J=7.1 Hz, 2H), 3.03 (s, 6H), 3.57 (t, J=5.1 Hz, 2H), 3.98 (s, 3H), 4.23 (t, J=6.6 Hz, 2H), 6.92 (s, 1H), 7.10 (dd, J=2.7 Hz, 9.3 Hz, 1H), 7.24 (d, J=2.7 Hz, 1H), 7.31 (s, 1H), 7.44 (s, 1H), 8.31 (d, J=9.0 Hz, 1H), 8.54 (s, 1H).

Mass analysis, found (ESI-MS, m/z): 504 (M$^+$+1).

Example 184

N-(2-Chloro-4-{[6-methoxy-7(3-piperidino-propoxy)-4-quinazolinyl]oxy}phenyl)-N'-methylurea N-{2-Chloro-4-[(7-hydroxy-6-methoxy-4-quinaz-olinyl) oxy]phenyl}-N'-methylurea (2.0 g) was dissolved in N,N-dimethylformamide (50 ml), and triphenylphosphine (2.8 g), piperidinopropanol (0.9 g), and diethyl azodicarboxylate (1.9 g) were added to the solution. The mixture was stirred at room temperature for 2 hr. Triphenylphosphine (2.8 g), piperidinopropanol (0.6 g), and diethyl azodicarboxylate (1.9 g) were then again added to the reaction solution, followed by stirring at room temperature for additional 10 hr. The solvent was removed by distillation under the reduced pressure. The residue was purified by chromatography on silica gel by development with chloroform/methanol (20/1) to give 650 mg (yield 25%) of the title compound.

$^1$H-NMR (DMSO-d$_6$, 400 MHz): δ 1.37–1.43 (m, 2H), 1.43–1.53 (m, 4H), 1.96–2.00 (m, 2H), 2.29–2.50 (m, 6H), 2.68 (d, J=4.6 Hz, 3H), 3.97 (s, 3H), 4.23 (t, J=6.3 Hz, 2H), 6.82–6.85 (m, 1H), 7.23 (dd, J=2.7 Hz, 9.0 Hz, 1H), 7.38 (s, 1H), 7.47 (d, J=2.7 Hz, 1H), 7.54 (s, 1H), 8.07 (s, 1H), 8.17 (d, J=9.0 Hz, 1H), 8.55 (s, 1H).

Mass analysis, found (ESI-MS, m/z): 500 (M$^+$+1).

Example 185

N-(-2-1-Chloro-4-{[6-methoxy-7-(3-piperidino-propoxy)-4-quinazolinyl]oxy}phenyl)-N'-ethylurea N-{2-Chloro-4-[(7-hydroxy-6-methoxy-4-quinaz-olinyl) oxy]phenyl}-N'-ethylurea (2.7 g) was dissolved in N,N-dimethylformamide (30 ml), and triphenylphosphine(3.6 g), piperidinopropanol (1.2 g), and diethyl azodicarboxylate (2.4 g) were added to the solution. The mixture was stirred at room temperature for 2 hr. Triphenylphosphine(3.6 g), piperidinopropanol (0.8 g), and diethyl azodicarboxylate (1.9 g) were then again added to the reaction solution. The mixture was stirred at room temperature for additional 10 hr. The solvent was removed by distillation under the reduced pressure, and the residue was purified by chromatography on silica gel by development with chloroform/methanol (20/1) to give 1.5 g (yield 42%) of the title compound.

$^1$H-NMR (DMSO-d$_6$, 400 MHz): δ 1.08 (t, J=7.0 Hz, 3H), 1.38–1.41 (m, 2H), 1.47–1.53 (m, 4H), 1.95–2.00 (m, 2H), 2.31–2.46 (m, 6H), 3.10–3.17 (m, 2H), 3.97 (s, 3H), 4.23 (t, J=6.3 Hz, 2H), 6.96 (t, J=5.6 Hz, 1H), 7.23 (dd, J=2.7 Hz, 9.0 Hz, 1H), 7.37 (s, 1H), 7.47 (d, J=2.7 Hz, 1H), 7.54 (s, 1H), 8.02 (s, 1H), 8.19 (d, J=9.3 Hz, 1H), 8.55 (s, 1H).

Mass analysis, found (ESI-MS, m/z): 514 ($M^+$+1).

Example 186

N-(2-Chloro-4-{[6-methoxy-7-(4-pyridyl-methoxy)-4-quinolyl]oxy}phenyl)-N'-(2,4-difluorophenyl)-urea N-{2-Chloro-4-[(7-hydroxy-6-methoxy-4-quinolyl)-oxy]phenyl}-N'-(2,4-difluorophenyl)urea (55 mg), potassium carbonate (62 mg), and 4-(chloromethyl)pyridine hydrochloride (22 mg) were dissolved in N,N-dimethylformamide (1 ml), and the solution was stirred at 80° C. for one hr. The solvent was removed by distillation under the reduced pressure. A saturated aqueous sodium hydrogencarbonate solution was added to the residue, and the mixture was extracted with chloroform. The organic layer was dried over anhydrous sodium sulfate, and the solvent was removed by distillation under the reduced pressure. The residue was washed with ether to give 35 mg (yield 55%) of the title compound.

$^1$H-NMR (DMSO, 400 MHz): δ 3.98 (s, 3H), 5.41 (s, 2H), 6.56 (d, J=5.1 Hz, 1H), 7.04–7.10 (m, 1H), 7.25–7.37 (m, 2H), 7.47 (s, 1H), 7.49–7.52 (m, 4H), 7.55 (s, 1H), 8.08–8.15 (m, 1H), 8.24 (d, J=9.0 Hz, 1H), 8.49 (d, J=5.4 Hz, 1H), 8.60–8.63 (m, 1H), 8.81–8.83 (m, 1H), 9.30–9.31 (m, 1H).

Mass analysis, found (ESI-MS, m/z): 563 ($M^+$+1).

The structures of the compounds described in the examples are as follows.

| | X | Z | R¹ | R² | R³ | R⁴ | R⁵ | R⁶ | R⁷ | R⁸ | R⁹ | R¹⁰ | R¹¹ |
|---|---|---|---|---|---|---|---|---|---|---|---|---|---|
| 1 | CH | CH | H | CH₃O | CH₃O | H | H | F | H | H | H | H | 3,5-difluorobenzyl |
| 2 | CH | CH | H | CH₃O | CH₃O | H | H | F | H | H | H | H | 3-fluoropropyl |
| 3 | CH | CH | H | CH₃O | CH₃O | H | H | F | H | H | H | H | (pyridin-2-yl)methyl |
| 4 | CH | CH | H | CH₃O | CH₃O | H | H | F | H | H | H | H | but-3-enyl |
| 5 | CH | CH | H | CH₃O | CH₃O | H | H | F | H | H | H | H | pentyl |
| 6 | CH | CH | H | CH₃O | CH₃O | H | H | F | H | H | H | H | 5-fluoropentyl |
| 7 | CH | CH | H | CH₃O | CH₃O | H | H | F | H | H | H | H | pent-4-ynyl |
| 8 | CH | CH | H | CH₃O | CH₃O | H | H | F | H | H | H | H | hexyl |
| 9 | CH | CH | H | CH₃O | CH₃O | H | H | F | H | H | H | H | 2-methylpentyl |
| 10 | CH | CH | H | CH₃O | CH₃O | H | H | F | H | H | H | H | 2-methylbutyl |
| 11 | CH | CH | H | CH₃O | CH₃O | H | H | F | H | H | H | H | 3-methylbutyl |
| 12 | CH | CH | H | CH₃O | CH₃O | H | H | F | H | H | H | H | 3-methylpentyl |

-continued

| | X | Z | R¹ | R² | R³ | R⁴ | R⁵ | R⁶ | R⁷ | R⁸ | R⁹ | R¹⁰ | R¹¹ |
|---|---|---|---|---|---|---|---|---|---|---|---|---|---|
| 13 | CH | CH | H | CH₃O | CH₃O | H | H | Cl | H | H | H | H | butyl |
| 14 | CH | CH | H | CH₃O | CH₃O | H | H | Cl | H | H | H | H | 2-methyl-4-fluorophenyl |
| 15 | CH | CH | H | CH₃O | CH₃O | H | H | Cl | H | H | H | H | 3-bromo-2,6-dimethylpyridyl |
| 16 | CH | CH | H | CH₃O | CH₃O | H | H | Cl | H | H | H | H | 5-chloro-2-methylpyridyl |
| 17 | CH | CH | H | CH₃O | CH₃O | H | H | Cl | H | H | H | H | 5-bromo-2-methylpyridyl |
| 18 | CH | CH | H | CH₃O | CH₃O | H | H | Cl | H | H | H | H | 2-methoxy-6-methylphenyl |
| 19 | CH | CH | H | CH₃O | CH₃O | H | H | Cl | H | H | H | H | 2,6-dimethylphenyl |
| 20 | CH | CH | H | CH₃O | CH₃O | H | H | Cl | H | H | H | H | 5-methyl-2-methylpyridyl |

-continued

| | X | Z | $R^1$ | $R^2$ | $R^3$ | $R^4$ | $R^5$ | $R^6$ | $R^7$ | $R^8$ | $R^9$ | $R^{10}$ | $R^{11}$ |
|---|---|---|---|---|---|---|---|---|---|---|---|---|---|
| 21 | CH | CH | H | $CH_3O$ | $CH_3O$ | H | H | Cl | H | H | H | H | 6-methylpyridin-2-yl (2,6-dimethylpyridin-2-yl with $CH_3$ at 6-position) |
| 22 | CH | CH | H | $CH_3O$ | $CH_3O$ | H | H | Cl | H | H | H | H | 4-methoxy-2-methylphenyl |
| 23 | CH | CH | H | $CH_3O$ | $CH_3O$ | H | H | Cl | H | H | H | H | 8-methylnaphthalen-1-yl |
| 24 | CH | CH | H | $CH_3O$ | $CH_3O$ | H | $CH_3$ | $CH_3$ | H | H | H | H | 2,5-difluoro-4-methylphenyl |
| 25 | CH | CH | H | $CH_3O$ | $CH_3O$ | H | $CH_3$ | $CH_3$ | H | H | H | H | 5-fluoro-2-methylphenyl |
| 26 | CH | CH | H | $CH_3O$ | $CH_3O$ | H | $CH_3$ | $CH_3$ | H | H | H | H | 2-fluoro-6-(methoxy)-methylphenyl (2-fluoro-6-methyl-phenoxymethyl-type) |

| | X | Z | R¹ | R² | R³ | R⁴ | R⁵ | R⁶ | R⁷ | R⁸ | R⁹ | R¹⁰ | R¹¹ |
|---|---|---|---|---|---|---|---|---|---|---|---|---|---|
| 27 | CH | CH | H | CH₃O | CH₃O | H | CH₃ | CH₃ | H | H | H | H | 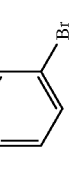 |
| 28 | CH | CH | H | CH₃O | CH₃O | H | CH₃ | CH₃ | H | H | H | H | 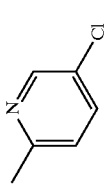 |
| 29 | CH | CH | H | CH₃O | CH₃O | H | CH₃ | CH₃ | H | H | H | H | 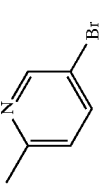 |
| 30 | CH | CH | H | CH₃O | CH₃O | H | CH₃ | CH₃ | H | H | H | H | 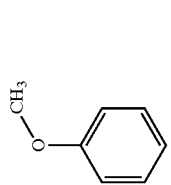 |
| 31 | CH | CH | H | CH₃O | CH₃O | H | CH₃ | CH₃ | H | H | H | H | 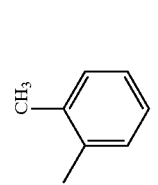 |
| 32 | CH | CH | H | CH₃O | CH₃O | H | CH₃ | CH₃ | H | H | H | H | 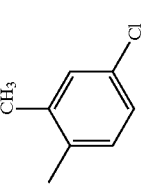 |
| 33 | CH | CH | H | CH₃O | CH₃O | H | CH₃ | CH₃ | H | H | H | H | 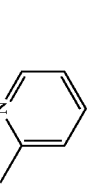 |

-continued

| | X | Z | R¹ | R² | R³ | R⁴ | R⁵ | R⁶ | R⁷ | R⁸ | R⁹ | R¹⁰ | R¹¹ |
|---|---|---|---|---|---|---|---|---|---|---|---|---|---|
| 34 | CH | CH | H | CH₃O | CH₃O | H | CH₃ | CH₃ | H | H | H | H | 5-methyl-2-pyridyl (6-methyl) |
| 35 | CH | CH | H | CH₃O | CH₃O | H | CH₃ | CH₃ | H | H | H | H | 2-methyl-6-methylpyridyl |
| 36 | CH | CH | H | CH₃O | CH₃O | H | CH₃ | CH₃ | H | H | H | H | 4-methoxyphenyl (4-methyl) |
| 37 | CH | CH | H | CH₃O | CH₃O | H | H | CH₃ | CH₃ | H | H | H | 2,4-difluorophenyl |
| 38 | CH | CH | H | CH₃O | CH₃O | H | H | CH₃ | CH₃ | H | H | H | butyl |
| 39 | CH | CH | H | CH₃O | CH₃O | H | H | CH₃ | CH₃ | H | H | H | 4-chloro-2-methylphenyl |
| 40 | CH | CH | H | CH₃O | CH₃O | H | H | CH₃ | CH₃ | H | H | H | 4-fluoro-2-methylphenyl |

-continued
| | X | Z | R¹ | R² | R³ | R⁴ | R⁵ | R⁶ | R⁷ | R⁸ | R⁹ | R¹⁰ | R¹¹ |
|---|---|---|---|---|---|---|---|---|---|---|---|---|---|
| 41 | CH | CH | H | CH₃O | CH₃O | H | H | CH₃ | CH₃ | H | H | H | 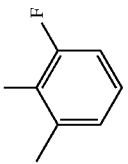 |
| 42 | CH | CH | H | CH₃O | CH₃O | H | H | CH₃ | CH₃ | H | H | H | 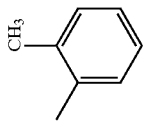 |
| 43 | CH | CH | H | CH₃O | CH₃O | H | H | CH₃ | CH₃ | H | H | H | 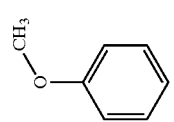 |
| 44 | CH | CH | H | CH₃O | CH₃O | H | H | CH₃ | CH₃ | H | H | H | 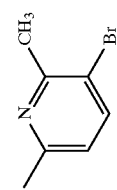 |
| 45 | CH | CH | H | CH₃O | CH₃O | H | H | CH₃ | CH₃ | H | H | H | 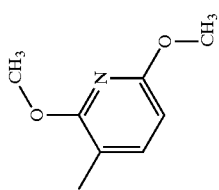 |
| 46 | CH | CH | H | CH₃O | CH₃O | H | H | CH₃ | CH₃ | H | H | H | 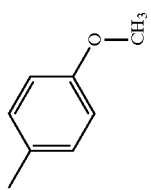 |

-continued

| | X | Z | R¹ | R² | R³ | R⁴ | R⁵ | R⁶ | R⁷ | R⁸ | R⁹ | R¹⁰ | R¹¹ |
|---|---|---|---|---|---|---|---|---|---|---|---|---|---|
| 47 | CH | CH | H | CH₃O | CH₃O | H | H | NO₂ | H | H | H | H | butyl |
| 48 | CH | CH | H | CH₃O | CH₃O | H | H | NO₂ | H | H | H | H | 2,4-difluoro-methylphenyl |
| 49 | CH | CH | H | CH₃O | CH₃O | H | Cl | H | Cl | H | H | H | 2,4-difluoro-methylphenyl |
| 50 | CH | CH | H | CH₃O | 2-methoxyethyl-morpholine | H | H | F | H | H | H | H | 2,4-difluoro-methylphenyl |
| 51 | CH | CH | H | CH₃O | 2-methoxyethyl-morpholine | H | H | Cl | H | H | H | H | 2,4-difluoro-methylphenyl |
| 52 | CH | CH | H | CH₃O | 2-methoxyethyl-morpholine | H | H | CH₃ | CH₃ | H | H | H | 2,4-difluoro-methylphenyl |

-continued
| | X | Z | R¹ | R² | R³ | R⁴ | R⁵ | R⁶ | R⁷ | R⁸ | R⁹ | R¹⁰ | R¹¹ |
|---|---|---|---|---|---|---|---|---|---|---|---|---|---|
| 53 | CH | CH | H | CH₃O | 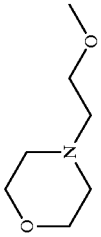 | H | H | CH₃ | CH₃ | H | H | H | 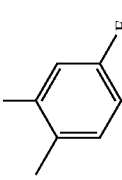 |
| 54 | CH | CH | H | CH₃O | CH₃O(CH₂)₂O | H | H | Cl | H | H | H | H | 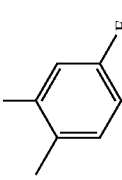 |
| 55 | CH | CH | H | CH₃O | CH₃O(CH₂)₂O | H | H | Cl | H | H | H | H | 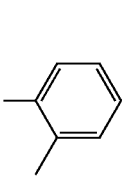 |
| 56 | CH | CH | H | CH₃O | CH₃O(CH₂)₂O | H | CH₃ | CH₃ | H | H | H | H | 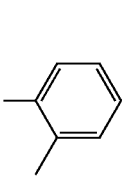 |
| 57 | CH | CH | H | CH₃O | CH₃O(CH₂)₂O | H | CH₃ | CH₃ | H | H | H | H | 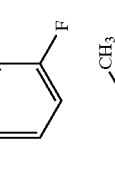 |
| 58 | CH | CH | H | CH₃O | CH₃O(CH₂)₂O | H | H | CH₃ | CH₃ | H | H | H | 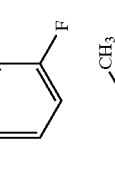 |

-continued

| | X | Z | R¹ | R² | R³ | R⁴ | R⁵ | R⁶ | R⁷ | R⁸ | R⁹ | R¹⁰ | R¹¹ |
|---|---|---|---|---|---|---|---|---|---|---|---|---|---|
| 59 | CH | CH | H | CH$_3$O | CH$_3$O(CH$_2$)$_2$O | H | H | CH$_3$ | CH$_3$ | H | H | H | 2-methoxy-6-methylphenyl |
| 60 | CH | CH | H | CH$_3$O | C$_6$H$_5$CH$_2$O | H | CH$_3$ | CH$_3$ | H | H | H | H | 2-methoxy-6-methylphenyl |
| 61 | N | CH | H | CH$_3$O | CH$_3$O | H | H | Cl | H | H | H | H | 2,4-difluoro-phenyl |
| 62 | N | CH | H | CH$_3$O | CH$_3$O | H | H | Cl | H | H | H | H | n-propyl |
| 63 | N | CH | H | CH$_3$O | CH$_3$O | H | H | H | H | H | H | H | n-butyl |
| 64 | N | CH | H | CH$_3$O | CH$_3$O | H | H | H | H | H | H | H | n-pentyl |
| 65 | N | CH | H | CH$_3$O | CH$_3$O | H | H | H | H | H | H | H | n-hexyl |
| 66 | N | CH | H | CH$_3$O | CH$_3$O | H | H | H | H | H | H | H | n-heptyl |
| 67 | N | CH | H | CH$_3$O | CH$_3$O | H | H | H | H | H | H | H | isobutyl |
| 68 | N | CH | H | CH$_3$O | CH$_3$O | H | H | H | H | H | H | H | but-3-enyl |

-continued

| | X | Z | R$^1$ | R$^2$ | R$^3$ | R$^4$ | R$^5$ | R$^6$ | R$^7$ | R$^8$ | R$^9$ | R$^{10}$ | R$^{11}$ |
|---|---|---|---|---|---|---|---|---|---|---|---|---|---|
| 69 | N | CH | H | CH$_3$O | CH$_3$O | H | H | H | H | H | H | H | but-3-yn-1-yl |
| 70 | N | CH | H | CH$_3$O | CH$_3$O | H | H | H | H | H | H | H | 2-(2,4-difluorophenyl)ethyl |
| 71 | N | CH | H | CH$_3$O | CH$_3$O | H | H | H | H | H | H | H | 2-(pyridin-2-yl)ethyl |
| 72 | N | CH | H | CH$_3$O | CH$_3$O | H | H | H | H | H | H | H | 2,5-difluoro-4-methylphenyl |
| 73 | N | CH | H | CH$_3$O | CH$_3$O | H | H | H | H | H | H | H | 4-fluoro-3-methylphenyl |
| 74 | N | CH | H | CH$_3$O | CH$_3$O | H | H | H | H | H | H | H | 2,3-dimethylphenyl |
| 75 | N | CH | H | CH$_3$O | CH$_3$O | H | H | H | H | H | H | H | 2-methoxy-3-methylphenyl |
| 76 | N | CH | H | CH$_3$O | CH$_3$O | H | H | Cl | H | H | H | H | propyl |
| 77 | N | CH | H | CH$_3$O | CH$_3$O | H | H | Cl | H | H | H | H | pentyl |

| | X | Z | R¹ | R² | R³ | R⁴ | R⁵ | R⁶ | R⁷ | R⁸ | R⁹ | R¹⁰ | R¹¹ |
|---|---|---|---|---|---|---|---|---|---|---|---|---|---|
| 78 | N | CH | H | CH₃O | CH₃O | H | H | Cl | H | H | H | H | hexyl |
| 79 | N | CH | H | CH₃O | CH₃O | H | H | Cl | H | H | H | H | isobutyl |
| 80 | N | CH | H | CH₃O | CH₃O | H | H | Cl | H | H | H | H | butenyl |
| 81 | N | CH | H | CH₃O | CH₃O | H | H | Cl | H | H | H | H | butynyl |
| 82 | N | CH | H | CH₃O | CH₃O | H | H | Cl | H | H | H | H | 2,4-difluorophenylethyl |
| 83 | N | CH | H | CH₃O | CH₃O | H | H | Cl | H | H | H | H | 2-pyridylethyl |
| 85 | N | CH | H | CH₃O | CH₃O | H | H | Cl | H | H | H | H | 4-fluoro-3-methylphenyl |
| 86 | N | CH | H | CH₃O | CH₃O | H | H | Cl | H | H | H | H | 2-methoxy-6-methylphenyl |
| 87 | N | CH | H | CH₃O | CH₃O | H | H | Cl | H | H | H | H | 5-chloro-2-methylpyridyl |
| 88 | N | CH | H | CH₃O | CH₃O | H | H | F | H | H | H | H | butyl |
| 89 | N | CH | H | CH₃O | CH₃O | H | H | F | H | H | H | H | pentyl |

-continued

| | X | Z | R¹ | R² | R³ | R⁴ | R⁵ | R⁶ | R⁷ | R⁸ | R⁹ | R¹⁰ | R¹¹ |
|---|---|---|---|---|---|---|---|---|---|---|---|---|---|
| 90 | N | CH | H | CH₃O | CH₃O | H | H | F | H | H | H | H | isobutyl |
| 91 | N | CH | H | CH₃O | CH₃O | H | H | F | H | H | H | H | allyl (but-3-enyl) |
| 92 | N | CH | H | CH₃O | CH₃O | H | H | F | H | H | H | H | but-3-ynyl |
| 93 | N | CH | H | CH₃O | CH₃O | H | H | F | H | H | H | H | 2,4-difluorophenethyl |
| 94 | N | CH | H | CH₃O | CH₃O | H | H | F | H | H | H | H | 2,5-difluorobenzyl |
| 95 | N | CH | H | CH₃O | CH₃O | H | H | F | H | H | H | H | 2-methylbenzyl (o-CH₃) |
| 96 | N | CH | H | CH₃O | CH₃O | H | H | F | H | H | H | H | 2-methoxybenzyl (o-OCH₃) |
| 97 | N | CH | H | CH₃O | CH₃O | H | CH₃ | H | H | H | H | H | n-pentyl |
| 98 | N | CH | H | CH₃O | CH₃O | H | CH₃ | H | H | H | H | H | n-hexyl |

-continued
| | X | Z | R¹ | R² | R³ | R⁴ | R⁵ | R⁶ | R⁷ | R⁸ | R⁹ | R¹⁰ | R¹¹ |
|---|---|---|---|---|---|---|---|---|---|---|---|---|---|
| 99 | N | CH | H | CH₃O | CH₃O | H | CH₃ | H | H | H | H | H |  |
| 100 | N | CH | H | CH₃O | CH₃O | H | CH₃ | H | H | H | H | H | 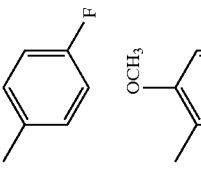 |
| 101 | N | CH | H | CH₃O | CH₃O | H | CH₃ | H | H | H | H | H | 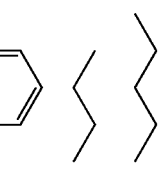 |
| 102 | N | CH | H | CH₃O | CH₃O | H | H | CH₃ | H | H | H | H | |
| 103 | N | CH | H | CH₃O | CH₃O | H | H | CH₃ | H | H | H | H | 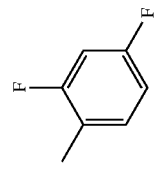 |
| 104 | N | CH | H | CH₃O | CH₃O | H | H | CH₃ | H | H | H | H | |
| 105 | N | CH | H | CH₃O | CH₃O | H | H | CH₃ | H | H | H | H | 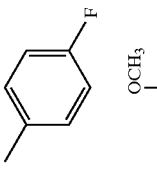 |
| 106 | N | CH | H | CH₃O | CH₃O | H | H | CH₃ | H | H | H | H | 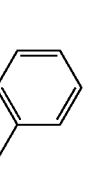 |

-continued

| | X | Z | R¹ | R² | R³ | R⁴ | R⁵ | R⁶ | R⁷ | R⁸ | R⁹ | R¹⁰ | R¹¹ |
|---|---|---|---|---|---|---|---|---|---|---|---|---|---|
| 107 | N | CH | H | CH₃O | CH₃O | H | H | H | H | H | H | H | alkyl |
| 108 | N | CH | H | CH₃O | CH₃O | H | H | NO₂ | H | H | H | H | alkyl |
| 109 | N | CH | H | CH₃O | CH₃O | H | H | NO₂ | H | H | H | H | alkyl |
| 110 | N | CH | H | CH₃O | CH₃O | H | H | Cl | H | H | CH₂OCH₃ | H | alkyl |
| 111 | N | CH | H | CH₃O | CH₃O | H | H | Cl | H | H | CH₃C(=O)— | H | alkyl |
| 112 | N | CH | H | CH₃O | CH₃O | H | H | Cl | H | H | H | CH₃ | alkyl |
| 113 | N | CH | H | CH₃O | CH₃O | H | H | Cl | H | H | H | CH₃CH₂ | alkyl |
| 114 | N | CH | H | CH₃O | CH₃O | H | H | Cl | H | H | H | CH₃(CH₂)₂ | alkyl |
| 115 | N | CH | H | CH₃O | CH₃O | H | H | Cl | H | H | H | CH₃ | 4-Cl-phenyl |
| 116 | N | CH | H | CH₃O | CH₃O | H | H | Cl | H | H | H | CH₃CH₂ | alkyl |
| 117 | N | CH | H | CH₃O | CH₃O | H | H | Cl | H | H | H | H | CH₃ |
| 118 | N | CH | H | CH₃O | CH₃O | H | H | Cl | H | H | H | CH₃ | CH₃ |
| 119 | N | CH | H | CH₃O | 4-(3-methoxypropyl)morpholin-yl | H | H | Cl | H | H | H | H | alkyl |
| 120 | N | CH | H | CH₃O | 4-(2-methoxyethyl)morpholin-yl | H | H | Cl | H | H | H | H | alkyl |
| 121 | N | CH | H | CH₃O | HO-CH₂CH₂CH₂-OCH₃ | H | H | Cl | H | H | H | H | alkyl |
| 122 | N | CH | H | CH₃O | HO-CH₂CH₂-OCH₃ | H | H | Cl | H | H | H | H | alkyl |

-continued

| | X | Z | R¹ | R² | R³ | R⁴ | R⁵ | R⁶ | R⁷ | R⁸ | R⁹ | R¹⁰ | R¹¹ |
|---|---|---|---|---|---|---|---|---|---|---|---|---|---|
| 123 | N | CH | H | CH₃O | 4-(methoxymethyl)pyridinyl | H | H | Cl | H | H | H | H | isopropyl |
| 124 | N | CH | H | CH₃O | 4-(4-methoxybutyl)morpholinyl | H | H | Cl | H | H | H | H | isopropyl |
| 125 | N | CH | H | CH₃O | 1-(4-methoxybutyl)pyrazolyl | H | H | Cl | H | H | H | H | isopropyl |
| 126 | N | CH | H | CH₃O | 4-(methoxymethyl)pyridinyl | H | H | Cl | H | H | H | CH₃CH₂ | isopropyl |
| 127 | N | CH | H | CH₃O | 4-(3-methoxypropyl)morpholinyl | H | H | Cl | H | H | H | H | isopropyl |
| 128 | N | CH | H | CH₃O | 1-methyl-4-(2-methoxyethyl)piperazinyl | H | H | Cl | H | H | H | H | isopropyl |
| 129 | N | CH | H | CH₃O | N-(2-hydroxyethyl)-N-(2-methoxyethyl)amino | H | H | Cl | H | H | H | H | isopropyl |
| 130 | N | CH | H | CH₃O | 1-methyl-4-(3-methoxypropyl)piperazinyl | H | H | Cl | H | H | H | H | isopropyl |
| 131 | N | CH | H | CH₃O | 1-(2-methoxyethyl)pyrazolyl | H | H | Cl | H | H | H | CH₃CH₂ | isopropyl |

-continued
| | X | Z | R¹ | R² | R³ | R⁴ | R⁵ | R⁶ | R⁷ | R⁸ | R⁹ | R¹⁰ | R¹¹ |
|---|---|---|---|---|---|---|---|---|---|---|---|---|---|
| 132 | N | CH | H | CH₃O | 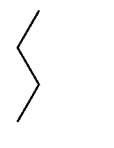 | H | H | Cl | H | H | H | CH₃CH₂ | 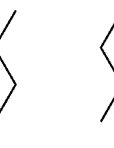 |
| 133 | N | CH | H | CH₃O |  | H | H | Cl | H | H | H | H | 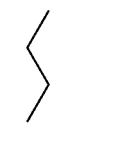 |
| 134 | N | CH | H | CH₃O | 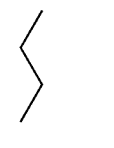 | H | H | Cl | H | H | H | H | 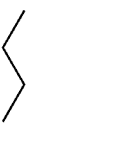 |
| 135 | N | CH | H | CH₃O |  | H | H | Cl | H | H | H | H | 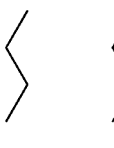 |
| 136 | N | CH | H | CH₃O |  | H | H | Cl | H | H | H | H | 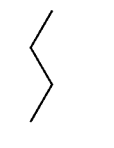 |
| 137 | N | CH | H | CH₃O |  | H | H | Cl | H | H | H | H |  |
| 138 | N | CH | H | CH₃O | 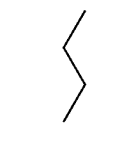 | H | H | Cl | H | H | H | H | |
| 139 | N | CH | H | CH₃O |  | H | H | Cl | H | H | H | H | |
| 140 | N | CH | H | CH₃O |  | H | H | Cl | H | H | H | H | |

-continued

| | X | Z | R¹ | R² | R³ | R⁴ | R⁵ | R⁶ | R⁷ | R⁸ | R⁹ | R¹⁰ | R¹¹ |
|---|---|---|---|---|---|---|---|---|---|---|---|---|---|
| 141 | CH | CH | H | CH₃O | 2-(methoxymethyl)pyridyl | H | H | Cl | H | H | H | H | iPr |
| 142 | CH | CH | H | CH₃O | 3-(methoxymethyl)pyridyl | H | H | Cl | H | H | H | H | iPr |
| 143 | CH | CH | H | CH₃O | 4-(methoxymethyl)pyridyl | H | H | Cl | H | H | H | H | iPr |
| 144 | CH | CH | H | CH₃O | 4-(2-methoxyethyl)morpholinyl | H | H | Cl | H | H | H | H | iPr |
| 145 | CH | CH | H | CH₃O | 1-(2-methoxyethyl)imidazolyl | H | H | Cl | H | H | H | H | iPr |
| 146 | CH | CH | H | CH₃O | 1-(2-methoxyethyl)imidazolyl | H | H | Cl | H | H | H | H | iPr |
| 147 | CH | CH | H | CH₃O | N-(2-methoxyethyl)-N-(2-hydroxyethyl) | H | H | Cl | H | H | H | H | iPr |
| 148 | CH | CH | H | CH₃O | 1-(2-methoxyethyl)-4-methylpiperazinyl | H | H | Cl | H | H | H | H | iPr |
| 149 | CH | CH | H | CH₃O | N,N-bis(2-methoxyethyl)-hydroxyethyl | H | H | Cl | H | H | H | H | iPr |
| 150 | CH | CH | H | CH₃O | N-methyl-N-(2-methoxyethyl)-N-(2-hydroxyethyl) | H | H | Cl | H | H | H | H | iPr |

| | X | Z | R¹ | R² | R³ | R⁴ | R⁵ | R⁶ | R⁷ | R⁸ | R⁹ | R¹⁰ | R¹¹ |
|---|---|---|---|---|---|---|---|---|---|---|---|---|---|
| 151 | CH | CH | H | CH₃O | 3-(morpholin-4-yl)propyl, O-methyl ether chain | H | H | Cl | H | H | H | H | iPr |
| 152 | CH | CH | H | CH₃O | 3-(4-methylpiperazin-1-yl)propyl with methoxy | H | H | Cl | H | H | H | H | iPr |
| 153 | CH | CH | H | CH₃O | 3-(pyrazol-1-yl)propyl-methoxy | H | H | Cl | H | H | H | H | iPr |
| 154 | CH | CH | H | CH₃O | 3-(imidazol-1-yl)propyl-methoxy | H | H | Cl | H | H | H | H | iPr |
| 155 | CH | CH | H | CH₃O | N,N-bis(2-hydroxyethyl)aminopropyl-methoxy | H | H | Cl | H | H | H | H | iPr |
| 156 | CH | CH | H | CH₃O | N,N-bis(2-hydroxyethyl)aminopropyl-methoxy | H | H | Cl | H | H | H | H | iPr |
| 157 | CH | CH | H | CH₃O | N-(2-hydroxyethyl)-N-methylaminopropyl-methoxy | H | H | Cl | H | H | H | H | iPr |
| 158 | CH | CH | H | CH₃O | 4-(pyrazol-1-yl)butyl-methoxy | H | H | Cl | H | H | H | H | iPr |
| 159 | CH | CH | H | CH₃O | 5-(pyrazol-1-yl)pentyl-methoxy | H | H | Cl | H | H | H | H | iPr |

-continued

| | X | Z | R¹ | R² | R³ | R⁴ | R⁵ | R⁶ | R⁷ | R⁸ | R⁹ | R¹⁰ | R¹¹ |
|---|---|---|---|---|---|---|---|---|---|---|---|---|---|
| 160 | CH | CH | H | CH₃O | 4-methoxybutyl-imidazolyl | H | H | Cl | H | H | H | H | butyl |
| 161 | N | CH | H | CH₃O | (methoxymethyl)pyridinyl | H | H | Cl | H | H | H | H | 2,4-difluoro-methylphenyl |
| 162 | N | CH | H | CH₃O | 2-methoxyethyl-morpholinyl | H | H | Cl | H | H | H | H | 2,4-difluoro-methylphenyl |
| 163 | N | CH | H | CH₃O | 3-methoxypropyl-morpholinyl | H | H | Cl | H | H | H | H | 2,4-difluoro-methylphenyl |
| 164 | N | CH | H | CH₃O | 3-methoxypropyl-(4-methylpiperazinyl) | H | H | Cl | H | H | H | H | 2,4-difluoro-methylphenyl |
| 165 | N | CH | H | CH₃O | N-(3-methoxypropyl)-N-methyl-2-hydroxyethylamino | H | H | Cl | H | H | H | H | 2,4-difluoro-methylphenyl |

-continued
| | X | Z | R¹ | R² | R³ | R⁴ | R⁵ | R⁶ | R⁷ | R⁸ | R⁹ | R¹⁰ | R¹¹ |
|---|---|---|---|---|---|---|---|---|---|---|---|---|---|
| 166 | CH | CH | H | CH₃O |  | H | H | Cl | H | H | H | H |  |
| 167 | CH | CH | H | CH₃O |  | H | H | Cl | H | H | H | H | 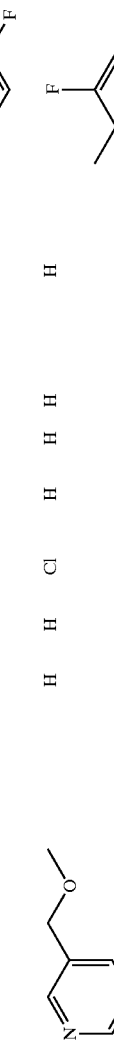 |
| 168 | CH | CH | H | CH₃O |  | H | H | Cl | H | H | H | H |  |
| 169 | CH | CH | H | CH₃O |  | H | H | Cl | H | H | H | H |  |
| 170 | CH | CH | H | CH₃O |  | H | H | Cl | H | H | H | H |  |
| 171 | N | CH | H | CH₃O |  | H | H | CH₃O | H | H | H | H |  |

-continued

| | X | Z | R¹ | R² | R³ | R⁴ | R⁵ | R⁶ | R⁷ | R⁸ | R⁹ | R¹⁰ | R¹¹ |
|---|---|---|---|---|---|---|---|---|---|---|---|---|---|
| 172 | N | CH | H | CH₃O | morpholine-propyl-OMe | H | H | CH₃O | H | H | H | H | 2,4-difluorophenylmethyl |
| 173 | CH | CH | H | CH₃O | morpholine-propyl-OMe | H | H | CH₃O | H | H | H | H | propyl |
| 174 | CH | CH | H | CH₃O | pyridyl-CH₂-OMe | H | H | CH₃O | H | H | H | H | propyl |
| 175 | CH | CH | H | CH₃O | morpholine-ethyl-OMe | H | H | CH₃ | H | H | H | H | ethyl |
| 176 | CH | CH | H | CH₃O | N-methylpiperazine-propyl-OMe | H | H | CH₃ | CH₃ | H | H | H | propyl |
| 177 | CH | CH | H | CH₃O | pyrazole-ethyl-OMe | H | H | CH₃ | CH₃ | H | H | H | propyl |
| 178 | N | CH | H | CH₃O | morpholine-ethyl-OMe | H | H | Cl | H | H | H | CH₃ | 2,4-difluorophenylmethyl |
| 179 | N | CH | H | CH₃O | morpholine-butyl-OMe | H | H | Cl | H | H | H | CH₃ | CH₃ |

-continued

| | X | Z | R¹ | R² | R³ | R⁴ | R⁵ | R⁶ | R⁷ | R⁸ | R⁹ | R¹⁰ | R¹¹ |
|---|---|---|---|---|---|---|---|---|---|---|---|---|---|
| 180 | N | CH | H | CH₃O | (methoxymethyl)pyridine | H | H | Cl | H | H | H | CH₃ | CH₃ |
| 181 | N | CH | H | CH₃O | methyl methoxyacetate | H | H | Cl | H | H | H | CH₃ | CH₃ |
| 182 | N | CH | H | CH₃O | 4-methyl-1-(3-methoxypropyl)piperazine | H | H | Cl | H | H | H | CH₃ | CH₃ |
| 183 | N | CH | H | CH₃O | N-(2-hydroxyethyl)-N-methyl-(3-methoxypropyl)amine | H | H | Cl | H | H | H | CH₃ | CH₃ |
| 184 | N | CH | H | CH₃O | 1-(3-methoxypropyl)piperidine | H | H | Cl | H | H | H | H | CH₃ |
| 185 | N | CH | H | CH₃O | 1-(3-methoxypropyl)piperidine | H | H | Cl | H | H | H | H | isopropyl |
| 186 | CH | CH | H | CH₃O | (methoxymethyl)pyridine | H | H | Cl | H | H | H | H | 2,4-difluorophenyl |

Pharmacological Test Example 1

Measurement of Inhibitory Activity Against Activation of MAPK Within Vascular Endothelial Cells Induced by VEGF Stimulation Human funicular venous vascular endothelial cells (purchased from Chronetics) were cultured in an EGM-2 medium (purchased from Chronetics) within an incubator containing 5% carbon dioxide until 50 to 70% confluent, and the culture was inoculated into wells, containing the same medium, in a 96-well flat-bottom plate in an amount of $1.5 \times 10^5$ per well. After cultivation at 37° C. overnight, the medium was replaced by an EBM-2 medium containing 0.5% fetal calf serum (purchased from Chronetics), followed by cultivation for 24 hr. A solution of the test compound in dimethyl sulfoxide was added to each well, and the cultivation was continued at 37° C. for additional one hr. A human recombinant vascular endothelial growth factor (hereinafter abbreviated to "VEGF") was added to a final concentration of 50 ng/ml, and the stimulation of cells was carried out at 37° C. for 8 min. The medium was removed, the cells were washed with phosphate buffered saline (pH 7.4), and 10 μl of a solubilization buffer (Tris buffered saline (pH 7.4) containing 1% Triton X100, 2 mM sodium orthovanadylate, and 1 mM disodium ethylenediaminetetraacetate) was then added thereto. The mixture was shaken at 4° C. for one hr to solubilize the cells. An equal amount of Tris buffered saline containing 1% sodium laurylsulfate was added to and thoroughly mixed with the solution. This solution (2 μl) was adsorbed on a PVDF filter by dot blotting, and this filter was subjected to immunoblotting with anti-tyrosine phosphorylated MAPK antibody (purchased from Daiichi Pure Chemicals).

The level of phosphorylated MAPK was quantitatively determined with a densitometer, and the percentage phosphorylated MAPK in the presence of the test compound was determined by presuming the level of phosphorylated MAPK with the addition of VEGF in the absence of the test compound to be 100% and the level of phosphorylated MAPK in the absence of the test compound and VEGF to be 0%. The test compound concentration ($IC_{50}$) necessary for inhibiting 50% of the activation of MAPK was calculated based on the percentage of phosphorylated MAPK.

The results were as summarized in Table 1.

TABLE 1

| Compound | $IC_{50}$ (nM) |
|---|---|
| 1 | 1.8 |
| 4 | 2.1 |
| 5 | 2.9 |
| 7 | 5.2 |
| 8 | 11.0 |
| 9 | 5.1 |
| 10 | 7.8 |
| 11 | 15.0 |
| 13 | 2.2 |
| 14 | 0.7 |
| 16 | 2.9 |
| 17 | 11.0 |
| 18 | 0.6 |
| 19 | 0.6 |
| 20 | 8.5 |
| 21 | 3.4 |
| 22 | 0.4 |
| 23 | 5.4 |
| 24 | 0.6 |
| 25 | 3.9 |
| 26 | 5.3 |
| 28 | 4.0 |
| 29 | 4.4 |
| 30 | 1.7 |
| 31 | 2.5 |
| 32 | 7.3 |
| 33 | 3.5 |
| 34 | 4.2 |
| 35 | 3.7 |
| 36 | 3.3 |
| 37 | 2.3 |
| 40 | 12.0 |
| 41 | 4.9 |
| 42 | 5.9 |
| 43 | 3.8 |
| 45 | 2.0 |
| 46 | 4.3 |
| 47 | 4.0 |
| 48 | 0.5 |
| 49 | 4.3 |
| 50 | 0.5 |
| 52 | 4.4 |
| 53 | 5.9 |
| 54 | 0.5 |
| 55 | 2.8 |
| 56 | 5.1 |
| 57 | 6.5 |
| 58 | 5.1 |
| 59 | 5.8 |
| 62 | 16.0 |
| 63 | 70.0 |
| 64 | 42.0 |
| 65 | 36.0 |
| 66 | 21.0 |
| 67 | 345.0 |
| 68 | 45.0 |
| 69 | 67.0 |
| 70 | 6.8 |
| 71 | 750.0 |
| 72 | 3.9 |
| 73 | <2 |
| 74 | 6.0 |
| 75 | 1.2 |
| 76 | 8.0 |
| 77 | 71.0 |
| 78 | 4.1 |
| 79 | 30.0 |
| 80 | 13.0 |
| 82 | 3.8 |
| 83 | >1000 |
| 85 | 0.7 |
| 86 | 0.6 |
| 87 | 58.0 |
| 89 | 45.0 |
| 90 | 42.0 |
| 92 | 46.0 |
| 93 | 14.0 |
| 94 | 1.8 |
| 95 | 2.7 |
| 96 | <1 |
| 97 | 518.0 |
| 98 | 450.0 |
| 99 | 8.8 |
| 100 | 5.2 |
| 102 | 150.0 |
| 103 | 53.0 |
| 104 | 5.3 |
| 105 | 2.3 |
| 106 | <1 |
| 107 | 10.2 |

Pharmacological Test Example 2

Measurement of Inhibitory Activity Against KDR Phosphorylation by ELISA

NIH 3T3 cells (Sawano A et al., Cell Growth & Differatation, 7, 213–221 (1996), "Flt-1 but not KDR/Flk-1 tyrosine kinase is a receptor for placenta growth factor, which is related to vascular endothelial growth factor") prepared by transfection of human KDR were cultured in a DMEM medium containing 10% fetal calf serum (purchased from GIBCO BRL) within a 5% carbon dioxide incubator until 50 to 70% confluent. The harvested cells were inoculated into wells, containing the same medium, in a collagen-type one-coat 96-well flat-bottom plate in an amount of 1.5 ×10$^4$ per well, followed by cultivation at 37° C. overnight. The medium was then replaced by a DMEM medium containing 0.1% fetal calf serum. A solution of the test compound in dimethyl sulfoxide was added to each well, and the cultivation was continued at 37° C for additional one hr. A human recombinant vascular endothelial growth factor (hereinafter abbreviated to "VEGF") was added to a final concentration of 100 ng/ml, and the stimulation of cells was carried out at 37° C. for 2 min. The medium was removed, the cells were washed with phosphate buffered saline (pH 7.4), and 50 μl of a solubilization buffer (20 mM HEPES (pH 7.4), 150 mM NaCl, 0.2% Triton X-100, 10% glycerol, 5 mM sodium orthovanadylate, 5 mM disodium ethylenediaminetetraacetate, and 2 mM Na$_4$P$_2$O$_7$) was then added thereto. The mixture was shaken at 4° C. for 2 hr to prepare a cell extract.

Separately, phosphate buffered saline (50 μl, pH 7.4) containing 5 μg/ml of anti-phospho-tyrosine antibody (PY20; purchased from Transduction Laboratories) was added to a microplate for ELISA (Maxisorp; purchased from NUNC), followed by standing at 4° C. overnight to form a solid phase on the wells. After washing of the plate, 300 =1 of a blocking solution was added, followed by standing at room temperature for 2 hr to perform blocking. After washing, the whole quantity of the cell extract was transferred to the wells, and the plate was then allowed to stand at 4° C. overnight. After washing, an anti-KDR antibody (purchased from Santa Cruz) was allowed to react at room temperature for one hr, and, after washing, a peroxidase-labeled anti-rabbit Ig antibody (purchased from Amersham) was allowed to react at room temperature for one hr. After washing, a chromophoric substrate for peroxidase (purchased from Sumitomo Bakelite Co., Ltd.) was added thereto to initiate a reaction. After a suitable level of color development, a reaction termination solution was added to stop the reaction, and the absorbance at 450 nm was measured with a microplate reader. The KDR phosphorylation activity for each well was determined by presuming the absorbance with the addition of VEGF and without the addition of the medicament to be 100% KDR phosphorylation activity and the absorbance without the medicament and VEGF to be 0% KDR phosphorylation activity. The concentration of the test compound was varied on several levels, the inhibition (%) of KDR phosphorylation was determined for each case, and the concentration of the test compound necessary for inhibiting 50% of KDR phosphorylation (IC$_{50}$) was ii calculated.

The results were as summarized in Table 2.

TABLE 2

| Compound | IC$_{50}$ (nM) |
| --- | --- |
| 62 | 11.0 |
| 63 | 150.0 |
| 64 | 150.0 |
| 65 | 27.0 |
| 66 | 15.0 |
| 67 | 63.0 |
| 68 | 24.0 |
| 69 | 64.0 |
| 70 | 32.0 |
| 71 | 350.0 |
| 72 | 3.5 |

TABLE 2-continued

| Compound | IC$_{50}$ (nM) |
| --- | --- |
| 73 | 1.0 |
| 74 | 11.0 |
| 75 | 1.4 |
| 76 | 3.5 |
| 77 | 6.0 |
| 78 | 3.4 |
| 79 | 18.0 |
| 80 | 2.7 |
| 81 | 4.1 |
| 82 | 8.4 |
| 83 | 840.0 |
| 85 | 0.5 |
| 86 | 1.5 |
| 87 | 110.0 |
| 88 | 61.0 |
| 89 | 24.0 |
| 90 | 57.0 |
| 92 | 63.0 |
| 93 | 37.0 |
| 94 | 2.3 |
| 95 | 3.8 |
| 96 | 0.4 |
| 97 | 490.0 |
| 98 | 330.0 |
| 99 | 25.0 |
| 100 | 13.0 |
| 101 | 3.0 |
| 102 | 105.0 |
| 103 | 78.0 |
| 104 | 3.9 |
| 105 | 2.0 |
| 106 | 1.5 |
| 107 | 11.0 |
| 108 | 5.0 |
| 110 | >1000 |
| 111 | >1000 |
| 112 | >1000 |
| 113 | >1000 |
| 114 | >1000 |
| 115 | >1000 |
| 116 | >1000 |
| 117 | 24.0 |
| 118 | >1000 |
| 119 | 3.6 |
| 120 | 3.9 |
| 121 | 12.5 |
| 122 | 5.8 |
| 123 | 8.9 |
| 124 | 1.9 |
| 125 | 2.6 |
| 126 | >1000 |
| 127 | 1.1 |
| 131 | >1000 |
| 132 | >1000 |
| 133 | 8.3 |
| 134 | 5.0 |
| 135 | 1.0 |
| 136 | 160.0 |
| 137 | 24.0 |
| 138 | 40.0 |
| 139 | 15.0 |
| 140 | 36.0 |
| 141 | 14.0 |
| 142 | 2.6 |
| 143 | 3.5 |
| 144 | 1.6 |
| 145 | 0.8 |
| 146 | 1.0 |
| 147 | 1.0 |
| 148 | 15.0 |
| 149 | 1.6 |
| 150 | 1.8 |
| 151 | 0.5 |
| 152 | 0.8 |
| 153 | 1.5 |
| 154 | 1.5 |
| 155 | 2.1 |

TABLE 2-continued

| Compound | IC$_{50}$ (nM) |
|---|---|
| 156 | 0.8 |
| 157 | 0.4 |
| 158 | 1.6 |
| 159 | 1.9 |
| 160 | 0.9 |
| 161 | 3.9 |
| 162 | 1.0 |
| 163 | 1.4 |
| 164 | 0.9 |
| 165 | 0.6 |
| 166 | 2.2 |
| 167 | 2.1 |
| 168 | 4.0 |
| 169 | 3.7 |
| 170 | 1.1 |
| 175 | 4.7 |
| 176 | 3.7 |
| 177 | 2.3 |
| 178 | >1000 |
| 179 | >1000 |
| 180 | >1000 |
| 181 | >1000 |
| 182 | >1000 |
| 183 | >1000 |
| 184 | 0.2 |
| 185 | 0.5 |
| 186 | 6.3 |

Pharmacological Test Example 3

Karyomorphosis Test

A375 human melanoma cells (2×10$^4$) (obtained from Japanese Foundation for Cancer Research) were incolulated on a culture slide (manufactured by Falcon) and were cultured at 37° C. . After the elapse of 5 hr from the initiation of the cultivation, the test compound was added to 10 μM and 1 μM, and the cultivation was continued for additional 48 hr. After the fixation of cells, 50 μg/ml propidium iodide solution containing ribonuclease (200 μg/ml) was added to stain nuclei. The stained nuclei were observed under a fluorescent microscope to analyze the nuclei for abnormality of karyomorphosis. The change in karyomorphosis for test compounds was evaluated as (2+) when the change in karyomorphosis of cells took place at 1 μM; was evaluated as (+) when the change in karyomorphosis of cells took place at 10 μM; and was evalauted as (−) when if the change in karyomorphosis of cells did not take place at 10 μM.

The results were as summarized in Table 3.

TABLE 3

| Compound No. | Change in morphosis |
|---|---|
| 13 | (−) |
| 14 | (−) |
| 15 | (−) |
| 16 | (−) |
| 17 | (−) |
| 18 | (−) |
| 20 | (−) |
| 21 | (−) |
| 22 | (−) |
| 24 | (−) |
| 25 | (−) |
| 26 | (−) |
| 28 | (−) |
| 29 | (−) |
| 30 | (−) |
| 31 | (−) |
| 32 | (−) |
| 33 | (−) |
| 34 | (−) |
| 35 | (−) |
| 36 | (−) |
| 37 | (−) |
| 38 | (−) |
| 39 | (−) |
| 40 | (−) |
| 41 | (−) |
| 42 | (−) |
| 43 | (−) |
| 44 | (−) |
| 45 | (−) |
| 46 | (−) |
| 47 | (−) |
| 48 | (−) |
| 49 | (−) |
| 52 | (−) |
| 53 | (−) |
| 55 | (−) |
| 58 | (−) |
| 59 | (−) |
| 60 | (−) |
| 61 | (−) |
| 62 | (−) |

Pharmacological Test Example 4

Antitumor Effect on Human Glioma Cells (GL07)

Human glioma cells GL07 (obtained from Central Laboratories for Experimental Animals) were transplanted into nude mice. When the tumor volume became about 100 mm$^3$, the mice were grouped. In this case, grouping was carried out so that each group consisted of four mice and the average tumor volume was even among the groups. The test compound was orally or intraperitoneally administered at a dose of 20 mg/kg to the test groups every once a day for 9 days, while the medium was administered to the control group in the manner as in the test groups. The tumor growth inhibition rate (TGIR) was calculated as follows: The tumor growth inhibition rate (TGIR)=(1−Tx/Cx)×100 wherein Cx represents the volume of tumor at day x for the control group when the tumor volume at the day of the start of the administration was presumed to be 1; and Tx represents the volume of tumor for test compound administration groups.

The tumor growth inhibition rate for representative examples of a group of compounds according to the present invention is shown in Table 4.

TABLE 4

| Ex. No. | Administration site | TGIR, % |
|---|---|---|
| 4 | Oral | 61 |
| 5 | Oral | 59 |
| 9 | Intraperitoneal | 59 |
| 13 | Intraperitoneal | 52 |
| 14 | Intraperitoneal | 81 |
| 16 | Intraperitoneal | 77 |
| 17 | Intraperitoneal | 85 |
| 18 | Oral | 57 |
| 24 | Oral | 63 |
| 25 | Intraperitoneal | 68 |
| 28 | Intraperitoneal | 84 |
| 29 | Oral | 64 |
| 37 | Intraperitoneal | 70 |
| 48 | Intraperitoneal | 90 |
| 50 | Oral | 59 |

TABLE 4-continued

| Ex. No. | Administration site | TGIR, % |
|---|---|---|
| 51 | Oral | 65 |
| 54 | Oral | 59 |
| 62 | Oral | 78 |
| 64 | Oral | 37 |
| 66 | Oral | 26 |
| 67 | Oral | 30 |
| 68 | Oral | 57 |
| 69 | Oral | 26 |
| 71 | Oral | 67 |
| 73 | Oral | 34 |
| 74 | Oral | 28 |
| 77 | Oral | 26 |
| 78 | Oral | 21 |
| 79 | Oral | 28 |
| 80 | Oral | 52 |
| 82 | Oral | 27 |
| 83 | Oral | 31 |
| 85 | Oral | 26 |
| 89 | Oral | 40 |
| 93 | Oral | 29 |
| 94 | Oral | 29 |
| 97 | Oral | 48 |
| 98 | Oral | 38 |
| 99 | Oral | 33 |
| 100 | Oral | 36 |
| 101 | Oral | 44 |
| 102 | Oral | 24 |
| 103 | Oral | 23 |
| 104 | Oral | 22 |
| 105 | Oral | 20 |
| 107 | Oral | 49 |
| 109 | Oral | 71 |
| 110 | Oral | 26 |
| 111 | Oral | 78 |
| 112 | Oral | 81 |
| 113 | Oral | 61 |
| 114 | Oral | 60 |
| 115 | Oral | 74 |
| 116 | Oral | 83 |
| 119 | Oral | 40 |
| 120 | Oral | 30 |
| 121 | Oral | 22 |
| 122 | Oral | 21 |
| 123 | Oral | 31 |
| 124 | Oral | 27 |
| 125 | Oral | 30 |
| 126 | Oral | 52 |
| 127 | Oral | 25 |
| 128 | Oral | 21 |
| 129 | Oral | 25 |
| 130 | Oral | 32 |
| 131 | Oral | 31 |
| 132 | Oral | 24 |
| 133 | Oral | 20 |
| 134 | Oral | 29 |
| 135 | Oral | 62 |
| 136 | Oral | 23 |
| 137 | Oral | 20 |
| 138 | Oral | 21 |
| 139 | Oral | 27 |
| 140 | Oral | 21 |
| 141 | Oral | 28 |
| 142 | Oral | 48 |
| 143 | Oral | 53 |
| 144 | Oral | 56 |
| 145 | Oral | 57 |
| 146 | Oral | 48 |
| 147 | Oral | 34 |
| 148 | Oral | 54 |
| 149 | Oral | 47 |
| 150 | Oral | 22 |
| 151 | Oral | 44 |
| 152 | Oral | 44 |
| 153 | Oral | 53 |
| 154 | Oral | 34 |
| 155 | Oral | 29 |
| 156 | Oral | 24 |
| 157 | Oral | 44 |
| 158 | Oral | 39 |
| 159 | Oral | 40 |
| 160 | Oral | 43 |
| 161 | Oral | 39 |
| 162 | Oral | 40 |
| 163 | Oral | 52 |
| 164 | Oral | 55 |
| 165 | Oral | 44 |
| 166 | Oral | 27 |
| 167 | Oral | 28 |
| 168 | Oral | 42 |
| 169 | Oral | 55 |
| 170 | Oral | 64 |
| 171 | Oral | 13 |
| 172 | Oral | 42 |
| 173 | Oral | 21 |
| 174 | Oral | 19 |
| 175 | Oral | 17 |
| 176 | Oral | 22 |
| 177 | Oral | 35 |
| 178 | Oral | 28 |
| 179 | Oral | 33 |
| 180 | Oral | 45 |
| 181 | Oral | 21 |
| 182 | Oral | 31 |
| 183 | Oral | 22 |
| 184 | Oral | 48 |
| 185 | Oral | 59 |
| 186 | Oral | 47 |

TGIR, % = Tumor growth inhibition rate (%)

What is claimed is:

1. A compound, wherein said compound has at least one chemical name selected from the group consisting of N-{2-chloro-4-[(6,7-dimethoxy-4-quinazolinyl)-oxy]phenyl}-N'-propylurea, N-{2-chloro-4-[(6,7-dimethoxy-4 quinazolinyl)oxy]phenyl}-N'-ethylurea, N-butyl-N'- {2-chloro-4-[(6,7-dimethoxy-4-quinazolinyl)oxy]phenyl}urea, N-{2-chloro-4-[(6,7-dimethoxy-4-quinazolinyl)oxy]phenyl}-N'-pentylurea, N-(sec-Butyl)-N'-{2-chloro-4-[(6,7-dimethoxy-4-quinazolinyl)oxy]phenyl}urea, N-allyl-N'-{2-chloro-4-[(6,7-dimethoxy4-quinazolinyl)oxy]phenyl}urea, and N-{2-chloro-4-[(6,7-dimethoxy-4-quinazolinyl)oxy]phenyl}-N' (2-propynyl)urea.

2. The compound according to claim 1, wherein said compound is N-{2-chloro-4-[(6,7-dimethoxy-4-quinazolinyl)-oxy]phenyl}-N'-propylurea.

3. The compound according to claim 1, wherein said compound is N-{2-chloro-4-[(6,7-dimethoxy-4quinazolinyl)oxy]phenyl}-N'-ethylurea.

4. The compound according to claim 1, wherein said compound is N-butyl-N'-{2-chloro-4-[(6,7-dimethoxy-4-quinazolinyl)oxy]phenyl}urea.

5. The compound according to claim 1, wherein said compound is N-{2-chloro-4-[(6,7-dimethoxy-4-quinazolinyl)oxy]phenyl}-N'-pentylurea.

6. The compound according to claim 1, wherein said compound is N-(sec-Butyl)-N'-{2-chloro-4-[(6,7-dimethoxy-4-quinazolinyl)oxy]phenyl}urea.

7. The compound according to claim 1, wherein said compound in N-allyl-N'-{2-chloro-4-[(6,7-dimethoxy-4-quinazolinyl)oxy]phenyl}urea.

8. The compound according to claim 1, wherein said compound is N-{2-chloro-4-[(6,7-dimethoxy-4-quinazolinyl)oxy]phenyl}-N'(2 propnyl)urea.

* * * * *